(12) United States Patent
Christie et al.

(10) Patent No.: US 11,759,526 B2
(45) Date of Patent: Sep. 19, 2023

(54) METHOD AND MOLECULES

(71) Applicants: MedImmune, LLC, Gaithersburg, MD (US); The Regents Of The University Of California, Oakland, CA (US)

(72) Inventors: Ronald James Christie, Gaithersburg, MD (US); Changshou Gao, Gaithersburg, MD (US); Andre Henri St. Amant, Oakland, CA (US); Javier Read de Alaniz, Oakland, CA (US)

(73) Assignees: MedImmune, LLC, Gaithersburg, MD (US); The Regents Of The University Of California, Oakland, CA (US)

( * ) Notice: Subject to any disclaimer, the term of this patent is extended or adjusted under 35 U.S.C. 154(b) by 292 days.

(21) Appl. No.: 16/615,582

(22) PCT Filed: May 25, 2018

(86) PCT No.: PCT/US2018/034535
§ 371 (c)(1),
(2) Date: Nov. 21, 2019

(87) PCT Pub. No.: WO2018/218093
PCT Pub. Date: Nov. 29, 2018

(65) Prior Publication Data
US 2020/0206359 A1 Jul. 2, 2020

Related U.S. Application Data

(60) Provisional application No. 62/511,415, filed on May 26, 2017.

(51) Int. Cl.
*A61K 47/68* (2017.01)
*A61K 47/69* (2017.01)
*C07C 271/22* (2006.01)
*C07D 207/46* (2006.01)

(52) U.S. Cl.
CPC ...... *A61K 47/6811* (2017.08); *A61K 47/6889* (2017.08); *A61K 47/6923* (2017.08); *C07C 271/22* (2013.01); *C07D 207/46* (2013.01); *C07C 2601/10* (2017.05); *C07C 2602/50* (2017.05)

(58) Field of Classification Search
CPC ............ A61K 47/6811; A61K 47/6889; A61K 47/6923; C07C 271/22; C07C 2601/10; C07C 2602/50; C07C 233/48; C07C 233/52; C07C 247/10; C07C 247/12; C07D 207/46; C07D 307/58; A61P 29/00; A61P 35/00; C07K 1/1077; C07K 1/13
See application file for complete search history.

(56) References Cited

U.S. PATENT DOCUMENTS

| 2003/0134826 | A1 | 7/2003 | Glusenkamp et al. |
| 2004/0059101 | A1* | 3/2004 | Weissler ............ C07H 15/26 536/17.4 |
| 2006/0223743 | A1 | 10/2006 | Abel et al. |
| 2007/0287735 | A1 | 12/2007 | Jordan et al. |
| 2011/0268654 | A1 | 11/2011 | Hilderbrand et al. |
| 2015/0005481 | A1 | 1/2015 | Chin et al. |

FOREIGN PATENT DOCUMENTS

| EP | 1 548 109 | 6/2005 |
| WO | 2013092998 A1 | 6/2013 |
| WO | 2014065860 A1 | 5/2014 |
| WO | 2014207245 A1 | 12/2014 |
| WO | 2015019192 A2 | 2/2015 |
| WO | WO-2020210535 A1 * | 10/2020 ............ C40B 40/10 |

OTHER PUBLICATIONS

Pozsgay, et al., Organic Letters 2002 vol. 4 No. 19 pp. 3191-3191 (Year: 2002).*
Kim, et al., Biomol. Ther. 2015 23(6), 493-509 (Year: 2015).*
Zimmerman, et al., Bioconjugate Chem. 2014 vol. 25, Issue 2, pp. 351-361 (Year: 2014).*
Amant, et al., Bioconjugate Chem. 2018 vol. 29, Issue 7, 2406-2414 (Year: 2018).*
Torres, et al. 2014 Dissertation for the Degree of Doctor of Philosophy, North Carolina State University (Year: 2014).*
Hill et al. 'Diels-Alder Bioconjugation of Diene-Modified Oligonucelotides', The Journal of Organic Chemistry, Jul. 12, 2001 (Jul. 12, 2001), vol. 66, pp. 5352-5358.
Pozsgay et al. 'A Method of Bioconjugation of Carbohydrates Using Diels-Alder Cycloaddition', Organic Letters, Aug. 23, 2002 (Aug. 23, 2002), vol. 4, pp. 3191-3194.
Gregoritza et al. 'The Diels-Alder reaction: A powerful tool for the design of drug delivery systems and biomaterials', European Journal of Pharmaceutics and Biopharmaceuticals, Nov. 27, 2015 (Nov. 27, 2015), vol. 97, pp. 438-453.
De Araujo et al., "Diels-Alder Ligation and Surface Immobilization of Proteins", Angew. Chem. 2006, vol. 118, pp. 302-307.
Palomo, J. M., "Diels-Alder Cycloaddition in Protein Chemistry", Eur. J. Org. Chem., 2010, pp. 6303-6314.
Pott et al., "Evolved Sequence Contexts for Highly Efficient Amber Suppression with Noncanonical Amino Acids", ACS Chem. Biol., 2014, vol. 9, pp. 2815-2822.
Lang et al., "Genetically encoded norbornene directs site-specific cellular protein labelling via a rapid bioorthogonal reaction", Nature Chemistry, 2012, vol. 4, pp. 298-304.

(Continued)

Primary Examiner — Julie Wu
Assistant Examiner — John L Van Druff

(57) ABSTRACT

The present invention provides a bioconjugation method and compounds for use therein. The bioconjugation method comprises the step of conjugating a biological molecule containing a first unsaturated functional group with a payload comprising a second unsaturated functional group, wherein the first and second unsaturated functional groups are complementary to each other such that conjugation is a reaction of said functional groups via a Diels-Alder reaction which forms a cyclohexene ring.

5 Claims, 81 Drawing Sheets

(56) References Cited

OTHER PUBLICATIONS

Plass et al., "Amino Acids for Diels-Alder Reactions in Living Cells", Angew. Chem. Int. Ed., 2012, vol. 51, pp. 4166-4170.
Shi et al., "Immuno-Polymeric Nanoparticles by Diels-Alder Chemistry", Angew. Chem. Int. Ed., 2007, vol. 46, pp. 6126-6131.
Shi et al., "Immuno-Polymeric Nanoparticles by Diels-Alder Chemistry—Supporting Information", Angewandte Chemie, vol. 119, No. 32, 2007, pp. 6238-6243.
Marchan V. et al., "Diels-Alder cycloadditions in water for the straightforward preparation of peptide-oligonucleotide conjugates", Nucleic Acids Research, 2006, vol. 34, No. 3 e24, pp. 1-9.
Baldwin, J.E. et al., "Use of L-aspartic acid β-semialdehyde in the synthesis of more complex non protein amino acids", Tetrahedron Letters, vol. 28, No. 31, Jan. 1, 1987, pp. 3605-3608.
Hoogewijs, Kurt et al., "Exploiting furan's versatile reactivity in reversible and irreversible orthogonal peptide labeling", *Chem. Comm.*, vol. 49, No. 28, Jan. 1, 2013, pp. 2927-2929.
Partial European Search Report, European Patent Office, European Patent App. No. 23166601, dated Jul. 17, 2023, 14 pages.
Schmidt, Mortiz J., et al., "Red-Light-Controlled Protein-RNA Crosslinking with a Genetically Encoded Furan", *Angew. Chem. Int. Ed.*, vol. 52, No. 17, Mar. 19, 2013, pp. 4690-4693.

\* cited by examiner

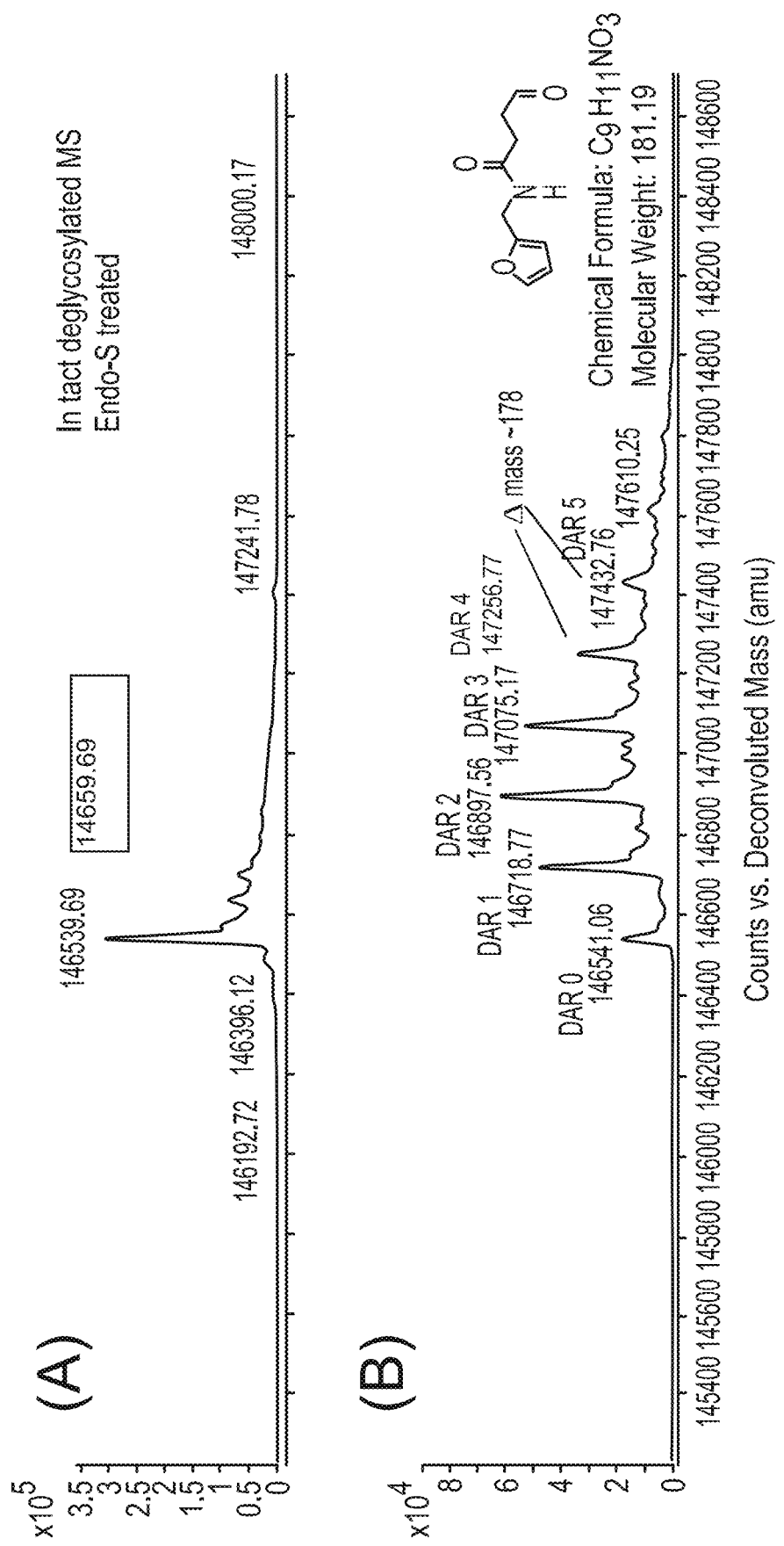
Figure 1.1. Intact deglycosylated mass spectrometry before (A) and after (B) reaction of mAb with furan-NHS.
DAR 0 - 146541.06; DAR 1 - 146718.77; DAR 2 - 146897.56; DAR 3 - 147075.17; DAR 4 - 147256.66; DAR 5 - 147432.76

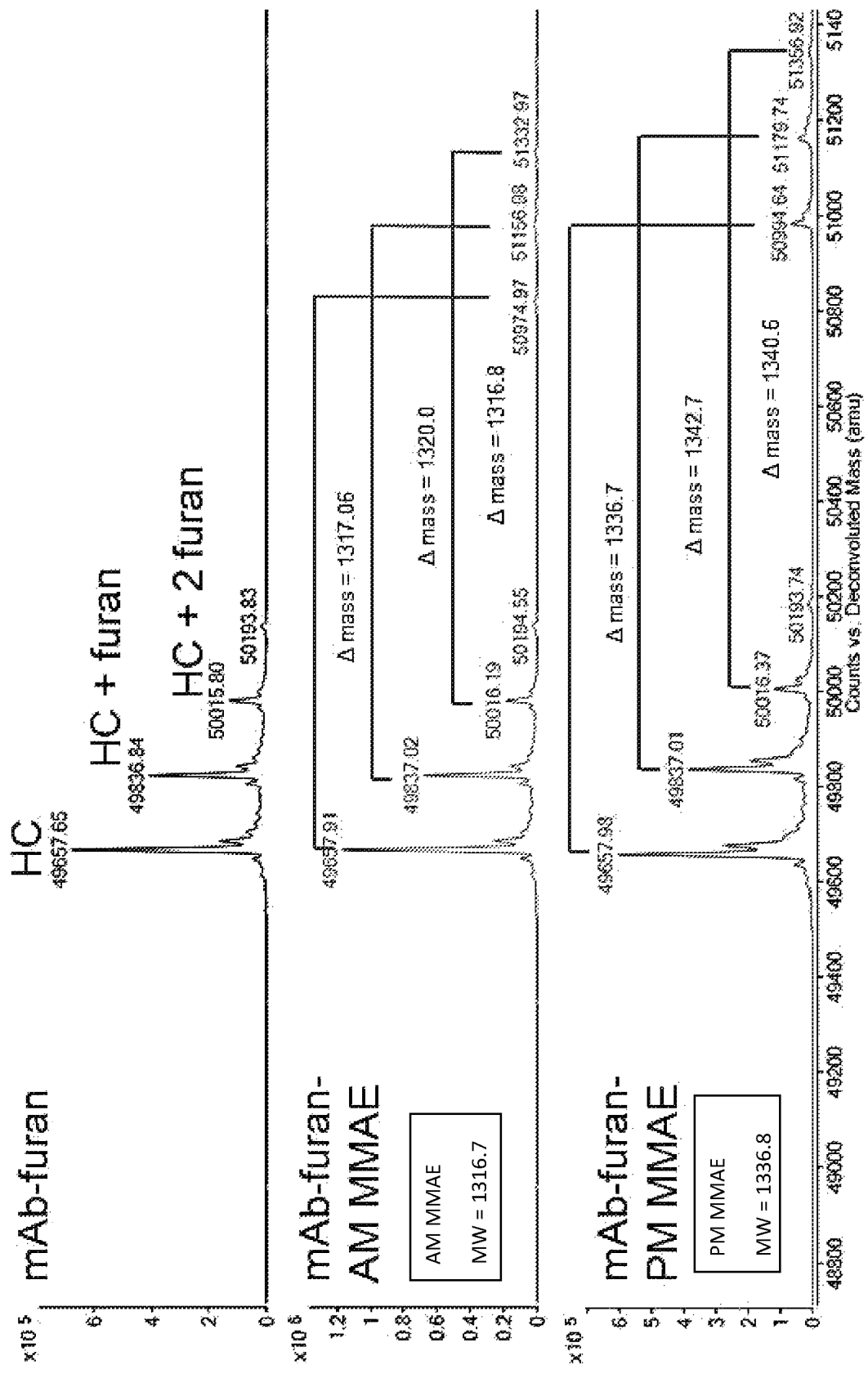
Figure 1.2. Reduced deglycosylated mass spectra of mAb-furan-linker samples after 20 h reaction with MMAEs.

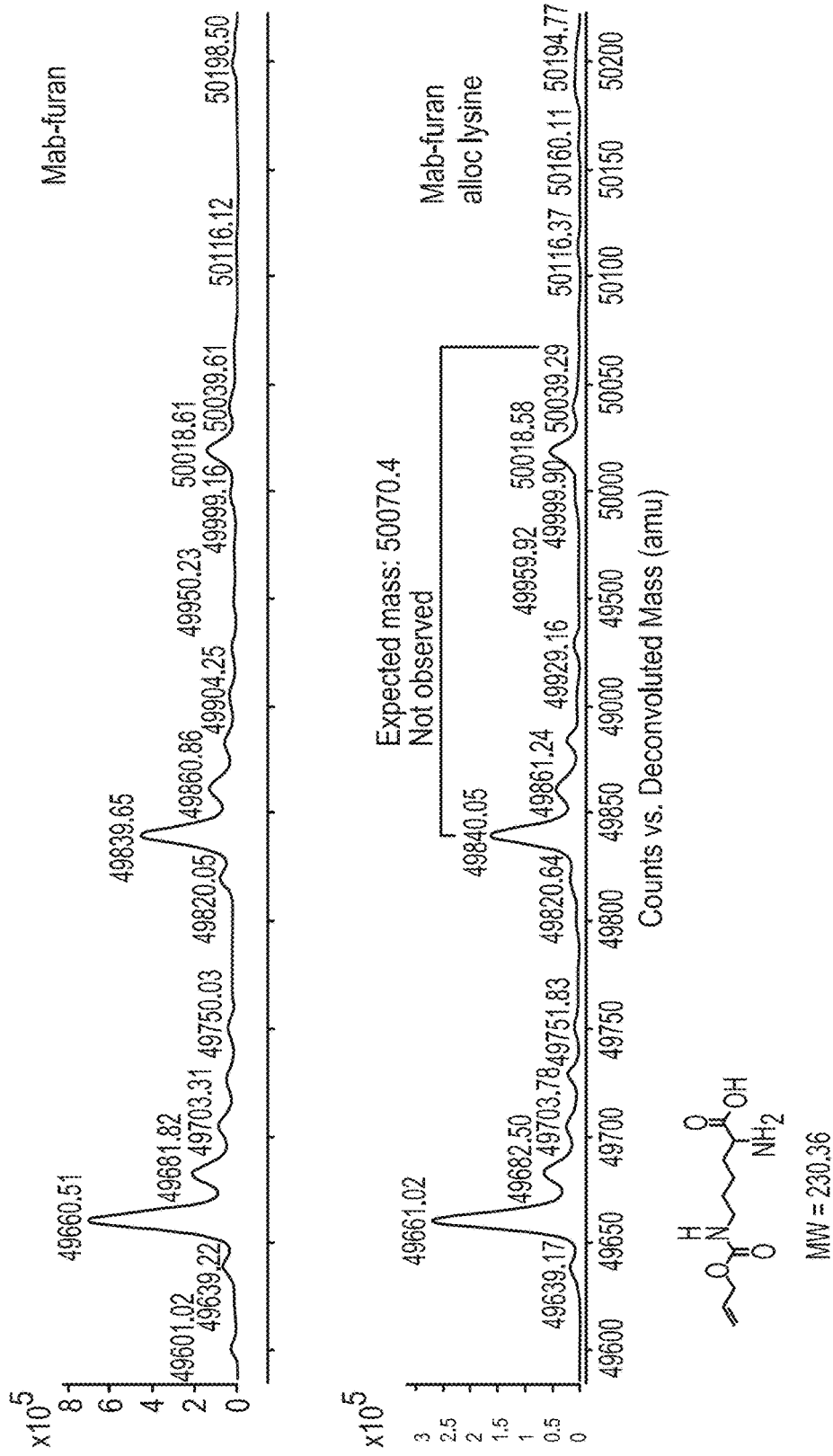
Figure 1.3. Reduced deglycosylated mass spectrometry analysis of mAb-furan-linker alloc lysine reaction product. No peaks corresponding to the expected mass of the conjugate were observed. The chemical structure of alloc-lysine is shown below the spectra.

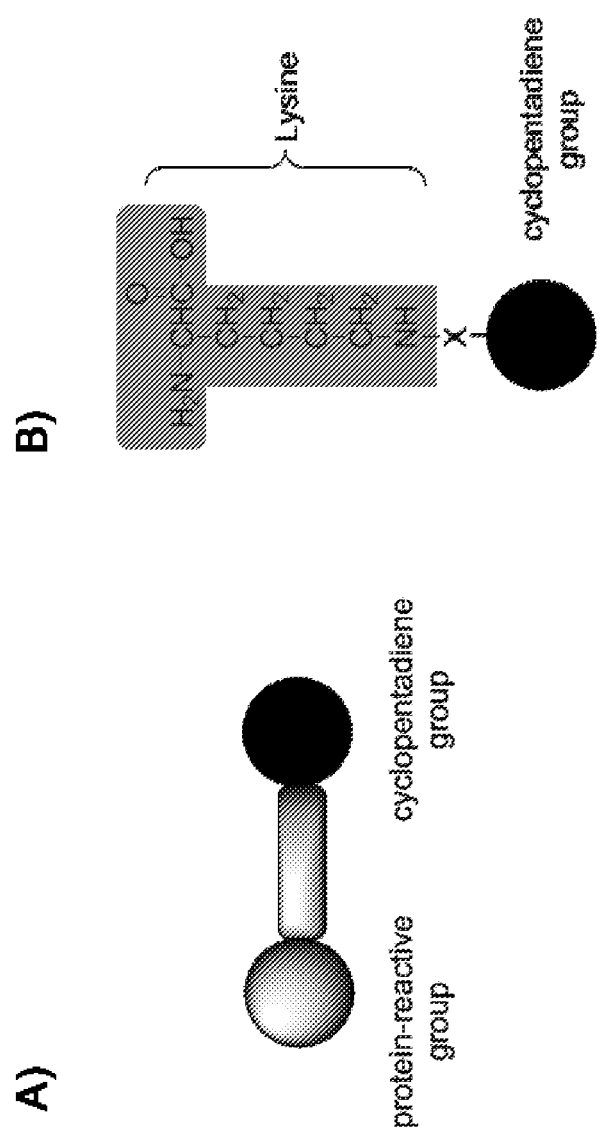
Figure 2.1. General design of cyclopentadiene crosslinkers (A) and cyclopentadiene NNAA (B) described in example 2.

Figure 3.1. Intact deglycosylated mass spectrometry before (A) and after (B) reaction of mAb with CP1-NHS
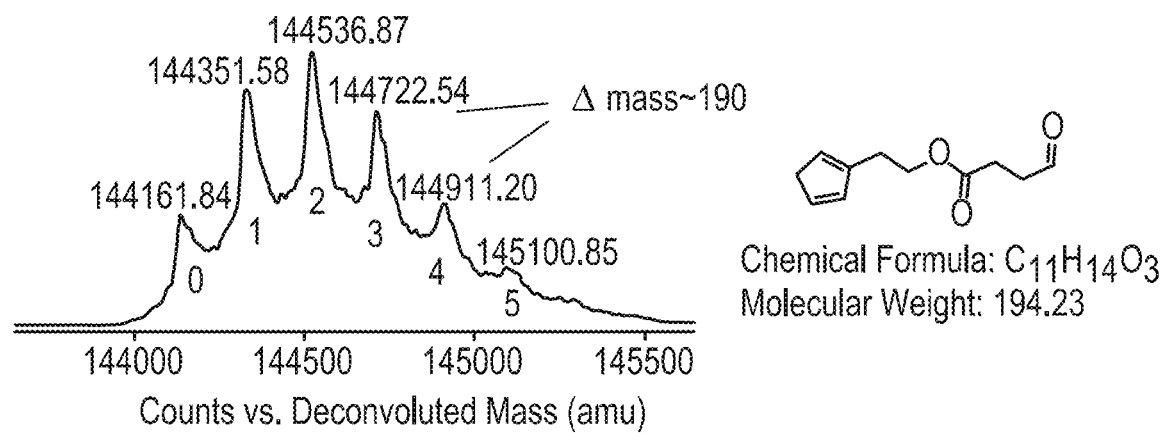

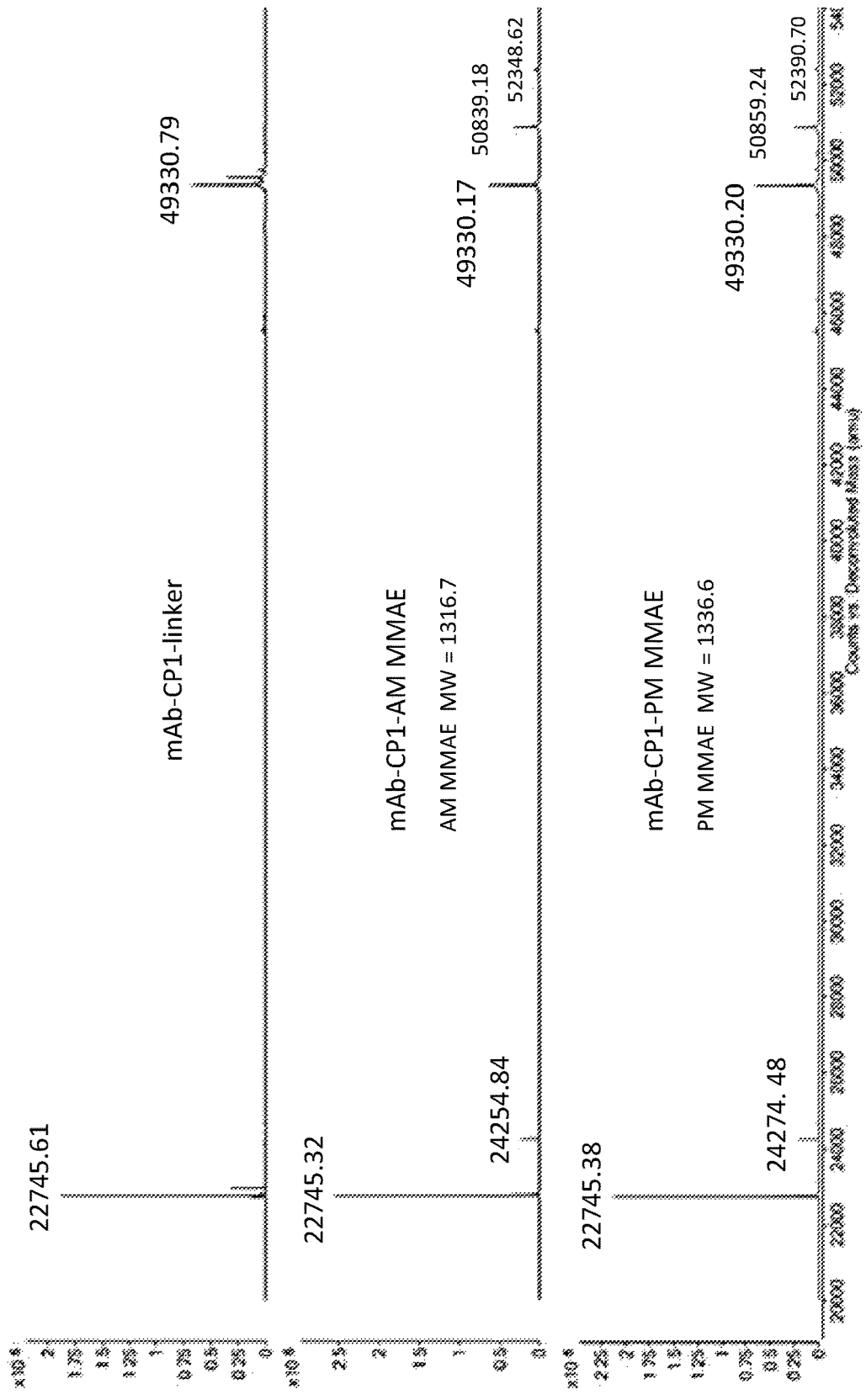
Figure 3.2. Reduced deglycosylated mass spectra of mAb-CP1-linker maleimido MMAE reaction products. Spectra are zoomed to show mAb heavy and light chains.

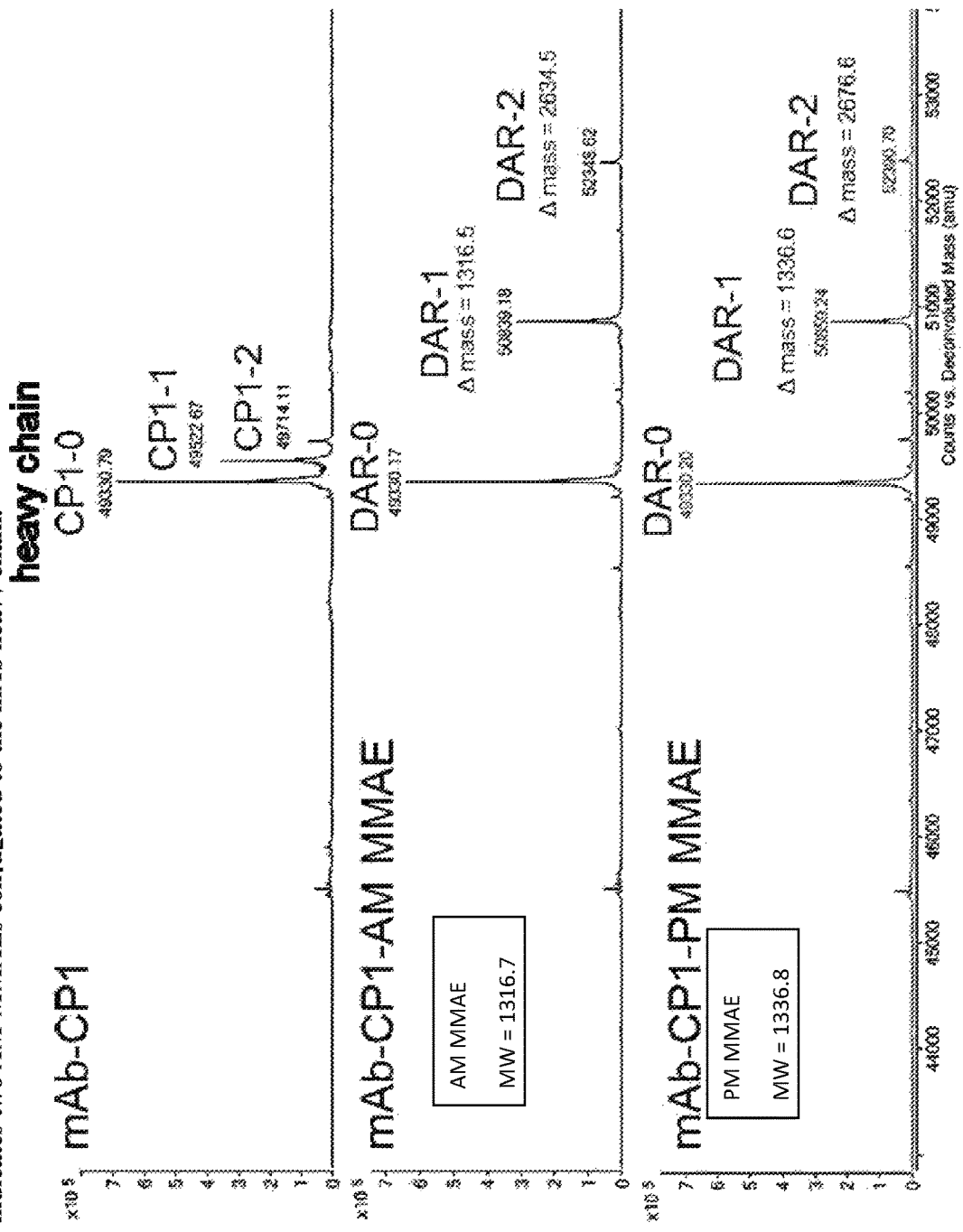
Figure 3.3. Reduced deglycosylated mass spectra of mAb-CP1-linker AM-MMAE reaction products zoomed in to show the mAb heavy chain region. DAR-0 indicates no AM-MMAE conjugated to the mAb heavy chain, DAR-1 indicates one AM-MMAE conjugated to the mAb heavy chain and DAR-2 indicates two AM-MMAEs conjugated to the mAb heavy chain.

Figure 3.4. Reduced deglycosylated mass spectrometry analysis of mAb-CP1-linker alloc lysine reaction product. No peaks corresponding to the expected mass of the conjugate were observed.
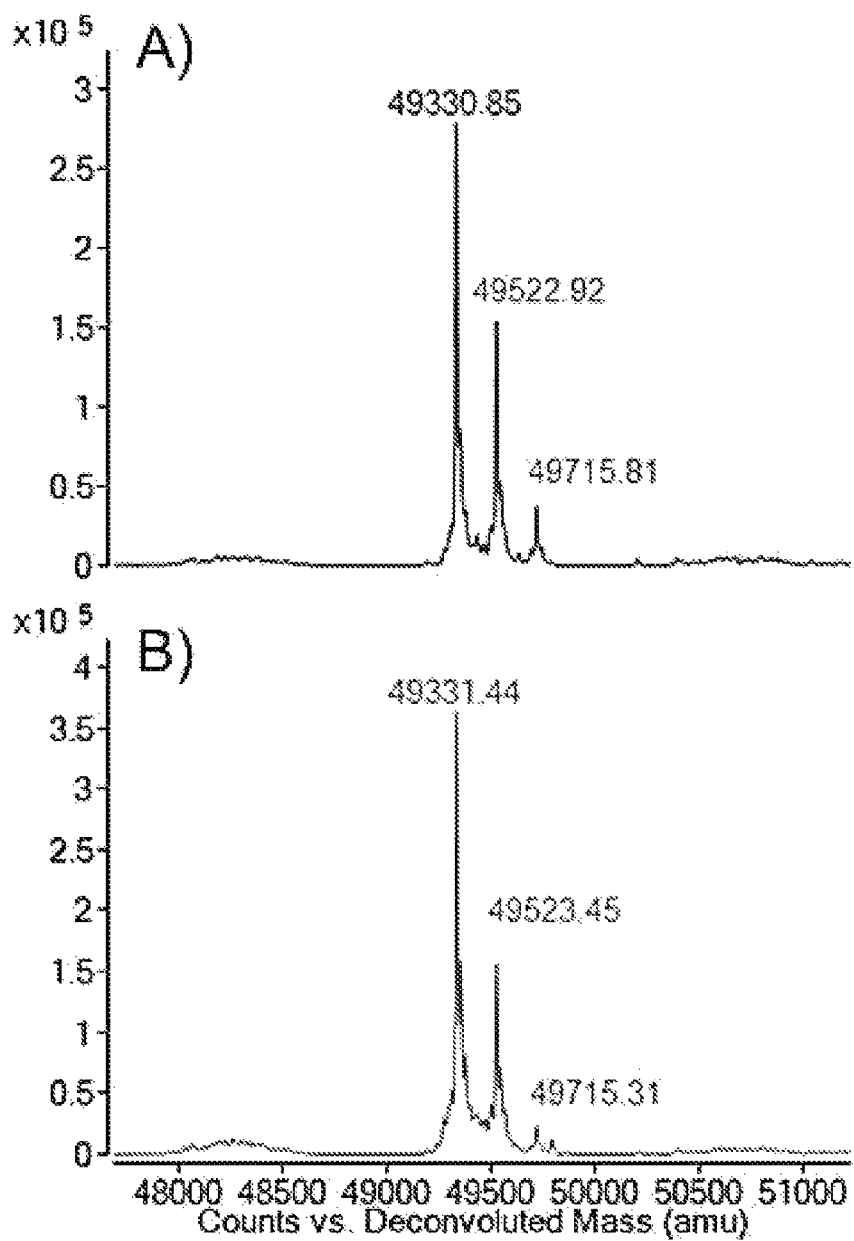

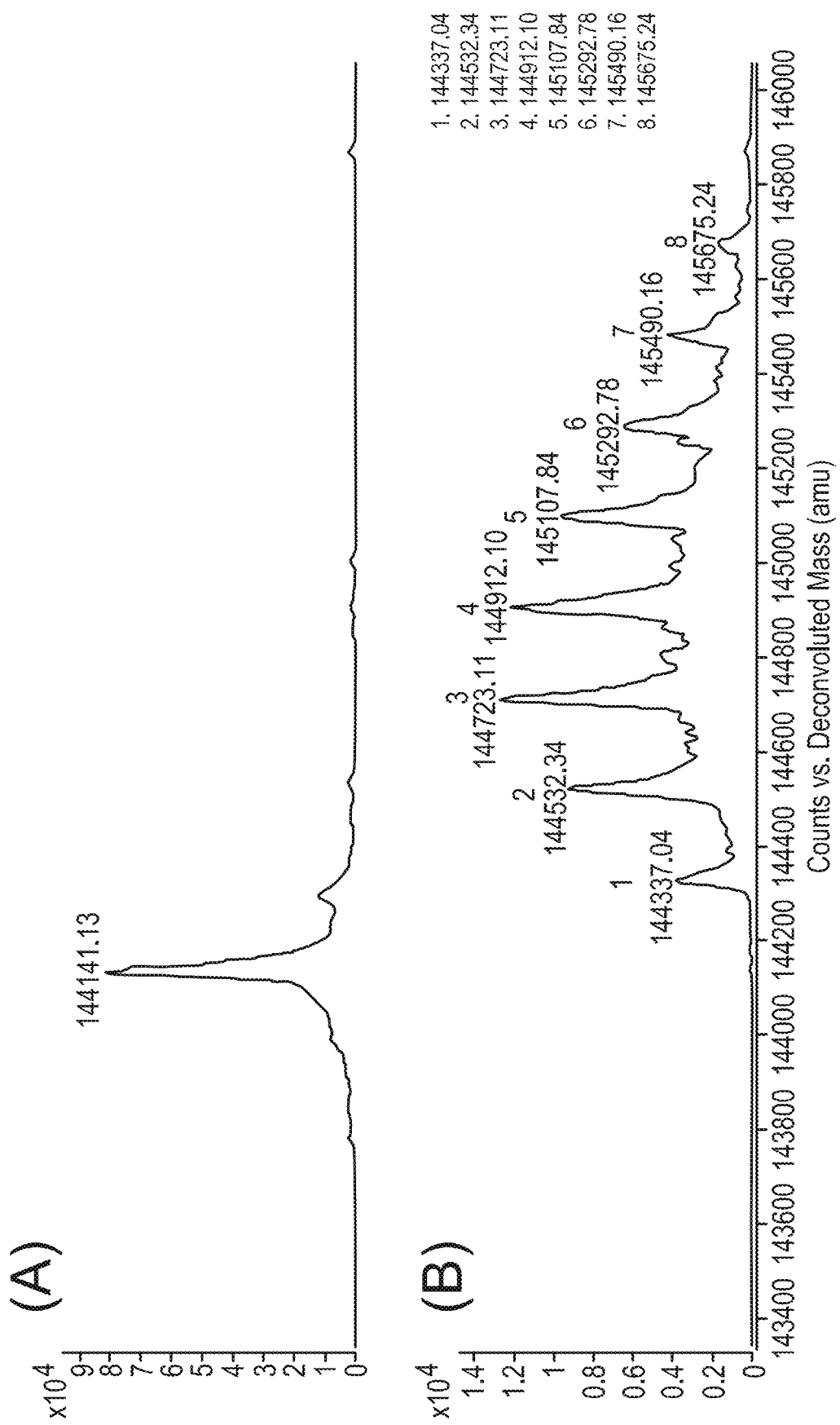
Figure 4.1. Intact deglycosylated mass spectrometry before (A) and after (B) reaction of mAb with CP1-NHS.

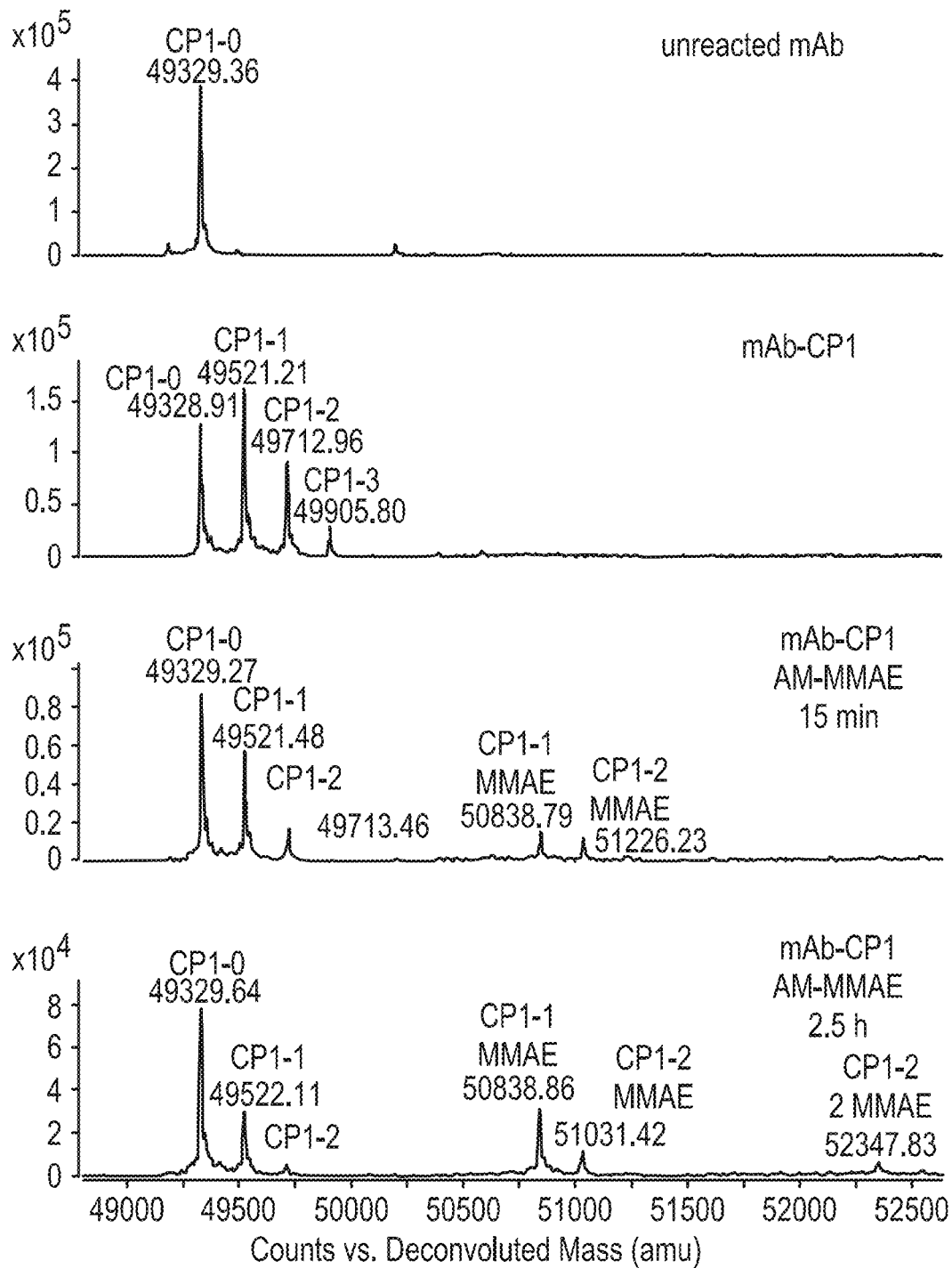
Figure 4.2. Reduced deglycosylated mass spectra of unmodified mAb, mAb-CP1-linker and AM-MMAE-reacted mAb-CP1-linker (mAb-CP1 AM-MMAE) at 15 min and 2.5 h.

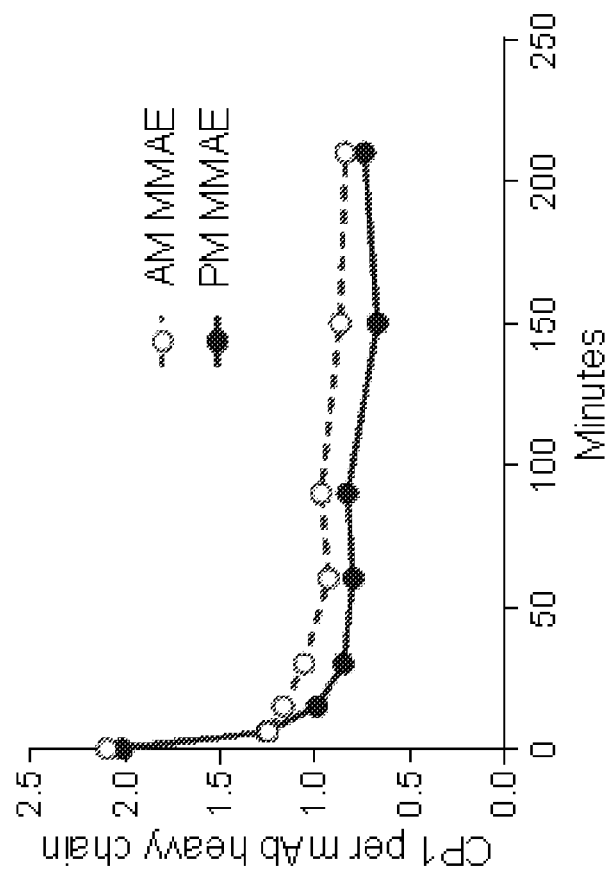
Figure 4.3. Reaction of mAb-CP1-linker with maleimido-MMAEs. Unreacted CP1 diene was determined from the pe

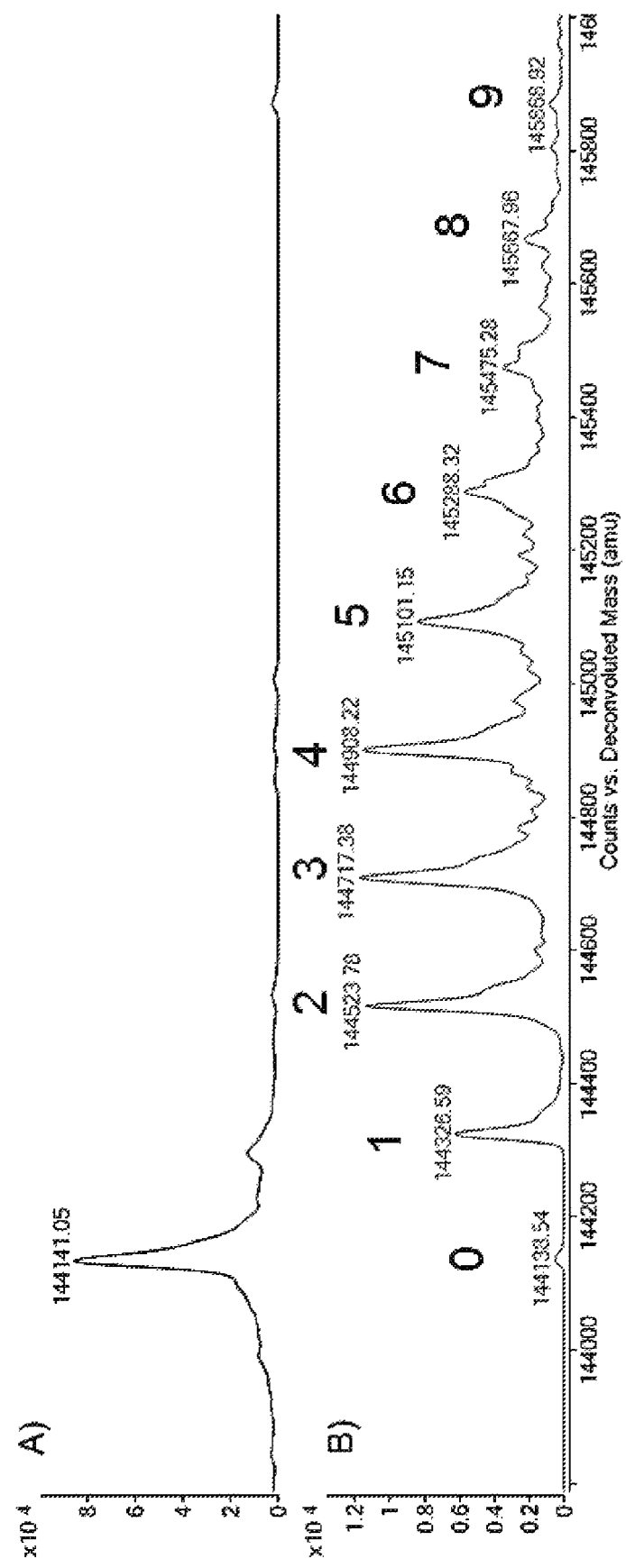
Figure 5.1. Intact deglycosylated mass spectrometry before (A) and after (B) reaction of mAb with CP1-NHS.

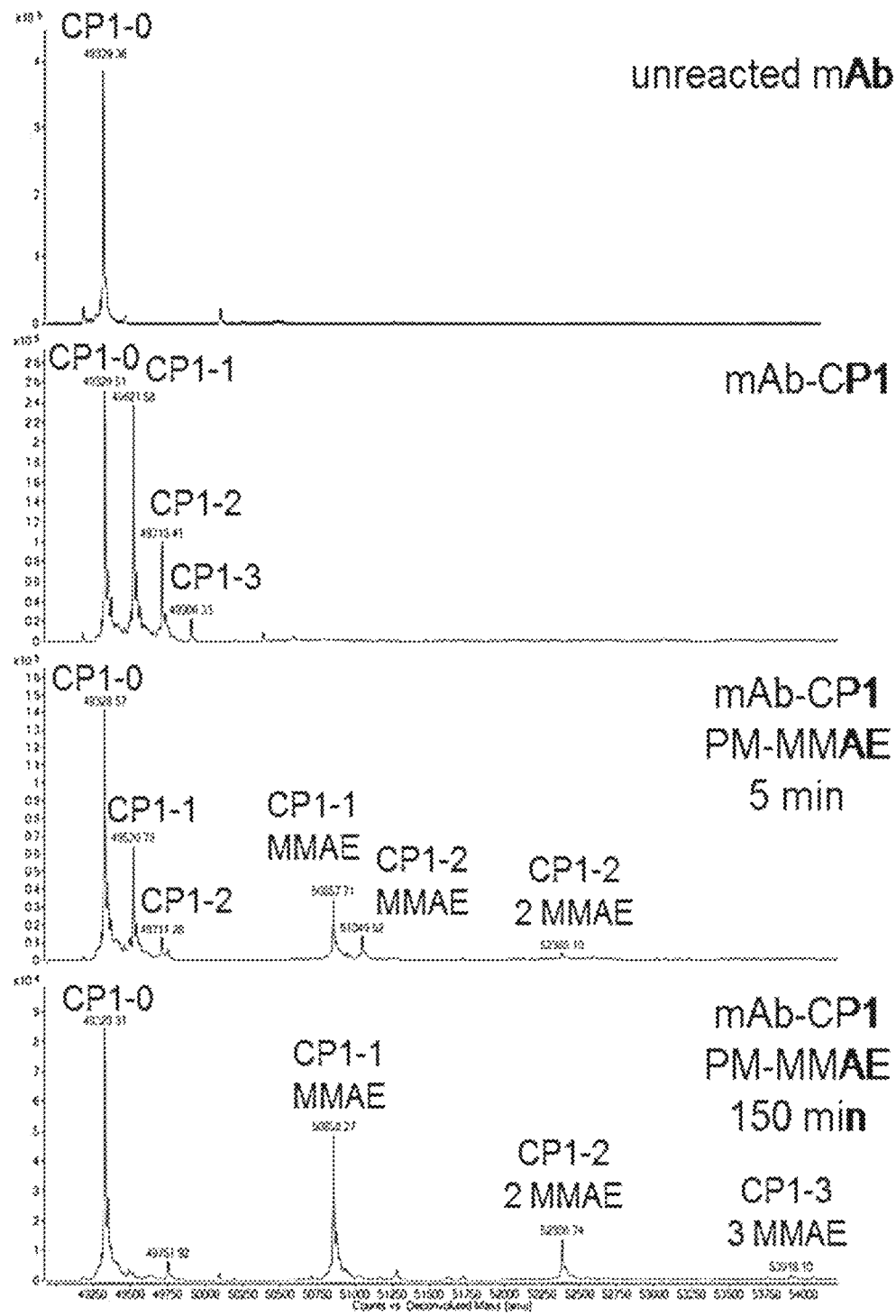
Figure 5.2. Reduced deglycosylated mass spectra of unmodified mAb, mAb-CP1-linker (mAb-CP1) and PM-MMAE-reacted mAb-CP1-linker at 5 min and 150 min.

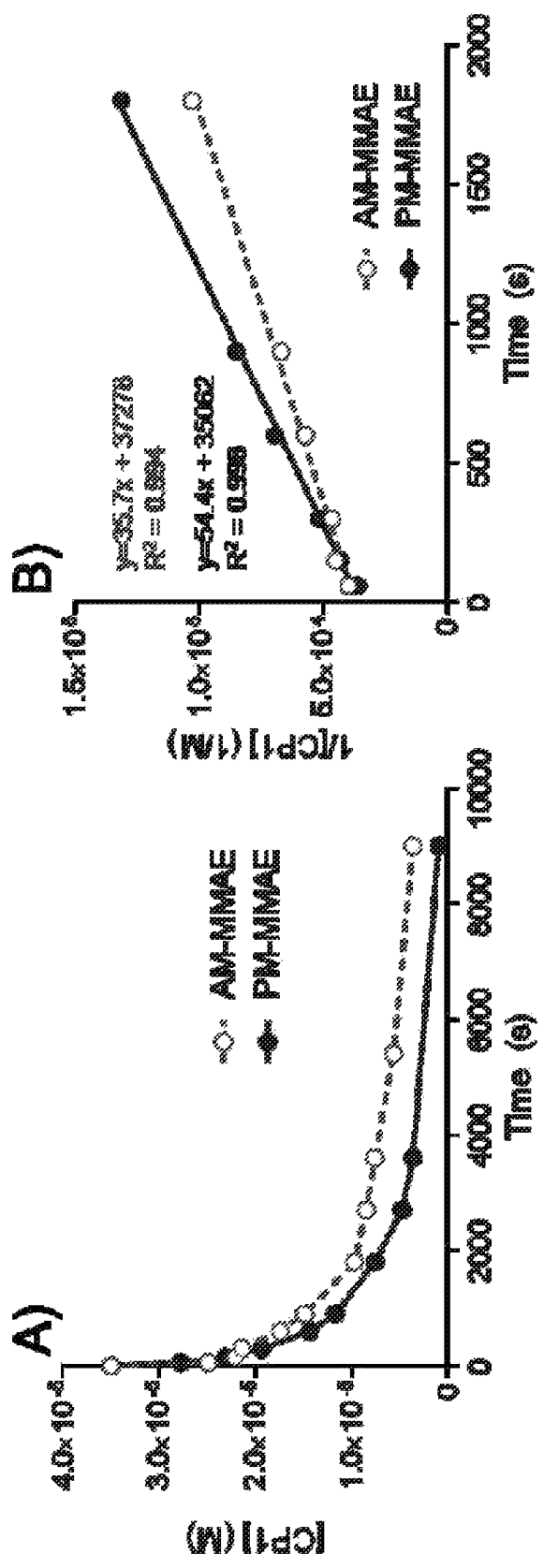
Figure 5.3. Reaction of mAb-CP1-linker with maleimido-MMAEs. A) Unreacted CP1 dienes per mAb, determined from the peak intensities of reduced deglycosylated mass spectra. B) Inverse concentration plot used to calculate rate constants.

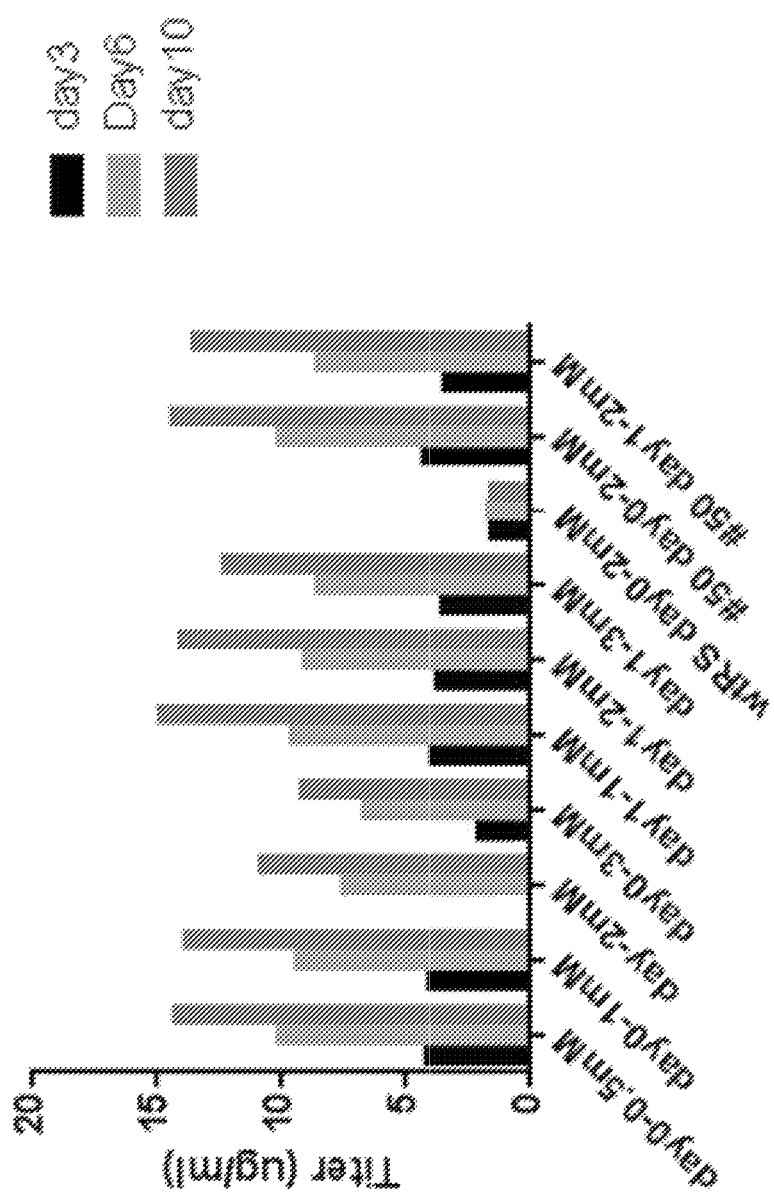
Figure 6.1. Titers of 12G3H11 K274CP1-NNAA-mAb after expression in mammalian cells comprising mutant or wt TRS. CP1-NNAA final concentration in media and feeding time was varied as indicated on the x-axis. Note that the structure of non-natural amino acid #50 is shown if Figure 6.8.

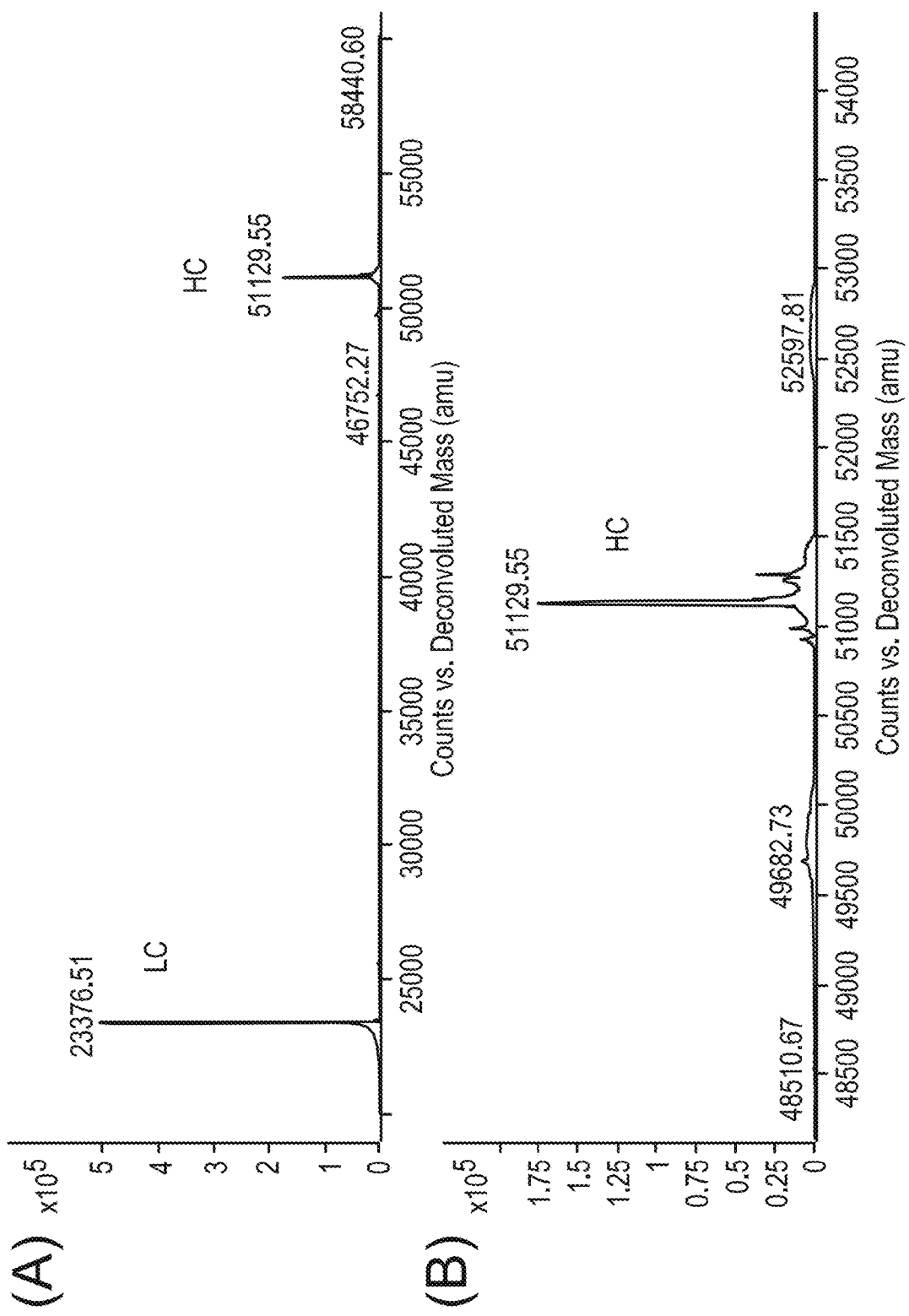
Figure 6.2. Reduced glycosylated mass spectrometry analysis of 12G3H11 K274CP1-NNAA mAb. A) Mass range showing mAb light chain (LC) and heavy chain (HC). B) Zoomed spectrum showing mAb heavy chain only.

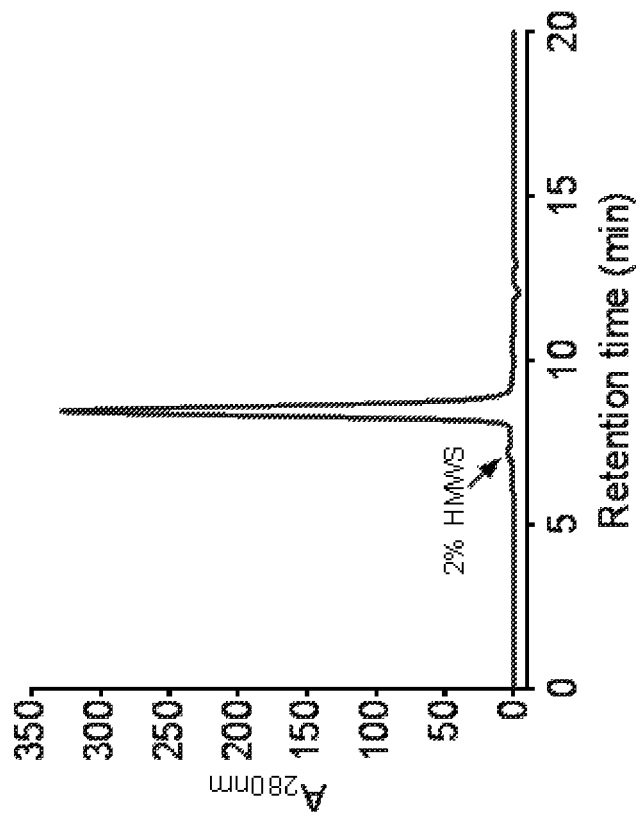
Figure 6.3. SEC analysis of 12G3H11 K274CP1-NNAA mAb indicating that monomeric product was obtained. High molecular weight species (HMWS) are indicated.

Figure 6.4. Analysis of 1C1-K274CP1-NNAA mAb (1C1.K274CP1) by SDS-PAGE.
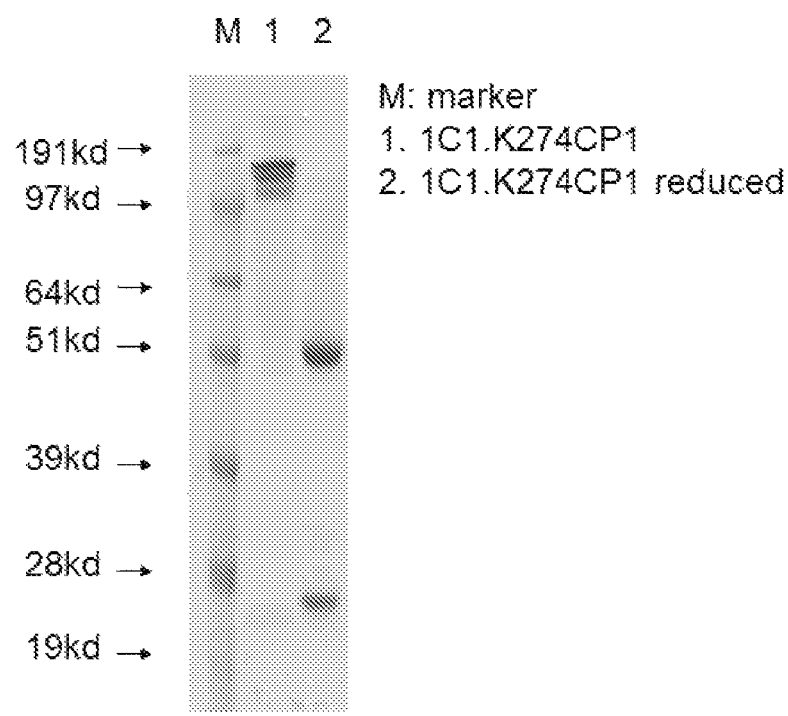

Figure 6.5. Reduced deglycosylated mass spectrometry analysis of 12G3H11 K274CP1-NNAA mAb-MMAE conjugation products. A) unreacted antibody, B) AM-MMAE reaction product, C) PM-MMAE reaction product. Spectra are zoomed in to show only the mAb heavy chain (HC).
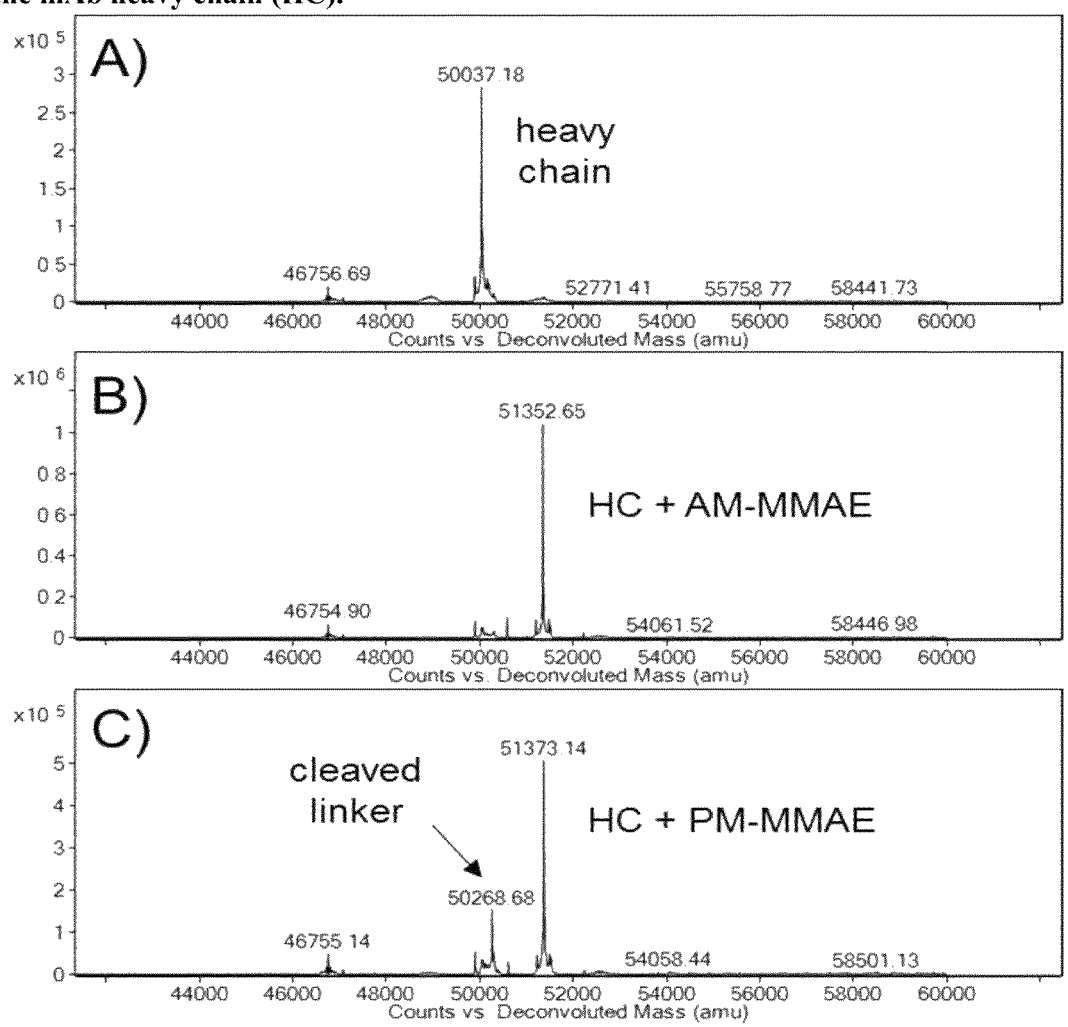

Figure 6.6. Reduced glycosylated mass spectrometry analysis of 1C1 K274CP1-NNAA mAb-AM-MMAE conjugation product. A) unreacted antibody, B) AM-MMAE reaction product. Spectra are zoomed in to show only the mAb heavy chain. Zoomed out spectra showing both heavy and light chains are shown in Figure 6.9 and 6.7.
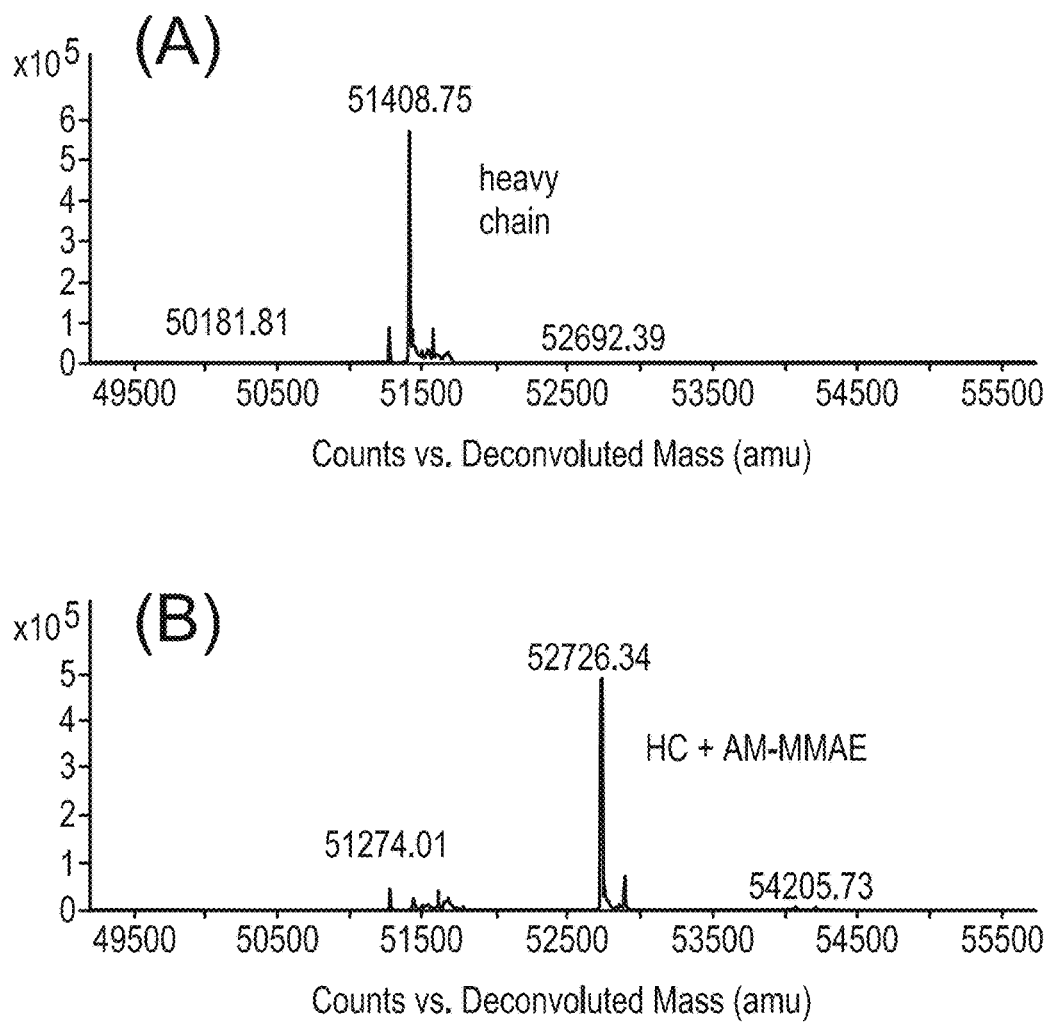

Figure 6.7. Chemical structure of CP1-NNAA showing compound isomers, which exist as a 1:1 ratio.
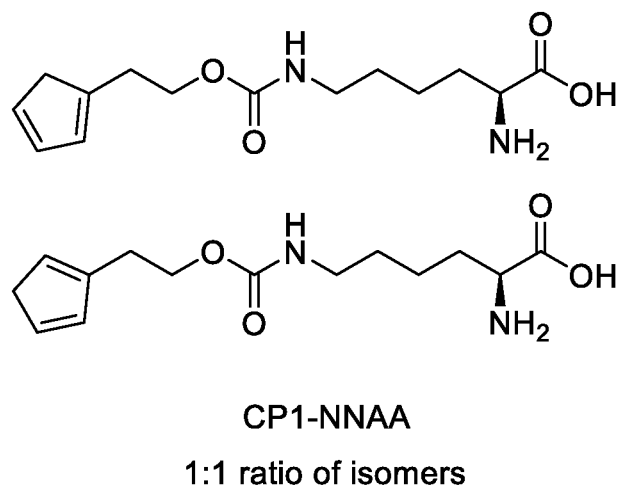
CP1-NNAA
1:1 ratio of isomers
Figure 6.8. Chemical structure of compound 50, a furan analogue of CP1 NNAA described in the literature. This compound was used as a control for expression studies with 12G3H11 mAb.
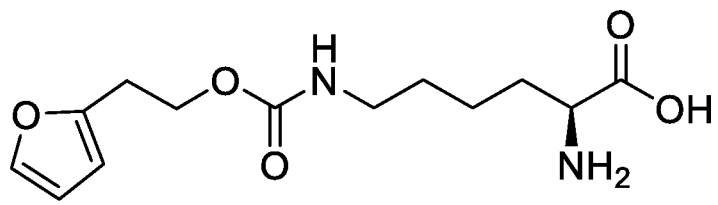

Figure 6.9. Reduced deglycosylated mass spectrometry analysis of 12G3H11 K274CP1-NNAA mAb-MMAE conjugation products. A) unreacted antibody, B) AM-MMAE reaction product, C) PM-MMAE reaction product. Spectra are zoomed to show both antibody heavy and light chains.
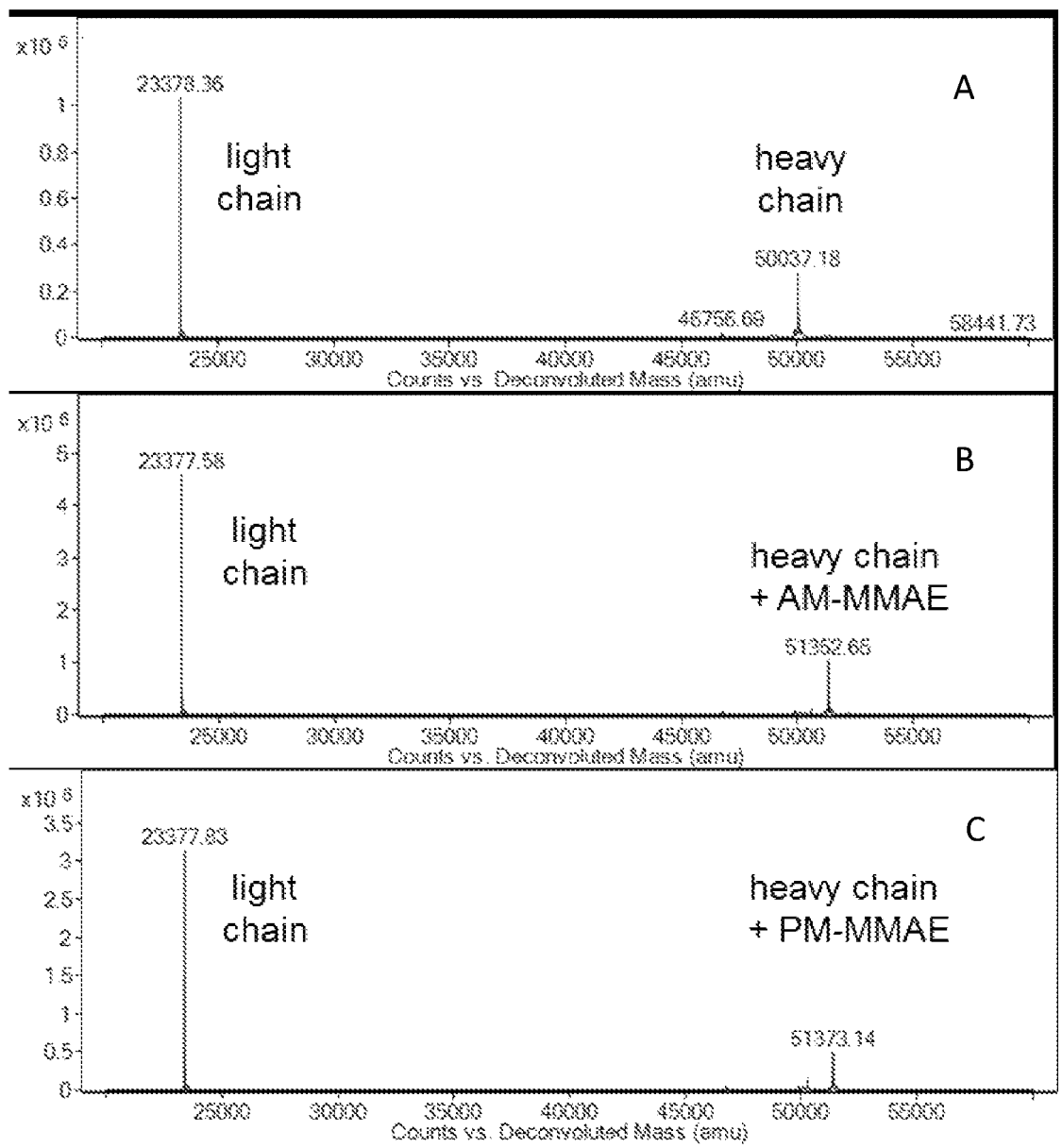

Figure 6.10. Reduced glycosylated mass spectrometry analysis of 1C1 K274CP1-NNAA mAb-AM-MMAE conjugation product. A) unreacted antibody, B) AM-MMAE reaction product. Spectra are zoomed to show both antibody heavy and light chains and also high molecular weight species.
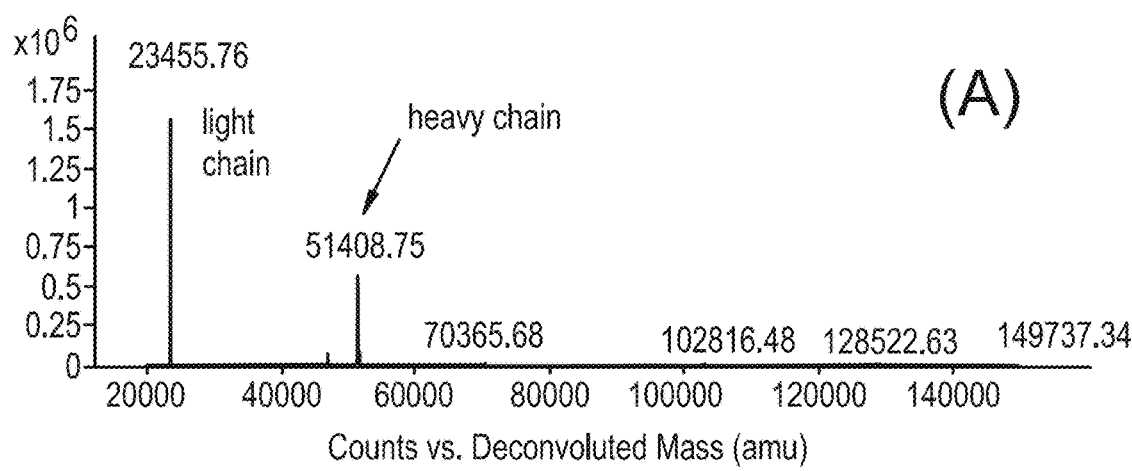
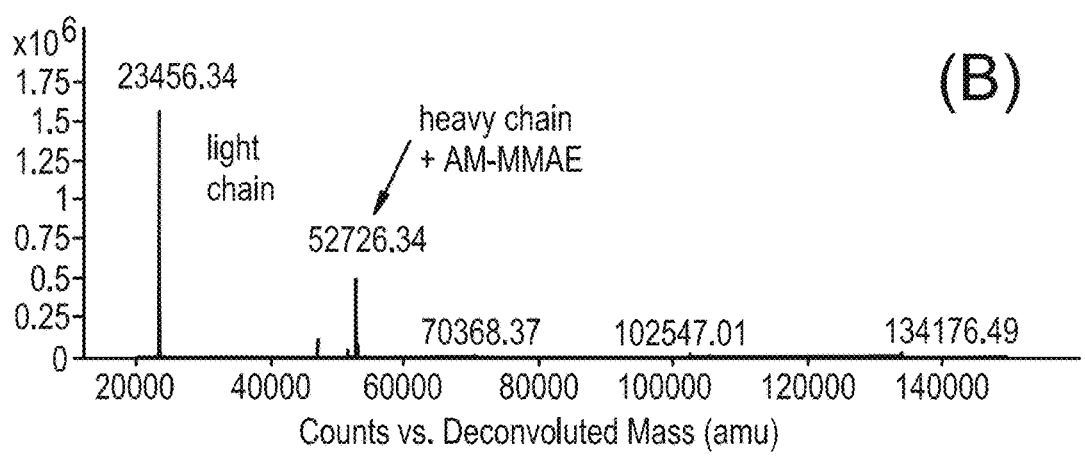

Figure 7.1. Rat serum stability of 12G3H11 K274CP1-NNAA AM-MMAE ADC.
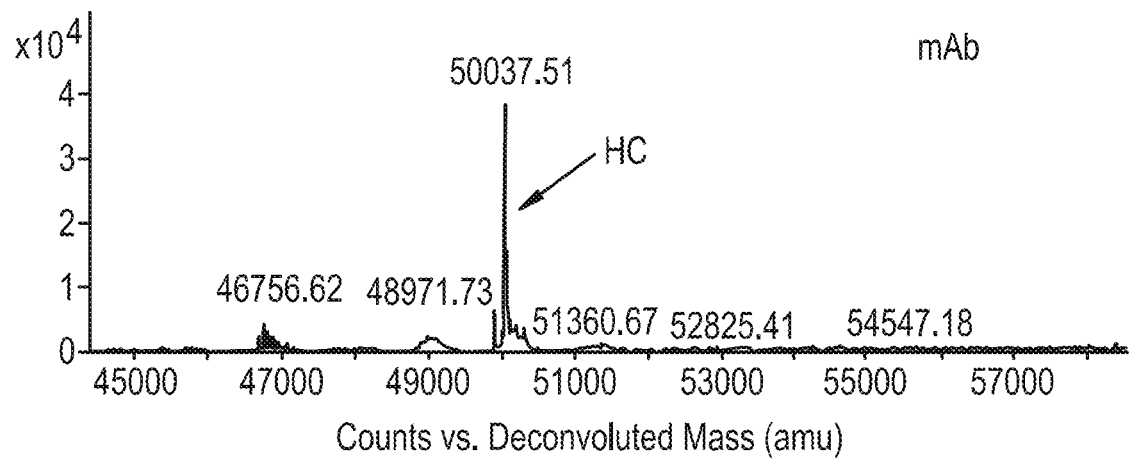
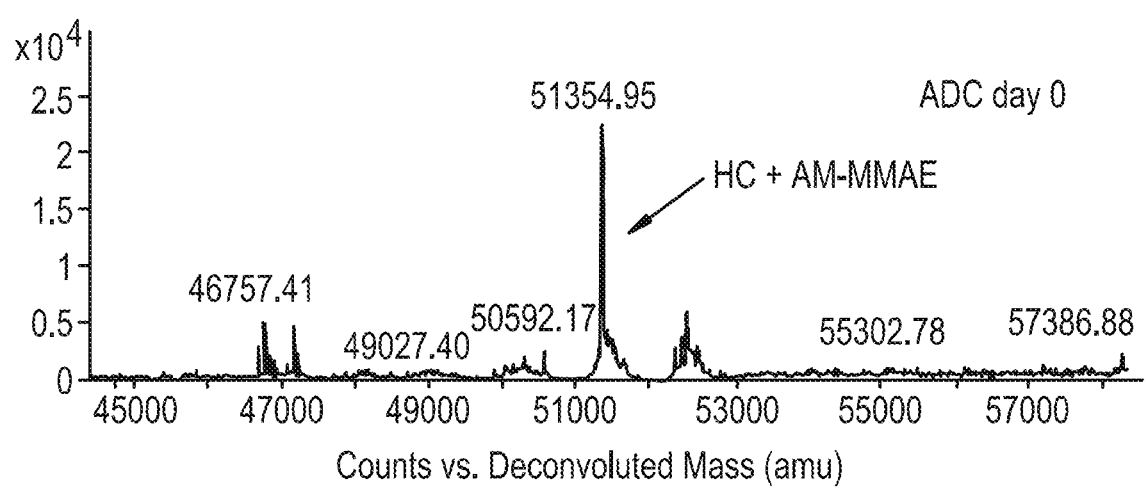
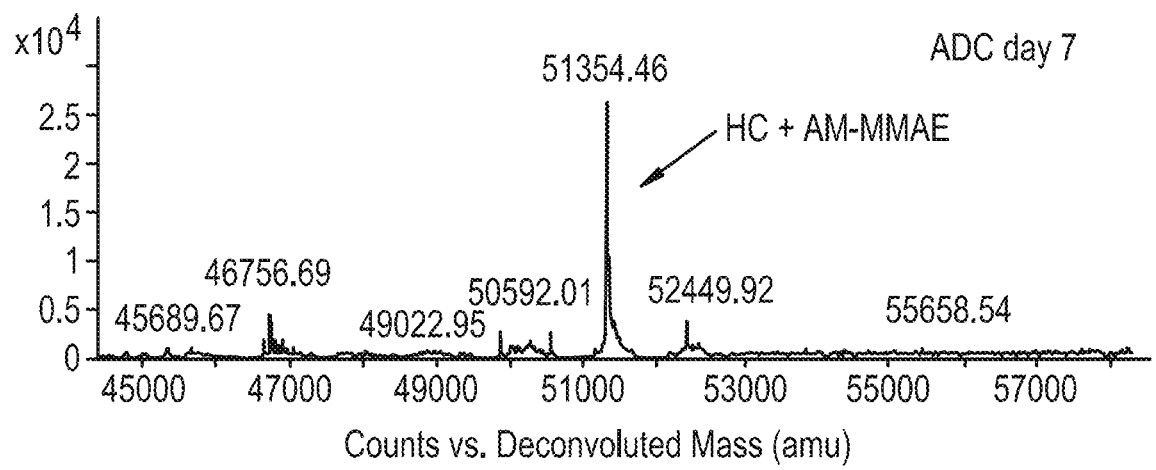

Figure 7.2. Rat serum stability of 12G3H11 K274CP1-NNAA PM-MMAE ADC.
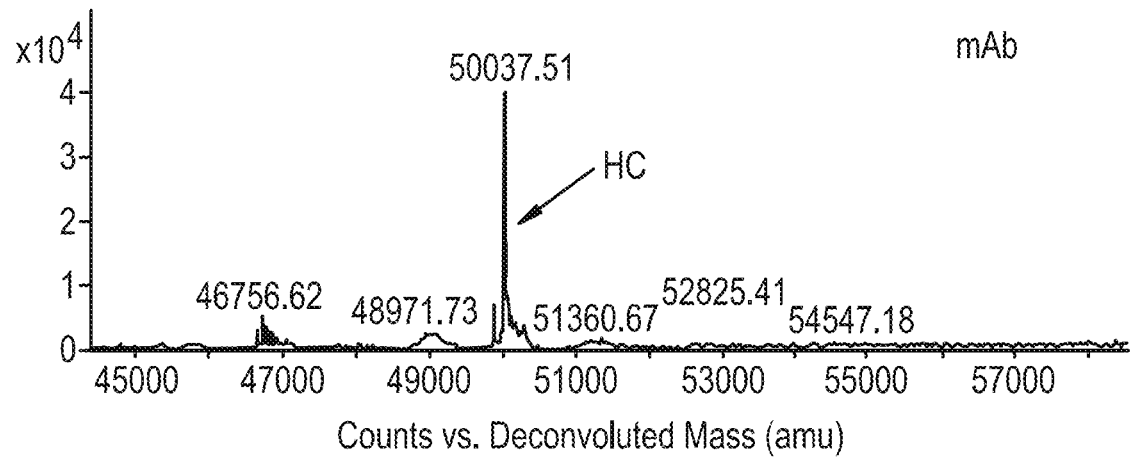
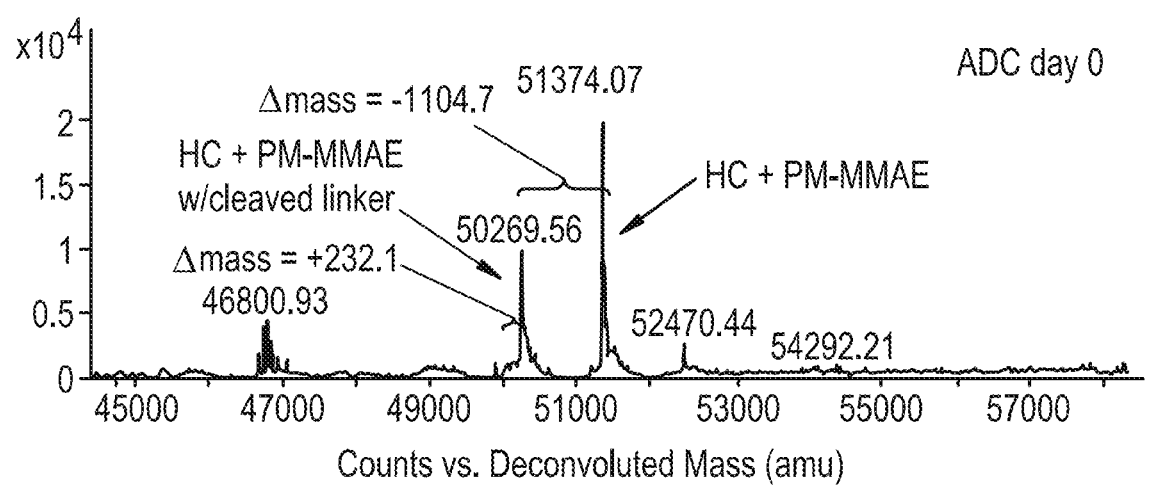
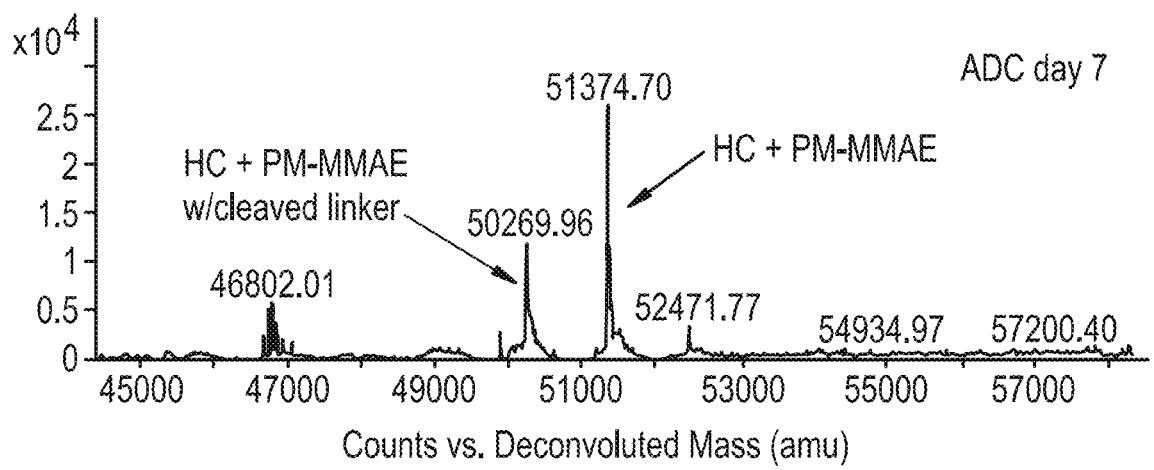

Figure 7.3. Mouse serum stability of 12G3H11 K274CP1-NNAA AM-MMAE ADC.
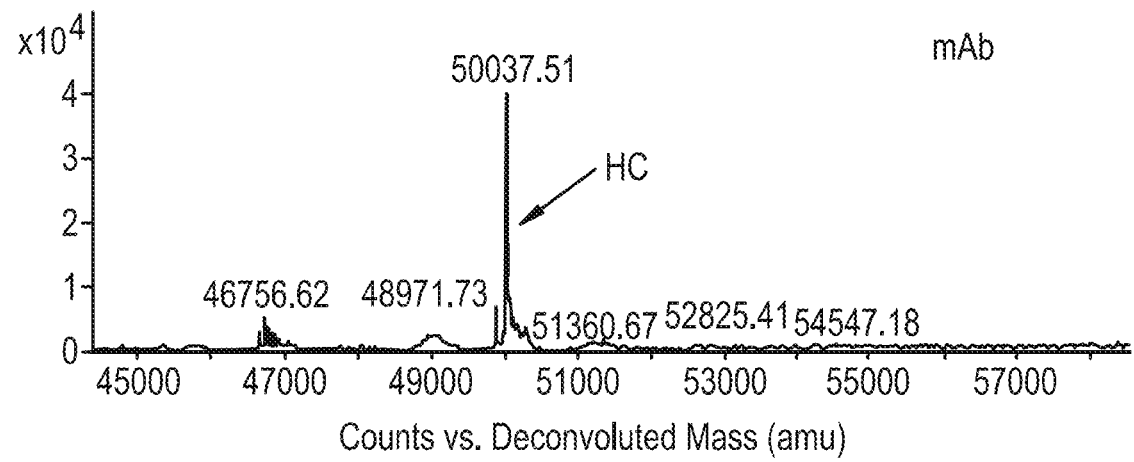
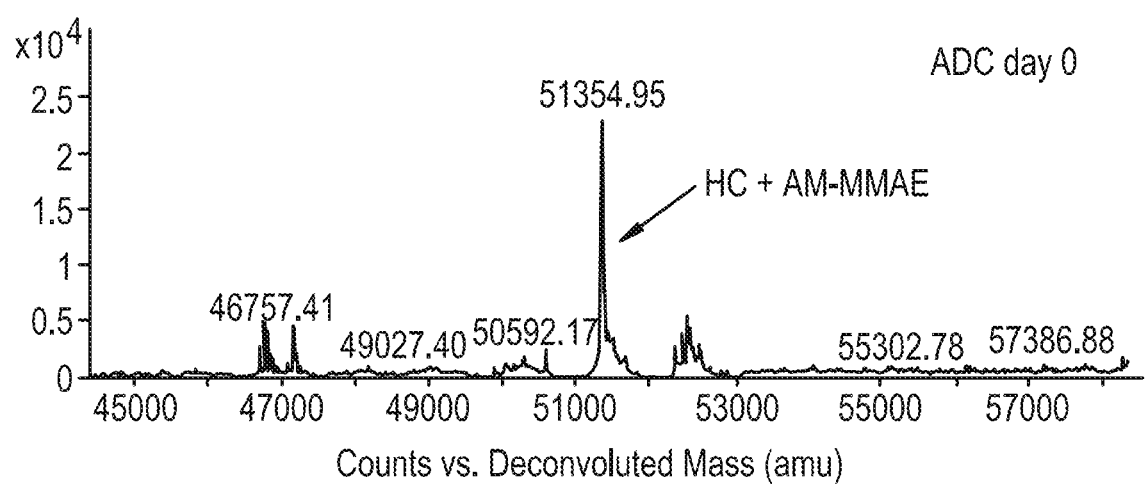
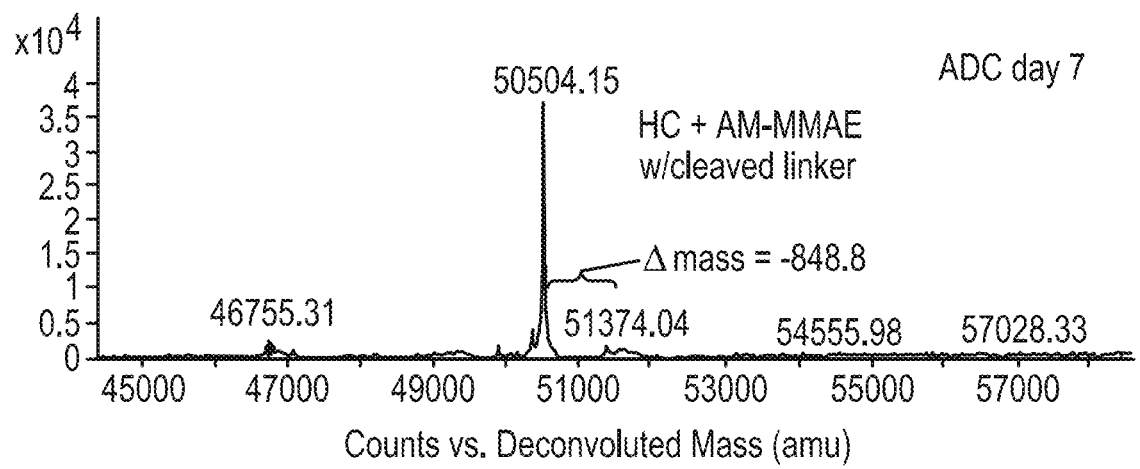

Figure 7.4. Mouse serum stability of 12G3H11 K274CP1-NNAA PM-MMAE ADC.
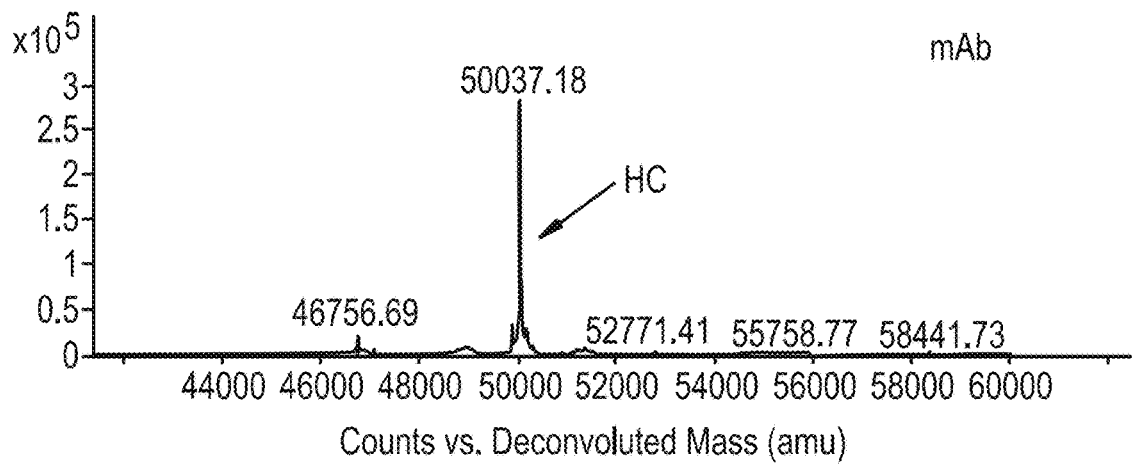
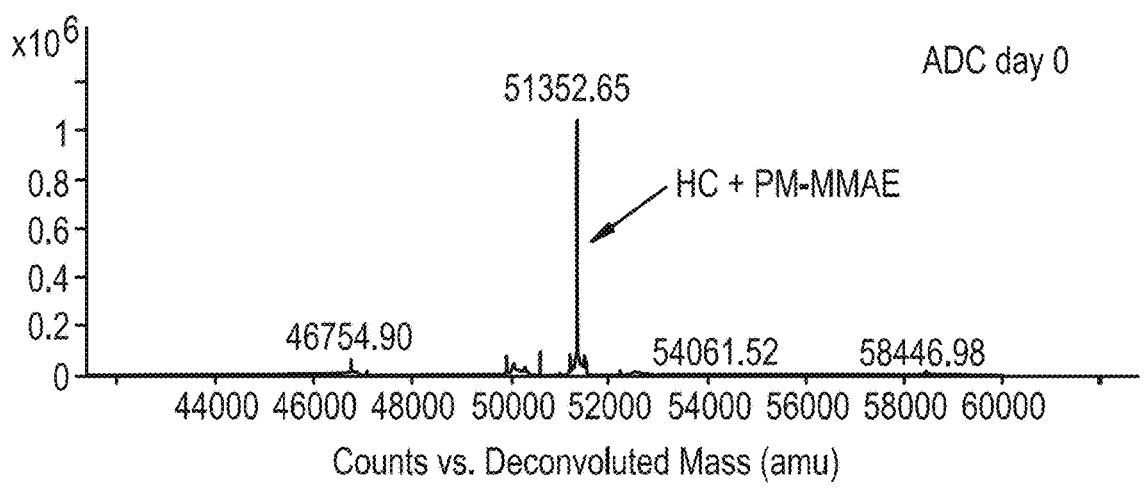
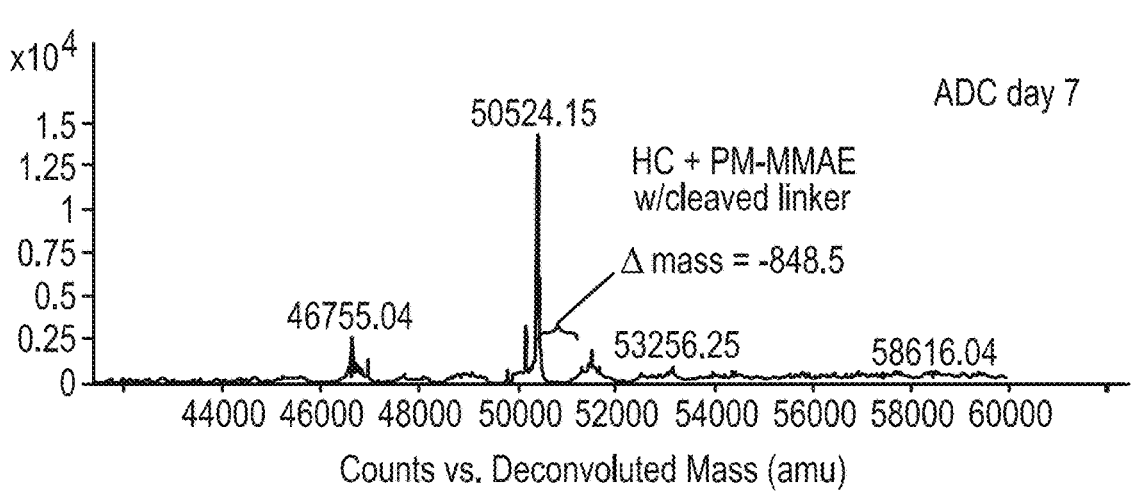

Figure 7.5. Chemical structures of MMAE payloads showing molecular weight.

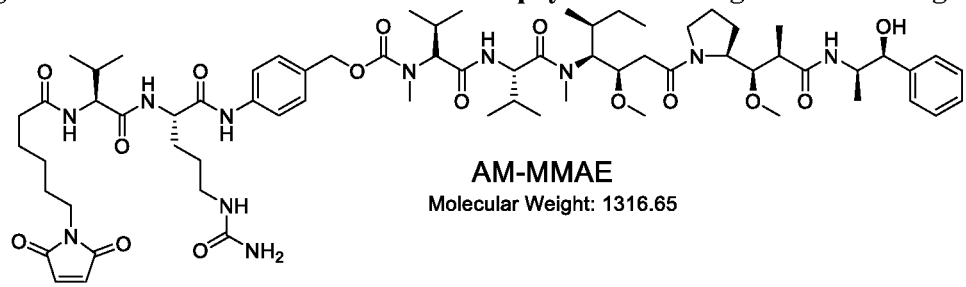

AM-MMAE
Molecular Weight: 1316.65

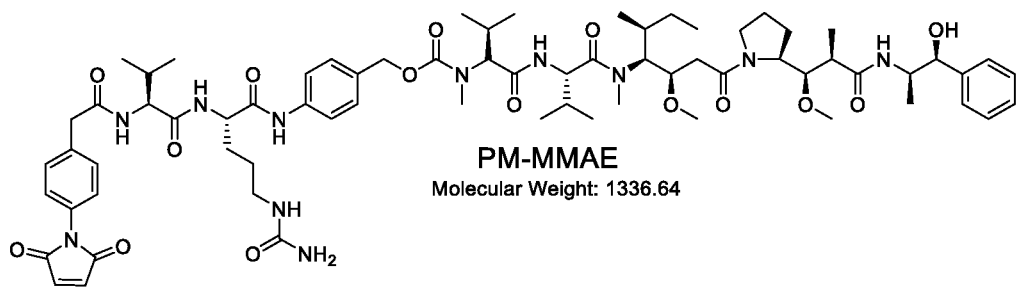

PM-MMAE
Molecular Weight: 1336.64

Figure 7.6 Chemical structure of predominant cleavage products observed following incubation of ADCs in mouse serum. A) and B) show the species remaining on the antibody (CP1-maleimide linkage not shown) for AM-MMAE and PM-MMAE conjugates, respectively. C) Shows the species liberated after val-cit dipeptide cleavage.

A)
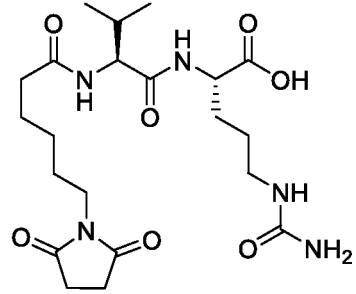
Molecular Weight: 469.54

B)
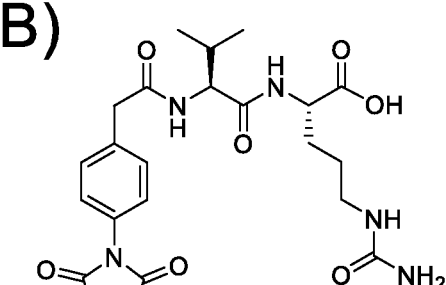
Molecular Weight: 489.53

C)
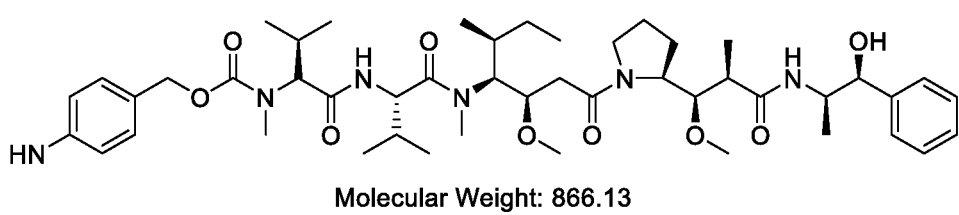
Molecular Weight: 866.13

Figure 7.7. Chemical structure of PM-MMAE cleavage products following serum incubation. A) species remaining on the antibody and B) liberated species.
A)
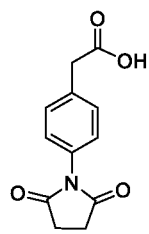
Molecular Weight: 233.22
B)
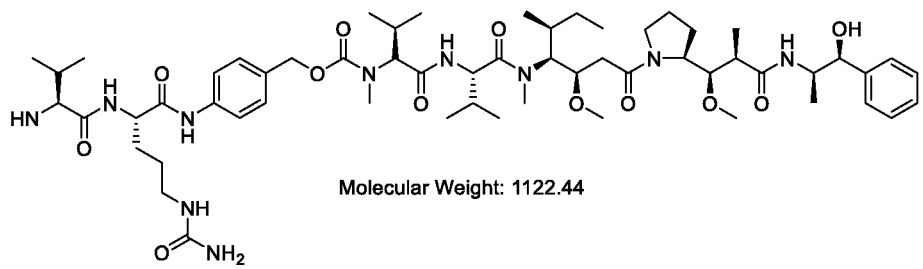
Molecular Weight: 1122.44
Figure 8.1. General design of spirocyclopentadiene crosslinkers (A) and spirocyclopentadiene NNAA (B) described in example 8.
A)
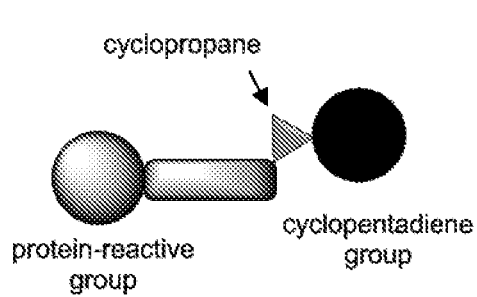
B)
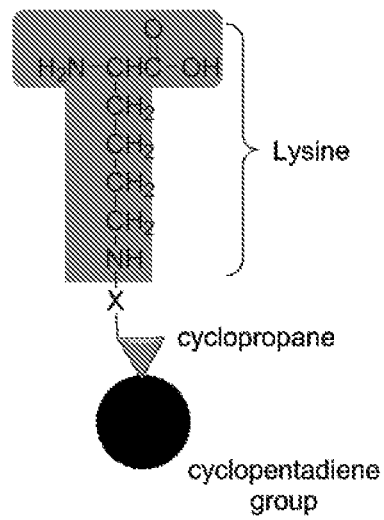

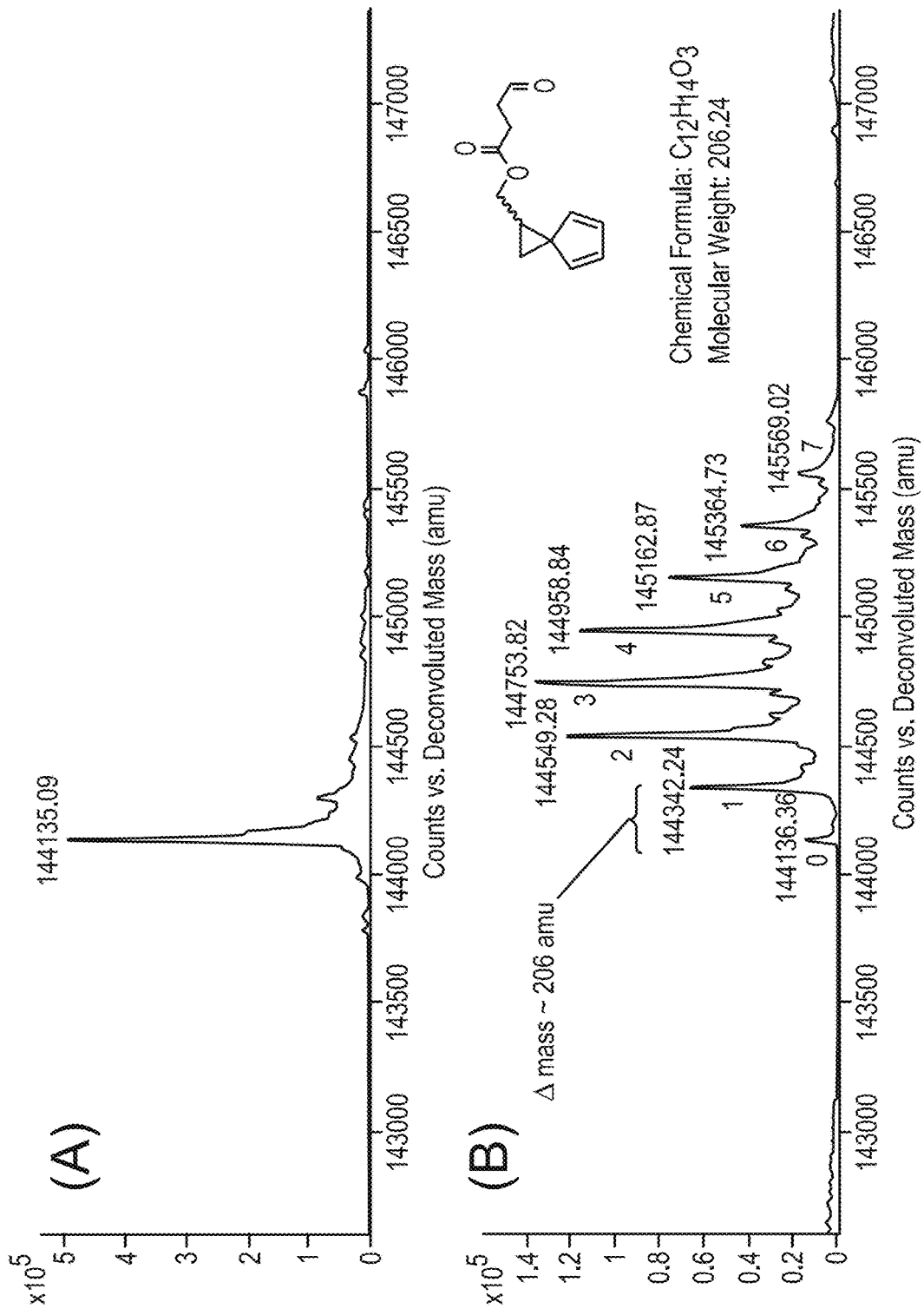
Figure 9.1. Intact deglycosylated mass spectrometry before (A) and after (B) reaction with CP2-NHS. Numbers below peaks in (B) indicate the number of CP2-linker groups introduced into the mAb. Estimation of CP2-linker introduction by peak intensities yields 3.29 CP2-linkers per mAb.

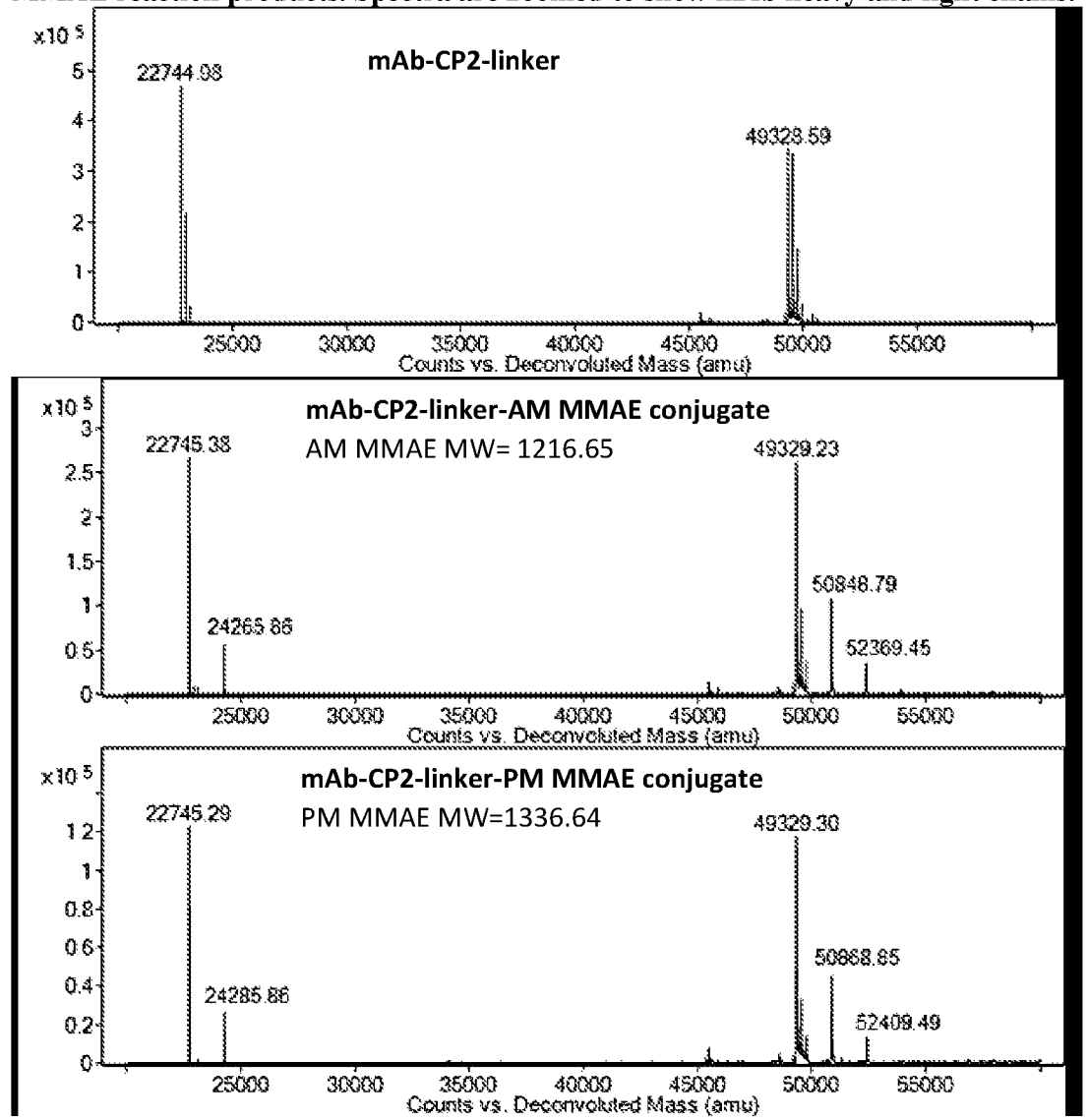
Figure 9.2. Reduced deglycosylated mass spectra of mAb-CP2-linker maleimido MMAE reaction products. Spectra are zoomed to show mAb heavy and light chains.

Figure 9.3 Reduced deglycosylated mass spectra of mAb-CP2-linker maleimido MMAE reaction products zoomed in to show the mAb heavy chain region. The number of conjugated species is indicated above each peak.
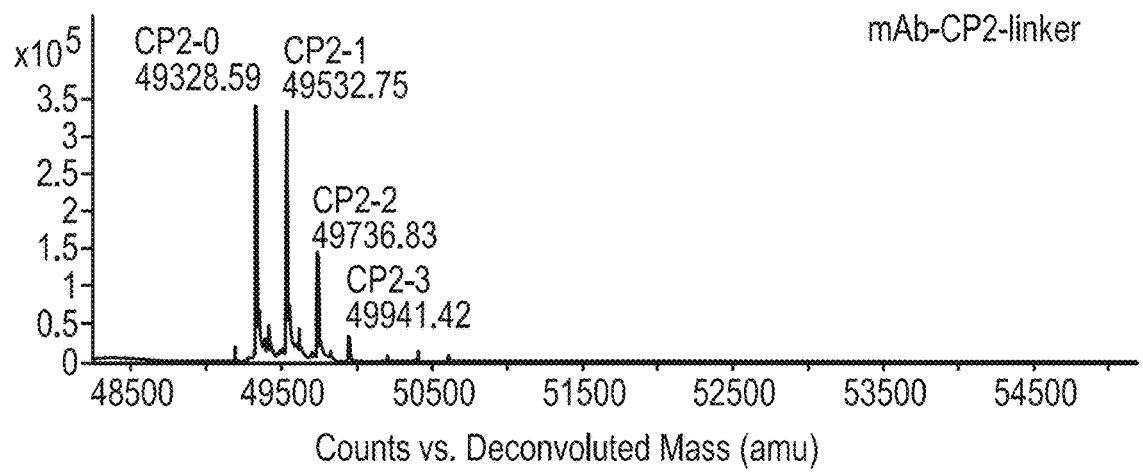
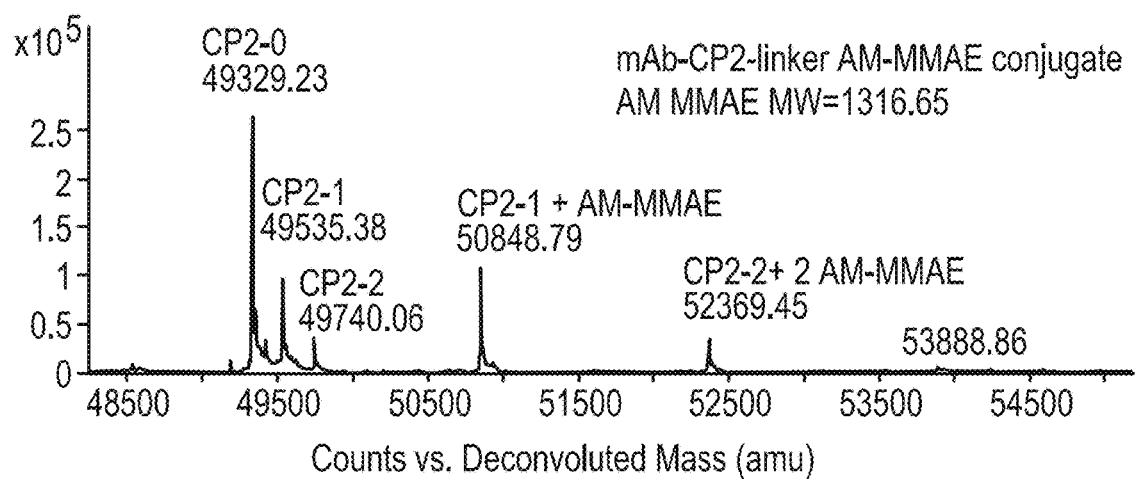
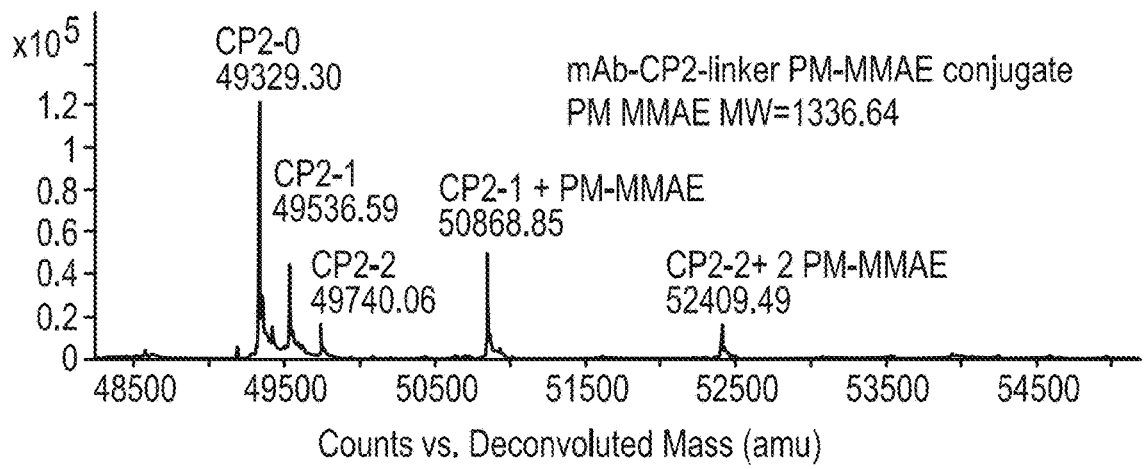

Figure 10.1 Reduced deglycosylated mass spectra of mAb-CP2-linker and AM-MMAE-reacted mAb-CP2-linker at 4 h and 48 h. Spectra are zoomed in to show the heavy chain only. Each peak is labelled to indicate the number of species conjugated.
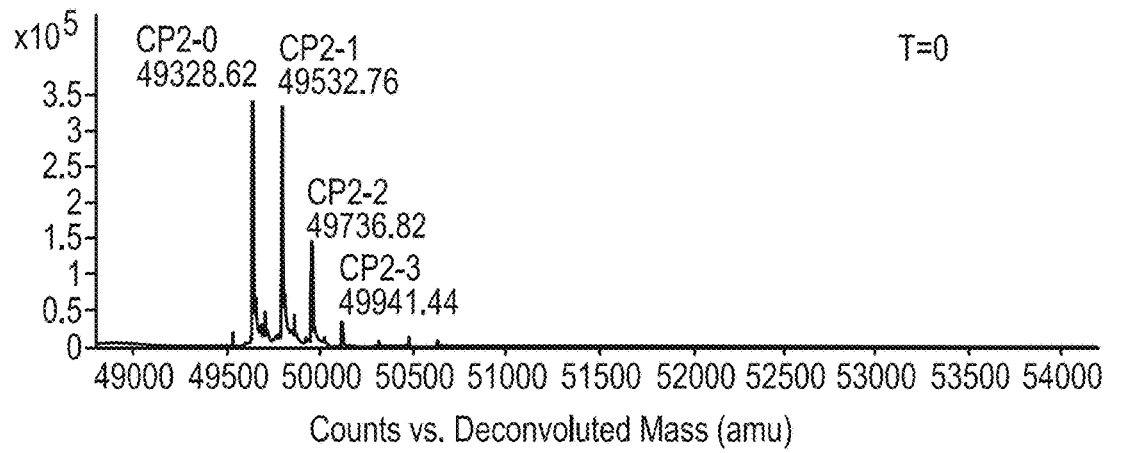
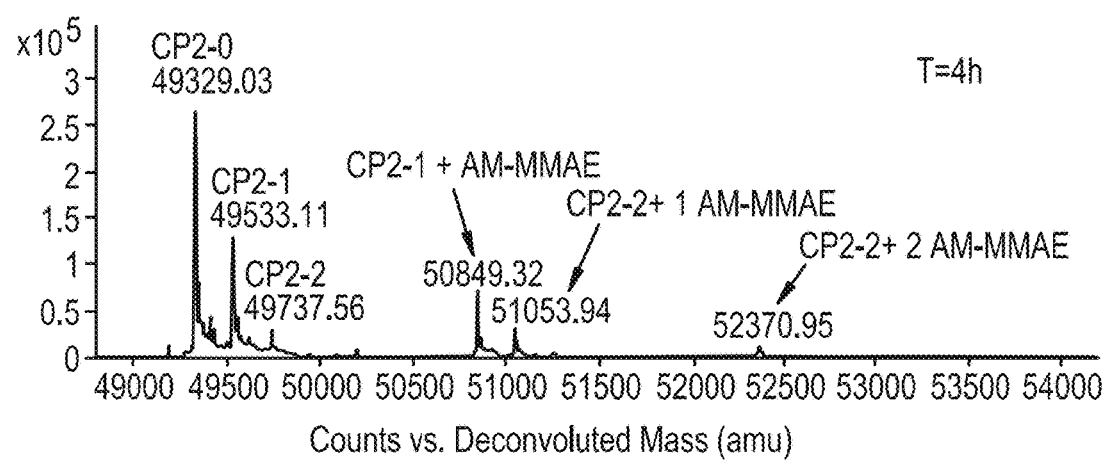
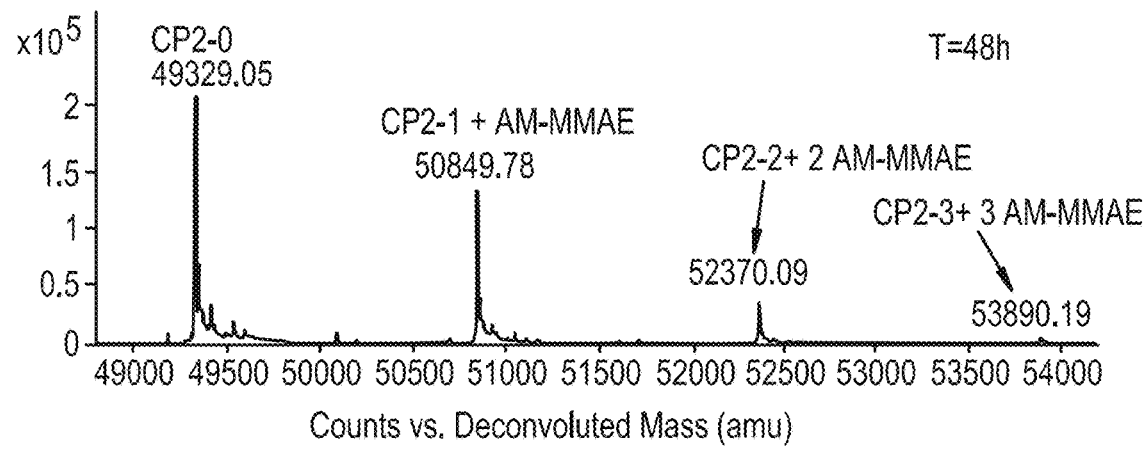

Figure 10.2 Reduced deglycosylated mass spectra of CP2-mAb and PM-MMAE-reacted CP2-mAb at 4 h and 48 h. Spectra are zoomed in to show the heavy chain only. Each peak is labelled to indicate the number of species conjugated.
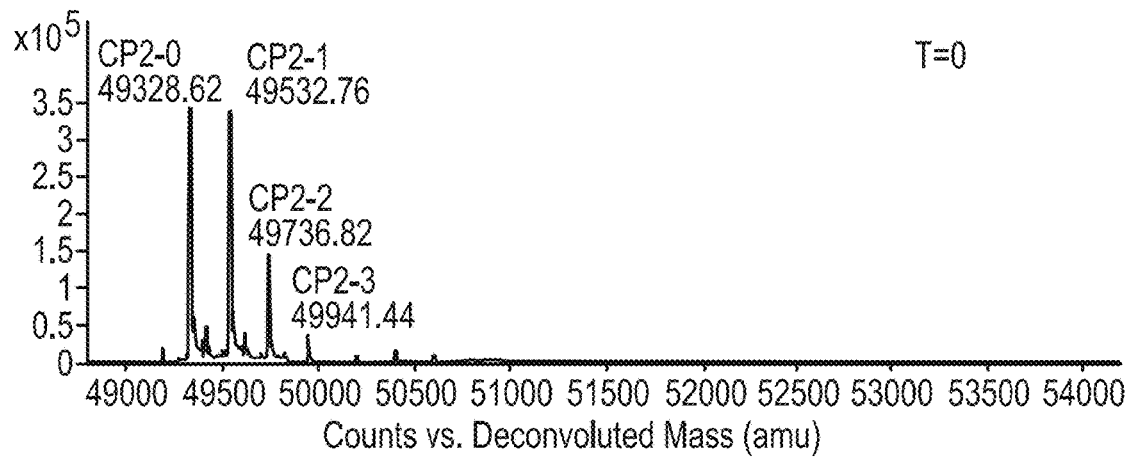
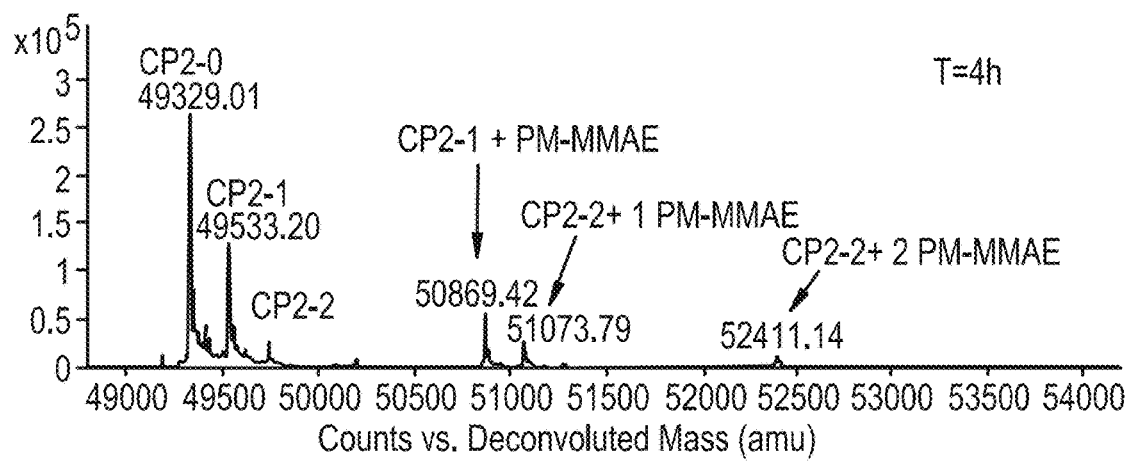
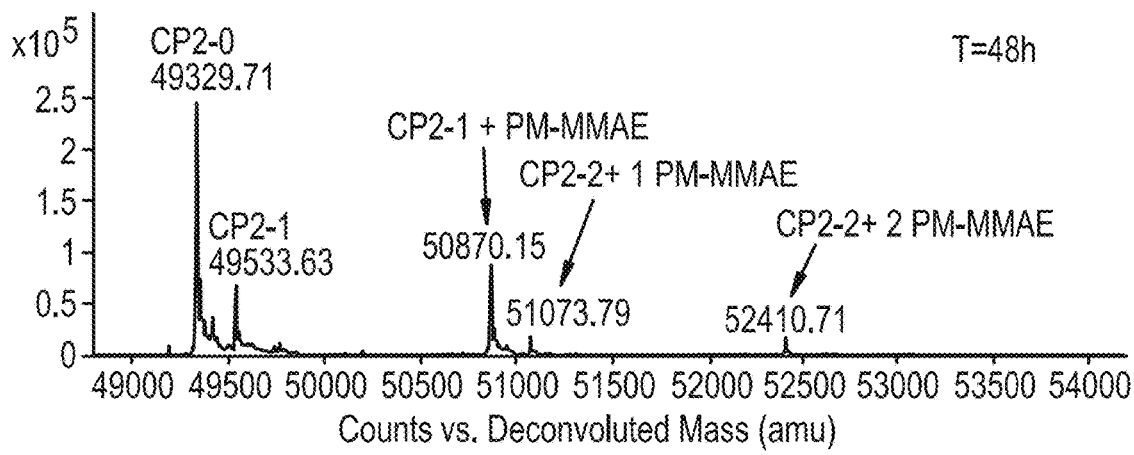

Figure 10.3 Reaction of mAb-CP2-liner dienes with maleimido-MMAEs. A) Molar concentration of unreacted CP2 over time. Unreacted CP2 diene per mAb was determined from the peak intensities of reduced deglycosylated mass spectra. B) Inverse concentration plot used to calculate reaction rates.
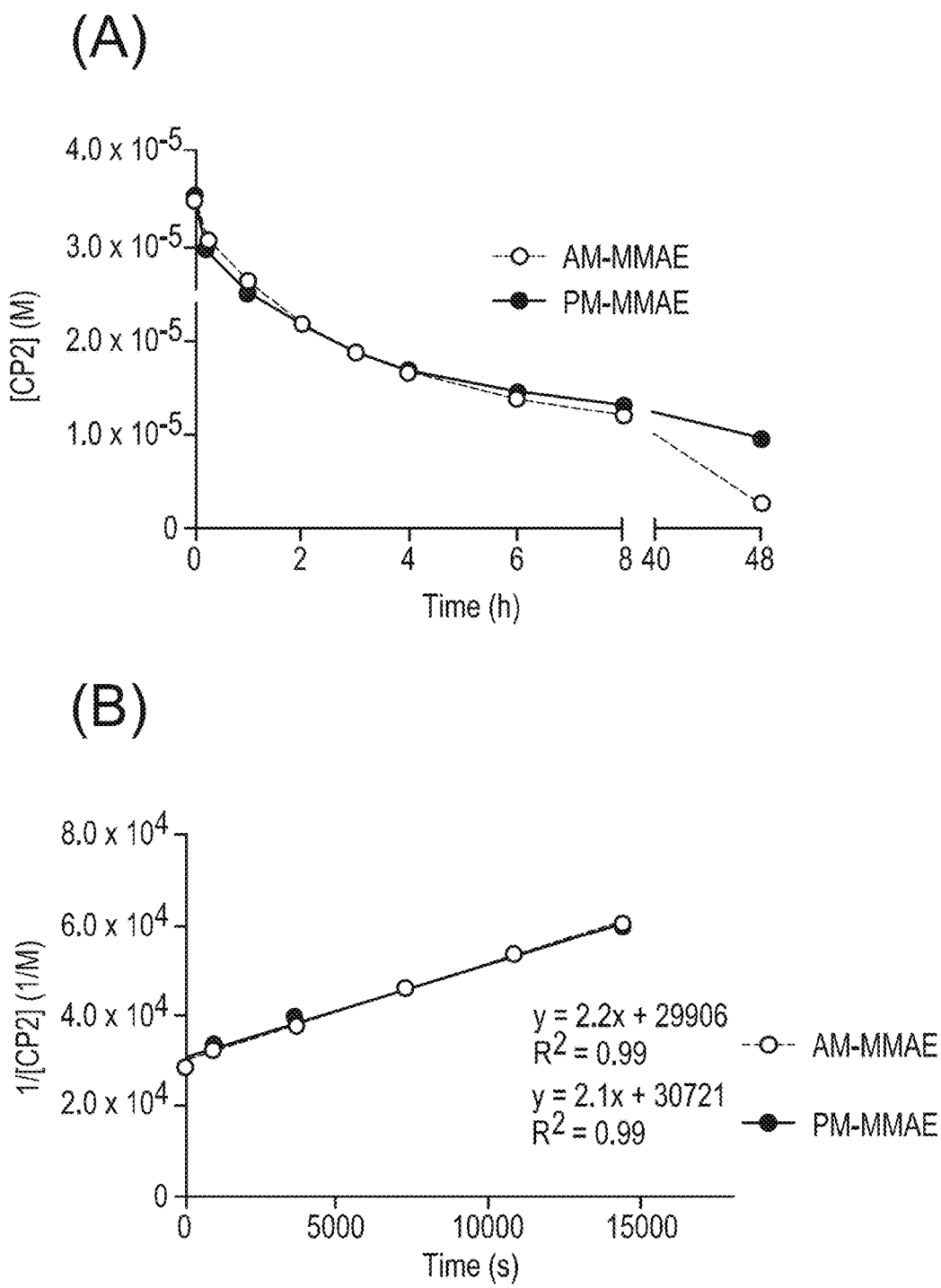

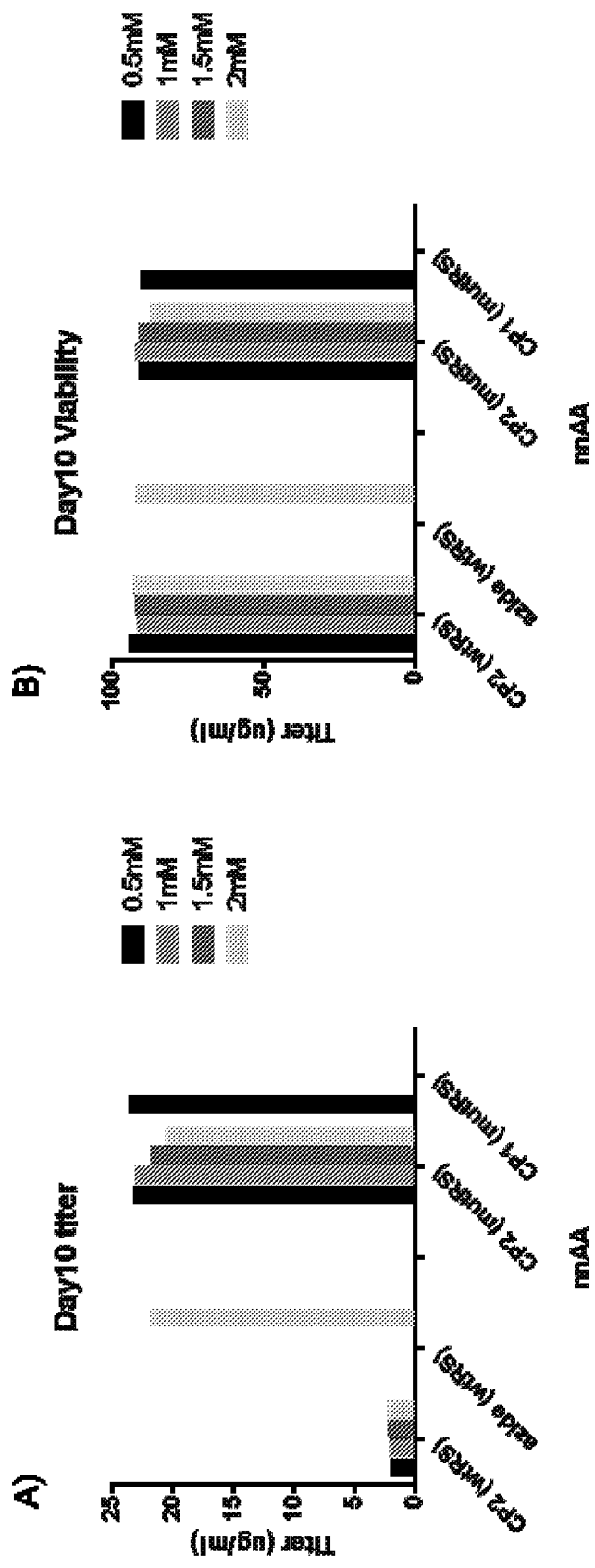
Figure 11.1. Titers & cell viability of 12G3H11 K274CP2-NNAA mAb after expression in mammalian cells comprising mutant or wild type tRS. CP2- NNAA final concentration in media is indicated in the figure legend. 12G3H11 K274CP2-NNAA mAb expression with mutant tRS was comparable to azido-lysine with wild-type tRS, with minimal toxicity.

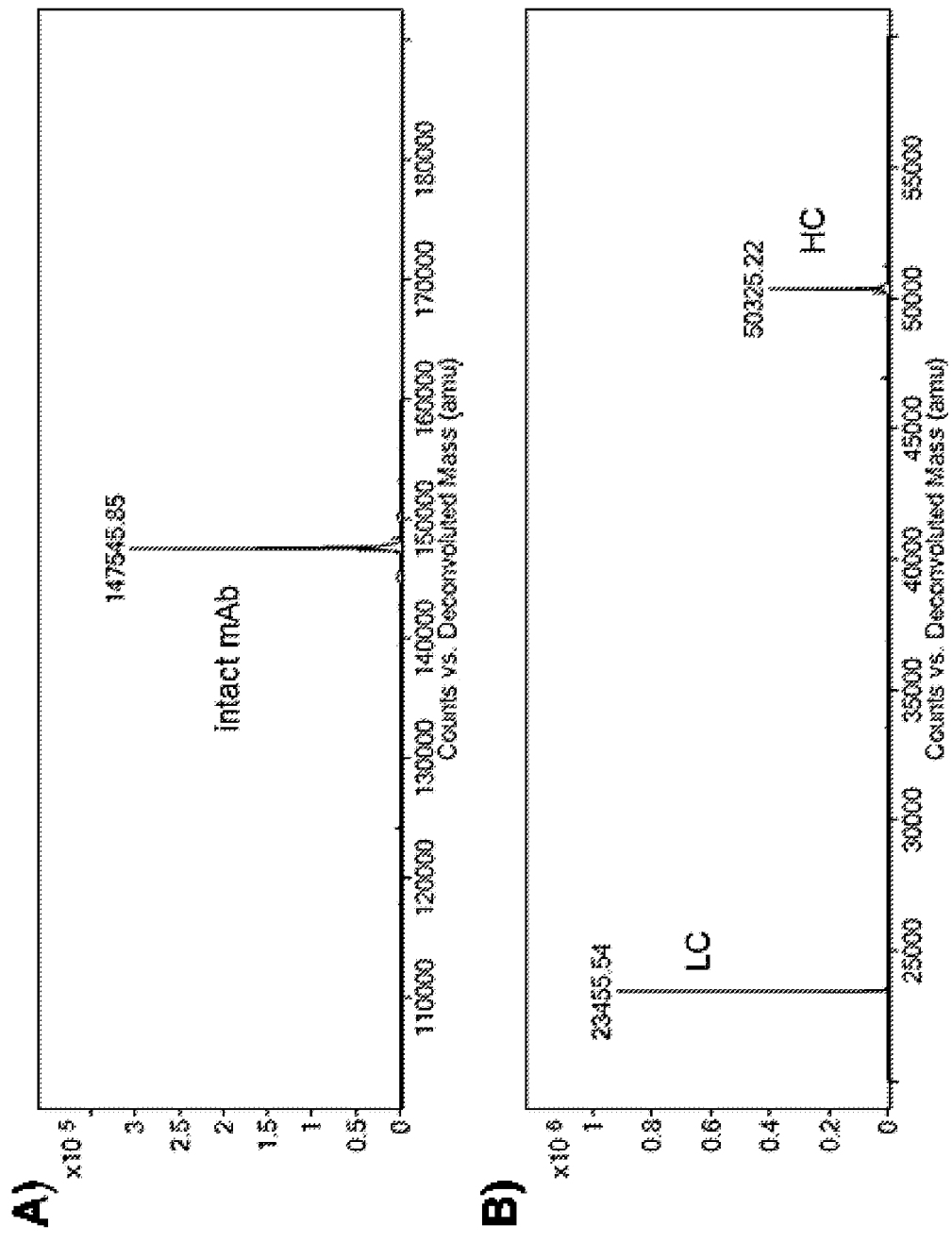
Figure 11.2. Mass spectrometry analysis of deglycosylated1C1 K274CP2-NNAA mAb. A) Intact mAb B) Reduced mAb zoomed to show the light chain (LC) and heavy chain (HC).

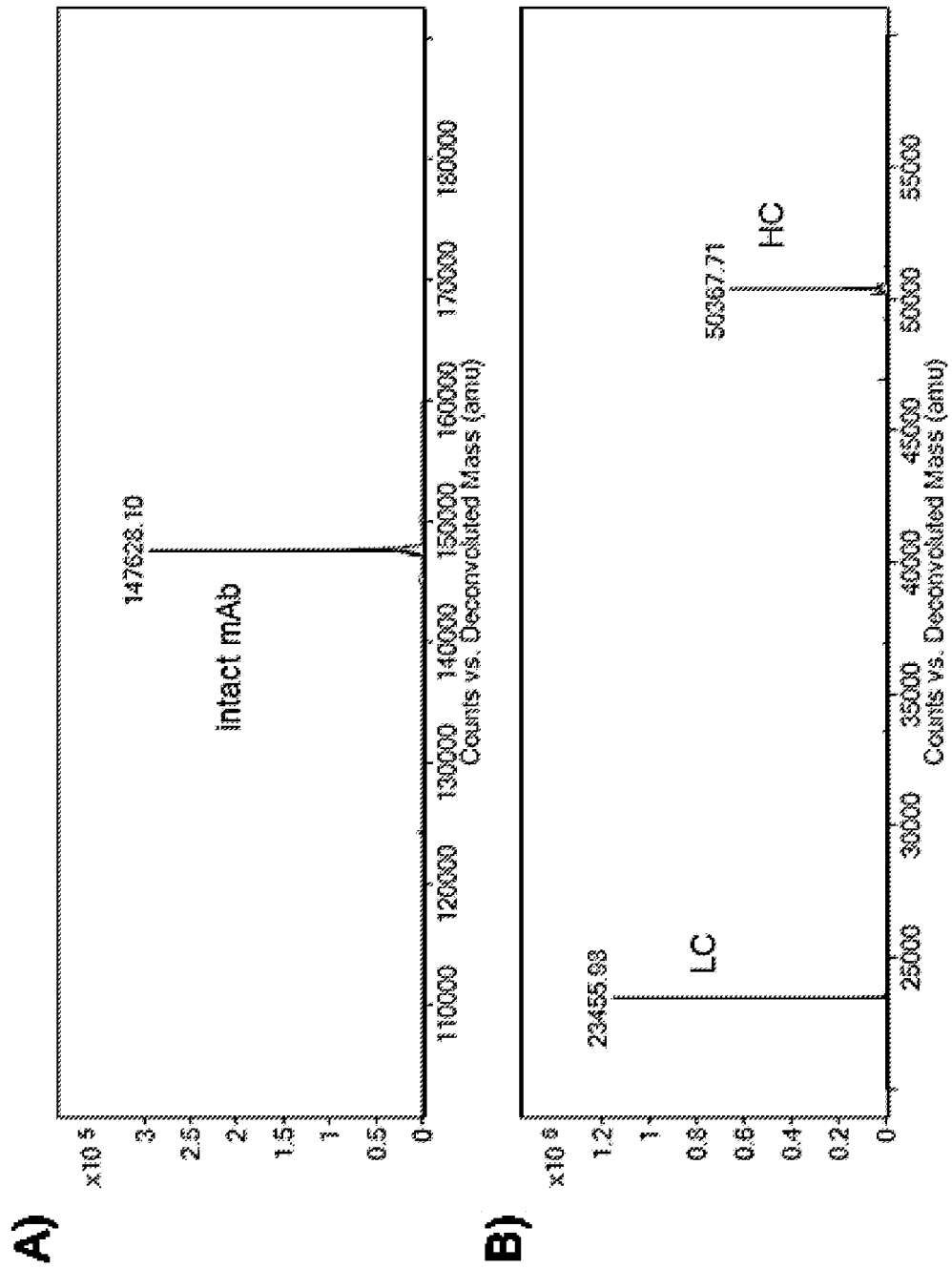
Figure 11.3. Mass spectrometry analysis of deglycosylated 1C1 S239CP2-NNAA mAb. A) Intact mAb B) Reduced mAb zoomed to show the light chain (LC) and heavy chain (HC).

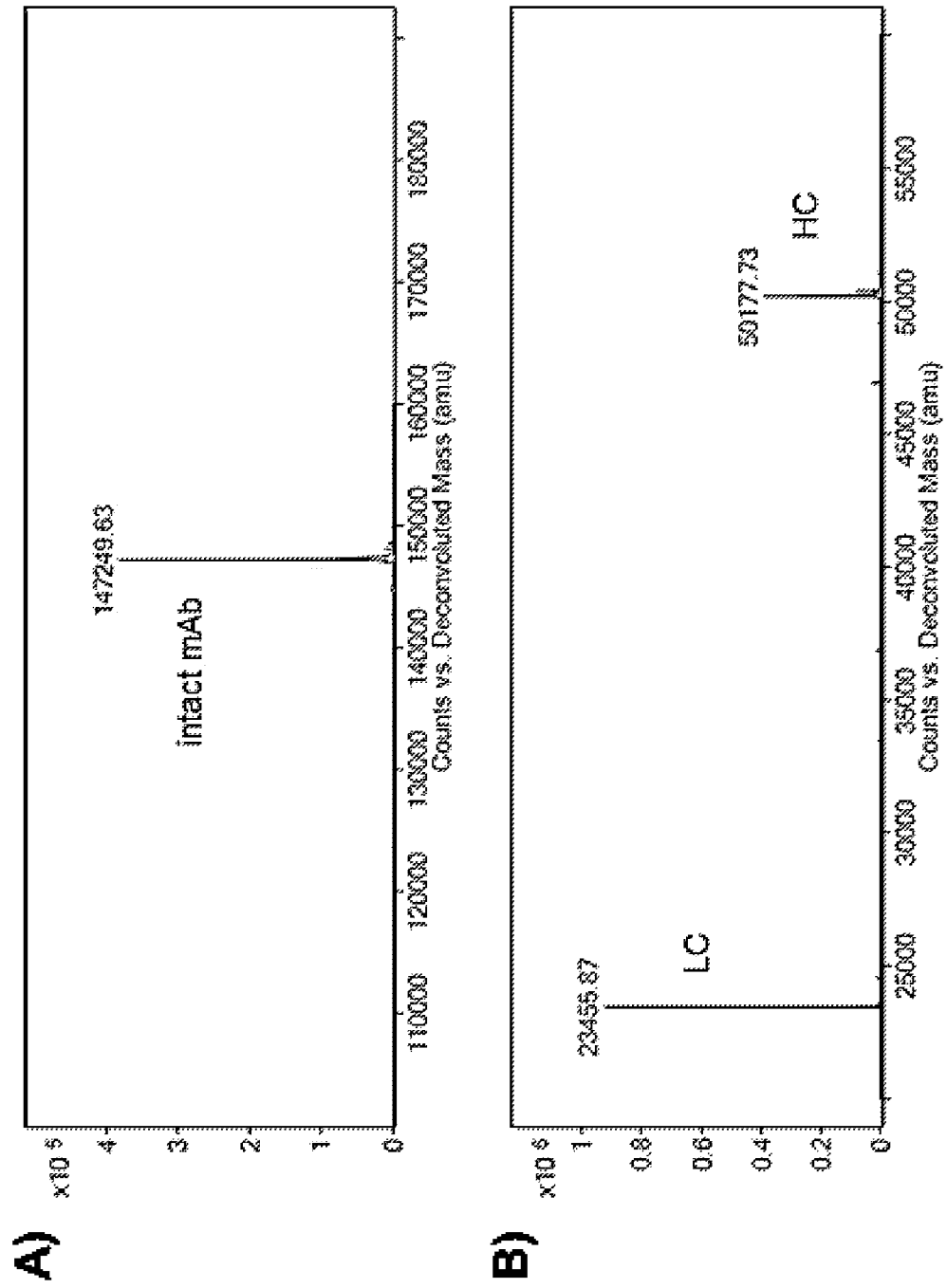
Figure 11.4. Mass spectrometry analysis of deglycosylated 1C1 wild-type mAb. A) Intact mAb B) Reduced mAb zoomed to show the light chain (LC) and heavy chain (HC).

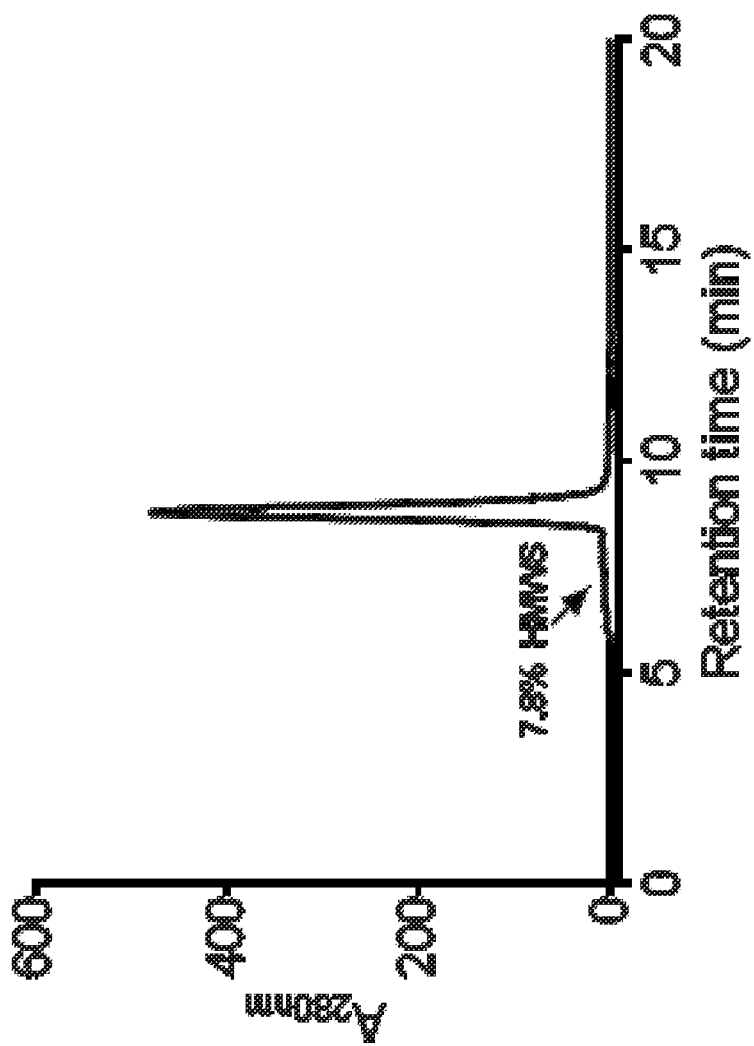
Figure 11.5. SEC analysis of 1C1 K274CP2-NNAA mAb indicating that monomeric product was obtained. High molecular weight species (HMWS) are indicated.

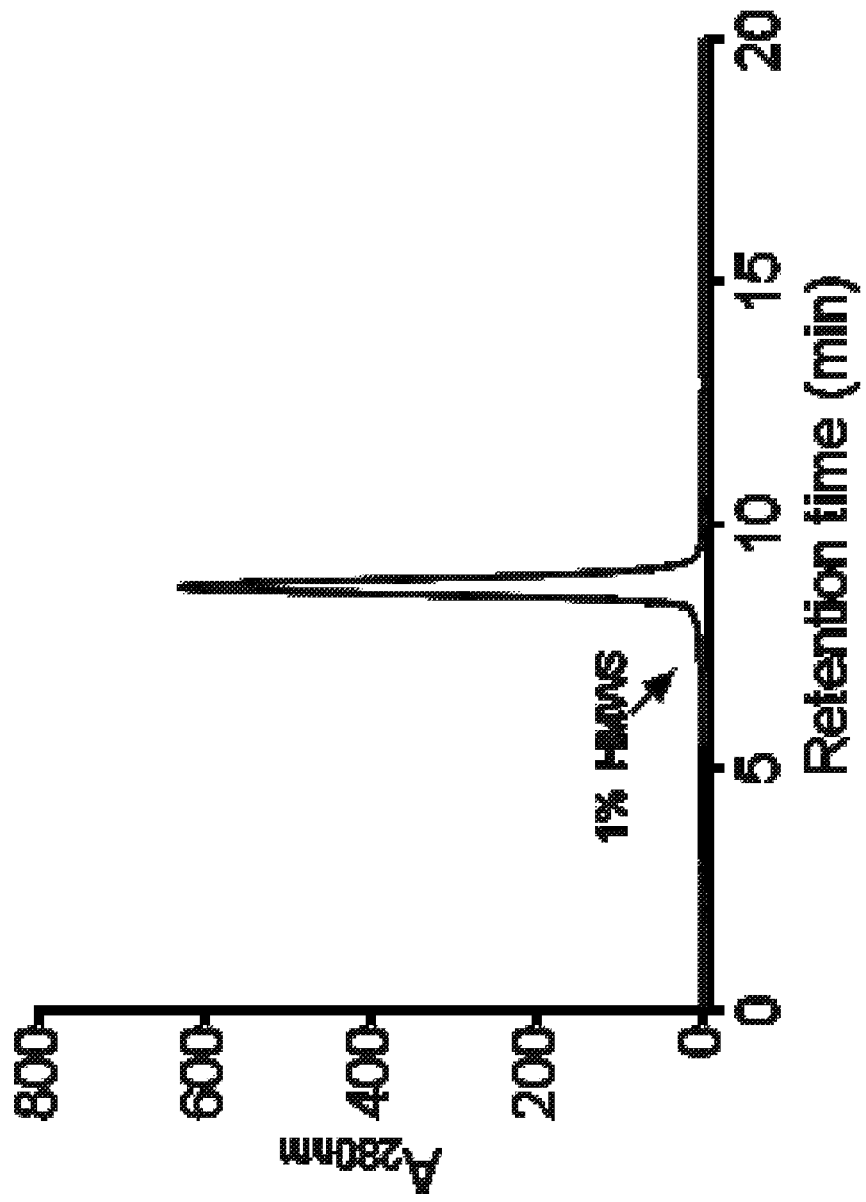
Figure 11.6. SEC analysis of 1C1 S239CP2-mAb indicating that monomeric product was obtained.

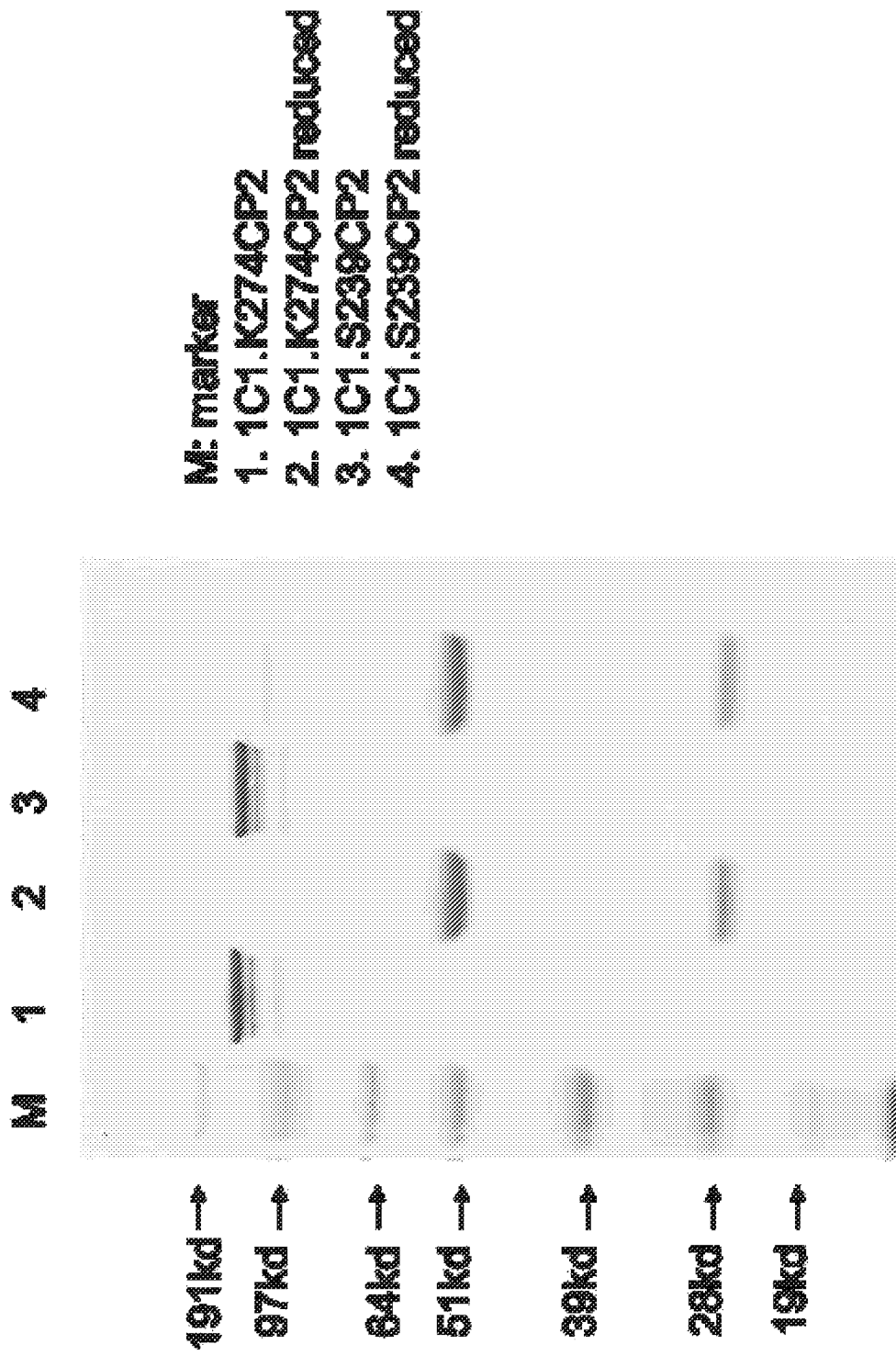
Figure 11.7. Analysis of 1C1-K274CP2 mAb and 1C1-S239CP2 mAb by SDS-PAGE.

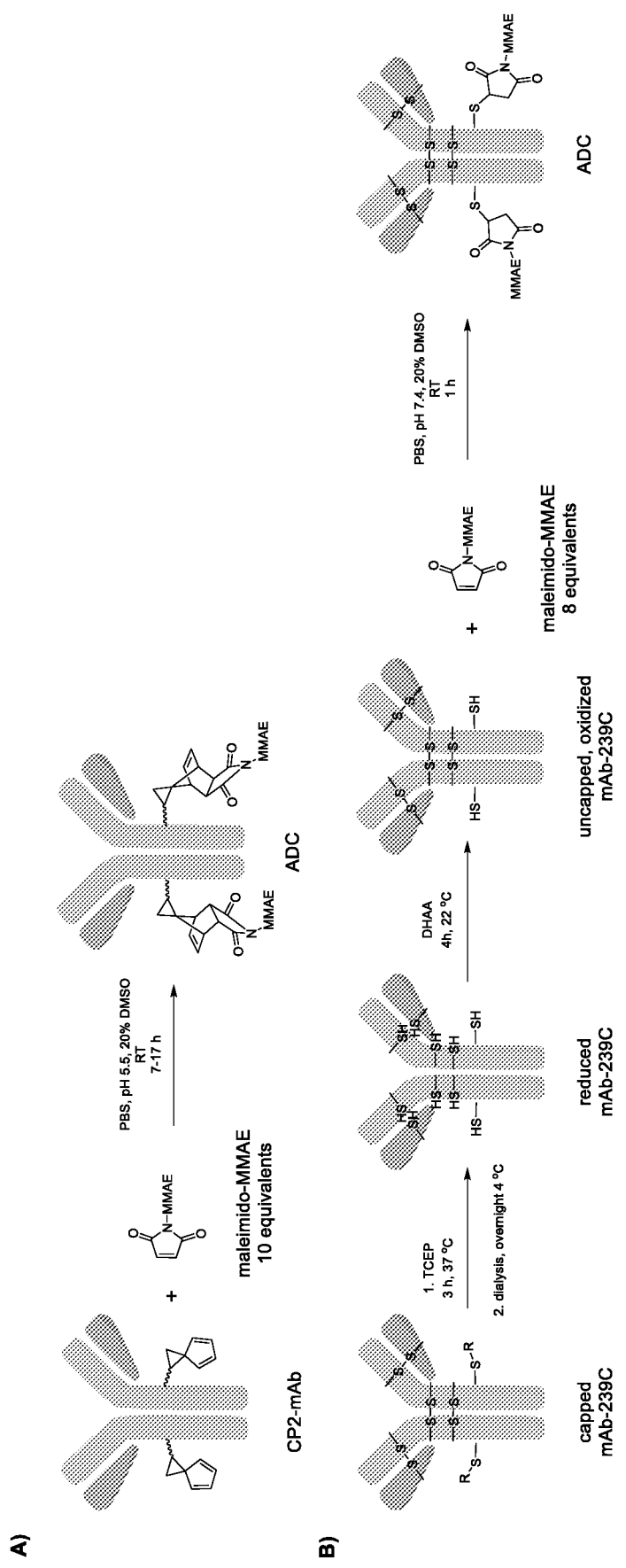
Figure 12.1. Generation of mAb-CP2-NNAA ADCs and mAb-239C ADCs.

Figure 12.2. Reduced, glycosylated mass spectrometry analysis of mAb-CP2-NNAAs and mAb-cysteine before and after reaction with AM-MMAE. Spectra zoomed in to shown mAb heavy chain (HC) region. DAR-0 indicates no drug conjugated to the mAb heavy chain and DAR-1 indicates one drug conjugated to the mAb heavy chain.
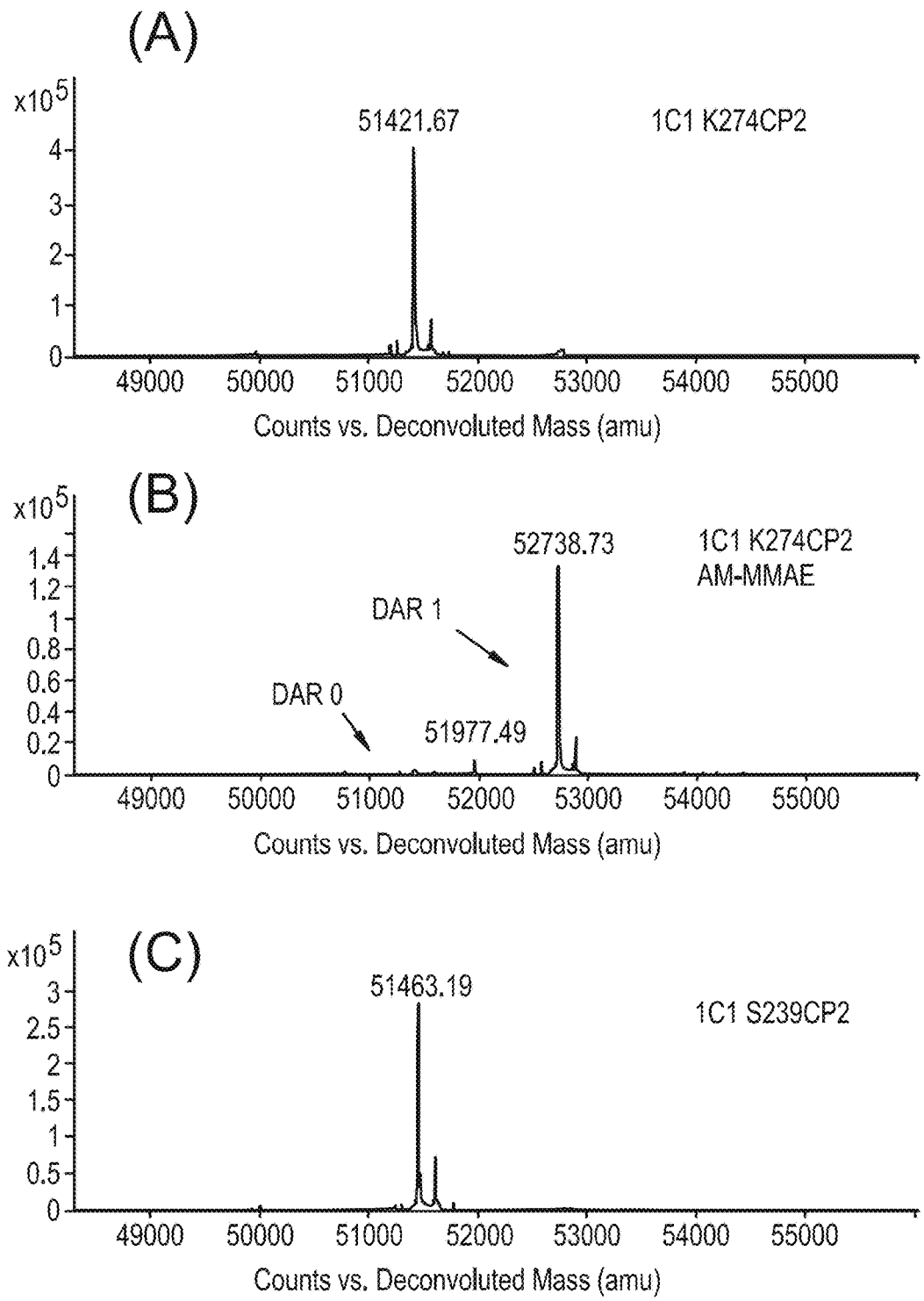

Figure 12.2. (continued) Reduced, glycosylated mass spectrometry analysis of mAb-CP2-NNAAs and mAb-cysteine before and after reaction with AM-MMAE. Spectra zoomed in to shown mAb heavy chain (HC) region.
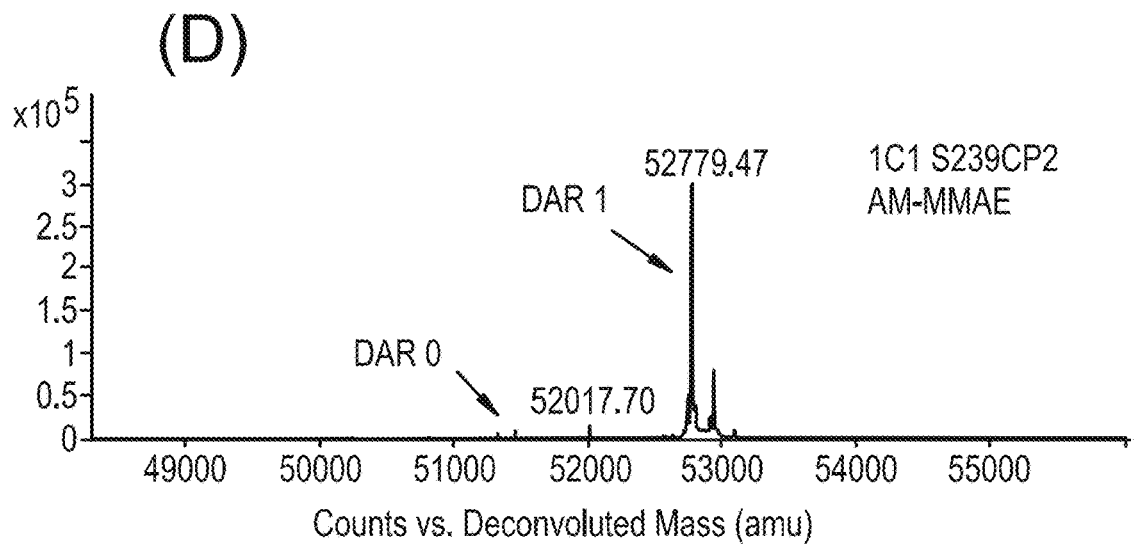
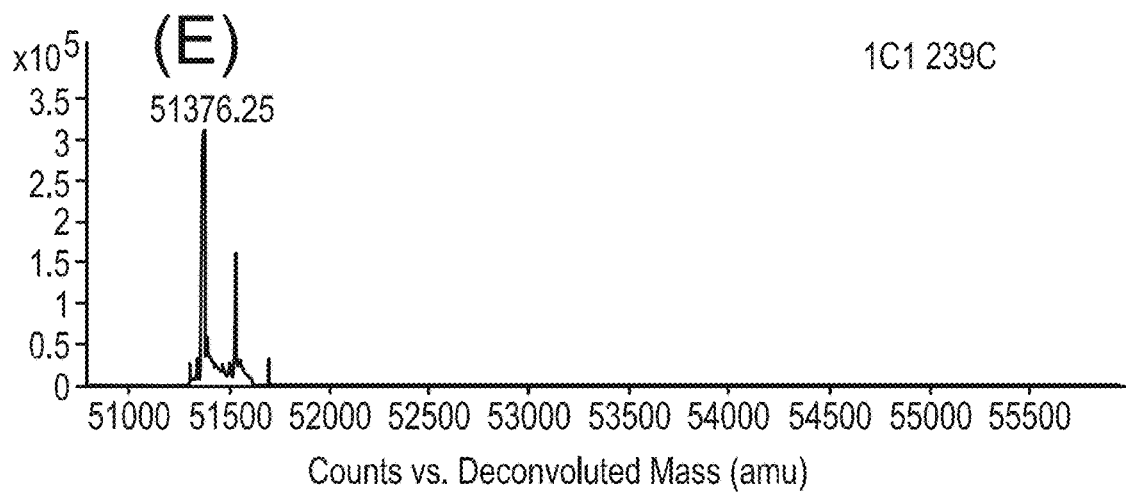
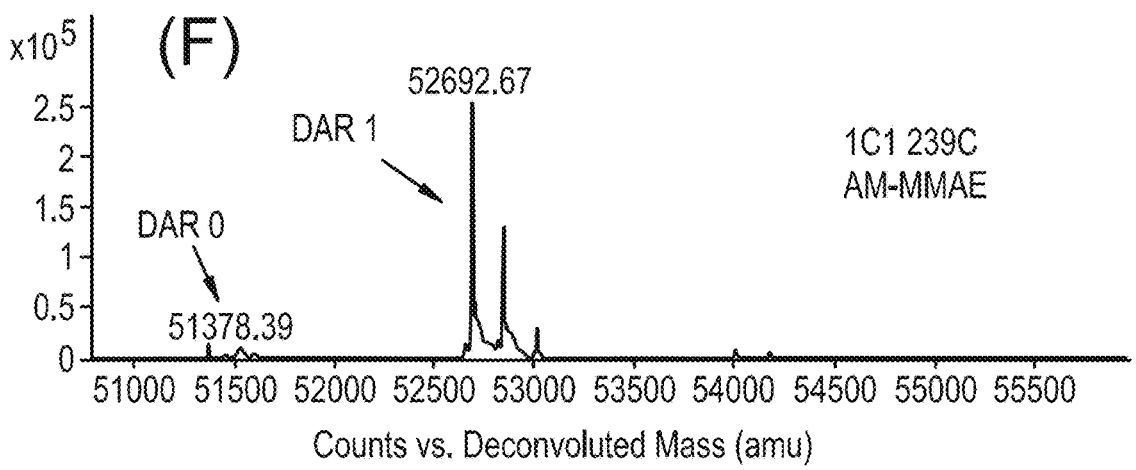

Figure 12.3. Reduced, glycosylated mass spectrometry analysis of mAb-CP2-NNAAs and mAb-cysteine before and after reaction with AM-MMAE. Spectra are zoomed to show mAb light chain.
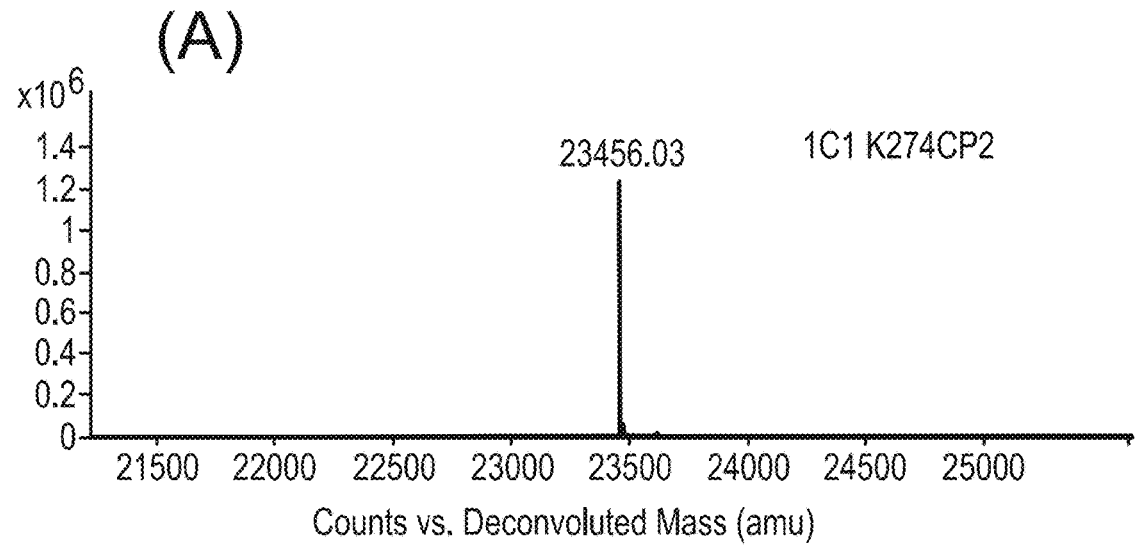
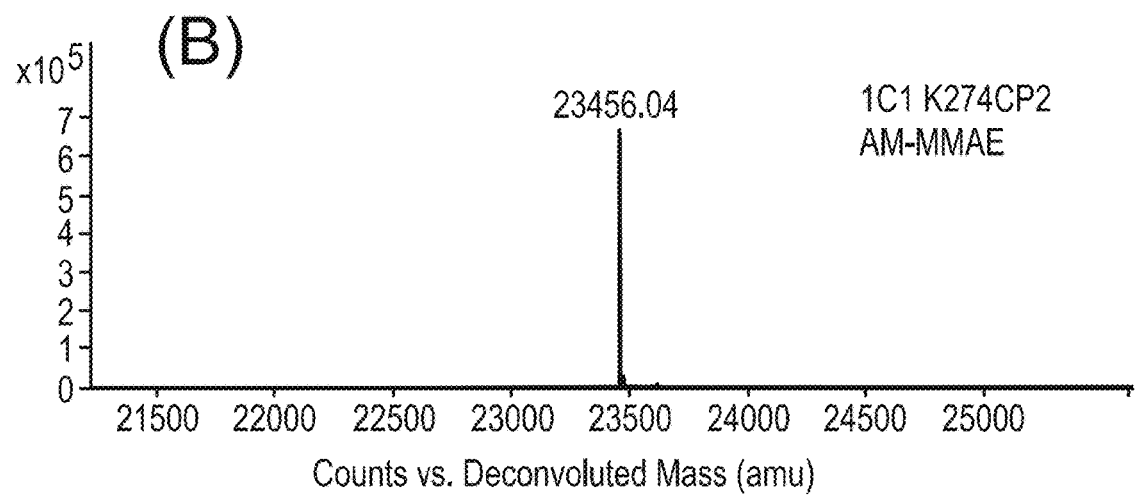
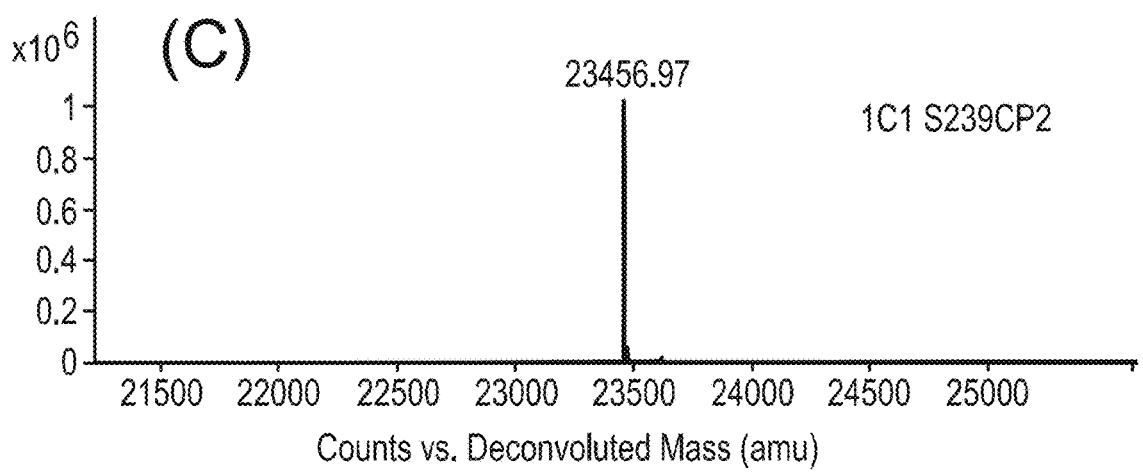

Figure 12.3. (continued) Reduced, glycosylated mass spectrometry analysis of mAb-CP2-NNAAs and mAb-cysteine before and after reaction with AM-MMAE. Spectra are zoomed to show mAb light chain.
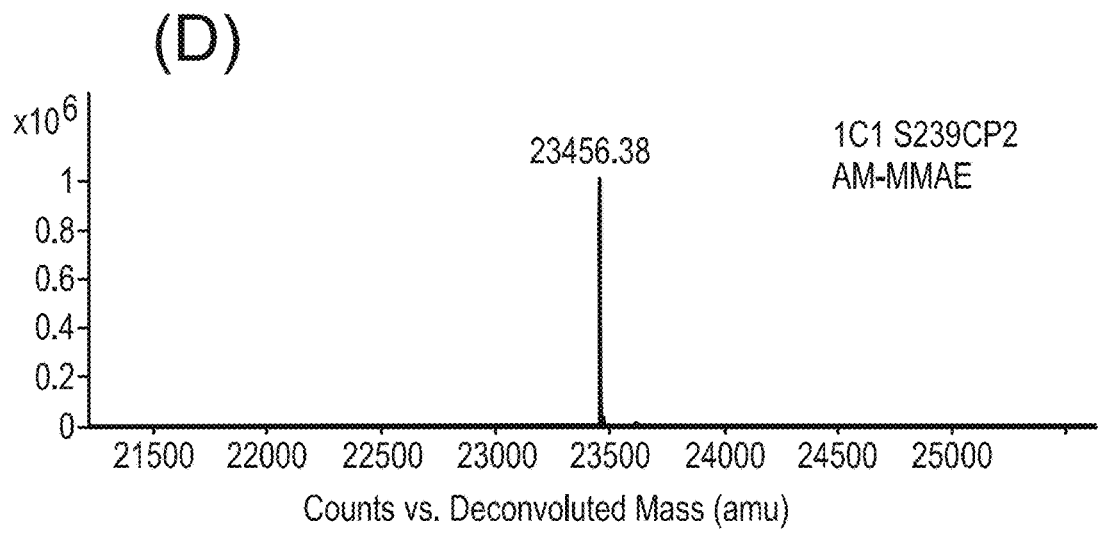
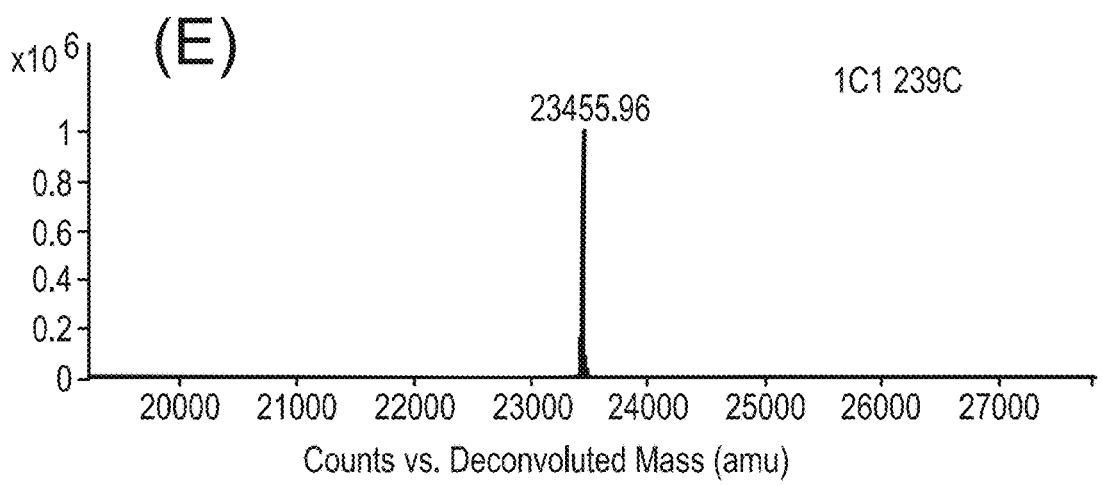
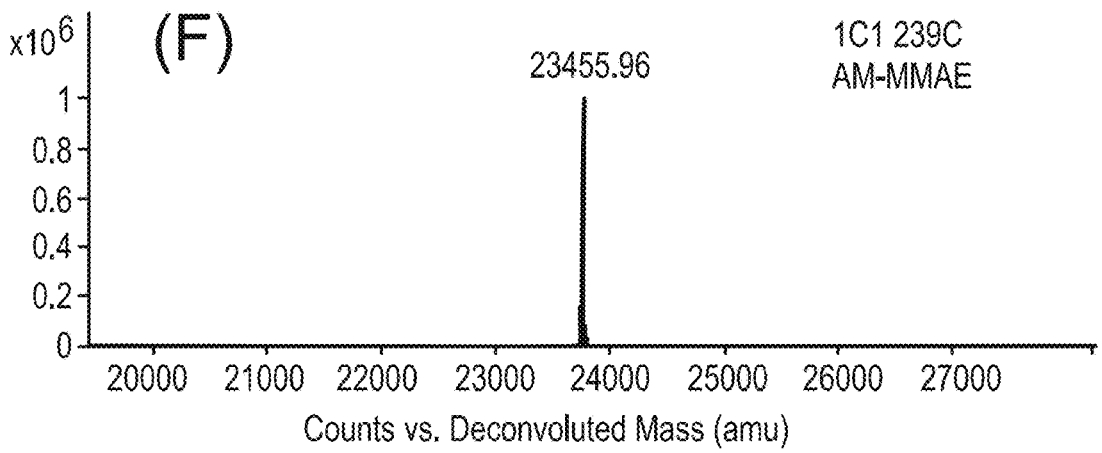

Figure 12.4. Hydrophobic interaction chromatography analysis of mAb-CP2-NNAA and mAb-cysteine ADCs.
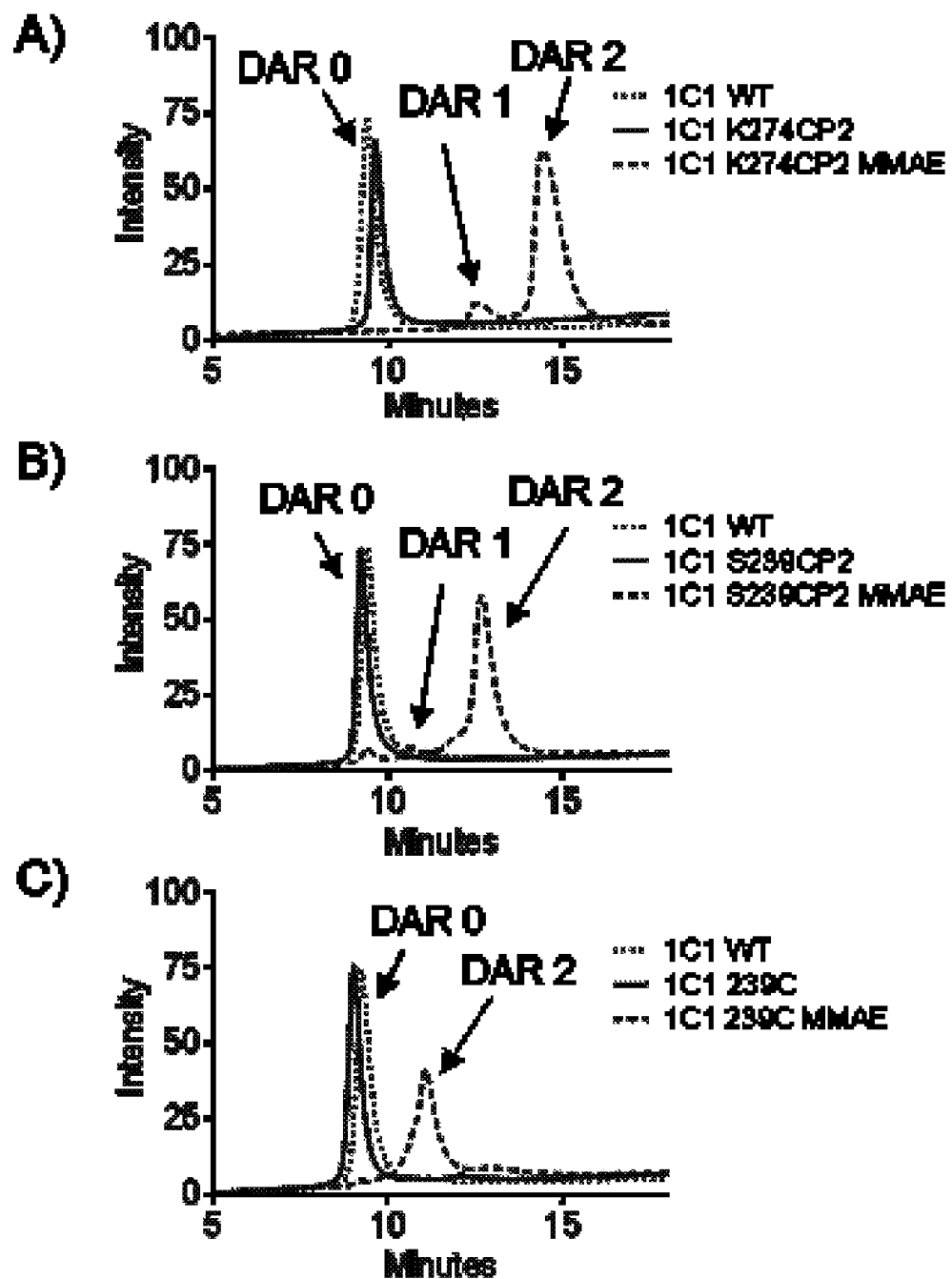

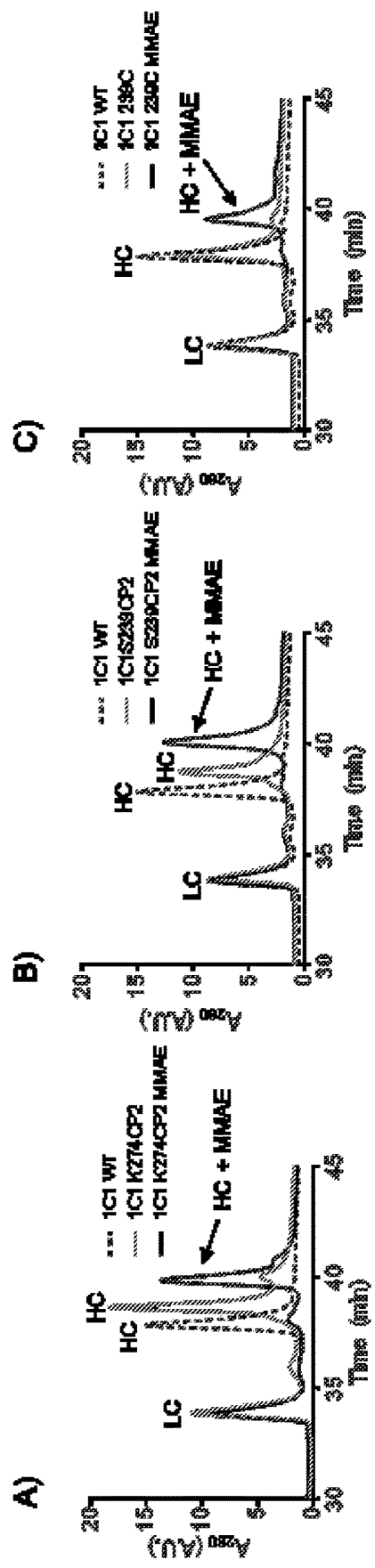
Figure 12.5. Reduced reverse-phase high-performance chromatography analysis of mAb-CP2-NNAA and mAb-cysteine ADCs.

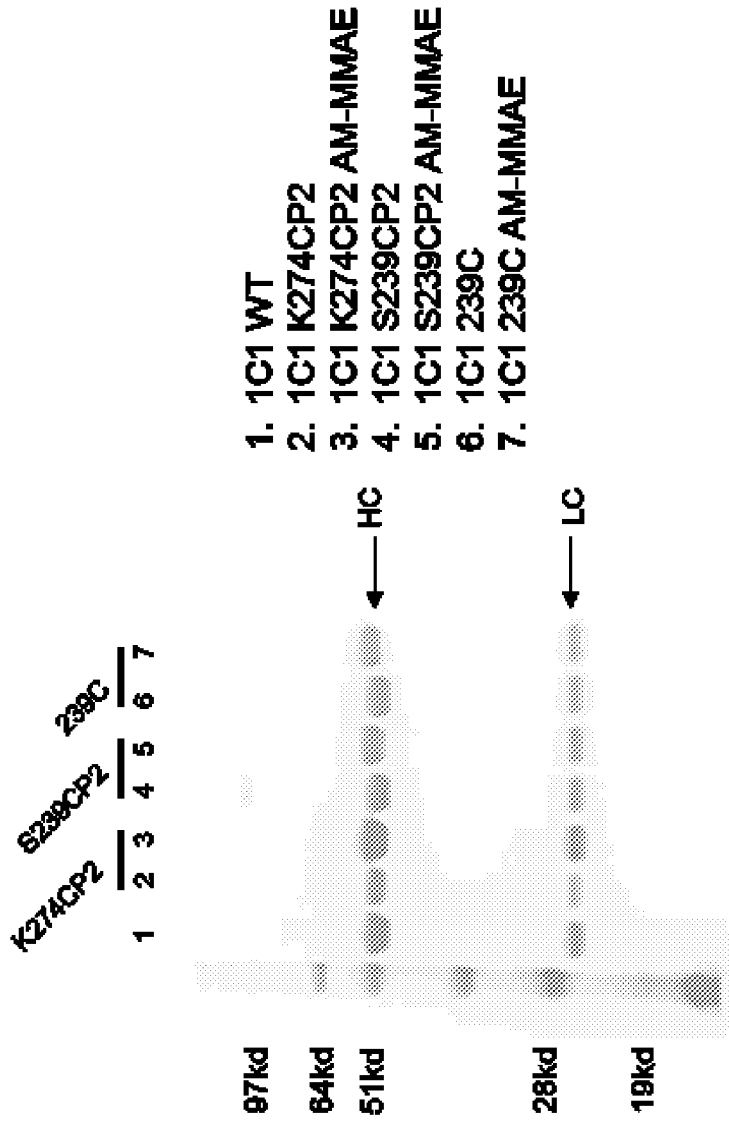
Figure 12.6. Reduced SDS-PAGE analysis of mAb-CP2-NNAA and mAb-cysteine ADCs.

Figure 12.7. Reduced, deglycosylated mass spectrometry analysis of mAb-CP2-NNAA ADCs before and after incubation in rat serum for 7 days at 37°C
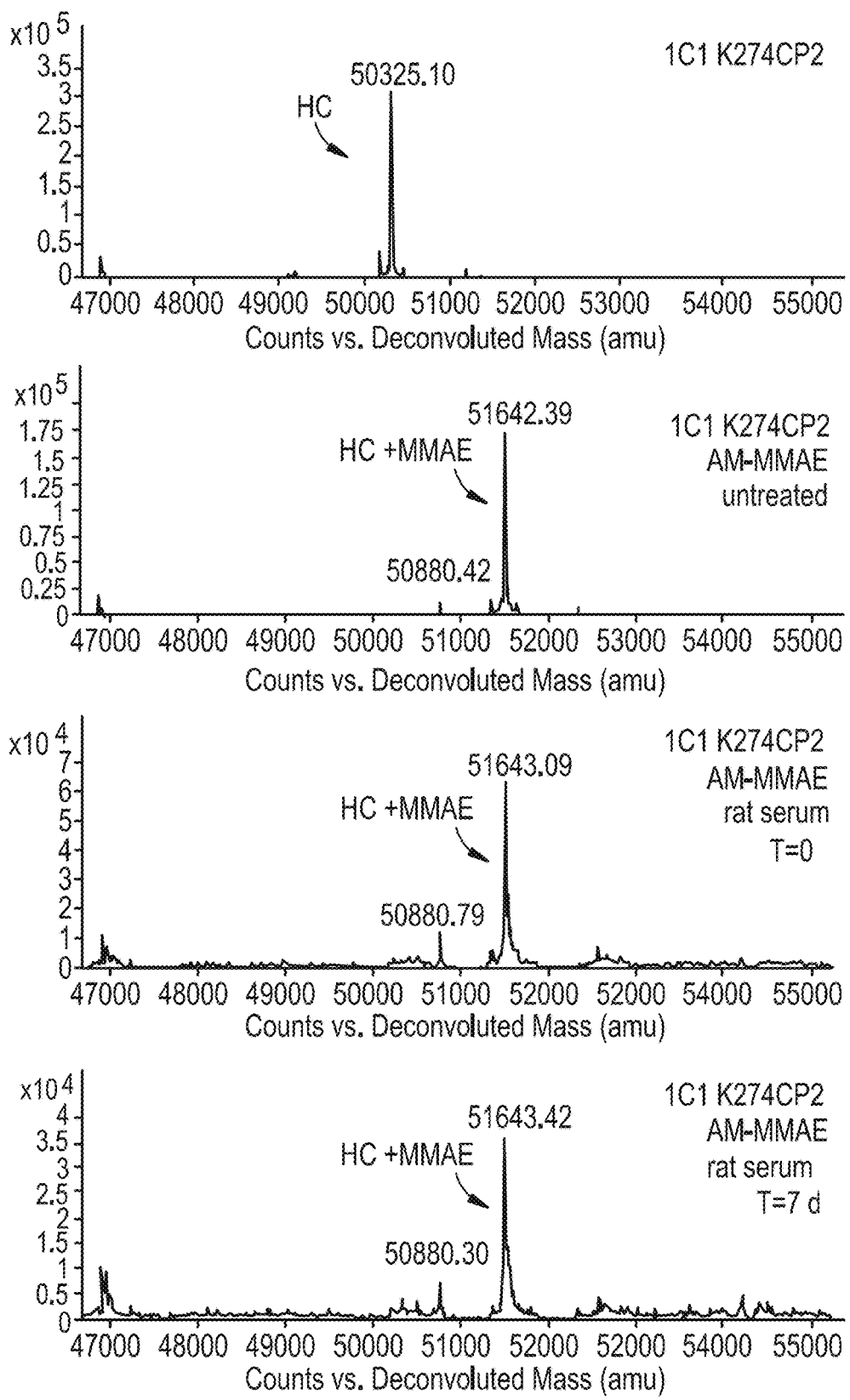

Figure 12.7. (Continued) Reduced, deglycosylated mass spectrometry analysis of mAb-CP2-NNAA ADCs before and after incubation in rat serum for 7 days at 37°C.
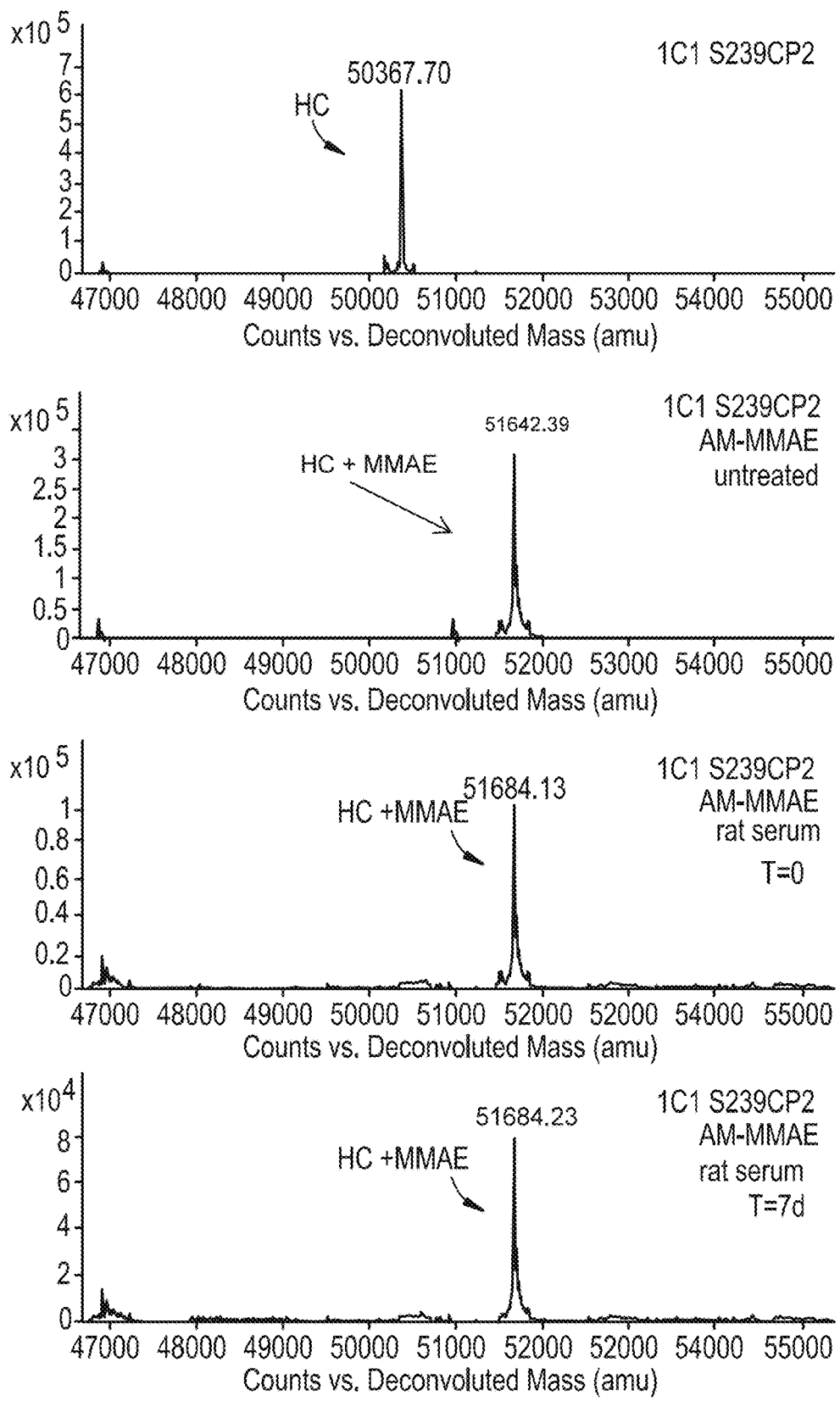

Figure 12.8. Quantification of mAb-CP2-NNAA ADC DARs before and after incubation in rat serum for 7 d at 37 °C. DARs were calculated from the peak heights of mass spectra shown in Figure 12.7. Values are reported as the mean ± standard deviation, n=3. No drug loss was detected under these conditions.
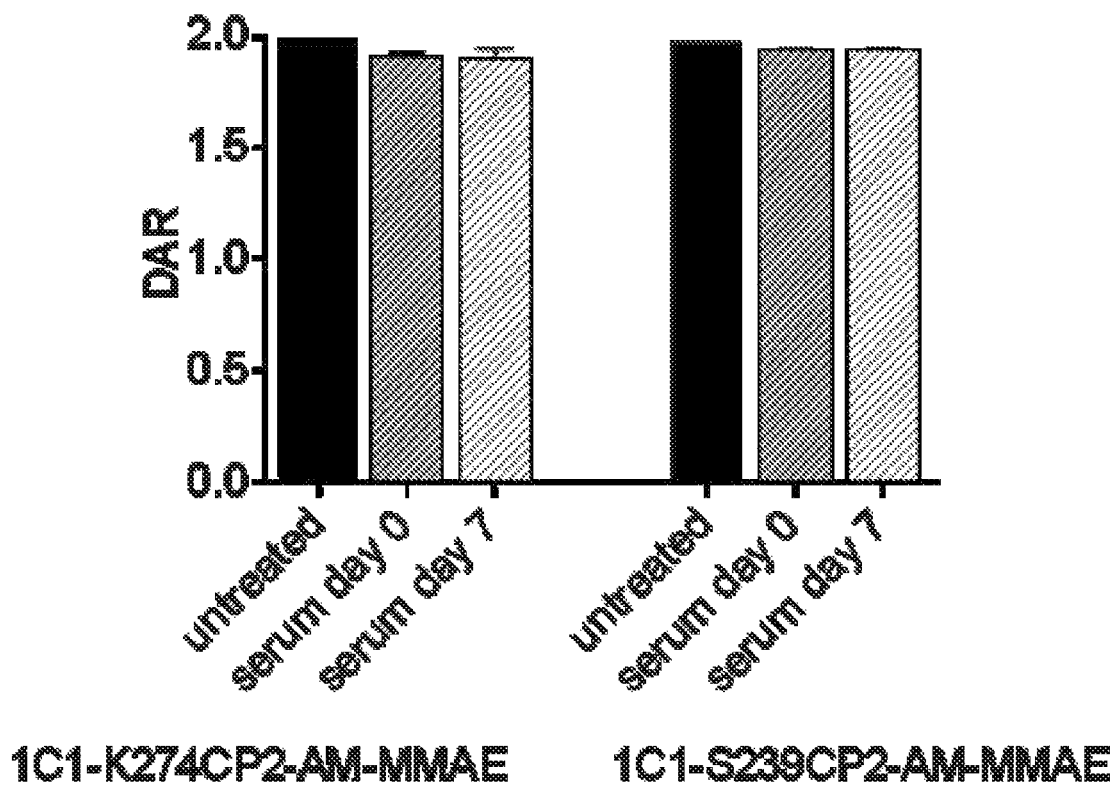

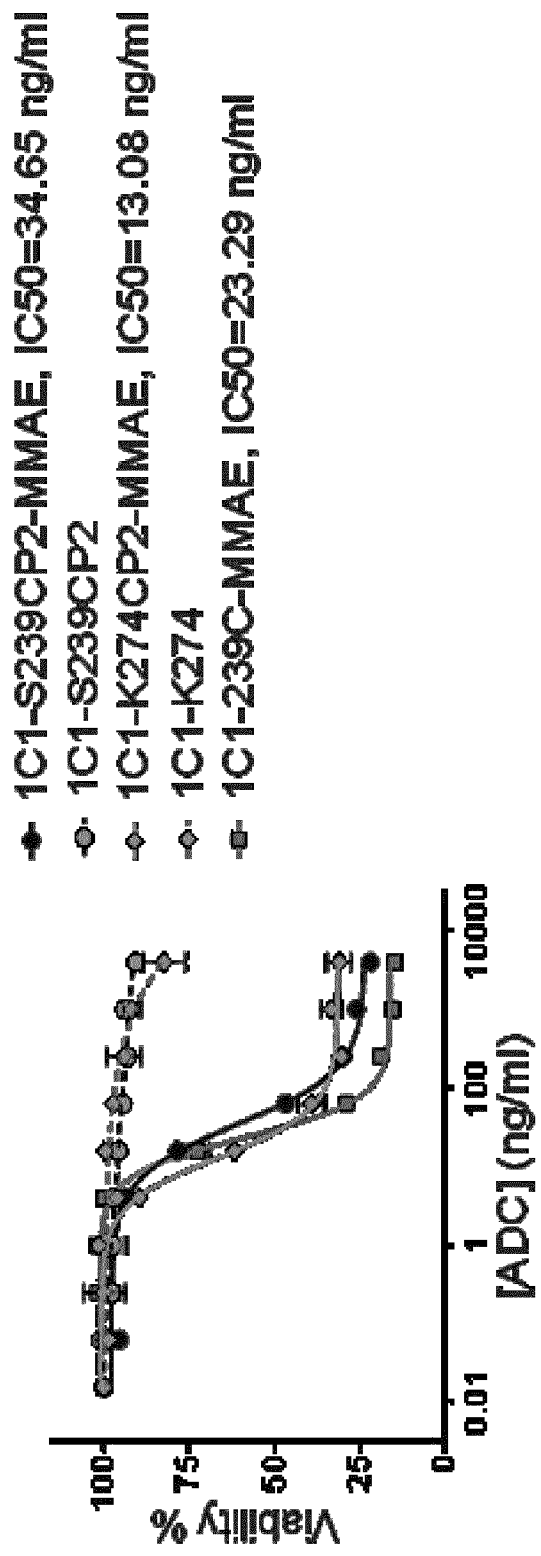
Figure 12.9. Cytotoxicity of mAb-CP2-NNAA and mAb-cysteine ADCs towards PC3 cancer cells *in vitro*. mAb-CP2-NNAA AM-MMAE ADCs exhibited similar potencies as the analogous ADC prepared by site-specific cysteine conjugation of AM-MMAE.

Figure 13.1. Overview of ester positions in A) CP1-NHS and B) CP1b-NHS linkers.
(A)
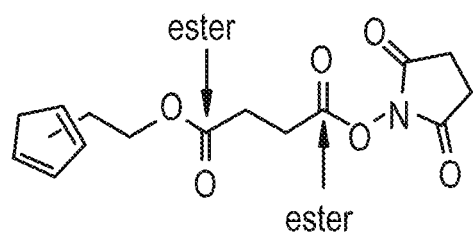
CP1-NHS
(B)
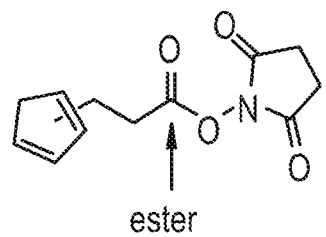
CP1b-NHS

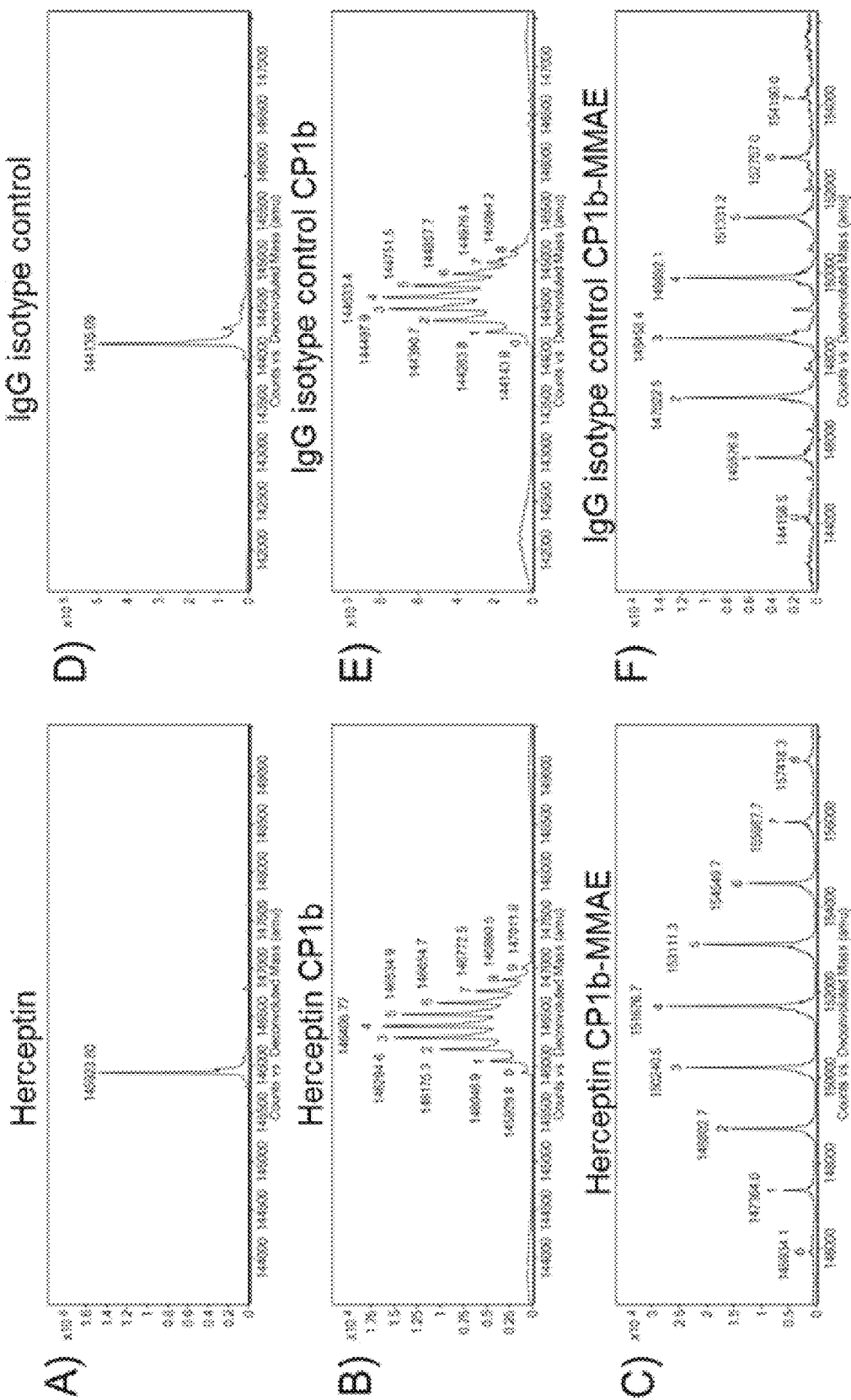
Figure 14.1. Mass spectrometry analysis of mAb-CP1b conjugates.

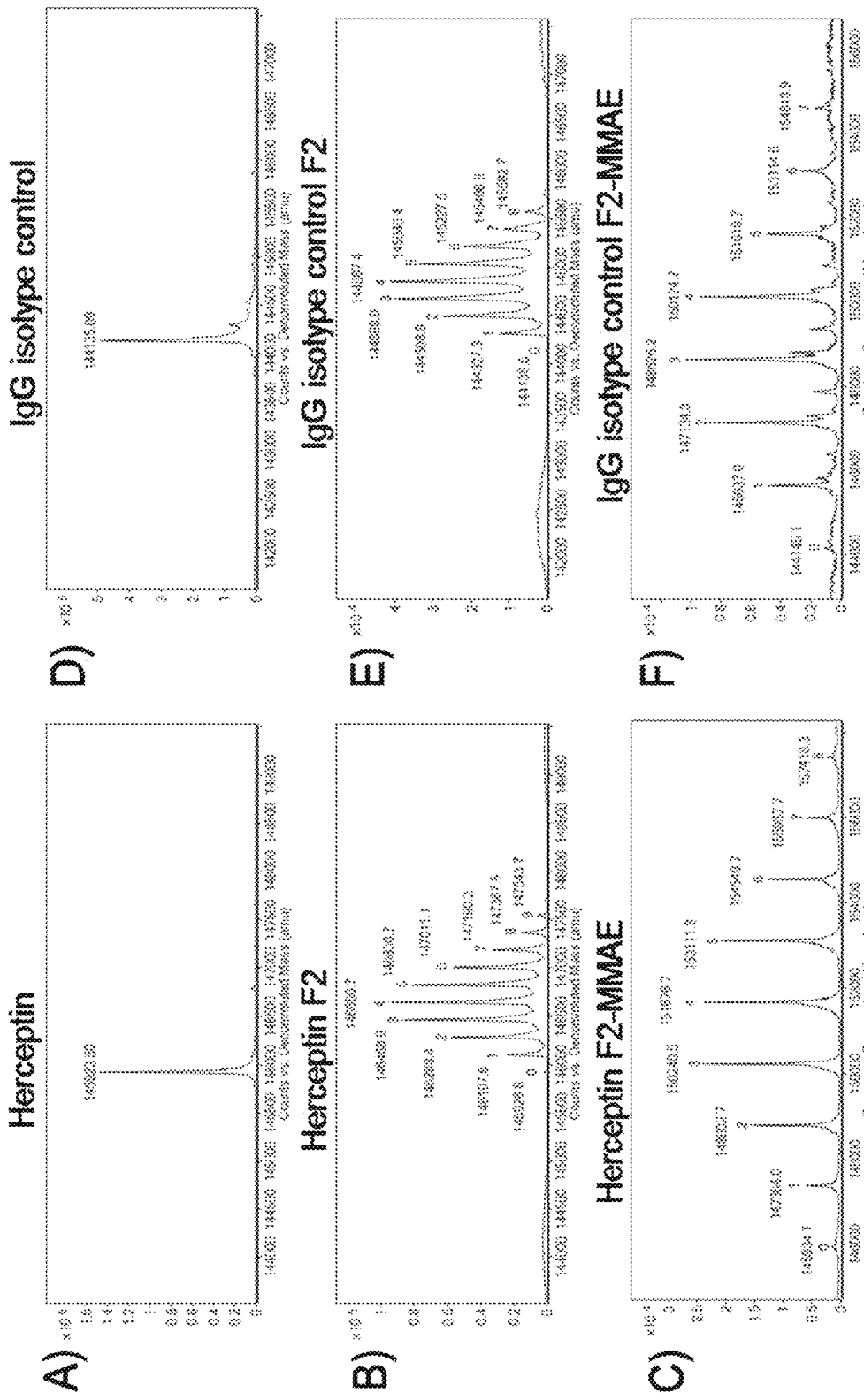
Figure 14.2. Mass spectrometry analysis of mAb-F2 conjugates.

Figure 14.3. Mass spectrometry analysis of mAb-Cys conjugates.
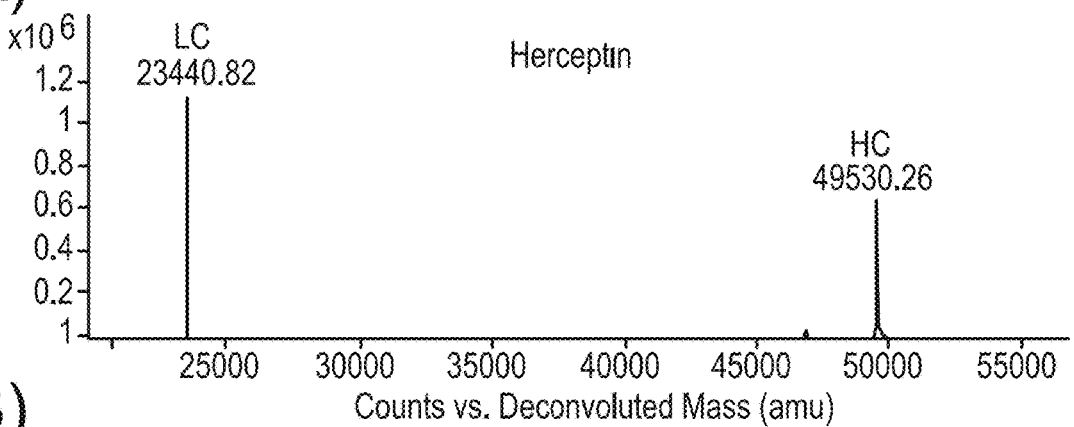
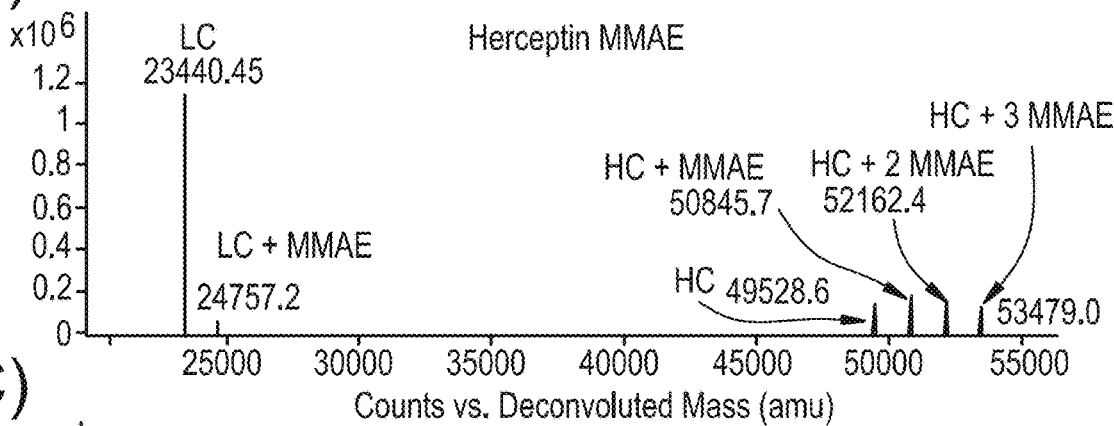
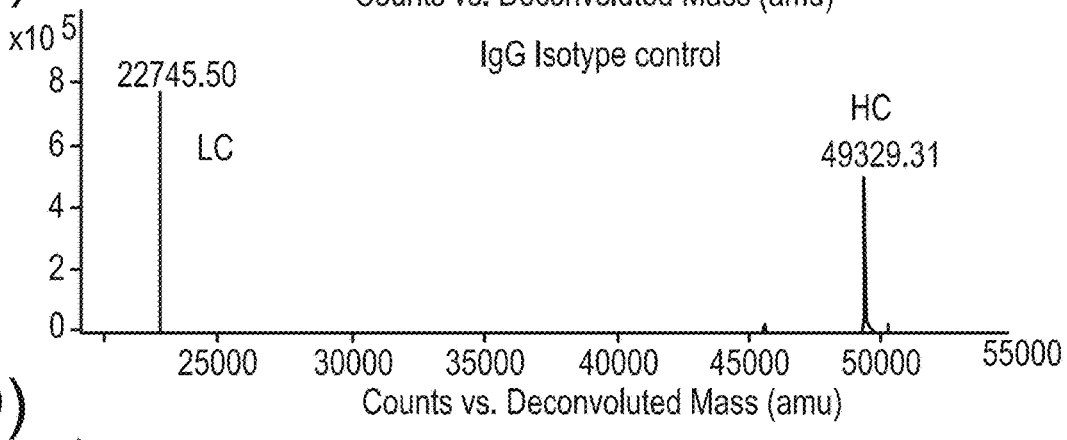
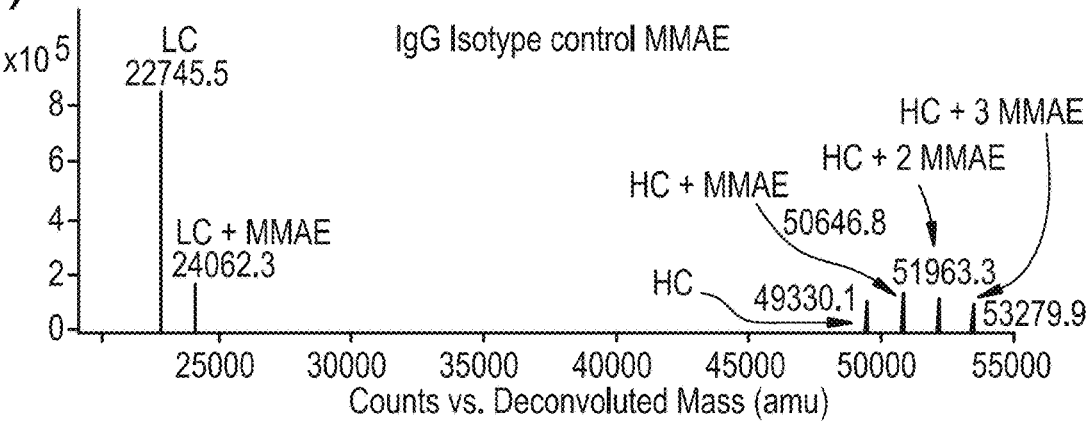

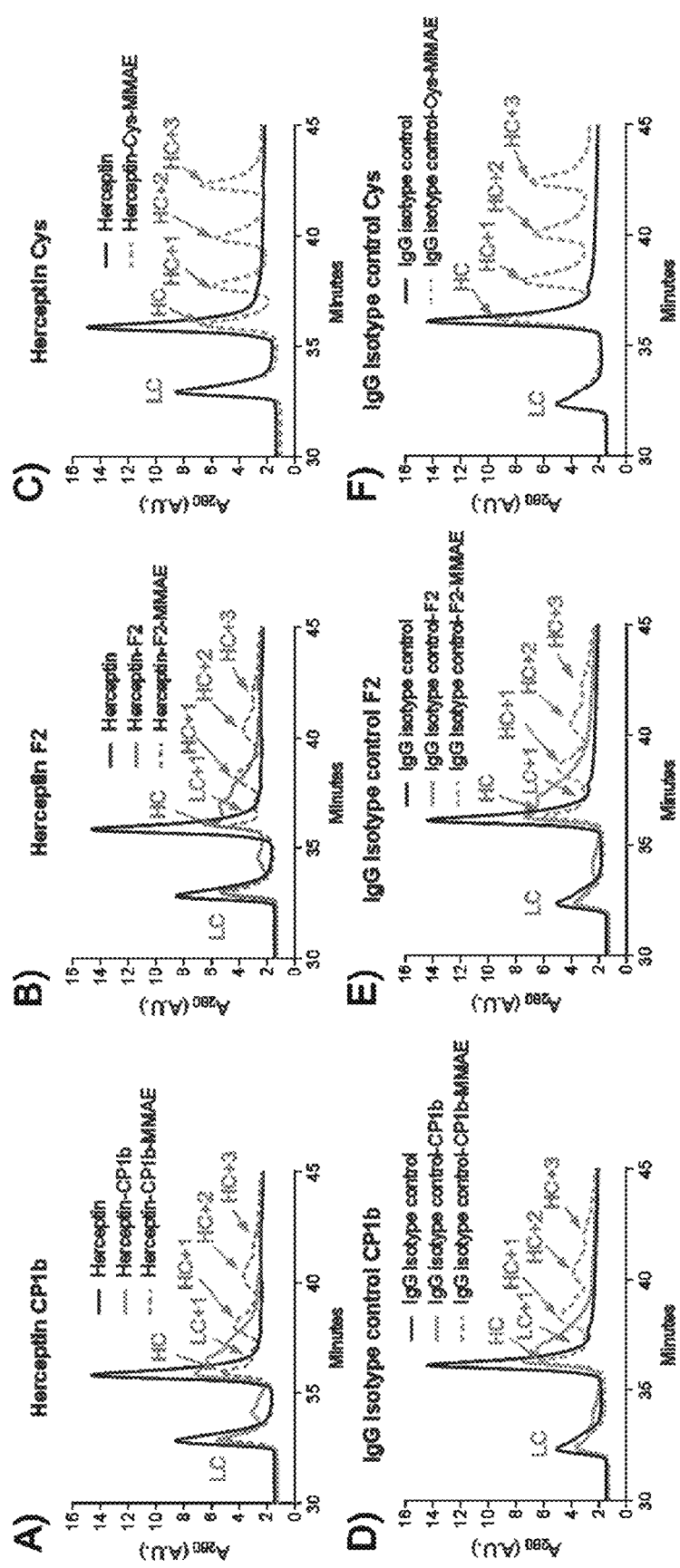
Figure 14.4. rRP-HPLC analysis of mAbs, mAb-linker conjugates and ADCs.

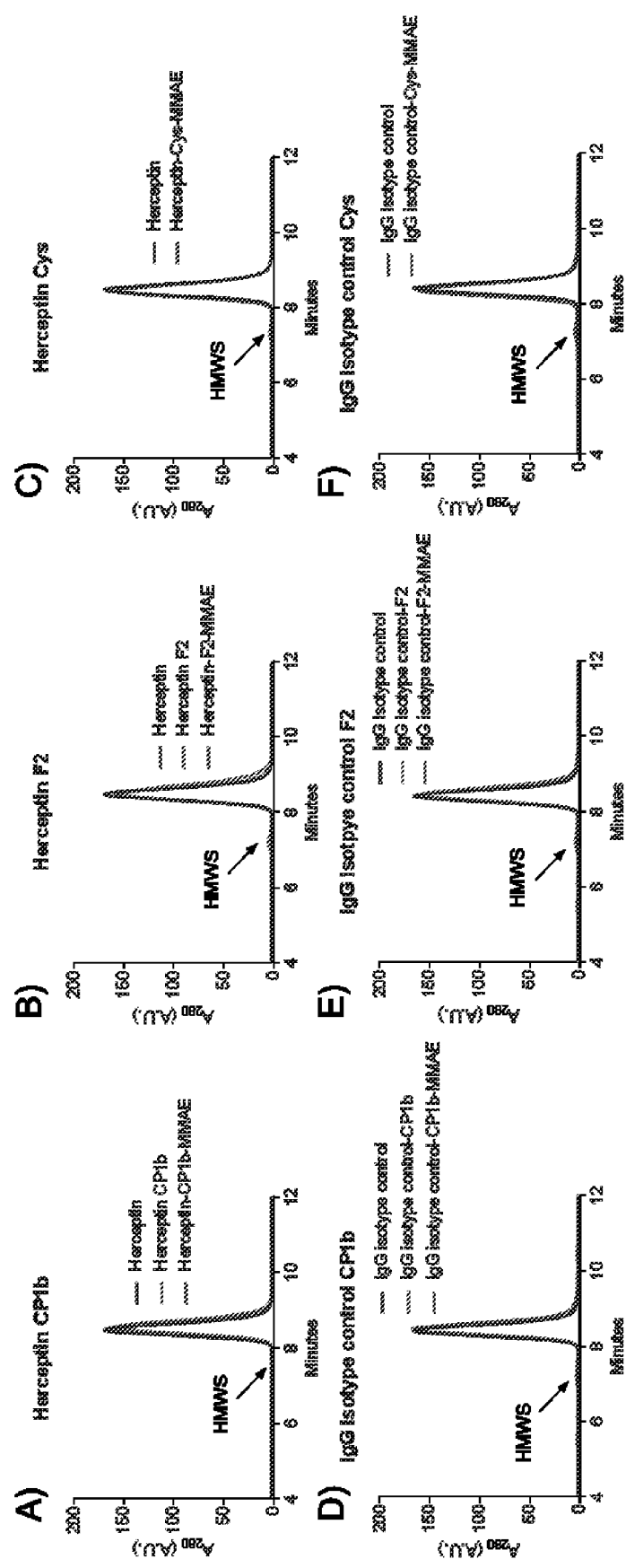
Figure 14.5. SEC Analysis of mAbs, mAb-linker conjugates and ADCs.

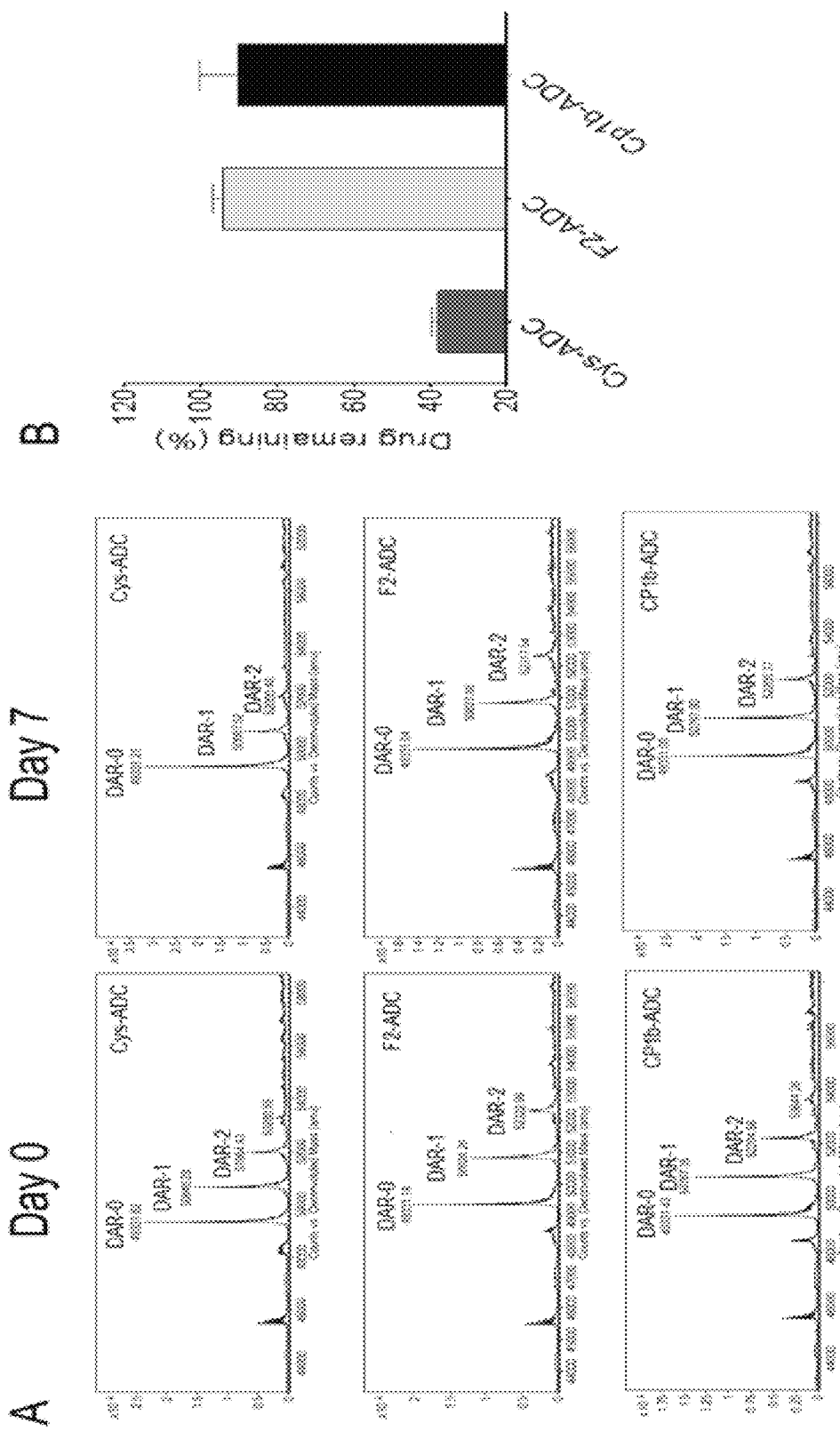
Figure 14.6. A) Mass spectrometry analysis of ADCs following incubation in rat serum for 7 d. B) Quantification of remaining drug (%) using mass spectrometry data. Data is shown as the average +/- the standard deviation, n=3. ADCs were prepared by Diels-Alder or Michael addition of maleimido-MMAE.

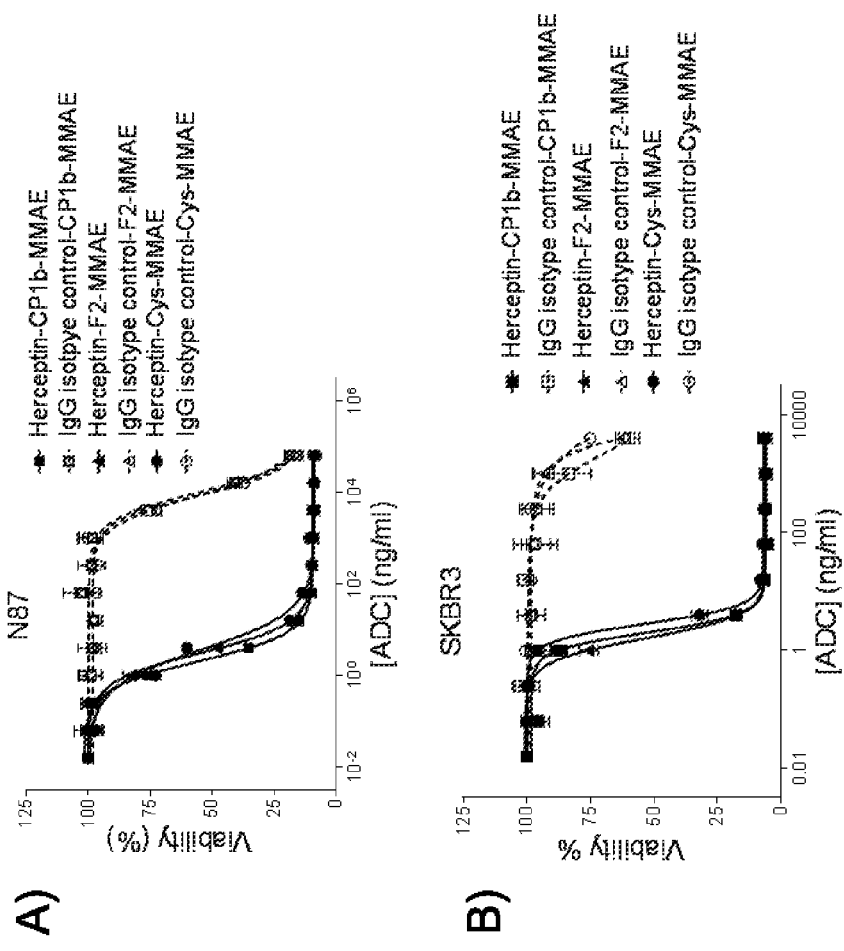
Figure 14.7. In vitro activity of ADCs.

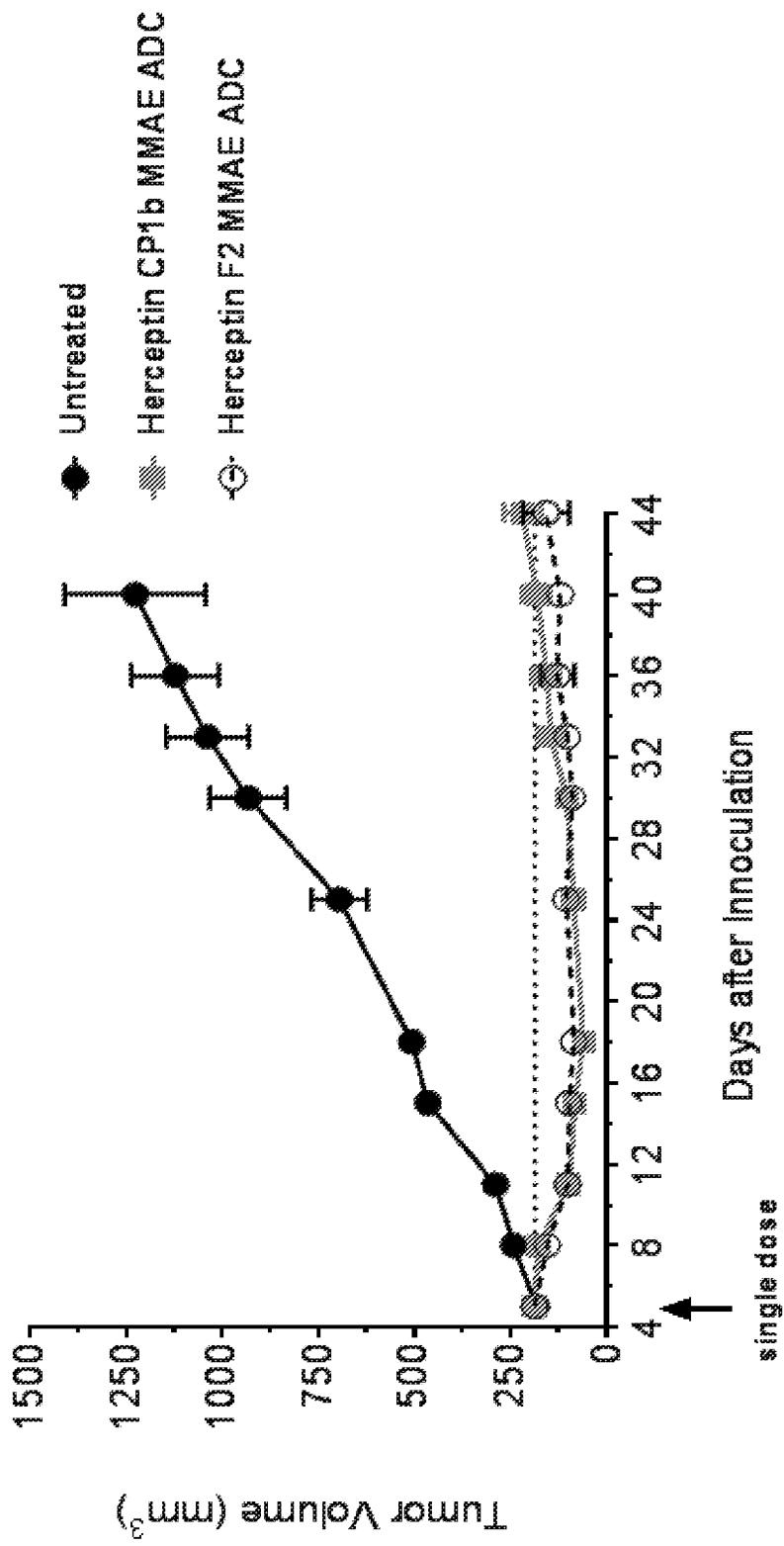
Figure 14.8. Tumor growth inhibition activity of Herceptin-linker MMAE ADCs towards subcutaneous N87 tumor models in mice.

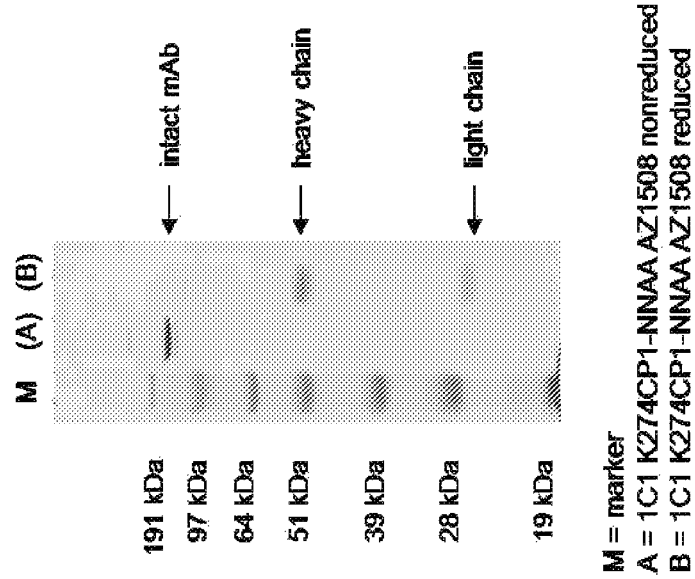
Figure 15.1. SDS-PAGE analysis of 1C1 K274CP1-NNAA mAb. A) Unreacted mAb. B) ADC prepared with AZ1508.

Figure 15.2. Reduced glycosylated mass spectrometry analysis of 1C1 K274CP1-NNAA mAb AZ1508 conjugation product. A) Unreacted mAb. B) AZ1508 reaction product. Spectra are zoomed to show both antibody heavy chain (HC) and light (LC) chain.
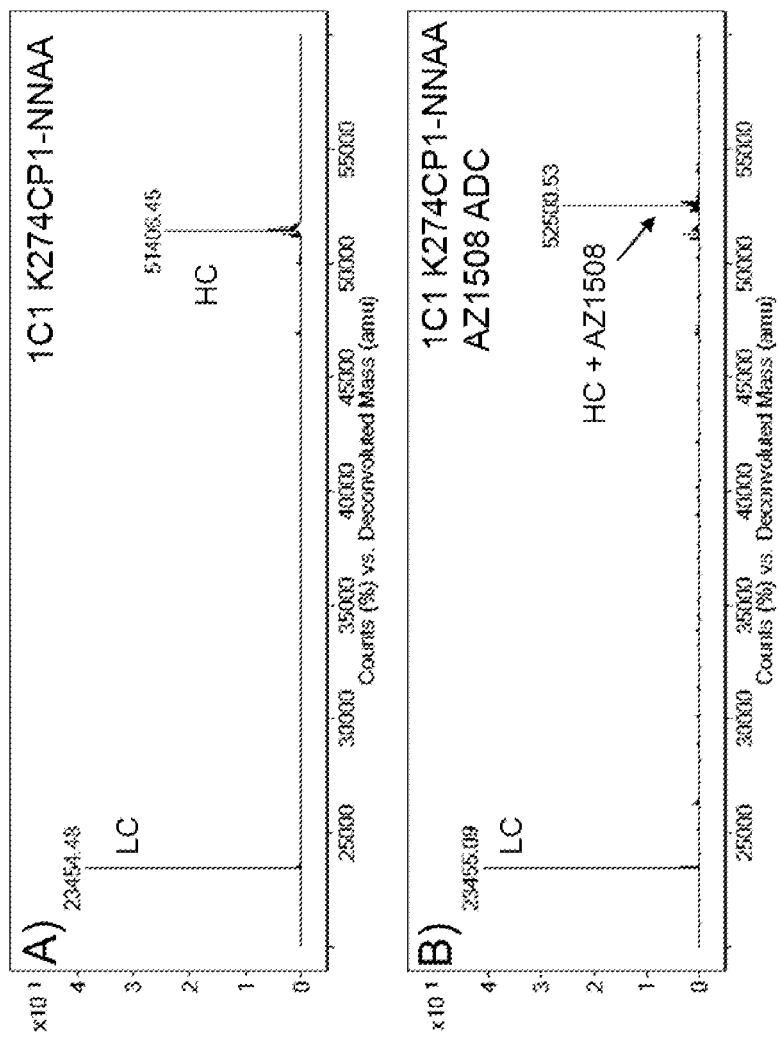

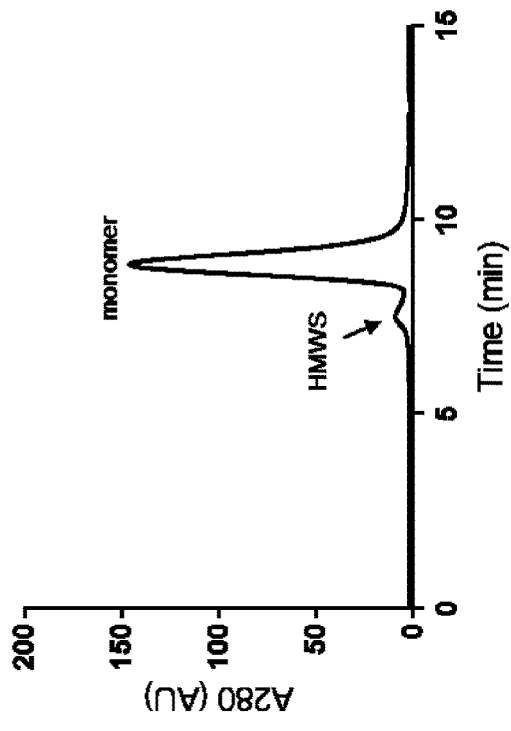
Figure 15.3. SEC analysis of 1C1 K274CP1-NNAA AZ1508 ADC indicating that high monomeric product was obtained. High molecular weight solids (HMWS) are indicated.

Figure 16.1. SDS-PAGE analysis of 1C1 CP2-NNAA AZ1508 ADCs and 1C1 cysteine AZ1508 ADCs. A) Non-reduced samples, B) reduced samples.
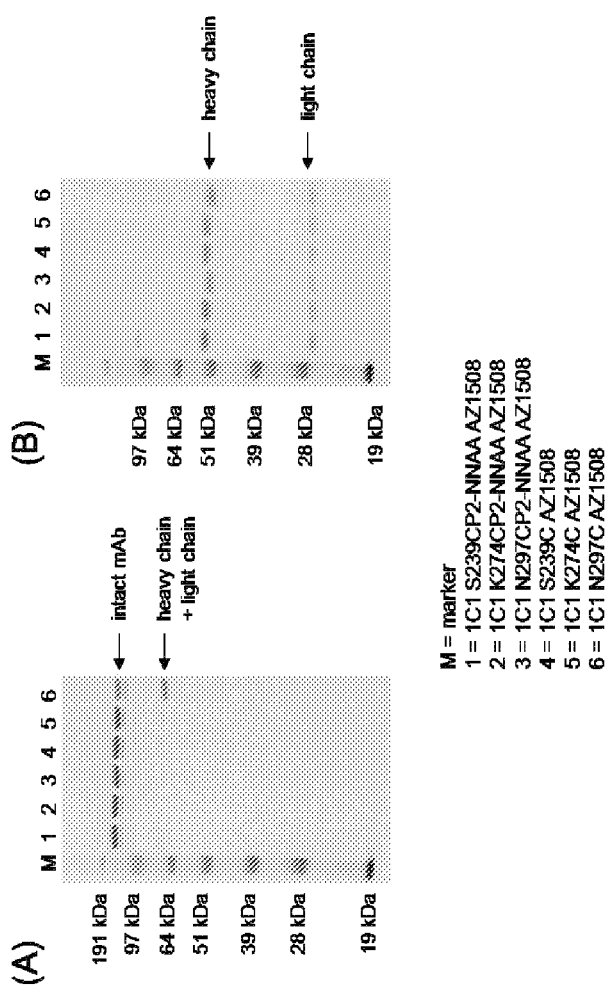

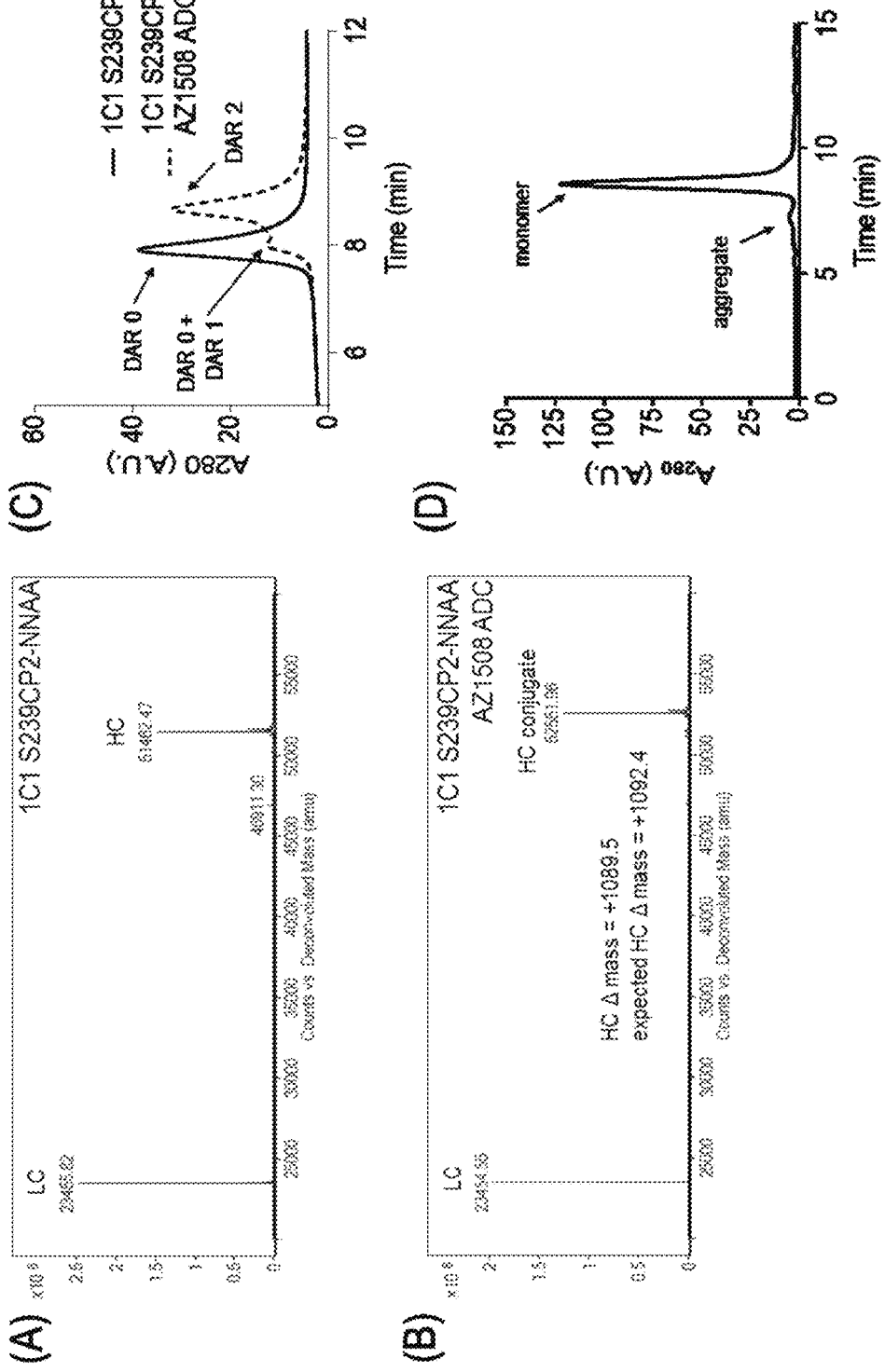
Figure 16.2. Analysis of 1C1 S239CP2-NNAA AZ1508 ADC. A) Reduced glycosylated mass spectrometry analysis of unreacted mAb. B) Reduced glycosylated mass spectrometry analysis of AZ1508 conjugation product. C) HIC analysis of unreacted antibody and AZ1508 reaction product. D) SEC analysis of AZ1508 reaction product. Spectra are zoomed to show both antibody heavy (HC) and light (LC) chains in (A) and (B).

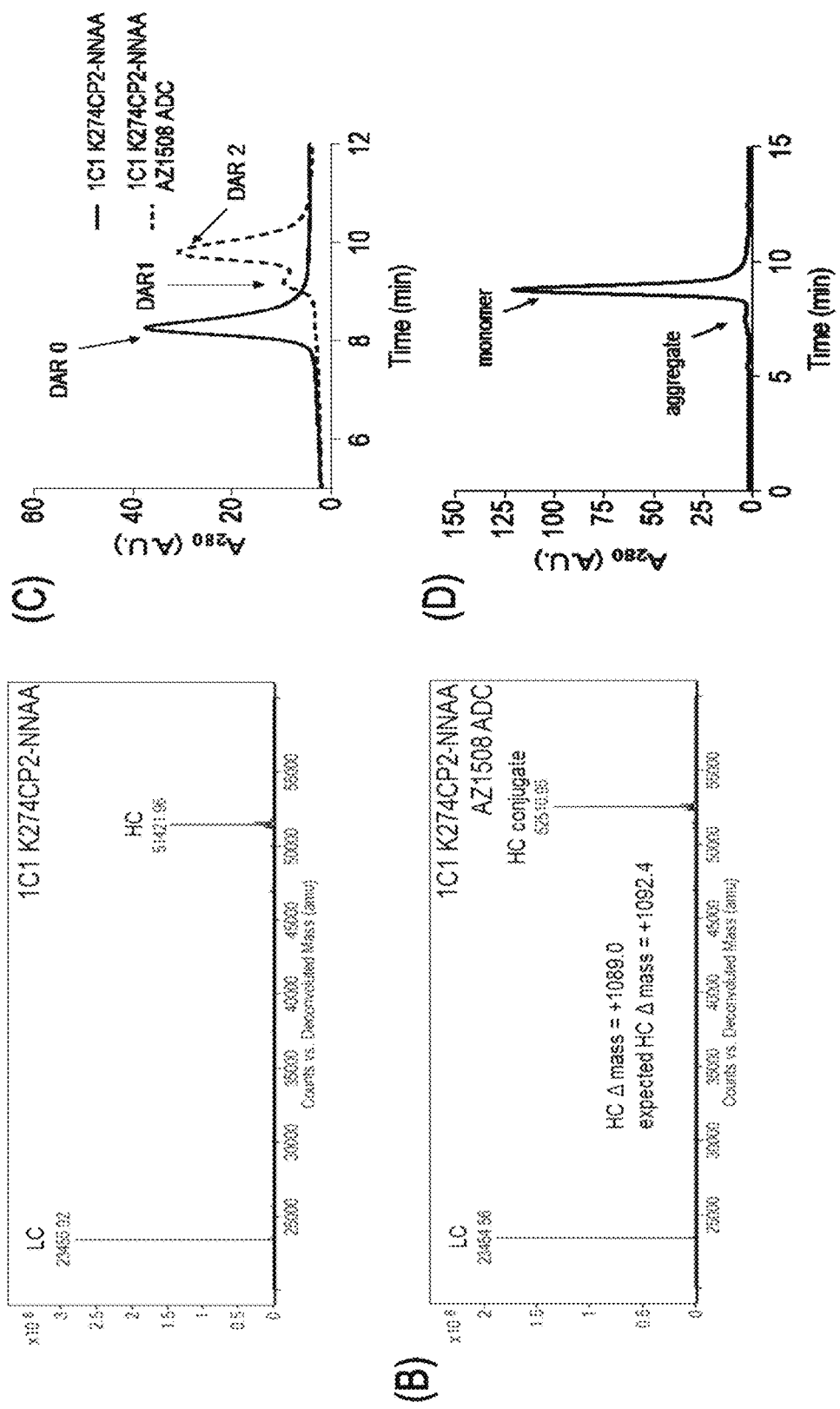
Figure 16.3. Analysis of 1C1 K274CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product. D) SEC analysis of AZ1508 reaction product. Spectra are zoomed to show both antibody heavy (HC) and light (LC) chains in (A) and (B).

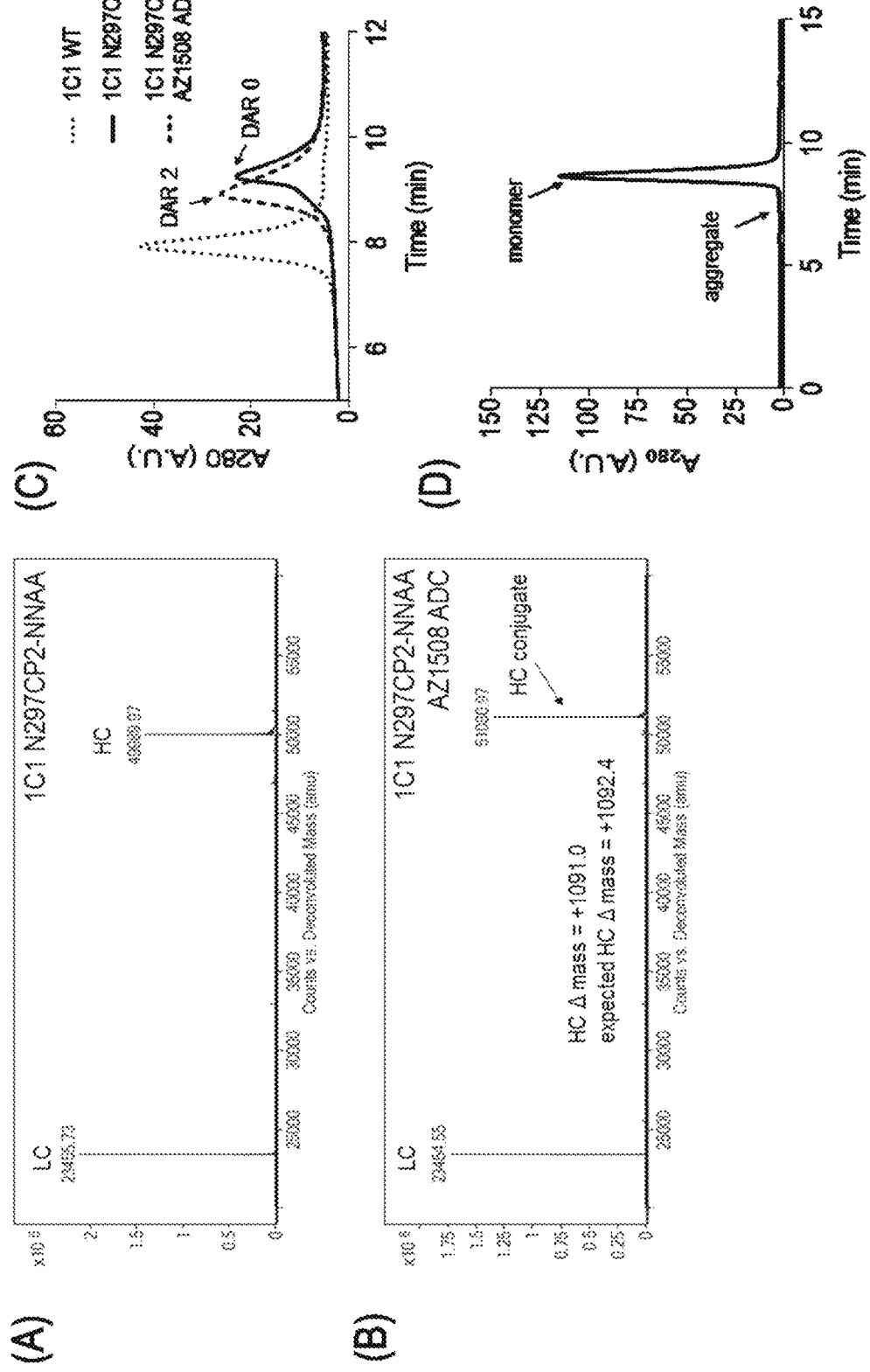
Figure 16.4. Analysis of 1C1 N297CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

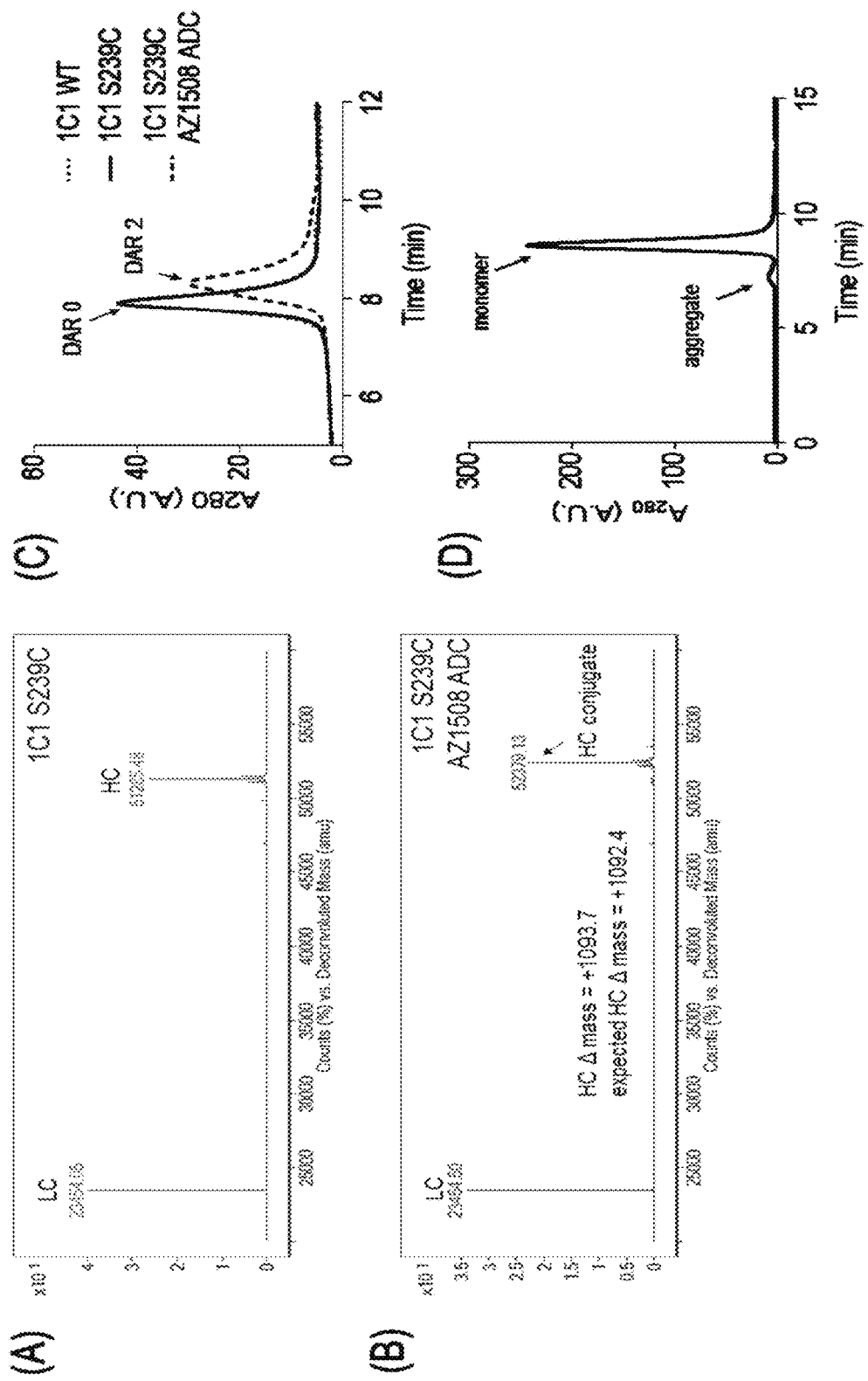
Figure 16.5. Analysis of 1C1 S239C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

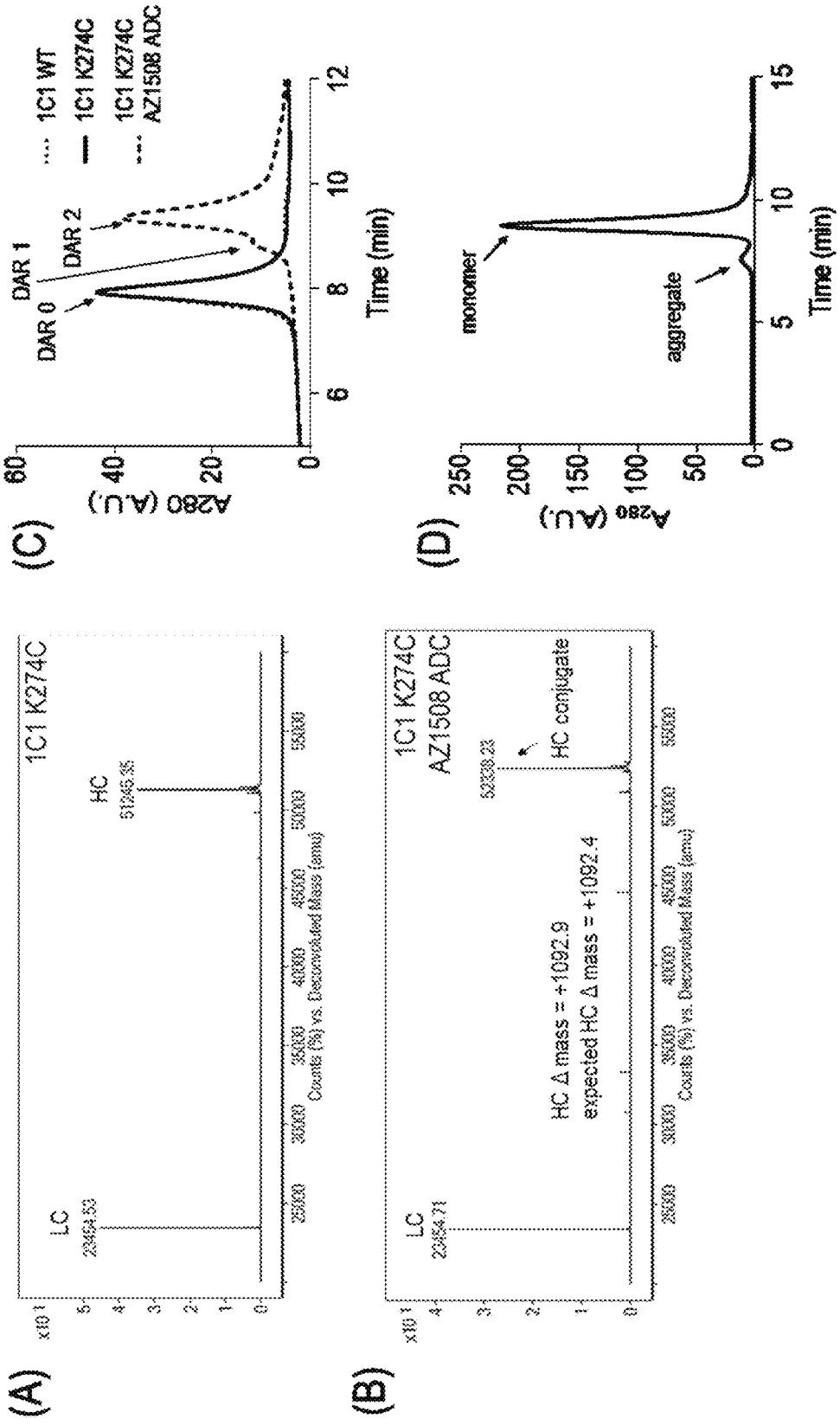
Figure 16.6. Analysis of 1C1 K274C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

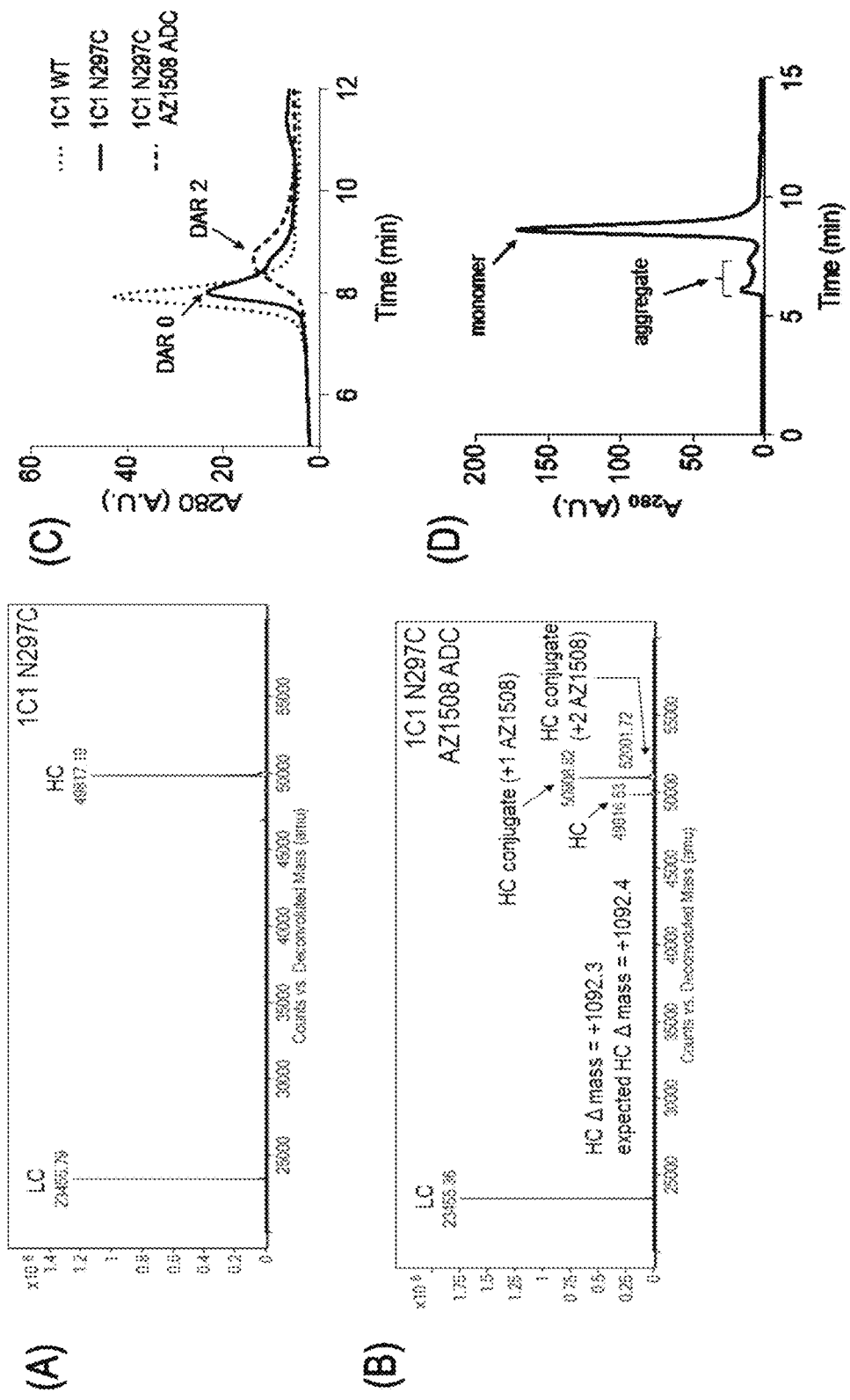
Figure 16.7. Analysis of 1C1 N297C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

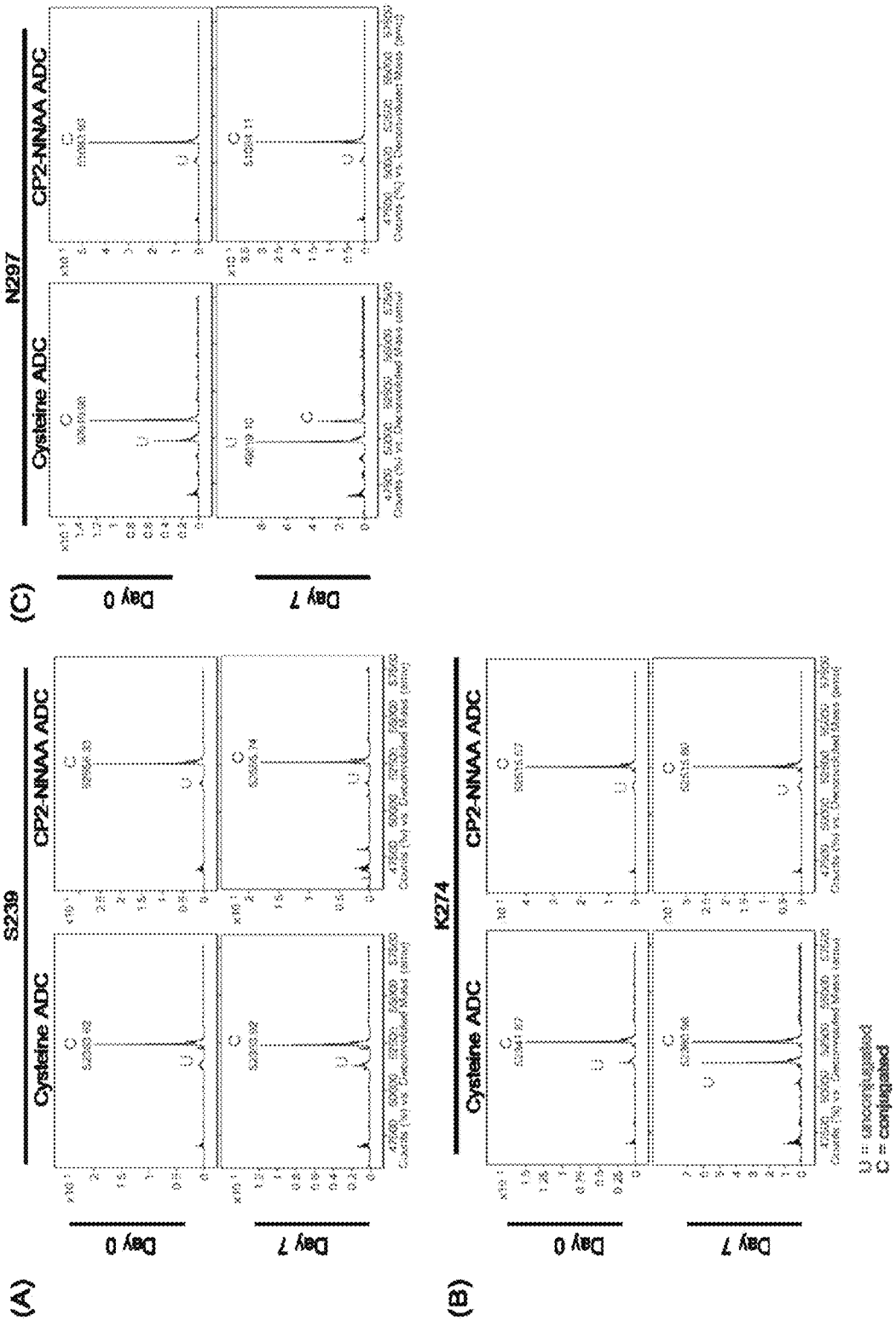
Figure 17.1. Representative reduced, glycosylated mass spectra of 1C1 CP2-NNAA- and 1C1 cysteine-AZ1508 ADCs before and after incubation in rat serum. Natural amino acids were mutated to CP2-NNAA or cysteine as indicated at (A) Position S239, (B) Position K274, (C) Position N297. Unconjugated and conjugated species are indicated.

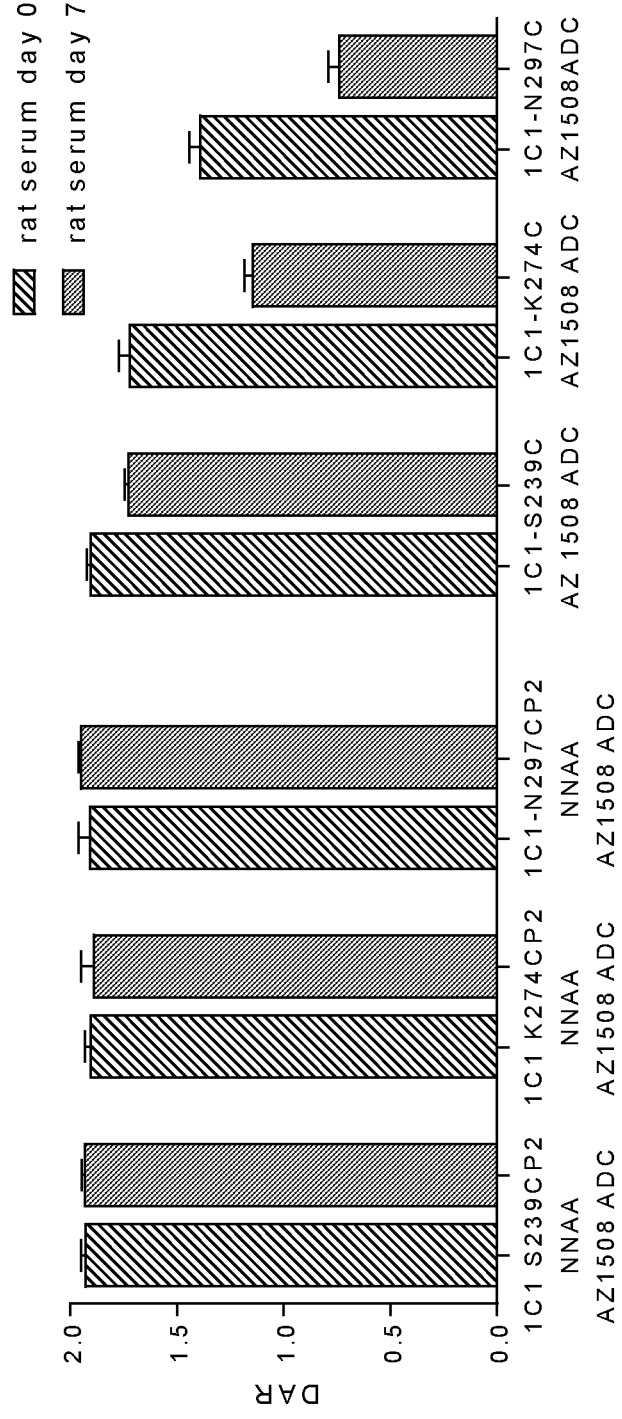
Figure 17.2. Quantification of AZ1508 remaining attached to CP2-NNAA or cysteine-engineered antibodies after incubation in rat serum for 7 d at 37 °C.

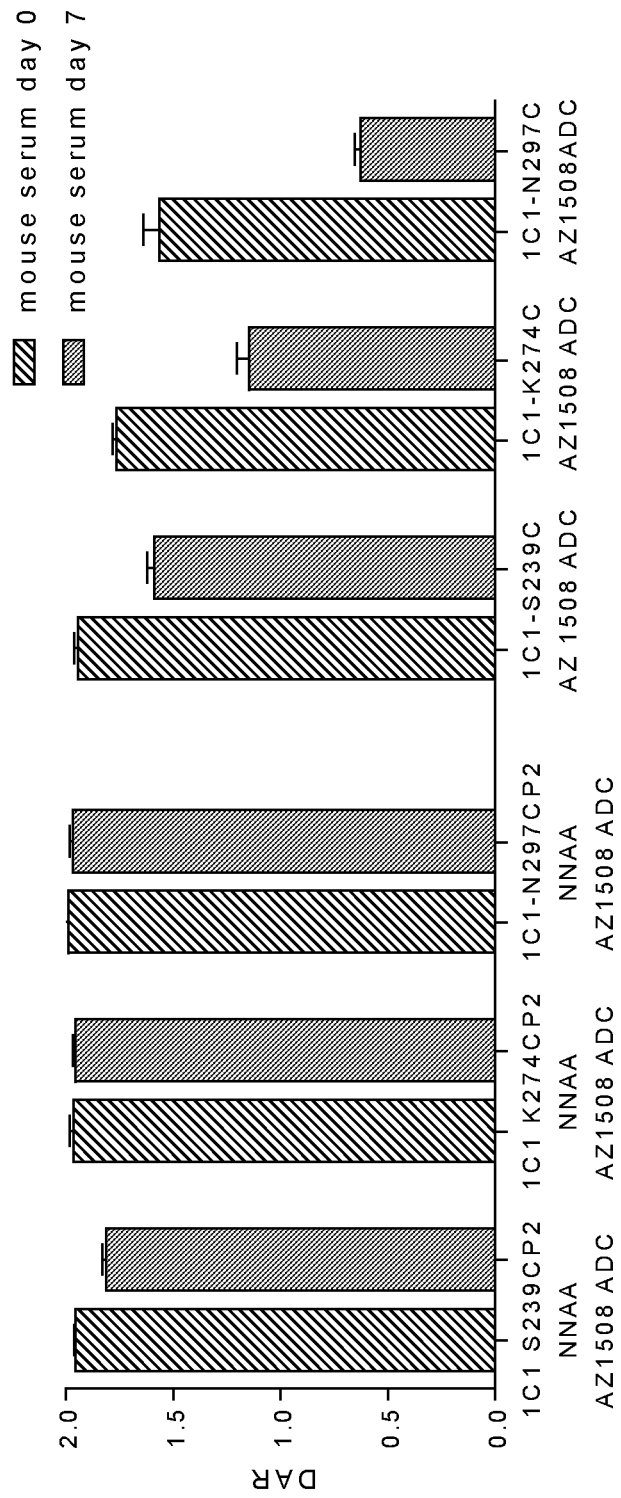
Figure 17.3. Quantification of AZ1508 remaining attached to CP2-NNAA or cysteine engineered antibodies after incubation in mou

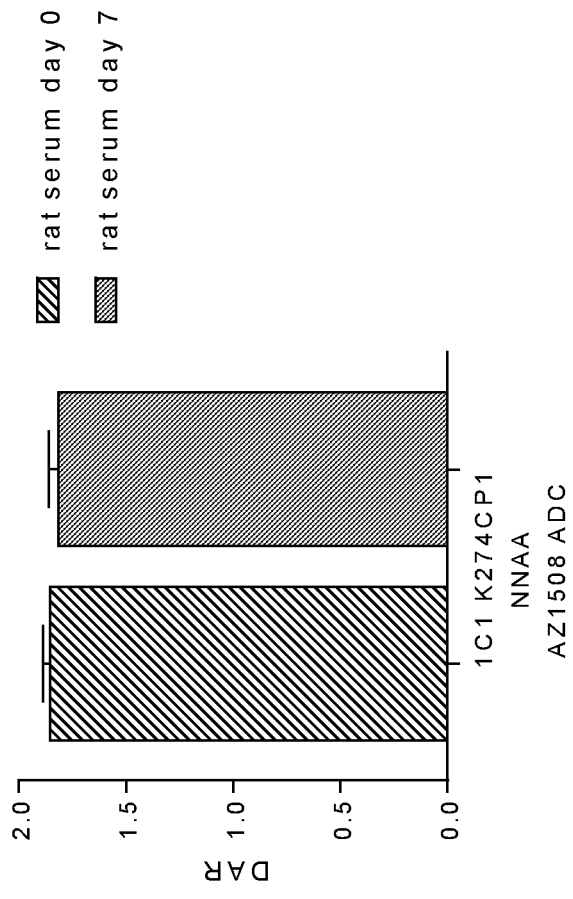
Figure 17.4. Quantification of AZ1508 remaining attached to CP1-NNAA antibodies after incubation in rat serum for 7 d at

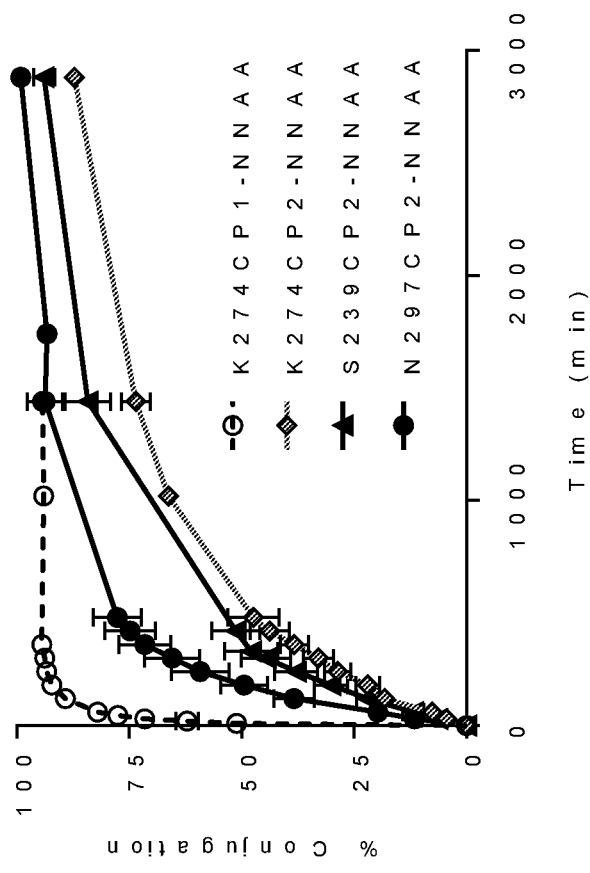
Figure 18.1. Conjugation kinetics of 1C1 CP1-NNAA and 1C1 CP2-NNAA mAbs with AZ1508 meas

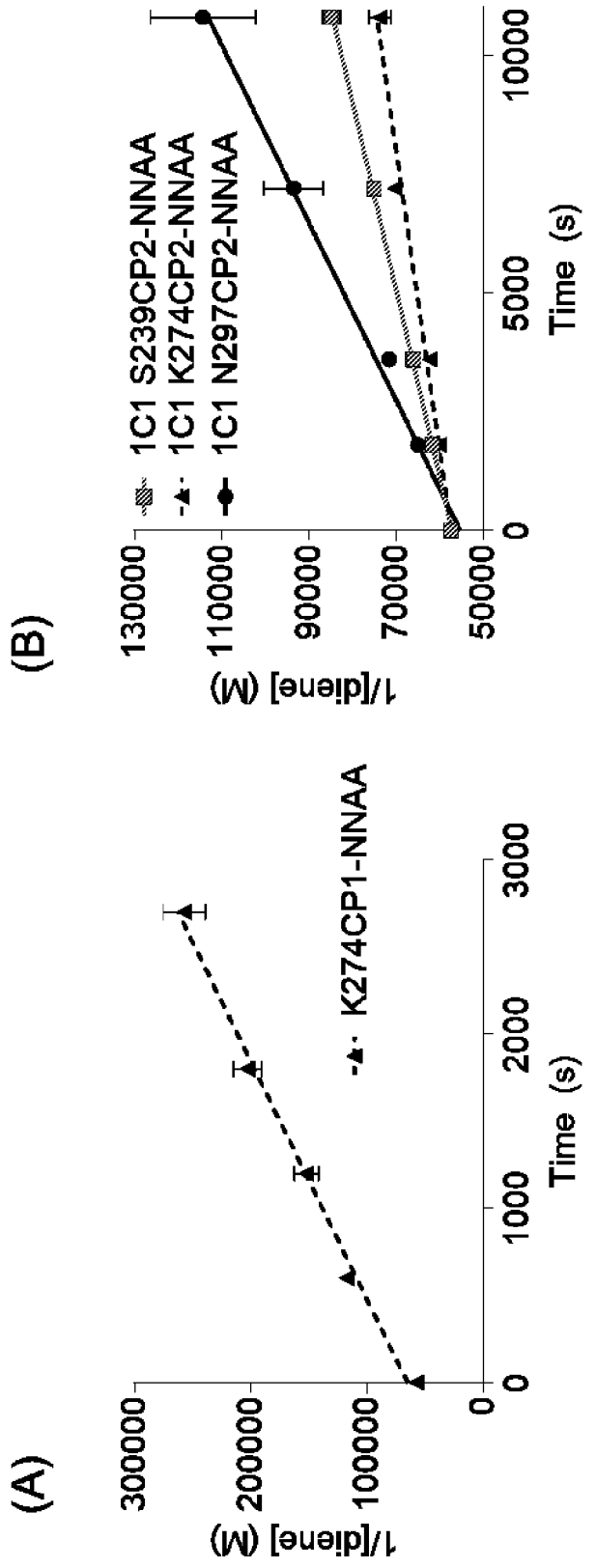
Figure 18.2. Inverse concentration plot showing consumption of diene upon reaction of CP1-NNAA and CP2-NNAA mAbs with AZ1508. (A) 1C1 K274CP1-NNAA, (B) 1C1 S239CP2, 1C1 K274CP2-NNAA, and N297CP2-NNAA mAbs. Data

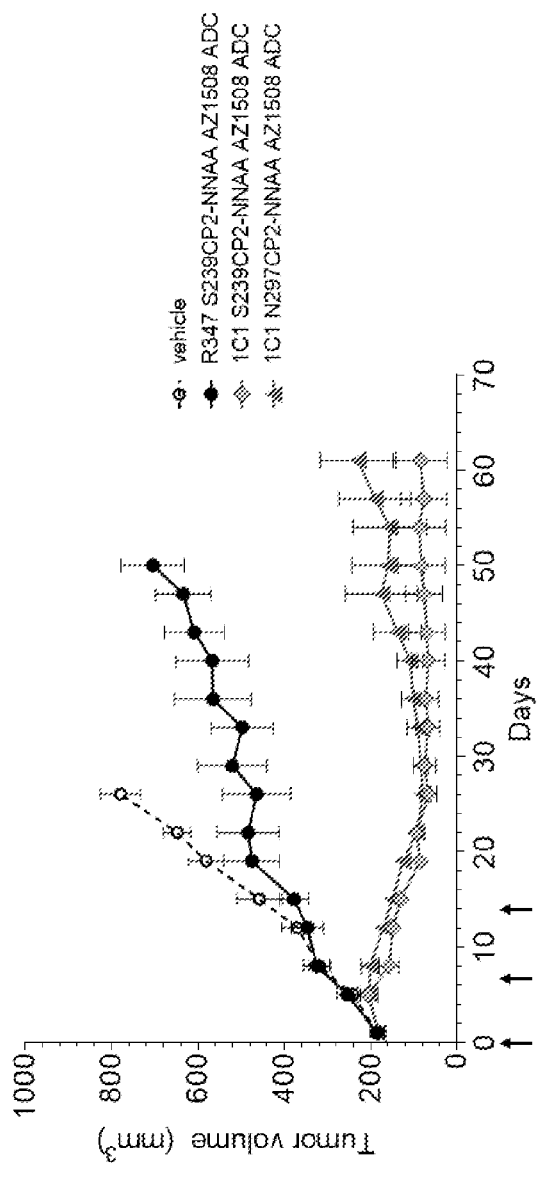
Figure 19.1. Tumor growth inhibition of PC3 xenografts in mice following administration of CP2-NNAA AZ1508 ADCs. On-target 1C1 mAb ADCs were prepared with CP2-NNAA incorporated at position S239 or N297 whereas non-targeting isotype control R347 mAb ADC was prepared with CP2 incorporated at position S239. ADCs were dosed intravenously at 3 mg/kg on days 0, 7 and 14 (indicated with arrows).

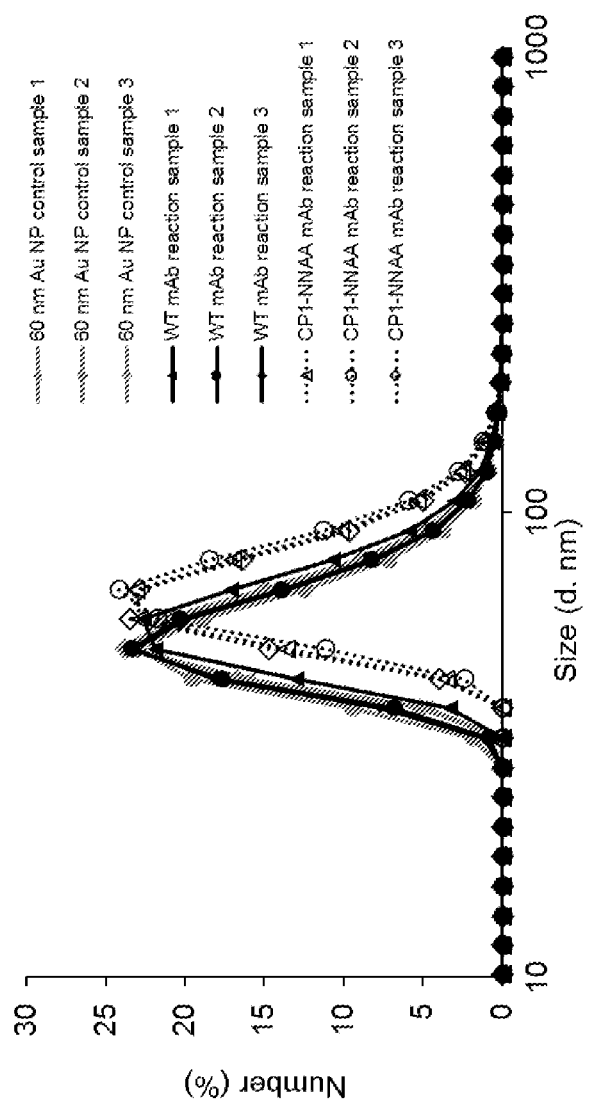
Figure 20.1. Dynamic light scattering analysis (DLS) of 60 nm maleimide-functionalized gold nanoparticles before and after incubation with 1C1 wild-type (WT) or 1C1 K274CP1-NNAA antibodies (CP1-NNAA mAb) for 2 h at 25 °C.

METHOD AND MOLECULES

The present disclosure relates to a method of conjugating a biological molecule to a payload, a molecule made by said method, compositions comprising the same, certain novel amino acid structures particularly suitable for use in the method and use of the biological molecules and compositions in treatment, in particular the treatment of inflammatory responses, including cancer.

CROSS-REFERENCE TO RELATED APPLICATIONS

This application is a U.S. National Stage application of International Application No. PCT/US2018/034535, filed on May 25, 2018, said International Application No. PCT/US2018/034535 claims benefit under 35 U.S.C. § 119(e) of the U.S. Provisional Application No. 62/511,415, filed May 26, 2017. Each of the above listed applications is incorporated by reference herein in its entirety for all purposes.

BACKGROUND

There are a number of registered pharmaceutical products which comprise a protein/polypeptide component linked to a polymer or toxin. Often the polymer is polyethylene glycol and it is conjugated to the polypeptide by reacting a cysteine or lysine amino acid residue (in particular the side chain of a lysine residue) with a maleimide group or NHS-ester group, respectively. Other therapeutic compounds such as antibody-drug conjugates (ADCs) are prepared in a similar fashion, where the toxin/drug bears a reactive maleimide or other appropriate functional groups for attachment to an antibody, Examples of such reactions are shown generically below:

Employing a native amino acid residue in the polypeptide can result in conjugation product that contains a mixture of species. Furthermore, if the target amino acid residue for the conjugation reaction is in a protein fold or is, for example solvent inaccessible, harsh conditions may be required to drive the conjugation reaction to completion. However, it is generally desirable to employ mild conditions in the presence of a biological molecule because the activity of the molecule can be damaged by harsh conditions.

The basic conjugation reactions for coupling to native residues in biological molecules have changed very little in the last five to ten years, with examples of such reactions shown below. However, these reactions are becoming more and more important as second generation biological products, such as antibody drug conjugates, are likely to make a significant contribution to the treatment of diseases, such as cancer. Chemistry, such as so-called Click-Chemistry may be used in bioconjugation to non-native functional groups employing, for example azide-alkyne cycloaddition reactions, strained azide-alkyne cycloadditions, alkyne-nitrone additions, reactions of an alkene and azide [3 plus 2 cycloaddition], alkene and tetrazine inverse-demand Diels-Alder reactions, or alkene and tetrazole [Husigen] reactions.

The non-natural functional groups required for these reactions can be installed onto proteins by chemical modification of native lysines, cysteines, or tyrosines, or, by expressing proteins that incorporated non-natural amino acids into the protein structure. Examples of such chemistries are shown below:

Conjugation to Natural Protein Functional Groups

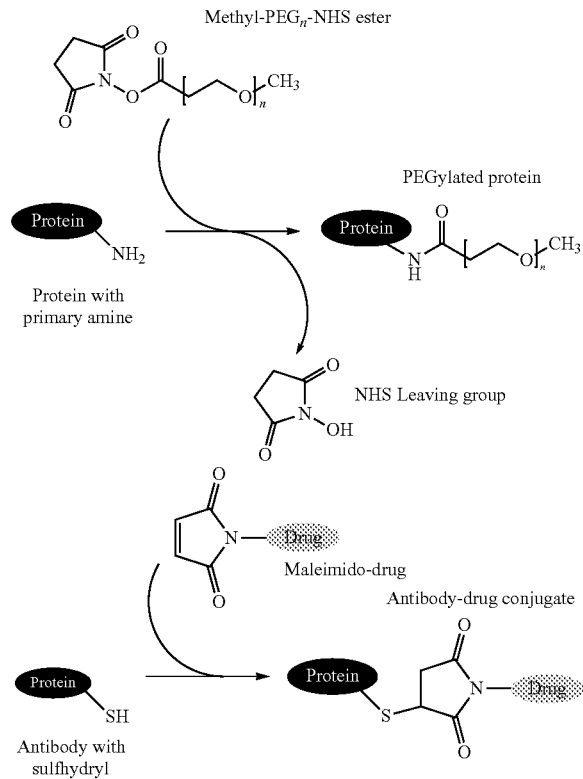

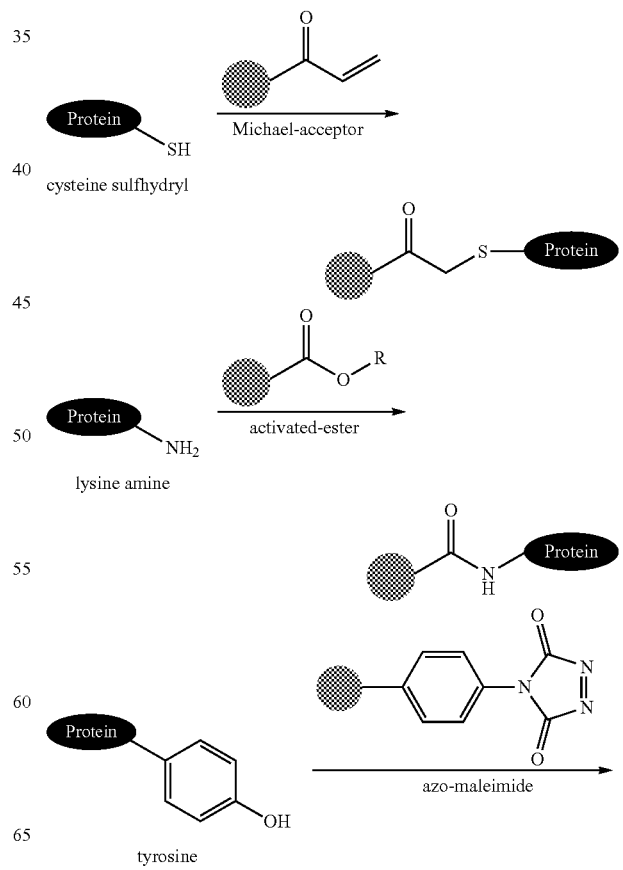

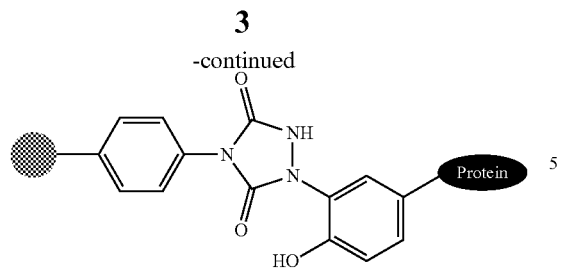
Conjugation to Unnatural Protein Functional Groups
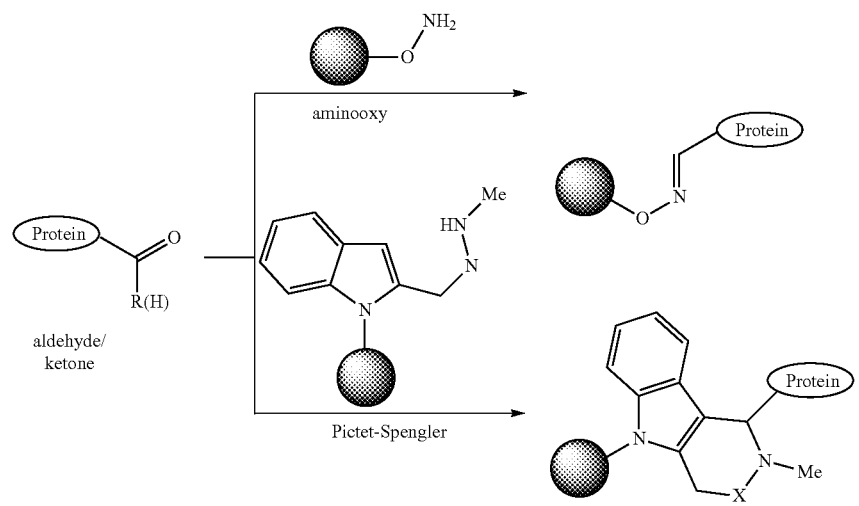
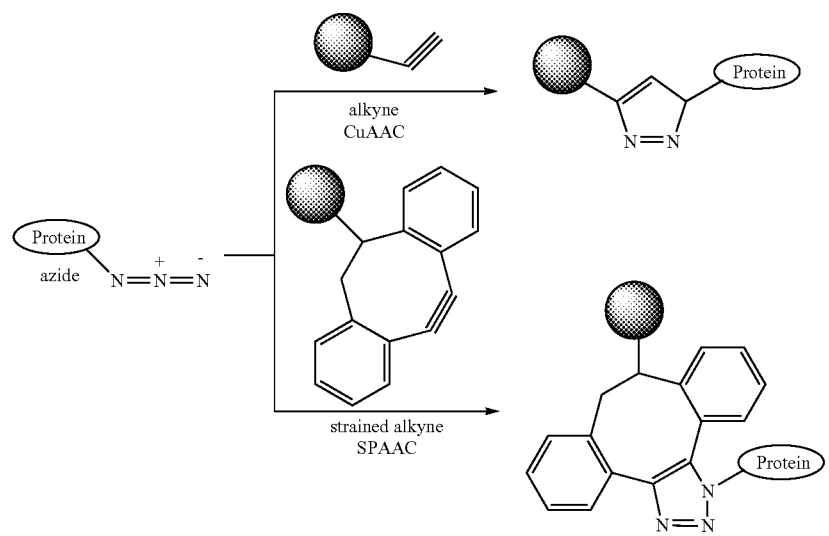
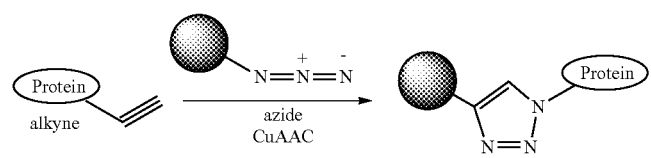

-continued

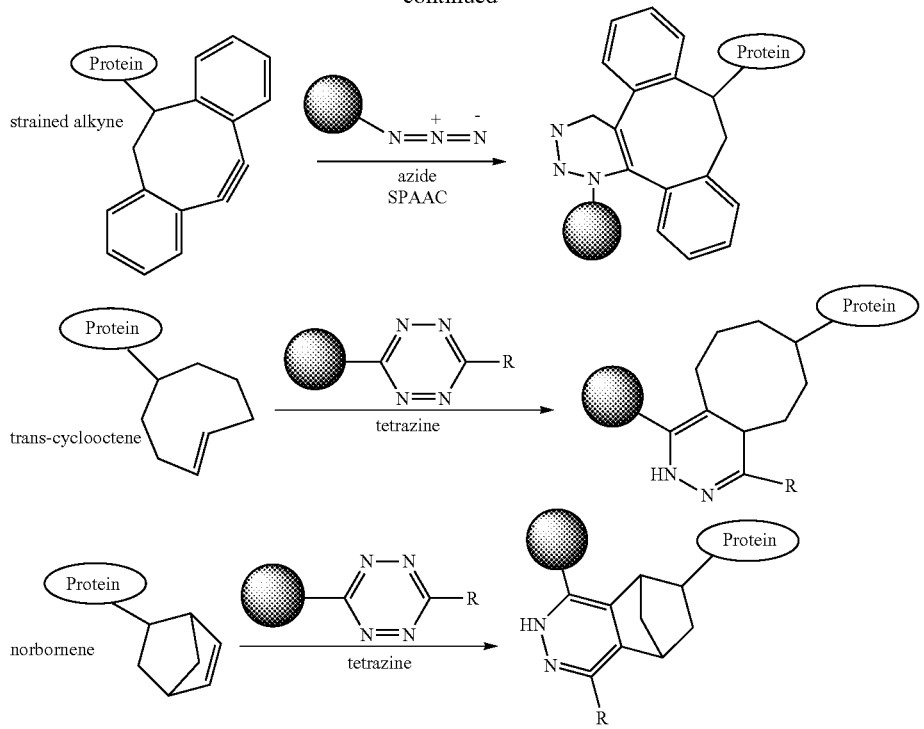

While many of the conjugation chemistries shown above have expanded the possibilities available for preparing bioconjugates, their applications to prepare therapeutic molecules may be limited due to; long reaction times, need for catalysts that could oxidize protein functional groups, hydrophobic reaction partners that affect protein properties such as tendency to aggregate, potential safety concerns with explosive intermediates (i.e. azide compounds), to name a few issues.

Furthermore, employing chemistries shown above to produce ADCs via coupling to unnatural protein functional groups requires development of a toxin/drug that contains the appropriate complimentary reactive group, which could complicate drug development as some reactive groups may not be compatible with certain payloads, and/or may impact payload properties such as hydrophobicity and solubility. Currently, many ADC payloads have been developed to include maleimide groups for conjugating to cysteine thiols. It would be useful to have an alternative method of conjugating a biological molecule to another entity, such as a polymer or payload, for example that utilizes a functional group that is currently available (such as maleimide) and known to be compatible with a large range of desired payloads. In addition, it would be useful to have a conjugation reaction that had one or more of the following properties, specific, fast, employs mild or moderate conditions, and able to react with amino acid residues that are not solvent exposed.

SUMMARY OF THE DISCLOSURE

Thus, in one aspect there is provided a bioconjugation method comprising the step of conjugating a biological molecule containing a first unsaturated functional group with a payload comprising a second unsaturated functional group, wherein the first and second unsaturated functional groups are complementary to each other such that conjugation is a reaction of said functional groups via a Diels-Alder reaction which forms a cyclohexene ring.

The Diels-Alder reaction as employed herein refers to a 4 plus 2 cycloaddition reaction which forms a cyclohexene ring, which may be part of a fused ring system. A generic example the reaction is shown below:

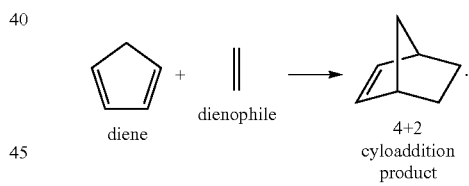

Surprisingly the present inventors have established that this reaction can be employed under mild conditions in specific conjugation reactions comprising a biological molecule. In some instances, the reactions take a little as two hours at room temperature. In other instances, the bioconjugation reaction can occur in one-step, without need for additional reagents other than payload, protein, and solvent.

Furthermore, reactive crosslinkers and non-natural amino acids comprising diene functionality desired for efficient Diels-Alder transformations are synthetically accessible and can be produced in high yields in simple and straightforward routes.

The diene or the dienophile may be incorporated into the biological molecule via the addition of a linker or by incorporating a non-natural amino acid into the polypeptide sequence. The requisite complementary functional group can then be incorporated into the payload.

The following is a schematic representation of conjugation of a payload to a non-natural amino acid comprising a diene in an amino acid:

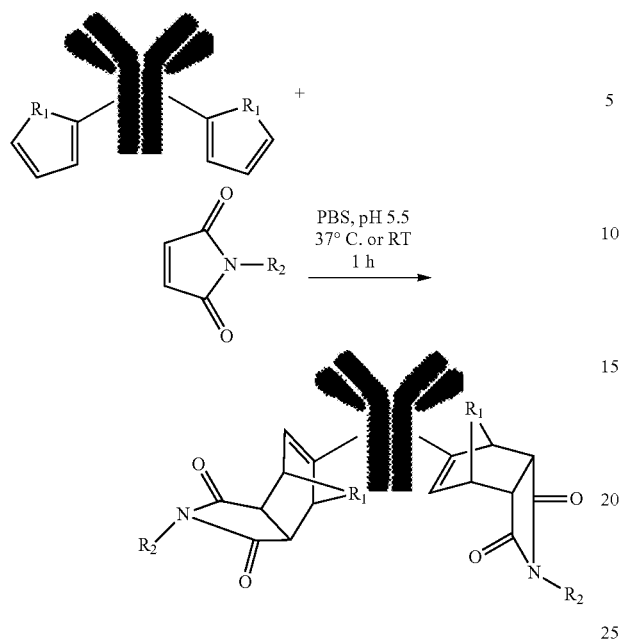

Advantageously, the product of the conjugation reaction is stable in biological milieu at body temperatures. However, if desired the reaction can be reversed by exposing the conjugation product to elevated temperatures, for example 60° C. or higher.

In one embodiment the first functional group (i.e. within the biological molecule) is a diene.

In one embodiment the second functional groups (i.e. in the payload) is a dienophile, for example selected from a maleimide, esters of maleic acid, esters of fumaric acid, esters of acrylic acid, methacrylic acid, acrylonitrile, acrylamide, methacrylamide, methyl vinyl ketone, vinyl pyridine, amides and esters of but-2-ynedioic acid, quinone, acetylenes.

In one embodiment the second functional group is a diene.

In one embodiment the first functional group (i.e. in the biological molecules) is a dienophile, for example esters of maleic acid, maleimide, esters of fumaric acid, esters of acrylic acid, methacrylic acid, acrylonitrile, acrylamide, methacrylamide, methyl vinyl ketone, vinyl pyridine, amides and esters of but-2-ynedioic acid, quinone, acetylenes.

In one embodiment the first functional group is a dienophile in a non-natural amino acid, for example a non-natural amino acid comprising norbornene.

In one embodiment the diene is a linear diene, carbocyclic diene, or heterocyclic diene, for example the diene comprises a butadiene, a cyclopentadiene, a 1,3-cyclohexadiene, furan or anthracene.

In one embodiment the diene is contained in a non-natural amino acid, for example a non-natural amino acid derived from lysine, cysteine, selenocysteine, aspartic acid, glutamic acid, serine, threonine, glycine, and tyrosine.

In one embodiment the diene is in a side chain of the amino acid.

In one embodiment the non-natural amino has a formula (I):

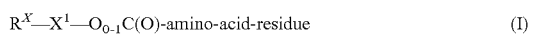

wherein:
$R^X$ represents an unsaturated group selected from a:
i) $C_{4-9}$ linear conjugated diene,
ii) $C_{5-14}$ carbocyclyl comprising a conjugated diene, and
iii) a 5 to 14 membered heterocyclyl comprising 1, 2 or 3 heteroatoms selected O, N and S, and a conjugated diene,
wherein i), ii) and iii) may bear up to five substituents, (such as one, two or three substituents) for example, the substituents are independently selected from $C_{1-3}$ alkyl, oxo, halogen, sulfo, sulfhydryl, amino, —$C_{1-3}$alkyleneN$_3$, or —$C_{2-5}$alkynyl; and
$X^1$ represents
i) a saturated or unsaturated branched or unbranched $C_{1-8}$ alkylene chain, wherein at least one carbon (for example 1, 2 or 3 carbons) is replaced by a heteroatom selected from O, N, $S(O)_{0-3}$, wherein said chain is optionally, substituted by one or more groups independently selected from oxo, halogen, amino, —$C_{1-3}$alkyleneN$_3$, or —$C_{2-5}$alkynyl; or
ii) together with a carbon from the carbocylcyl or heterocyclyl represents a cyclopropane ring linked to a saturated or unsaturated (in particular saturated) branched or unbranched $C_{1-6}$ alkylene chain, wherein at least one carbon (for example 1, 2 or 3 carbons) is replaced by a heteroatom selected from O, N, $S(O)_{0-3}$, wherein said chain is optionally, substituted by one or more groups independently selected from oxo, halogen, amino, —$C_{1-3}$alkyleneN$_3$, or —$C_{2-5}$alkynyl and
—$O_{0-1}C(O)$— is linked through a side chain of an amino acid.

In one embodiment the non-natural amino acid is a residue of the structure of formula (II):

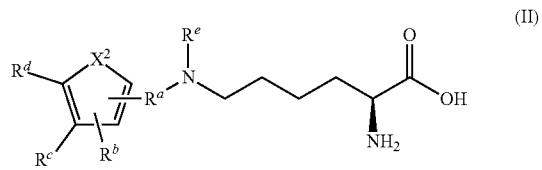

wherein
$X^2$ represents —C—, —C(R')—, —CH$_2$ or O;
R' represents H or $C_{1-3}$ alkyl,
$R^a$ represents
i) a saturated or unsaturated branched or unbranched $C_{1-8}$ alkylene chain, wherein at least one carbon (for example 1, 2 or 3 carbons) is replaced by a heteroatom selected from O, N, $S(O)_{0-3}$, wherein said chain is optionally, substituted by one or more groups independently selected from oxo, halogen, amino; or
ii) together with a carbon from the 5 membered ring represents a cyclopropane ring linked to a saturated or unsaturated (in particular saturated) branched or unbranched $C_{1-6}$ alkylene chain, wherein at least one carbon (for example 1, 2 or 3 carbons) is replaced by a heteroatom selected from O, N, $S(O)_{0-3}$, wherein said chain is optionally, substituted by one or more groups independently selected from oxo, halogen, amino;
$R^b$ represents H, —OC$_{1-3}$ alkyl, $C_{1-6}$alkyl optionally bearing a hydroxyl substituent, —$C_{1-3}$alkyleneN$_3$, or —$C_{2-5}$ alkynyl;
$R^c$ represents H, —OC$_{1-3}$ alkyl, $C_{1-6}$alkyl optionally bearing a hydroxyl substituent, —$C_{1-3}$ alkyleneN$_3$, or —$C_{2-5}$ alkynyl;

$R^d$ represents H, —$OC_{1-3}$alkyl, $C_{1-6}$alkyl optionally bearing a hydroxyl substituent, —$C_{1-3}$ alkyleneN$_3$, or —$C_{2-5}$ alkynyl;

$R^e$ represents H, saturated or unsaturated (in particular saturated) branched or unbranched $C_{1-8}$ alkylene chain, wherein one or more carbons are optionally replaced by —O— and the chain is optionally substituted by one or more halogen atoms (such as iodo), N$_3$ or —$C_{2-5}$alkynyl.

In one embodiment $R^a$ is —(CH$_2$)mC(O)—, —CH$_2$(CH$_3$)C(O)—, —(CH$_2$)mCH$_2$OC(O)—, —CHCHCH$_2$OC(O)—, or —OCH$_2$CH$_2$COC(O)— and m represents 0 or 1.

In one embodiment $R^b$ is H, —$OC_{1-3}$alkyl, —CH$_3$, —CH(CH$_3$)$_2$, CH$_2$OH, —CH$_2$N$_3$, or —CCH.

In one embodiment $R^c$ is H, —$OC_{1-3}$alkyl, —CH$_3$, —CH(CH$_3$)$_2$, CH$_2$OH, —CH$_2$N$_3$, or —CCH.

In one embodiment $R^d$ is H, —$OC_{1-3}$alkyl, —CH$_3$, —CH(CH$_3$)$_2$, CH$_2$OH, —CH$_2$N$_3$, or —CCH.

In one embodiment $R^e$ represents H or —CH$_2$OCH$_2$CH$_2$N$_3$.

In one embodiment the non-natural amino is a residue of the structure of formula (IIa):

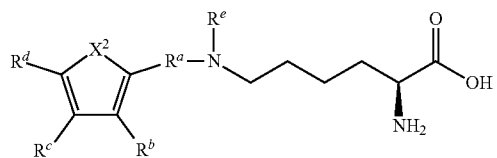

(IIa)

wherein $R^a$, $R^b$, $R^c$, $R^d$, $R^e$ and X are defined above.

In one embodiment the non-natural amino acid has the structure of formula (IIb):

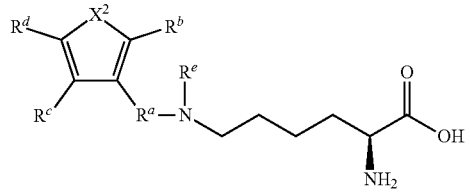

(IIb)

wherein $R^a$, $R^b$, $R^c$, $R^d$, $R^e$ and $X^2$ are defined above.

In one embodiment the non-natural amino acid has the structure of formula (IIc):

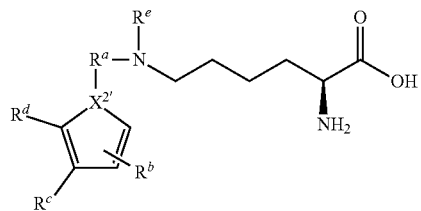

(IIc)

wherein $R^a$, $R^b$, $R^c$, $R^d$, $R^e$ are defined above and $X^2$, is —C— or —CR' as defined above.

Generally compounds, for example formula (I), (II), (IIa), (IIb) and (IIc) will at most contain only one azide group.

In one embodiment the non-natural amino acid is selected from the group comprising:

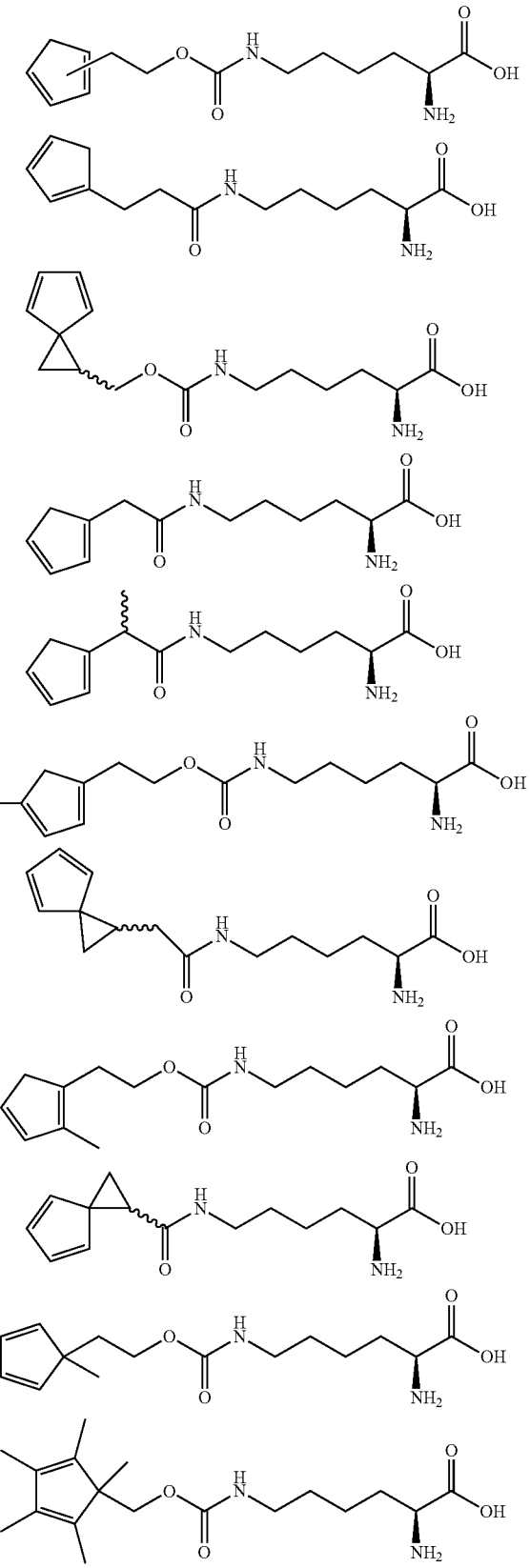

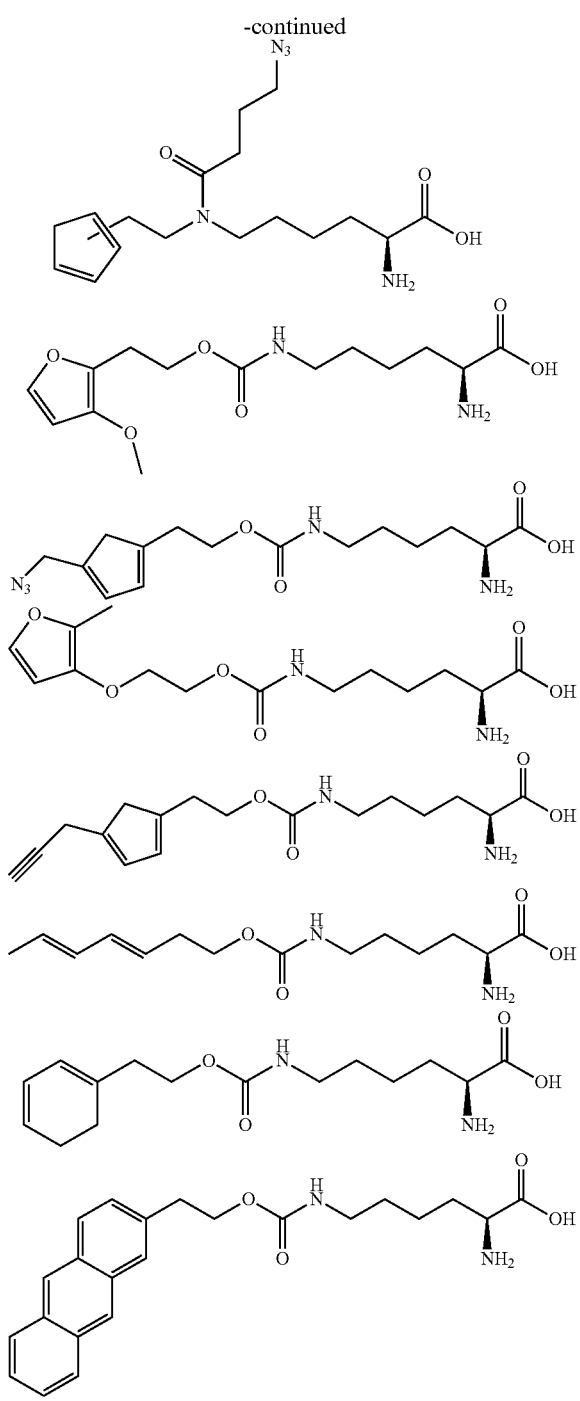

In one embodiment the method comprises a pre-step of conjugating the diene or dienophile (in particular the diene) via a linker to an amino acid residue in the biological molecule, for example where the amino acid is a cysteine or lysine.

In one embodiment the diene before addition to said amino acid residue in the biological molecule has the structure of formula (III):

wherein
n represents 0 or 1;
m represents 0 or 1;
p represents 0 or 1;

$R^X$ represents an unsaturated group selected from a:
i) $C_{4-9}$ linear conjugated-diene,
ii) $C_{5-14}$ carbocyclyl comprising a conjugated-diene, and
iii) a 5 to 14 membered heterocyclyl comprising 1, 2 or 3 heteroatoms selected O, N and S, and a conjugated diene,
wherein i), ii) and iii) may bear up to five substituents, (such as one, two or three substituents) for example where the substituents are independently selected from $C_{1-3}$ alkyl, oxo, halogen, sulfo, sulfhydryl, amino, —$C_{1-3}$alkyleneN$_3$, or —$C_{2-5}$alkynyl; and B represents $C_{1-6}$ alkylene, —$C_{3-4}$ cycloalkyl$C_{1-6}$ alkylene-; wherein a optionally a sugar residue (such as glucose, glucosamine, galactose, galactosamine, lactose, mannose, and fructose) is contained in the alkylene chain of any one of the same, and wherein the alkylene chain of any one of said variables defined for B bears optionally bears one or two substituents independently selected from an N- and O-linked sugar residue (such as glucose, glucosamine, galactose, galactosamine, lactose, mannose, and fructose):

$X^3$ represents —(R$^1$)NC(O)—, —C(O) N(R$^1$)—, —OC(O)—, —OC(O)N—;

$R^1$ represents H or —CH$_2$OCH$_2$CH$_2$R$^2$;

$R^2$ represents —N$_3$, $C_{2-5}$ alkynyl, or halogen, such as iodo;

Y represents —(OCH$_2$)qC$_{2-6}$alkylene, or —C$_{2-6}$ alkylene optionally substituted with —NR$^3$R$^4$,
wherein q is 1 to 7000;

$R^3$ and $R^4$ independently represents H or $C_{1-3}$ alkyl;

Z represents —C(O)OR$^5$, R$^{5'}$, —NC(O)R$^6$, —C$_{2-5}$ alkylene, CH$_2$—O—NH$_2$, alkyne, azide, 3-arylpropiolonitrile, or halogen such as iodo;

$R^5$ represents $C_{1-6}$ alkyl, succinimide, C$_6$F$_4$H (tetrafluorohexyl), or H:

$R^{5'}$ represents a sulfur bridging group, for example a dibromomaleimide, a dichloroacetone or a derivative of any one of the same, $R^6$ represents:

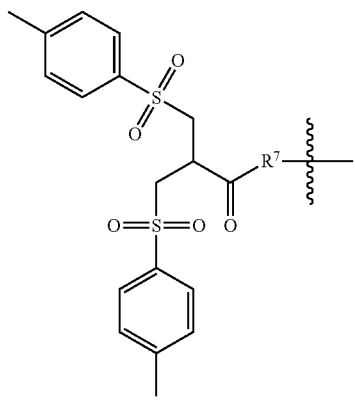

wherein
$R^7$ is $C_{1-6}$ alkylene optionally bearing one or more (such as one, two or three) groups selected from hydroxyl, sulfo, amino and —(OCH$_2$)$_r$C$_{2-6}$alkylene, and phenyl optionally bearing one or more (such as one, two or three) groups selected from hydroxyl, sulfo, amino and —(OCH$_2$)$_r$C$_{2-6}$alkylene, v is an integer 1, 2, 3, 4 or 5

〰 represents where the fragment is connected to the rest of the molecule.

In one embodiment the diene has a structure:

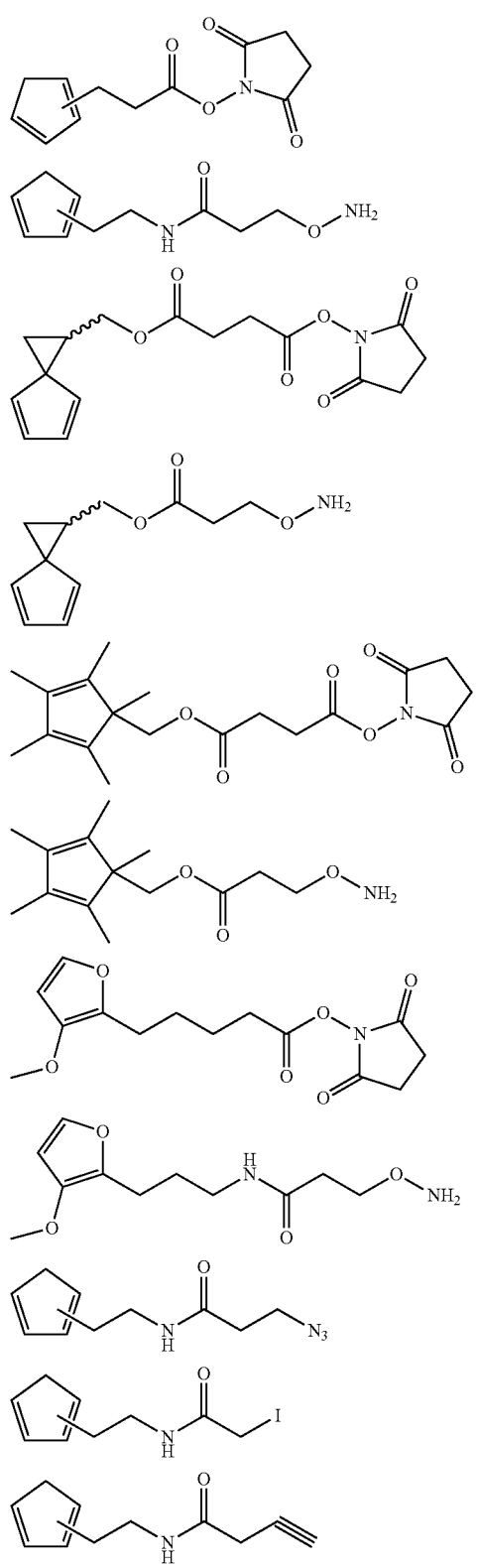

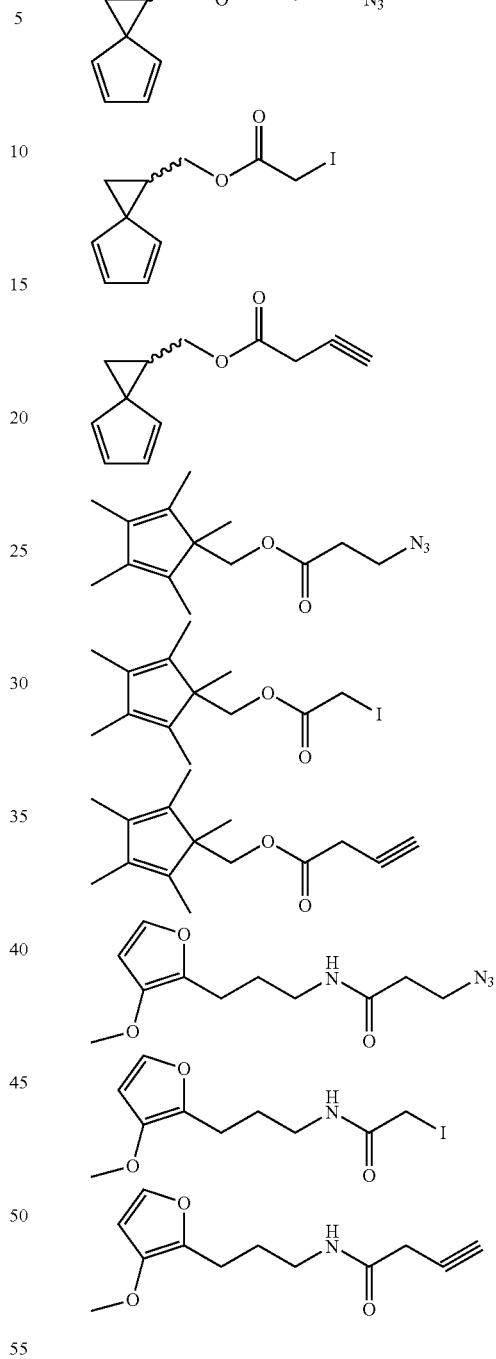

In one embodiment the reaction is performed at a temperature in the range 10 to 40° C., for example ambient temperature.

In one embodiment the reaction is performed in aqueous solvent, for example aqueous organic solvent systems, a buffer such as PBS optionally comprising a polar aprotic solvent, such as DMSO or a surfactant, such as polysorbate 80 or combinations thereof.

In one embodiment the therapeutic biological molecule is a polypeptide, for example selected from the group comprising a ligand, receptor, antibody molecule.

In one embodiment the biological molecule is engineered to add or remove one or more lysine residues from the original or native sequence.

In one embodiment the biological molecule is engineered to add or remove one or more cysteine residues from the original or native sequence.

In one embodiment the biological molecule is engineered to add or remove one or more tyrosine residues from the original or native sequence.

In one embodiment the biological molecule is engineered to add one or more natural or non-natural amino acid residues to the original or the native sequence.

In one embodiment the biological molecule is a therapeutic molecule.

In one embodiment the payload is selected from:
a. an auristatin, for example selected from the group comprising MMAE (monomethyl auristatin E), MMAF (monomethyl auristatin F), doxorubicin, tubulysin and duocarmycin;
b. comprising a maytansinoid, for example N 2'-deacetyl-N 2'-(3-mercapto-1-oxopropyl)-maytansine (DM1), N 2'-deacetyl-N 2'-(4-mercapto-1-oxopentyl)-maytansine (DM3) and N 2'-deacetyl-N 2'(4-methyl-4-mercapto-1-oxopentyl)-maytansine (DM4),
c. a pyrrolobenzodiazepine (PBD) or iminobenzodiazepine (IBD)
d. a topoisomerase inhibitor, such as SN-38, irinotecan, exatecan, or DxD1.
e. is a toxin, and
f. a polymer, for example a natural polymer, for example starch, poly(glutamic acid), poly(aspartic acid), poly (lysine) or albumin or a synthetic polymer, such as PEG.

In a further independent aspect there is provided a biological molecule conjugated to a payload obtained or obtainable form a method according to the present disclosure.

In one independent aspect there is also provided the biological molecule conjugated to a payload via a Diels-Alder reaction between a diene and a dienophile to form a cyclohexene ring.

In one embodiment the cyclohexene ring is part of a fused ring system, for example comprising up to 20 atoms.

In one embodiment the fused ring system has a formula (IVa):

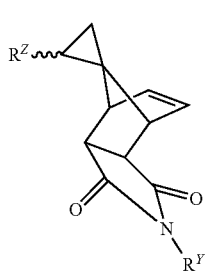

(IVa)

wherein $R^Y$ represents the payload, for example as defined herein; and $R^Z$ represents the biological molecule, for example as defined herein, or a formula (IVb):

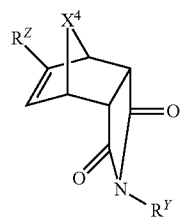

(IVb)

wherein
$R^Y$ represents the payload, for example as defined herein;
$R^Z$ represents the biological molecule, for example as defined herein; and
$X^4$ represents —O— or —$CH_2$—.

In one embodiment the biological molecule is an antibody or binding fragment thereof.

Also provided a biological molecule conjugated to a payload according to the present disclosure wherein the payload is selected from:
a. an auristatin, for example selected from the group comprising a tubulysin or a pyrrolobenzodiazepine (PBD) MMAE (monomethyl auristatin E), MMAF (monomethyl auristatin F), doxorubicin and duocarmycin;
b. comprising a maytansinoid, for example N 2'-deacetyl-N 2'-(3-mercapto-1-oxopropyl)-maytansine (DM1), N 2'-deacetyl-N 2'-(4-mercapto-1-oxopentyl)-maytansine (DM3) and N 2'-deacetyl-N 2'(4-methyl-4-mercapto-1-oxopentyl)-maytansine (DM4),
c. is a toxin,
d. a polymer, for example a natural polymer, for example starch, poly(glutamic acid) or albumin or a synthetic polymer, such as PEG.

Also provided is a pharmaceutical composition comprising a biological molecule conjugated to a payload according to the present disclosure and diluent, carrier and/or excipient, for example where the composition is a parenteral formulation.

The present disclosure further provides a method of treating a patient comprising administering a therapeutically effective amount of a biological molecule conjugated to a payload or a pharmaceutical composition as disclosed herein.

Thus, there is provided a biological molecule conjugated to a payload or a pharmaceutical composition as disclosed herein, for use in treatment.

Use of a biological molecule conjugated to a payload or a pharmaceutical composition as disclosed herein for the manufacture of a medicament is a further aspect of the present of the present invention.

In an independent aspect there is provided a non-natural amino acid comprising a diene or a dieneophile, for example wherein the diene or dieneophile is in a side chain.

In one embodiment the non-natural amino acid of the present disclosure is derived from lysine asparagine, glutamine, cysteine, selenocysteine, aspartic acid, glutamic acid, serine, threnonine, glycine and tyrosine.

In one embodiment non-natural amino acid according to the present disclosure has a formula (I):

$R^X$—$X^1$—$O_{0\text{-}1}$CO)-amino-acid-residue     (I)

wherein:

$R^x$ represents a unsaturated group selected from a:
- i) $C_{4-9}$ linear conjugated diene,
- ii) $C_{5-14}$ carbocyclyl comprising a conjugated diene, and
- iii) a 5 to 14 membered heterocyclyl comprising 1, 2 or 3 heteroatoms selected O, N and S, and a conjugated diene, wherein i), ii) and iii) may bear one, two or three substituents; and $X^1$ represents $C_{1-5}$ alkyl, and $O_{0-1}C(O)$ is linked through a side chain of an amino acid.

In one embodiment the non-natural amino acid has a formula (II):

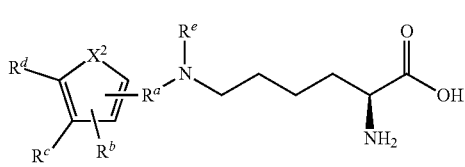

(II)

or a salt thereof wherein $X^2$ represents —C—, CR', —CH$_2$ or O;

$R^a$ represents
- i) a saturated or unsaturated branched or unbranched $C_{1-8}$ alkylene chain, wherein at least one carbon (for example 1, 2 or 3 carbons) is replaced by a heteroatom selected from O, N, S(O)$_{0-3}$, wherein said chain is optionally, substituted by one or more groups independently selected from oxo, halogen, amino; or
- ii) together with a carbon from the 5 membered ring represents a cyclopropane ring linked to a saturated or unsaturated (such as saturated) branched or unbranched $C_{1-6}$ alkylene chain, wherein at least one carbon (for example 1, 2 or 3 carbons) is replaced by a heteroatom selected from O, N, S(O)$_{0-3}$, wherein said chain is optionally, substituted by one or more groups independently selected from oxo, halogen, amino;

$R^b$ represents H, —OC$_{1-3}$alkyl, C$_{1-6}$alkyl optionally bearing a hydroxyl substituent, —C$_{1-3}$alkyleneN$_3$, or —C$_{2-5}$alkynyl;

$R^c$ represents H, —OC$_{1-3}$ alkyl, C$_{1-6}$ alkyl optionally bearing a hydroxyl substituent, —C$_{1-3}$ alkyleneN$_3$, or —C$_{2-5}$ alkynyl;

$R^d$ represents H, —OC$_{1-3}$ alkyl, C$_{1-6}$ alkyl optionally bearing a hydroxyl substituent, —C$_{1-3}$ alkyleneN$_3$, or —C$_{2-5}$ alkynyl;

$R^e$ represents H, saturated or unsaturated branched or unbranched C$_{1-8}$ alkylene chain, wherein one or more carbons are optionally replaced by —O— and the chain is optionally substituted by one or more halogen atoms (such as iodo), N$_3$ or —C$_{2-5}$alkynyl.

In one embodiment $R^a$, $R^b$, $R^c$, $R^d$ and $R^e$ are as defined herein.

In one embodiment the non-natural amino acid is a residue of the structure of formula (IIa):

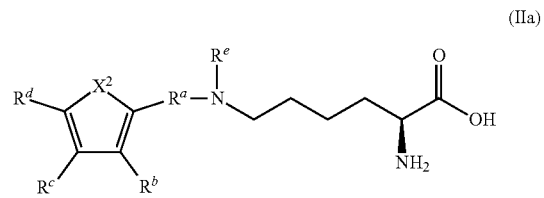

(IIa)

or a salt thereof wherein $R^a$, $R^b$, $R^c$, $R^d$, $R^e$ and $X^2$ are defined above compounds of formula (II).

In one embodiment the non-natural amino acid has the structure of formula (IIb):

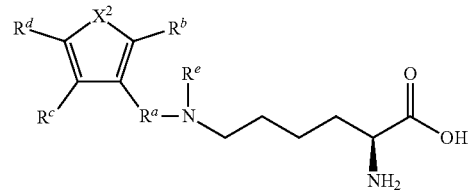

or a salt thereof wherein $R^a$, $R^b$, $R^c$, $R^d$, $R^e$ and $X^2$ are defined above compounds of formula (II).

In one embodiment the non-natural amino acid has the structure of formula (IIc):

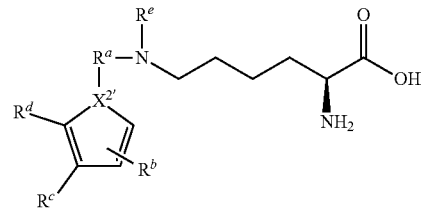

or a salt thereof wherein $R^a$, $R^b$, $R^C$, $R^d$, $R^e$ and $X^2$ are defined above compounds of formula (II).

In one embodiment the non-natural amino acid is selected from the group comprising:

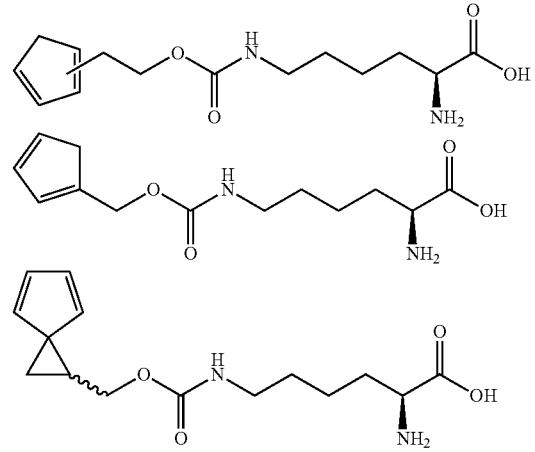

19
-continued

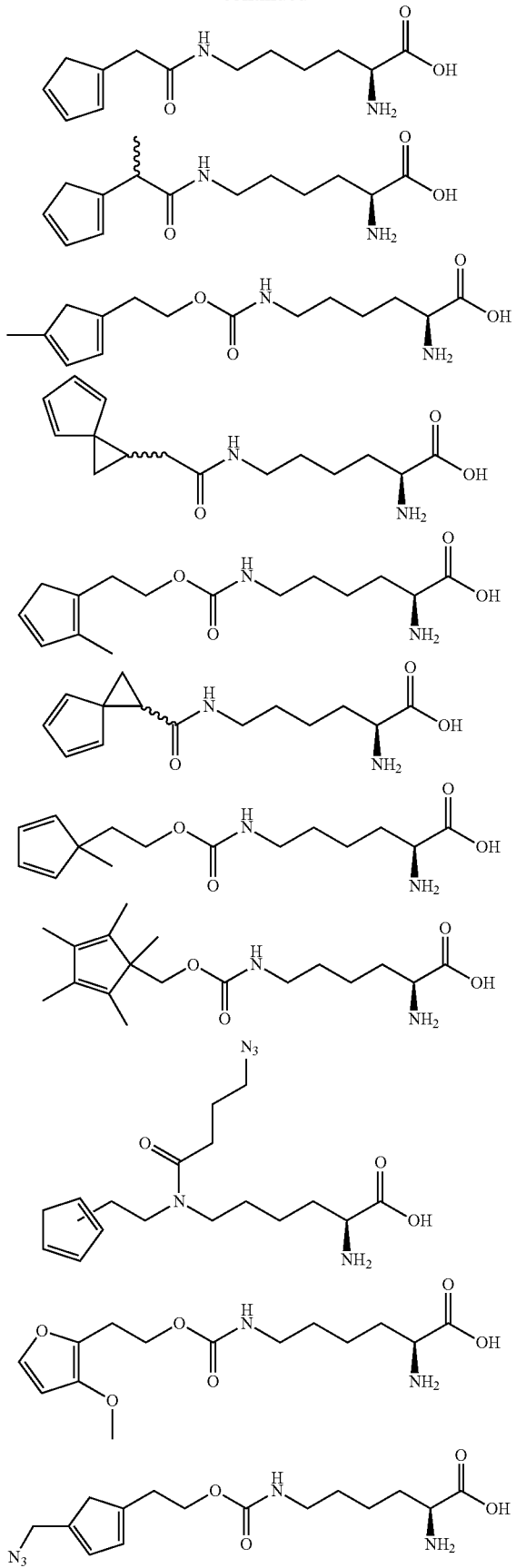

20
-continued

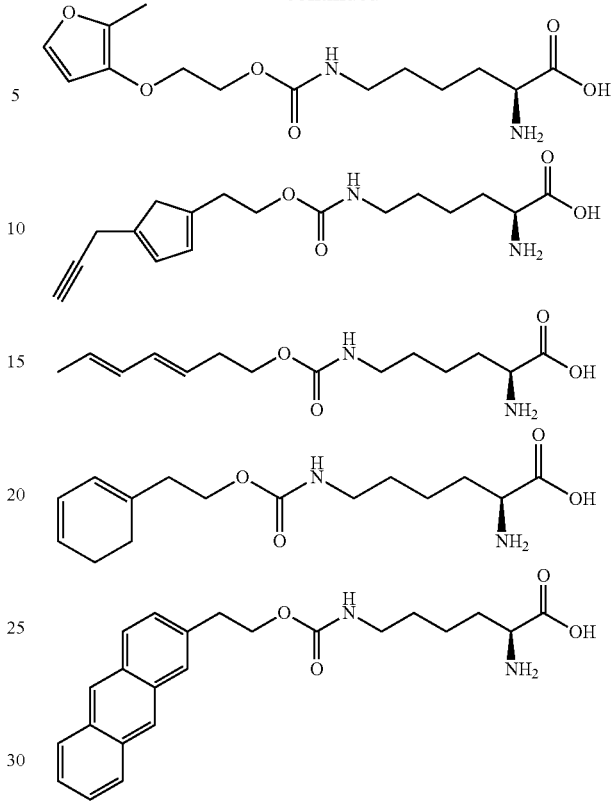

or a salt of any one of the same.

Also provided is a polypeptide comprising a non-natural amino acid according to the present disclosure.

In one embodiment the bioconjugation reaction does not conjugate a biological molecule to a gel or particle.

In one independent aspect there is provided a bioconjugation method comprising the step of conjugating a biological molecule containing a first unsaturated functional group with an entity comprising a second unsaturated functional group, wherein the first and second unsaturated functional groups are a complementary couple to each other such that one functional group of the complementary couple is a diene and the other functional group in the complementary couple is a dienophile and the conjugation is a reaction of said functional groups via a Diels-Alder reaction which forms a cyclohexene ring, with the proviso that the diene is not an unsubstituted furan.

In one independent aspect there is provided a bioconjugation method comprising the step of conjugating a biological molecule containing a first unsaturated functional group in a non-natural amino acid with an entity comprising a second unsaturated functional group, wherein the first and second unsaturated functional groups are a complementary couple to each other such that one functional group of the complementary couple is a diene and the other functional group in the complementary couple is a dienophile and the conjugation is a reaction of said functional groups via a Diels-Alder reaction which forms a cyclohexene ring.

DETAILED DISCLOSURE

A biological molecule as employed herein a polypeptide with at least one biological activity.

In one embodiment the biological molecule is a therapeutic biological molecule, namely a biological molecule that may be employed in therapy, in particular human therapy.

Conjugation (reaction) as employed herein is a simply a reaction linking a molecule to another entity. In the context of the present specification a biological molecule conjugated to, for example a payload is the product obtained from a conjugation reaction.

A bioconjugation method as employed herein refers to a method for linking a biological molecule to another entity, for example a payload.

An entity in the context of the present specification includes payload such as a polymer and/or toxin, a solid surface (such as a plate), a particle or the like. Examples of payloads are described in more detail below.

An amino acid residue as employed herein refers to a natural or non-natural amino acid linked, for example to another amino acid, via the N and/or C terminal of the amino acid, in particular where at least one link is a peptide bond.

A non-natural amino acid as employed herein refers to an amino acid which is other than one of the twenty-one naturally occurring amino acids. For example, the non-natural amino acid comprises a diene or dienophile and also contains the amino and carboxylic functional groups in the relative positions that are characteristic of natural amino acids. Certain non-natural amino acids and methods for making the same are disclosed in WO2015/019192, incorporated herein by reference. In one embodiment the dienophile is contained in a non-natural amino acid, such as norbornene lysine, which is disclosed in US2015/0005481 incorporated herein by reference.

The non-natural amino acids are generally derived from natural amino acid. Derived from a natural amino acid refers to the fact that the non-natural amino acid is based on (or incorporates) or is similar to the structure of natural amino acid, for example the alkylene chain in lysine may be shortened to provide a 3-carbon chain as opposed to the natural 4 carbon chain but the structural relationship or similarity to lysine still exists. Thus, derivatives of natural amino acids include modifications such as incorporating the diene or dienophile, lengthening or shortening an alkylene chain, adding one or more substituents to a nitrogen, oxygen, sulfur in a side chain or converting a nitrogen, oxygen or sulfur into a different functional group or a combination of any of the same. Usually the majority of modifications will be the addition of structure in the non-natural amino acid. However, modification may include removed or replacing an atom naturally found in an amino acid.

Natural amino acid as employed herein refers to the 21 proteinogenic amino acids (namely arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan).

In one embodiment the non-natural amino acid comprising a diene or dienophile is incorporated in the amino acid sequence of the biological molecule, for example in the expression process of a recombinant polypeptide. This is advantageous because it locates the amino acid is precisely position, which then facilitates a very specific conjugation reaction with the payload.

In one embodiment the non-natural amino acid may be appended to the biological molecule via a linker and conjugation reaction.

Dienophile as employed herein is a functional group which reacts with a diene. In one embodiment the dienophile comprises an alkene (with at one double bond, in particular one double bond).

Diene as employed herein refers to two double bonds (two -ene groups). However, said two groups need to in proximity of each other. Therefore, generally a diene as employed herein will refer to a conjugated diene, unless the context indicates otherwise.

Conjugated-diene as employed herein refers to refers to double-bond-single-bond-double-bond in a linear or cyclic context.

A conjugated-diene in a linear context includes, C4-9 linear conjugated dienes, such as butadiene, pentadiene, hexadiene, heptadiene, octadiene and nonadiene. Linear in this context refers to non-cyclic and therefore includes branched version of C4-9 carbon chains comprising a conjugated diene.

Conjugated-dienes in a cyclic context include, for example a monocylic carbocycle, such as cyclopentadiene or cyclohexadiene, or in bi or tricyclic carbocyclic system, such as a system comprising cyclopentadiene or cyclohexadiene fused to another ring. In one embodiment the conjugated diene is not aromatic. Conjugated-diene is not to be confused with conjugation reaction, the two are "unrelated".

Carbocycle as employed herein refers to a ring system, where the rings making up the system are made of carbon atoms i.e. heteroatoms do no contribute the ring structure. However, the carbocycle may bear one or substituents and the substituent may contain heteroatoms. In one embodiment the carbocycle is partially unsaturated or aromatic.

Cyclopropane is a three membered carbocycle. In some embodiments a cyclopropane ring is appended from a carbocyclic diene ring or heterocyclic diene ring, for example as shown in some of the structures herein. This is advantageous because it minimises the propensity of the diene to self-react, which may occur with reactive dienes. This cyclopropane ring in the present specification is not defined as a substituent per se, rather it defined in terms of the chain which or "linker" which is attached the ring system comprising diene.

C5-14 carbocyclyl comprising a conjugated diene as employed herein refers a 5 to 14 membered carbocyclic ring system, which may bear one or more substituents, for example one, two, three, three, four substituents.

The carbocycle comprising a conjugated-diene or a dieneophile is part one of the reactive functional groups found in the non-natural amino acid or will be a component of linker added prior to conjugation with the "payload". Example of C5-14 carbocycles include cyclopentadiene (including substituted or unsubstituted cyclopentadiene), cyclohexadiene (including substituted or unsubstituted cyclohexadiene), anthracene (including substituted or unsubstituted anthracene).

In one embodiment the cyclopentadiene in a non-natural amino acid or linker is unsubstituted. In one embodiment the cyclopentadiene is connected to the non-natural amino acid or liner via a cyclopropane ring.

In one embodiment the cyclopentadiene in a non-natural amino acid or linker comprises one, two, three, four or five, C1-3 alkyl substituents, for example the cyclopentadiene bears five methyl substituents.

Heterocyclyl as employed herein refers to a saturated or partially unsaturated or aromatic ring comprising one or more, for example 1, 2, 3 or 4 heteroatoms independently selected from O, N and S optionally one or two carbons in the ring may bear an oxo substituent. Clearly any valancies of a heteroatom not employed in forming or retaining the ring structure may be filled by hydrogen or a substituent, as appropriate. Thus, substituents on heterocycles may be on carbon or on a heteroatom, such as N as appropriate.

5 to 14 membered heterocycle will contains 5 to 14 members making the ring system, for example comprising one, two or three heteroatoms. The hetercycle may, for example bear one, two or three substituents. Generally the heterocycle will generally comprise diene or dienophile and therefore will be at least partially unsaturated and may be aromatic.

5 to 14 membered heterocycle will generally comprise a diene or a dienophile for incorporating into a non-natural amino acid or linker. Example of heterocycles comprising a diene include furan (including substituted or unsubstituted furan, in particular substituted furan), and 2H-pyran (including substituted or unsubstituted forms thereof). Examples of heterocycles comprising a dienophile include maleimide, vinyl pyridine, pyrroline (such as 2-pyrroline and 3-pyrroline), and 3,4-dihydropyran.

In one furan is bears at least one substituent, for example an electron donating substituent, such as alkoxy, in particular at one (such as one) methoxy.

Where the diene or dienophile is introduced into the biological molecule via a linker, functionality such as $N_3$, halo, succinimide or an alkyne can be reacted with, for example lysine in the amino acid sequence of the biological molecule.

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —C1-3 alkylOC1-3 alkyl, such as —CH2CH2OCH3 or —CH2OCH3. Thus in one embodiment the alkoxy is linked through carbon to the remainder of the molecule. In one embodiment the alkoxy is linked through oxygen to the remainder of the molecule, for example —CO alkylOC1-6 alkyl. In one embodiment the disclosure relates to straight chain alkoxy.

Amino as employed herein refers to —NH2, C1-4 mono or di-acyl amino is intended to refer to —NHC(O)C1-3 alkyl and to (—NC(O)C1-3 alkyl) C(O)C1-3 alkyl) respectively.

C1-4 mono or di-alkyl amino is intended to refer to —NHC1-4 alkyl and —N(C1-4 alkyl) (C1-4 alkyl) respectively.

Halogen or halo includes fluoro, chloro, bromo or iodo, in particular fluoro, chloro or bromo, especially fluoro or chloro.

Oxo as used herein refers to C=O and will usually be represented as C(O).

Alkylene as employed herein refers to branched or unbranched carbon radicals, such as methylene (—CH2-) or chains thereof.

$C_{2-5}$ alkyne as employed herein refers to a group or radical containing: a triple bond; and between two and 5 carbon atoms in a linear or branched arrangement.

In relation to a saturated or unsaturated, branched or unbranched $C_{1-8}$ alkyl chain, wherein at least one carbon (for example 1, 2 or 3 carbons, suitably 1 or 2, in particular 1) is replaced by a heteroatom selected from O, N, S(O)0-3, wherein said chain is optionally, substituted by one or more groups independently selected from oxo, halogen, it will be clear to persons skilled in the art that the heteroatom may replace a primary, secondary or tertiary carbon, that is $CH_3$, —$CH_2$— or a —CH— or a branched carbon group, as technically appropriate.

$N_3$ as employed herein refers to an azide.

Sulfo as employed herein refers to a sulphur atom bonded to one, two or three oxygen atoms.

Sulfohydryl as employed herein refers to a sulfur atom bonded to one or more hydrogen atoms, which can exist in equilibrium between the protonated and unprotonated forms.

The cyclohexene ring, which is the characterising feature of the conjugated product of the reaction according to the present disclosure via Diels-Alder mechanism, a mononcyclic system or part of a fused ring system, such as a bicyclic system.

Suitable sugars for addition to compounds of formula (III) include glucose, glucosamine, galactose, galactosamine, mannose, fructose, galactose, maltose and lactose. Advantageously the addition of a sugar molecule may increase solubility.

Polypeptides for Use in the Present Disclosure

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the instant disclosure are based upon antibodies.

Polypeptide as employed herein refers to a sequence of 5 or more amino acids, with or without secondary or tertiary structure comprising at least one thiol group. Thus in the present disclosure the term "polypeptides" includes peptides, polypeptides and proteins. These are used interchangeably unless otherwise specified.

In one embodiment the polypeptide is a protein. Proteins generally contain secondary and/or tertiary structure and may be monomeric or multimeric in form.

In one embodiment the protein is an antibody as single chains or associated chains or binding fragment thereof.

Antibody molecule as employed herein is a generic term referring to antibodies, antibody binding fragments and antibody formats such as multispecific antibodies comprising said antibodies or binding fragments thereof.

The terms "antibody" or "immunoglobulin," as used interchangeably herein, include whole antibodies and any antigen binding fragment or single chains thereof.

A typical antibody comprises at least two heavy (H) chains and two light (L) chains interconnected by disulfide bonds. Each heavy chain is comprised of a heavy chain variable region (abbreviated herein as VH, VH region, or VH domain) and a heavy chain constant region. The heavy chain constant region is comprised of three or four constant domains, CH1, CH2, CH3, and CH4. The Fc region includes the polypeptides comprising the constant region of an antibody excluding the first constant region immunoglobulin domain, and fragments thereof. Thus, for IgG the "Fc region" refers to CH2 and CH3 and optionally all or a portion of the flexible hinge region N-terminal to these domains. The term "Fc region" can refer to this region in isolation, or this region in the context of an antibody, antibody fragment, or Fc fusion protein.

Each light chain is comprised of a light chain variable region (abbreviated herein as VL, VL region, or VL domain) and a light chain constant region. The light chain constant region is comprised of one domain, CL.

The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. Framework regions can be designated according to their respective VH and VL regions. Thus, e.g., VH-FW1 would refer to the first framework region of VH. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1 q) of the classical complement system.

The term "antibody" means an immunoglobulin molecule or antigen binding fragment thereof that recognizes and specifically binds to a target, such as a protein, polypeptide, peptide, carbohydrate, polynucleotide, lipid, or combinations of the foregoing through at least one antigen recognition site (also referred to as a binding site) within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain antibody fragments (scFv and disulfide stabilized scFv (dsFv)), multispecific antibodies such as bispecific antibodies generated from at least two different antibodies or multispecific antibodies formed from antibody fragments (see, e.g., PCT Publications WO96/27011, WO2007/024715, WO2009018386, WO2009/080251, WO2013006544, WO2013/070565, and WO2013/096291), chimeric antibodies, humanized antibodies, human antibodies, fusion proteins comprising an antigen-binding fragment of an antibody, and any other modified immunoglobulin molecule comprising an antigen-binding fragment so long as the antibodies exhibit the desired biological activity.

An antibody can be of any the five major classes of immunoglobulins: IgA, IgD, IgE, IgG, and IgM, or subclasses (isotypes) (e.g. IgG1, IgG2, IgG3, IgG4, IgA1 and IgA2), or allotype (e.g., Gm, e.g., G1m (f, z, a or x), G2m (n), G3m (g, b, or c), Am, Em, and Km (1, 2 or 3)). The different classes of immunoglobulins have different and well-known subunit structures and three-dimensional configurations. Antibodies may be derived from any mammal, including, but not limited to, humans, monkeys, pigs, horses, rabbits, dogs, cats, mice, etc., or other animals such as birds (e.g. chickens).

The terms "antigen-binding fragment" refers to a fragment comprising antigenic determining variable regions of an intact antibody. It is known in the art that the antigen binding function of an antibody can be performed by fragments of a full-length antibody. Examples of antibody fragments include, but are not limited to Fab, Fab', F(ab')2, Fv fragments, scFvs, linear antibodies, single chain antibodies, and multispecific antibodies formed from antibody fragments.

Thus in one embodiment the antibody used in the present invention may comprise a complete antibody molecule having full length heavy and light chains or a fragment thereof and may be, but are not limited to Fab, modified Fab, Fab', modified Fab', F(ab')2, Fv, single domain antibodies (e.g. VH or VL or VHH), scFv, bi, tri or tetra-valent antibodies, Bis-scFv, diabodies, triabodies, tetrabodies, combinations of the same and epitope-binding fragments of any of the above.

Other antibodies specifically contemplated are "oligoclonal" antibodies which are a predetermined mixture of distinct monoclonal antibodies. See, e.g., PCT publication WO 95/20401; U.S. Pat. Nos. 5,789,208 and 6,335,163. Preferably oligoclonal antibodies consist of a predetermined mixture of antibodies against one or more epitopes are generated in a single cell. More preferably oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. Those skilled in the art will know or can determine what type of antibody or mixture of antibodies is applicable for an intended purpose and desired need.

Other moieties specifically contemplated for use in the present disclosure are small, engineered protein domains such as scaffold (see for example, U.S. Patent Publication Nos. 2003/0082630 and 2003/0157561). Scaffolds are based upon known naturally-occurring, non-antibody domain families, specifically protein extracellular domains, which typically of small size (~100 to ~300 AA) and containing a highly structured core associated with variable domains of high conformational tolerance allowing insertions, deletions or other substitutions. These variable domains can create a putative binding interface for any targeted protein. In general, the design of a generic protein scaffold consists of two major steps: (i) selection of a suitable core protein with desired features and (ii) generation of complex combinatorial libraries by mutagenizing a portion or all of the domains accepting high structural variability, display of these libraries in an appropriate format (i.e., phage, ribosome, bacterial, or yeast) and screening of the library for mutagenized scaffold having the desired binding characteristics (e.g. target specificity and/or affinity). The structure of the parental scaffolds can be highly diverse and include highly structured protein domains including but not limited to, FnIII domains (e.g., AdNectins, see, e.g., Protein Eng. Des. Sel. 18, 435-444 (2005), US2008/00139791, and WO 2005/056764, TN3, see e.g., WO2009/058379 and WO2011/130324); Z domains of protein A (Affibody, see, e.g., Protein Eng. Des. Sel. 17,455-462 (2004) and EP1641818A1); domain A from LDL receptor (Avimers, see, e.g., Nature Biotechnology 23(12), 1556-1561 (2005) and Expert Opinion on Investigational Drugs 16(6), 909-917 (June 2007)); Ankyrin repeat domains (DARPins, J. Mol. Biol. 332,489-503 (2003), PNAS (2003) and Biol. 369, (2007) and WO02/20565); C-type lectin domains (Tetranectins, see, e.g., WO02/48189). If desired two or more such engineered scaffold domains can be linked together, to form a multivalent binding protein. The individual domains can target a single type of protein or several, depending upon the use/disease indication.

Virtually any molecule (or a portion thereof, e.g., subunits, domains, motifs or a epitope) may be targeted by and/or incorporated into a moiety including, but not limited to, integral membrane proteins including ion channels, ion pumps, G-protein coupled receptors, structural proteins; adhesion proteins such as integrins; transporters; proteins involved in signal tranduction and lipid-anchored proteins including G proteins, enzymes such as kinases including membrane-anchored kinases, membrane-bound enzymes, proteases, lipases, phosphatases, fatty acid synthetases, digestive enzymes such as pepsin, trypsin, and chymotrypsin, lysozyme, polymerases; receptors such as hormone receptors, lymphokine receptors, monokine receptors, growth factor receptors, cytokine receptors; cytokines; and more.

In some aspects a polypeptide employed in the present disclosure targets and/or incorporates all or a portion (e.g., subunits, domains, motifs or a epitope) of a growth factor, a cytokine, a cytokine-related protein, a growth factor, a receptor ligand or a receptor selected from among, for example, BMP1, BMP2, BMP3B (GDF10), BMP4, BMP6, BMP8, CSF1 (M-CSF), CSF2 (GM-CSF), CSF3 (G-CSF), EPO, FGF1 (αFGF), FGF2 (βFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, FGFR, FGFR1, FGFR2, FGFR3, FGFR4, FGFRL1, FGFR6, IGF1, IGF2, IGF1R, IGF2R, IFNA1, IFNA2, IFNA4, IFNA5, IFNA6, IFNA7, IFNAR1, IFNAR2, IFNB1, IFNG, IFNW1, FIL1, FIL1 (EPSILON), FIL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, IL2RA, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL17RA, IL17RB, IL17RC, IL17RD, IL18R1, IL20RA, IL20RB, IL21R, IL22R, IL22RA1, IL23R, IL27RA, IL28RA, PDGFA, PDGFB, PDGFRA, PDGFRB, TGFA, TGFB1, TGFB2, TGFB3, TGFBR1, TGFBR2, TGFBR3, ACVRL1, GFRA1, LTA (TNF-beta), LTB, TNF (TNF-alpha), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, TNFRSF1A, TNFRSF1B, TNFRSF10A (Trail-receptor), TNFRSF10B (Trail-receptor 2), TNFRSF10C (Trail-receptor 3), TNFRSF10D (Trail-receptor 4), FIGF (VEGFD), VEGF, VEGFB, VEGFC, KDR, FLT1, FLT4, NRP1, IL1HY1, IL1RAP, IL1RAPL1, IL1RAPL2, IL1RN, IL6ST, IL18BP, IL18RAP, IL22RA2, AIF1, HGF, LEP (leptin), PTN, ALK and THPO.

In some aspects a polypeptide employed in the present disclosure targets and/or incorporates all or a portion (e.g., subunits, domains, motifs or a epitope) of a chemokine, a chemokine receptor, or a chemokine-related protein selected from among, for example, CCL1 (I-309), CCL2 (MCP-1/MCAF), CCL3 (MIP-la), CCL4 (MIP-1b), CCL5 (RANTES), CCL7 (MCP-3), CCL8 (mcp-2), CCL11 (eotaxin), CCL13 (MCP-4), CCL15 (MIP-Id), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EB11), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10 (C10), EPO, FY (DARC), GDF5, HIF1A, IL8, PRL, RGS3, RGS13, SDF2, SLIT2, TLR2, TLR4, TREM1, TREM2, and VHL.

In some aspects a polypeptide employed in the present disclosure targets and/or incorporates all or a portion (e.g., subunits, domains, motifs or a epitope) of a protein selected from among, for example renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; epidermal growth factor (EGF); insulin-like growth factor binding proteins; CD proteins such as CD2, CD3, CD4, CD8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD18, CD61, CD104, beta5, beta6, beta7 and beta8; Integrin subunit combinations including but not limited to, αVβ, αVβ5 and α4β7; a member of an apoptosis pathway; IgE; blood group antigens; flk2/flt3 receptor; obesity (OB) receptor; mpl receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIbα, GPIIb/IIIa and CD200.

Also contemplated are moieties that specifically bind and/or comprises cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, C017-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16, NY-BR-16, HER2 antigen (p185HER2), and HER3; polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; VIM-D5; D156-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 variant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4a, MAGE-4b and MAGE-X2; Cancer-Testis Antigen (NY-EOS-1) and fragments of any of the above-listed polypeptides.

In one embodiment the polypeptide employed is recombinant. A "recombinant" polypeptide or protein refers to a polypeptide or protein produced via recombinant DNA technology. Recombinantly produced polypeptides and proteins expressed in engineered host cells are considered isolated for the purpose of this disclosure, as are native or recombinant polypeptides which have been separated, fractionated, or partially or substantially purified by any suitable technique. The polypeptides disclosed herein can be recombinantly produced using methods known in the art. Alternatively, the proteins and peptides disclosed herein can be chemically synthesized.

Payload Molecules

Entity includes a particle (such as a nanoparticle or microparticle), solid support (such as a plate) and also includes a payload.

Payload does not generally extend to include a particle or solid support. Generally, a payload will bring some improvement to the biological molecule and, for example augment or optimised the properties of the resulting therapeutic conjugation product. Improvements include targeting, increased solubility, increased half-life, effector function, additional (a further new activity), increased activity, providing a detectable label, reducing toxicity (for example the payload may convert the biological molecule to be a prodrug).

Payload as employed herein refers to a molecule or component, which is intended for "delivery" to a target region location by conjugation to the polypeptide. Generally the payload will generally be an effector molecule, for example selected from the group consisting of a toxin, for example a cytotoxin, such as a chemotherapeutic agent, a drug, a pro-drug, an enzyme, an immunomodulator, an anti-angiogenic agent, a pro-apoptotic agent, a cytokine, a hormone, an antibody or fragment thereof, synthetic or naturally occurring polymers, nucleic acids and fragments thereof e.g. DNA, RNA and fragments thereof (e.g., an antisense molecule or a gene), radionuclides, particularly radioiodide, radioisotopes, chelated metals, nanoparticles and reporter groups such as fluorescent compounds or compounds which may be detected by NMR or ESR spectroscopy.

In one embodiment the payload is selected from the group comprising a toxin, drug, radionuclide, immunomodulator, cytokine, lymphokine, chemokine, growth factor, tumor necrosis factor, hormone, hormone antagonist, enzyme, oligonucleotide, DNA, RNA, siRNA, RNAi, microRNA, peptide nucleic acid, photoactive therapeutic agent, anti-angiogenic agent, pro-apoptotic agent, non-natural amino acid, peptide, lipid, a polymer, carbohydrate, scaffolding molecule, fluorescent tag, visualization peptide, biotin, serum half-life extender, capture tag, chelating agent, solid support, or a combination thereof.

In one embodiment the payload is a drug molecule (also referred to herein as a drug). Examples of drug molecules for use in the present disclosure include nitrogen mustard, ethylenimine derivative, alkyl sulfonates, nitrosourea, gemcitabine, triazene, folic acid analog, anthracycline, taxane, COX-2 inhibitor, pyrimidine analog, purine analog, antibiotic, enzyme inhibitor, epipodophyllotoxin, platinum coordination complex, vinca alkaloid, substituted urea, methyl hydrazine derivative, adrenocortical suppressant, hormone antagonist, endostatin, taxol, camptothecin, doxorubicin, doxorubicin analog, antimetabolite, alkylating agent, antimitotic, anti-angiogenic agent, tyrosine kinase inhibitor, mTOR inhibitor, topoisomerase inhibitor, heat shock protein (HSP90) inhibitor, proteosome inhibitor, HDAC inhibitor, pro-apoptotic agent, methotrexate, CPT-11, or a combination thereof, and wherein conjugation is.

In particular aspects, the drug is amifostine, cisplatin, dacarbazine, dactinomycin, mechlorethamine, streptozocin, cyclophosphamide, carrnustine, lomustine, doxorubicin lipo, gemcitabine, daunorubicin, daunorubicin lipo, procarbazine, mitomycin, cytarabine, etoposide, methotrexate, 5-fluorouracil, vinblastine, vincristine, bleomycin, paclitaxel, docetaxel, aldesleukin, asparaginase, busulfan, carboplatin, cladribine, 10-hydroxy-7-ethyl-camptothecin (SN38), gefitinib, dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil aromatase inhibitors, and combinations thereof.

In one embodiment the drug is selected from the group comprising alkylphosphocholines, topoisomerase I inhibitors, taxoids and suramin.

In one embodiment the payload comprises a tubulysin, for example tubulysin A, which is a cytotoxic peptide with antimiotic activity.

In one embodiment toxin comprise cytotoxins or cytotoxic agents including any agent that is detrimental to (e.g. kills) cells. Examples include aplidin, anastrozole, azacytidine, bortezomib, bryostatin-1, busulfan, combrestatins, carmustine, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In one embodiment the drug (also a cytotoxin in this instance) comprises an antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), carboplatin, anthracyclines (e.g. daunorubicin (formerly daunomycin) and doxorubicin or doxorubicin glucuronide), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

In some aspects, the drug is an auristatin (U.S. Pat. Nos. 5,635,483; 5,780,588), for example, MMAE (monomethyl auristatin E) or MMAF (monomethyl auristatin F). In other aspects, the drug is a dolastatin or dolastatin peptidic analog or derivative. Dolastatins and auristatins have been shown to interfere with microtubule dynamics, GTP hydrolysis, and nuclear and cellular division (Woyke et al., Antimicrob. Agents and Chemother. 45:3580-3584 (2001)) and have anticancer activity (U.S. Pat. No. 5,663,149). The dolastatin or auristatin drug moiety can be attached to the conjugate compound through the N (amino) terminus or the C (carboxyl) terminus of the peptidic drug moiety. See, e.g., Intl. Publ. No. WO2002/088172, which is herein incorporated by reference in its entirety.

In other aspects, the drug is a maytansinoid. In some aspects, the maytansinoid is N 2'-deacetyl-N 2'-(3-mercapto-1-oxopropyl)-maytansine (DM1), N 2'-deacetyl-N2'-(4-mercapto-1-oxopentyl)-maytansine (DM3) or N 2'-deacetyl-N 2'(4-methyl-4-mercapto-1-oxopentyl)-maytansine (DM4). Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533, which are herein incorporated by reference in their entireties.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Conjugates containing maytansinoids, methods of making same, and their therapeutic use are disclosed, for example, in U.S. Pat. Nos. 5,208,020, 5,416, 064 and European Patent EP0425235; Liu et al., Proc. Natl. Acad. Sci. USA 93:8618-8623 (1996) (described immunoconjugates comprising a maytansinoid designated DM1); and Chari et al., Cancer Research 52:127-131 (1992), which are herein incorporated by reference in their entireties.

Maytansinoids are well known in the art and can be synthesized by known techniques or isolated from natural sources. Suitable maytansinoids are disclosed, for example, in U.S. Pat. No. 5,208,020. Exemplary maytansinoid drug moieties include those having a modified aromatic ring, such as: C-19-dechloro (U.S. Pat. No. 4,256,746) prepared by lithium aluminum hydride reduction of ansamytocin P2); C-20-hydroxy (or C-20-demethyl)+/-C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions. Exemplary maytansinoid drug moieties also include those having modifications such as: C-9-SH, prepared by the reaction of maytansinol with H2S or P2S5 (U.S. Pat. No. 4,424,219); C-14-alkoxymethyl (demethoxy/CH2OR) (U.S. Pat. No. 4,331,598); C-14-hydroxymethyl or acyloxymethyl (CH2OH or CH2OAc), prepared from *Nocardia* (U.S. Pat. No. 4,450,254); C-15-hydroxy/acyloxy, prepared by the conversion of maytansinol by *Streptomyces* (U.S. Pat. No. 4,364,866); C-15-methoxy, isolated from Trewia nudiflora (U.S. Pat. Nos. 4,313,946 and 4,315,929); C-18-N-demethyl, prepared by the demethylation of maytansinol by *Streptomyces* (U.S. Pat. Nos. 4,362, 663 and 4,322,348); and 4,5-deoxy, prepared by the titanium trichloride/LAH reduction of maytansinol (U.S. Pat. No. 4,371,533). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

In some aspects, the drug is calicheamicin. The calicheamicin family of antibiotics is capable of producing double-stranded DNA breaks at sub-picomolar concentrations. For the preparation of conjugates of the calicheamicin family see, e.g., U.S. Pat. Nos. 5,712,374, 5,714,586, 5,739, 116, 5,767,285, 5,770,701, 5,770,710, 5,773,001, 5,877,296, which are herein incorporated by reference in their entireties. Structural analogues of calicheamicin that can be used include, but are not limited to, γ1I, α2I, α3I, N-acetyl-γ1I, PSAG and θ11 (Hinman et al., Cancer Research 53:3336-

3342 (1993), Lode et al., Cancer Research 58:2925-2928 (1998) and the aforementioned U.S. patents to American Cyanamid).

In some aspects, the drug is tubulysin. Tubulysins are members of a class of natural products isolated from myxobacterial species (Sasse et al., J. Antibiot. 53:879-885 (2000)). As cytoskeleton interacting agents, tubulysins are mitotic poisons that inhibit tubulin polymerization and lead to cell cycle arrest and apoptosis (Steinmetz et al., Chem. Int. Ed. 43:4888-4892 (2004); Khalil et al., Chem Bio Chem. 7:678-683 (2006); Kaur et al., Biochem. J. 396: 235-242 (2006)). Tubulysins are extremely potent cytotoxic molecules, exceeding the cell growth inhibition of any clinically relevant traditional chemotherapeutic, e.g., epothilones, paclitaxel, and vinblastine. Furthermore, they are potent against multidrug resistant cell lines (Domling et al., Mol. Diversity 9:141-147 (2005)). These compounds show high cytotoxicity tested against a panel of cancer cell lines with IC50 values in the low picomolar range; thus, they are of interest as anticancer therapeutics. See, e.g., Intl. Publ. No. WO/2012019123, which is herein incorporated by reference in its entirety. Tubulysin conjugates are disclosed, e.g., in U.S. Pat. No. 7,776,814.

In some aspects, the drug is a pyrrolobenzodiazepine (PBD). PBDs are relatively small molecules and some have the ability to recognize and covalently bind to specific sequences in the minor groove of DNA and thus exhibit antibiotic/antitumor activity. A number of PBDs and derivatives thereof are known in the art, for example, PBD dimers (e.g., SJG-136 or SG2000), C2-unsaturated PBD dimers, pyrrolobenzodiazepine dimers bearing C2 aryl substitutions (e.g., SG2285), PBD dimer pro-drug that is activated by hydrolysis (e.g., SG2285), and polypyrrole-PBD (e.g., SG2274). PBDs are further described in Intl. Publ. Nos. WO2000/012507, WO2007/039752, WO2005/110423, WO2005/085251, and WO2005/040170, and U.S. Pat. No. 7,612,062, each of which is incorporated by reference herein in its entirety.

In some aspects, the drug is a topoisomerase inhibitor. Topoisomerase inhibitors are compounds that block the action of topisomerase (topoisomerase I and II), which are enzymes that control the changes in DNA structure by catalyzing the breaking and rejoining of the phosphodiester backbone of DNA strands during the normal cell cycle.

In some aspects, the toxin comprises, for example, abrin, brucine, cicutoxin, diphteria toxin, botulinum toxin, shiga toxin, endotoxin, tetanus toxin, pertussis toxin, anthrax toxin, cholera toxin, falcarinol, alpha toxin, geldanamycin, gelonin, lotaustralin, ricin, strychnine, tetrodotoxin, saponin, ribonuclease (RNase), DNase I, Staphylococcal enterotoxin-A, pokeweed antiviral protein, *Pseudomonas* exotoxin, *Pseudomonas* endotoxin, or a combination thereof. In other aspects, the toxin comprises, for example, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, mitogellin, restrictocin, phenomycin, neomycin, tricothecenes, or a combination thereof. See, for example, Intl. Publ. No. WO1993/021232.

In some aspects, the chelating agent is DTPA, EC, DMSA, EDTA, Cy-EDTA, EDTMP, DTPA, CyDTPA, Cy2DTPA, BOPTA, DTPA-MA, DTPA-BA, DTPMP, DOTA, TRITA, TETA, DOTMA, DOTA-MA, HP-DO3A, pNB-DOTA, DOTP, DOTMP, DOTEP, DOTPP, DOTBzP, DOTPME, HEDP, DTTP, an N3S triamidethiol, DADS, MAMA, DADT, an N2S4 diaminetetrathiol, an N2P2 dithiol-bisphosphine, a 6-hydrazinonicotinic acid, a propylene amine oxime, a tetraamine, a cyclam, or a combination thereof.

In one embodiment the drug is an auristatin, a tubulysin or a pyrrolobenzodiazepine (PBD).

In one embodiment the auristatin is MMAE (monomethyl auristatin E) or MMAF (monomethyl auristatin F).

In one embodiment the drug is a maytansinoid, for example N 2'-deacetyl-N 2'-(3-mercapto-1-oxopropyl)-maytansine (DM1), N 2'-deacetyl-N2'-(4-mercapto-1-oxopentyl)-maytansine (DM3) or N 2'-deacetyl-N 2'(4-methyl-4-mercapto-1-oxopentyl)-maytansine (DM4).

Examples of radionuclides include 3H, 1 C, 13N, 15O, 18F, 32P, 33P, 35S, 47Sc, 51Cr, 54Mn, 57Co, 58Co, 59Fe, 62Cu, 65Zn, 67Cu, 67Ga, 68Ge, 75Br, 75Se, 76Br, 77Br, 77As, 80mBr, 85Sr, 89Sr, 90Y, 95Ru, 97Ru, 99Mo and 99mTc, 103Pd, 103m Rh, 103 Ru, 105Rh, 105Ru, 107Hg, 109Pd, 109Pt, 111Ag, 111In, 112In, 113mIn, 113Sn, 115In, 117Sn, 119Sb, 121mTe, 121I, 122mTe, 125mTe, 125I, 126I, 131I, 133I, 133Xe, 140La, 142Pr, 143Pr, 149Pm, 152Dy, 153Sm, 153Gd, 159Gd, 161Ho, 161Tb, 165Tm, 166Dy, 166Ho, 167Tm, 168Tm, 169Er, 169Yb, 175Yb, 177Lu, 186Re, 188Re, 188W, 189mOs, 189Re, 192Ir, 194Ir, 197Pt, 198Au, 199Au, 201Tl, 203Hg, 211At, 211Bi, 211Pb, 212Pb, 212Bi, 213Bi, 215Po, 217At, 219Rn, 221Fr, 223Ra, 224Ac, 225Ac, 225Fm, 252Cf and a combination thereof.

In one embodiment the radionuclide is selected from the group comprising or consisting of chromium (51Cr), cobalt (57Co), fluorine (18F), gadolinium (153Gd, 159Gd), germanium (68Ge), holmium (166Ho), indium (115In, 113In, 112In, 111In), iodine (131I, 125I, 123I, 121I), lanthanum (140La), lutetium (177Lu), manganese (54Mn), molybdenum (99Mo), palladium (103Pd), phosphorous (32P), praseodymium (142Pr), promethium (149Pm), rhenium (186Re, 188Re), rhodium (105Rh), ruthenium (97Ru), samarium (153Sm), scandium (47Sc), selenium (75Se), strontium (85Sr), sulfur (35S), technetium (99Tc), thallium (201Tl), tin (113Sn, 117Sn), tritium (3H), xenon (133Xe), ytterbium (169Yb, 175Yb), yttrium (90Y), zinc (65Zn), or a combination thereof.

In one embodiment the radionuclide is attached to the conjugate compound of the present disclosure by a chelating agent.

In one embodiment the payload is a serum half-life extender, for example comprising albumin, albumin binding polypeptide, PAS, the p subunit of the C-terminal peptide (CTP) of human chorionic gonadotropin, polyethylene glycol (PEG), hydroxyethyl starch (HES), XTEN, albumin-binding small molecules, or a combination thereof.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific naturally occurring polymers include lactose, hyaluronic acid, heparan sulphate, chondroitin sulphate, alginate, cellulose amylose, dextran, glycogen or derivatives thereof.

In some embodiments, the polymer is polyethylene glycol (PEG), branched PEG, polysialic acid (PSA), hydroxyalkyl starch (HAS), hydroxyethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC). In some embodiments, the polymer is polyethylene glycol. In one embodiment of the invention, the polyethylene glycol has a molecular weight range of 300 to 10,000,000, 500 to 100,000, 1000 to 50,000, 1500 to 30,000, 2,000 to 20,000 Da, 3,000 to 5,000 Da, and 4,000 to 5,000 Da. In other embodiments, the polyethylene glycol has a molecular weight of about 1,000 Da, about 1,500 Da, about 2,000 Da, about 3,000 Da, about 4,000 Da, about 5,000 Da, about 10,000 Da, about 20,000 Da, about 30,000 Da, about 40,000 Da, about 50,000 Da or more. This may translate to 1 to 7000 PEG monomer units, for example 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000 units (defined a q elsewhere herein).

In one embodiment payload or polypeptide (the biological molecule) comprises a visualization label. Visualization labels include, without limitation, a chromophore, a fluorophore, a fluorescent protein, a phosphorescent dye, a tandem dye, a particle, a hapten, an enzyme, a radioisotope, or a combination thereof.

In one embodiment the visualization label is a visualization peptide. In some aspects, the visualization peptide enables visualization or localization of the conjugate compound in vitro, in vivo, ex vivo, or any combination thereof. In some aspects, the visualization peptide is, for example, a biotin acceptor peptide, a lipoic acid acceptor peptide, a fluorescent protein, a cysteine-containing peptide for ligation of a biarsenical dye or for conjugating metastable technetium, a peptide for conjugating europium clathrates for fluorescence resonance energy transfer (FRET)-based proximity assays, or any combination thereof. In some aspects, the fluorescent protein is, for example, green fluorescent protein (GFP), red fluorescent protein (RFP), yellow fluorescent protein (YFP), enhanced green fluorescent protein (EGFP), enhanced yellow fluorescent protein (EYFP), or any combination thereof. In some aspects, the fluorescent protein is a phycobiliprotein or a derivative thereof.

Fluorescent proteins, especially phycobiliprotein, are useful for creating tandem dye labeled labeling reagents. These tandem dyes comprise a fluorescent protein and a fluorophore for the purposes of obtaining a larger stokes shift where the emission spectra is farther shifted from the wavelength of the fluorescent protein's absorption spectra. This can be effective for detecting a low quantity of a target in a sample where the emitted fluorescent light is maximally optimized, in other words little to none of the emitted light is reabsorbed by the fluorescent protein. For this to work, the fluorescent protein and fluorophore function as an energy transfer pair where the fluorescent protein emits at the wavelength that the fluorophore absorbs at and the fluorophore then emits at a wavelength farther from the fluorescent proteins than could have been obtained with only the fluorescent protein. A functional combination can be phycobiliproteins and sulforhodamine fluorophores, or sulfonated cyanine fluorophores as known in the art. The fluorophore sometimes functions as the energy donor and the fluorescent protein is the energy acceptor.

In other aspects, the biarsenical dye is 4',5'-bis(1,3,2-dithioarsolan-2-yl)fluorescein (FlAsH). In some aspects, the biotin acceptor peptide facilitates conjugation of avidin- and streptavidin-based reagents. In some aspects, the lipoic acid acceptor peptide facilitates conjugation of thiol-reactive probes to bound lipoic acid or direct ligation of fluorescent lipoic acid analogs.

In one embodiment R1 or the polypeptide (in particular R1) comprises a fluorescent tag. In some aspects, the fluorescent tag comprises, for example, a fluorescein-type dye, a rhodamine-type dye, dansyl-type dye, a lissamine-type dye, a cyanine-type dye, a phycoerythrin-type dye, a Texas Red-type dye, or any combination thereof. Fluorophores suitable for conjugation to the cysteine-engineered antibodies or antigen-binding fragments thereof disclosed herein include, without limitation; a pyrene (including any of the corresponding derivative compounds), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds), a carbocyanine (including any corresponding compounds), a carbostyryl, a porphyrin, a salicylate, an anthranilate, an azulene, a perylene, a pyridine, a quinoline, a borapolyazaindacene (including any corresponding compounds), a xanthene (including any corresponding compounds), an oxazine (including any corresponding compounds) or a benzoxazine, a carbazine (including any corresponding compounds), a phenalenone, a coumarin (including an corresponding compounds disclosed), a benzofuran (including an corresponding compounds) and benzphenalenone (including any corresponding compounds) and derivatives thereof. As used herein, oxazines include resorufins (including any corresponding compounds), aminooxazinones, diaminooxazines, and their benzo-substituted analogs, or any combination thereof.

In certain aspects, the fluorophores include, for example, xanthene (rhodol, rhodamine, fluorescein and derivatives thereof) coumarin, cyanine, pyrene, oxazine, borapolyazaindacene, or any combination thereof. In some embodiments, such fluorophores are, for example, sulfonated xanthenes, fluorinated xanthenes, sulfonated coumarins, fluorinated coumarins, sulfonated cyanines, or any combination thereof. Also included are dyes sold under the tradenames, and generally known as, ALEXA FLUOR®, DYLIGHT®, CY DYES®, BODIPY®, OREGON GREEN®, PACIFIC BLUE®, IRDYES®, FAM®, FITC®, and ROX®.

The choice of the fluorophore attached via a linker "Z" as disclosed herein will determine the absorption and fluorescence emission properties of the final compound. Physical properties of a fluorophore label that can be used include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain aspects, the fluorophore has an absorption maximum at wavelengths greater than 480 nm. In some aspects, the fluorophore absorbs at or near 488 nm to 514 nm (particularly suitable for excitation by the output of the argon-ion laser excitation source) or near 546 nm (particularly suitable for excitation by a mercury arc lamp). In some aspects, a fluorophore can emit in the NIR (near infrared region) for tissue or whole organism applications. Other desirable properties of the fluorescent label can include cell permeability and low toxicity, for example if labeling of the antibody is to be performed in a cell or an organism (e.g., a living animal).

In one embodiment the polypeptide comprises a capture tag. In some aspects, the capture tag is biotin or a His6 tag. Biotin is useful because it can function in an enzyme system to further amplify a detectable signal, and it can also function as a tag to be used in affinity chromatography for isolation purposes. For detection purposes, an enzyme conjugate that has affinity for biotin can be used, such as avidin-HRP.

Subsequently a peroxidase substrate can be added to produce a detectable signal. In addition to biotin, other haptens can be used, including hormones, naturally occurring and synthetic drugs, pollutants, allergens, effector molecules, growth factors, chemokines, cytokines, lymphokines, amino acids, peptides, chemical intermediates, nucleotides and the like.

In one embodiment the payload comprises an enzyme. Enzymes are effective labels because amplification of the detectable signal can be obtained resulting in increased assay sensitivity. The enzyme itself often does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the measurable product, e.g., colorimetric, fluorescent or chemiluminescence. Such substrates are extensively used in the art and are known in the art.

In some embodiments, colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants and reduced dihydroxanthenes, including dihydrofluoresceins and dihydrorhodamines including dihydrorhodamine 123.

The present disclosure extends to employing peroxidase substrates that are tyramides represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

The present disclosure extends to a colorimetric (and in some cases fluorogenic) substrate and enzyme combination sometimes uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates.

The disclosure also extends to payload comprising a glycosidase, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. In some embodiments, fluorogenic substrates include resorufin beta-D-galactopyranoside, fluorescein digalactoside (FDG), fluorescein diglucuronide and their structural variants, 4-methylumbelliferyl beta-D-galactopyranoside, carboxyumbelliferyl beta-D-galactopyranoside and fluorinated coumarin beta-D-galactopyranosides.

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are useful for incorporation into molecules of the present disclosure. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally productive.

Other Definitions

Before describing the provided embodiments in detail, it is to be understood that this disclosure is not limited to specific compositions or process steps, and as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes. Where the position of amino acid residues within an antibody are referred to by number, the numbering is according to the KABAT numbering system.

The term "subject" refers to any animal (e.g., a mammal), including, but not limited to humans, non-human primates, rodents, and the like, which is to be the recipient of a particular treatment. Typically, the terms "subject" and "patient" can be used interchangeably in reference to a human subject.

The term "pharmaceutical composition" refers to a preparation which is in such form as to permit the biological activity of the active ingredient (e.g., a conjugate compound disclosed herein) to be effective, and which contains no additional components which are unacceptably toxic to a subject to which the composition would be administered. Such composition may comprise one or more pharmaceutically acceptable excipients. Such composition can be sterile.

An "effective amount" of a conjugate compound as disclosed herein is an amount sufficient to carry out a specifically stated purpose. An "effective amount" can be determined empirically and in a routine manner, in relation to the stated purpose.

The term "therapeutically effective amount" refers to an amount of conjugate compound disclosed herein or other drug effective to "treat" a disease or disorder in a subject or mammal.

The word "label" when used herein refers to a detectable compound or composition which is conjugated directly or indirectly to an engineered antibody or fragment thereof disclosed herein (e.g., a cysteine engineered antibody or fragment thereof) so as to generate a "labeled" conjugate compound. The label can be detectable by itself (e.g., radioisotope labels or fluorescent labels) or, in the case of an enzymatic label, can catalyze chemical alteration of a substrate compound or composition that is detectable.

Terms such as "treating" or "treatment" or "to treat" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for a disease or condition, for example, cancer, according to the methods of the present disclosure if the patient shows, e.g., total, partial, or transient remission of the disease or condition, for example, a certain type of cancer.

The terms "polynucleotide" and "nucleic acid" are used interchangeably herein and refer to polymers of nucleotides of any length, including DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs.

As used herein, the term "vector" refers to a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, the term "comprising" in context of the present specification should be interpreted as "including".

"Employed in the present disclosure" as used herein refers to employed in the method disclosed herein, employed in the molecules including intermediates disclosed herein or both, as appropriate to the context of the term used.

It is understood that wherever aspects are described herein with the language "comprising," otherwise analogous aspects described in terms of "consisting of" and/or "consisting essentially of" are also provided.

Any positive embodiment or combination thereof described herein may be the basis of a negative exclusion i.e. a disclaimer.

Compositions

The present disclosure extends to compositions comprising a molecule described herein (such as hydrolysed molecules of the disclosure), in particular a pharmaceutical composition (or diagnostic composition) comprising a molecule of the present disclosure and pharmaceutical excipient, diluent or carrier.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant in the context of vaccine formulation.

The disclosure also extends to processes of preparing said compositions, for example preparation of a pharmaceutical or diagnostic composition comprising adding and mixing a molecule of the present disclosure, such as hydrolysed molecule of the disclosure of the present invention together with one or more of a pharmaceutically acceptable excipient, diluent or carrier.

The antibody of the disclosure may be the sole active ingredient in the pharmaceutical or diagnostic composition or may be accompanied by other active ingredients.

The pharmaceutical compositions suitably comprise a therapeutically effective amount of a molecule according to the disclosure. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

Compositions may be administered individually to a patient or may be administered in combination (e.g. simultaneously, sequentially or separately) with other agents, drugs or hormones.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the molecule of the disclosure may be in dry form, for reconstitution before use with an appropriate sterile liquid.

Suitably in formulations according to the present disclosure, the pH of the final formulation is not similar to the value of the isoelectric point of the antibody, for example if the pH of the formulation is 7 then a pI of from 8-9 or above may be appropriate. Whilst not wishing to be bound by theory it is thought that this may ultimately provide a final formulation with improved stability, for example the antibody remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

A thorough discussion of pharmaceutically acceptable carriers is available in Remington's Pharmaceutical Sciences (Mack Publishing Company, N.J. 1991).

Treatment

The present disclosure also extends to methods of treating a patient in need thereof by administering a therapeutically effective amount of a molecule according to the present disclosure or a composition, such as pharmaceutical composition comprising the same.

In one embodiment there is provided a molecule of the present disclosure or a composition comprising same, for use in treatment, in particular for use of the treatment of a disease or condition described herein, such as cancer.

In one embodiment is provided use of a molecule of the present disclosure or a composition comprising the same in the manufacture of a medicament for treating a condition or disease described herein, such as cancer.

Thus the molecules of the present invention are useful in the treatment and/or prophylaxis of a pathological condition.

The antibodies provided by the present invention are useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, colon, lung, kidney, pancreas, stomach, bladder or bowel. Cancers tend to infiltrate into adjacent tissue and spread (metastasise) to distant organs, for example: to bone, liver, lung or the brain.

The subjects to be treated can be animals. However, in one or more embodiments the compositions are adapted for administration to human subjects.

In the context of this specification "comprising" is to be interpreted as "including".

Embodiments of the invention comprising certain features/elements are also intended to extend to alternative embodiments "consisting" or "consisting essentially" of the relevant elements/features.

Where technically appropriate, embodiments of the invention may be combined.

Technical references such as patents and applications are incorporated herein by reference.

Any embodiments specifically and explicitly recited herein may form the basis of a disclaimer either alone or in combination with one or more further embodiments.

The present invention is further described by way of illustration only in the following examples, which refer to the accompanying Figures, in which:

ACRONYMS

NNAA Non-natural amino acid
DAR Drug:antibody ratio, also used generally to describe the ratio for any conjugated species such as linkers.

BRIEF SUMMARY OF THE FIGURES

FIG. 1.1. Shows intact deglycosylated mass spectrometry before (A) and after (B) reaction of mAb with furan-NHS.

FIG. 1.2. Shows reduced deglycosylated mass spectra of mAb-furan-linker samples after 20 h reaction with MMAEs.

FIG. 1.3. Shows reduced deglycosylated mass spectrometry analysis of mAb-furan-linker alloc lysine reaction product.

FIG. 2.1. General design of cyclopentadiene crosslinkers (A) and cyclopentadiene NNAA (B) described in example 2.

FIG. 3.1. Shows intact deglycosylated mass spectrometry before (A) and after (B) reaction of mAb with CP1-NHS.

FIG. 3.2. Shows reduced glycosylated mass spectra of mAb-CP1-linker maleimido MMAE reaction products zoomed to show both heavy and light mAb chains.

FIG. 3.3. Shows reduced declycosylated mass spectra of mAb-CP1-linker maleimido MMAE reaction products zoomed in to show the mAb heavy chain region.

FIG. 3.4. Shows reduced deglycosylated mass spectrometry analysis of mAb-CP1-linker alloc lysine reaction product, indicating no conjugation occurred.

FIG. 4.1. Shows intact deglycosylated mass spectrometry before (A) and after (B) reaction of mAb with CP1-NHS.

FIG. 4.2. Shows reduced deglycosylated mass spectra of unmodified mAb, mAb-CP1-linker (denoted as mAb-CP1 within figure) and AM-MMAE-reacted mAb-CP1-linker (denoted as mAb-CP1 AM-MMAE within figure) at 15 min and 2.5 h.

FIG. 4.3. Reaction of mAb-CP1-linker with maleimido-MMAEs. Unreacted CP1diene was determined from the peak intensities of reduced deglycosylated mass spectra.

FIG. 5.1. Shows intact deglycosylated mass spectrometry before (A) and after (B) reaction of mAb with CP1-NHS.

FIG. 5.2. Shows reduced deglycosylated mass spectra of unmodified mAb, CP-1 modified mAb and PM-MMAE-reacted CP1-mAb-linker at 5 min and 150 min.

FIG. 5.3. Shows reaction of mAb-CP1-linker with maleimido-MMAEs. A) Molar concentration of unreacted CP1 diene over time. Unreacted CP1 diene per mAb was determined from the peak intensities of reduced deglycosylated mass spectra. B) Inverse concentration plot used to calculate reaction rates.

FIG. 6.1. Shows titers of 12G3H11 K274CP1-NNAA mAb after expression in mammalian cells comprising mutant or wt TRS. CP1-NNAA final concentration in media and feeding time was varied as indicated on the x-axis.

FIG. 6.2. Shows reduced glycosylated mass spectrometry analysis of 12G3H11 K274CP1-NNAA mAb. A) Mass range showing mAb light chain (LC) and heavy chain (HC). B) Zoomed spectrum showing mAb heavy chain only.

FIG. 6.3. Shows SEC analysis of 12G3H11 K274CP1-NNAA mAb indicating that monomeric product was obtained. High molecular weight solids (HMWS) are indicated.

FIG. 6.4. Shows analysis of 1 C1 K274CP1-NNAA mAb by SDS-PAGE.

FIG. 6.5. Shows reduced deglycosylated mass spectrometry analysis of 12G3H11 K274CP1-NNAA mAb-MMAE conjugation products.

FIG. 6.6. Shows reduced glycosylated mass spectrometry analysis of 1C1 K274CP1-NNAA mAb-AM-MMAE conjugation product.

FIG. 6.7. Shows chemical structure of CP1-NNAA and compound isomers, which exist as a 1:1 ratio.

FIG. 6.8. Shows chemical structure of compound 50, a furan analogue of CP1-NNAA described in the literature. This compound was used as a control for expression studies with 12G3H11 mAb.

FIG. 6.9. Shows reduced deglycosylated mass spectrometry analysis of 12G3H11 K274CP1-NNAA mAb-MMAE conjugation products. A) unreacted antibody, B) AM-MMAE reaction product, C) PM-MMAE reaction product. Spectra are zoomed to show both antibody heavy and light chains.

FIG. 6.10. Shows reduced glycosylated mass spectrometry analysis of 1C1 K274CP1-NNAA mAb-AM-MMAE conjugation product. A) unreacted antibody, B) AM-MMAE reaction product. Spectra are zoomed to show both antibody heavy and light chains and also high molecular weight species.

FIG. 7.1. Shows rat serum stability of 12G3H11 K274CP1-NNAA AM-MMAE ADC. ADC was incubated in rat serum at 37° C. for 7 days and recovered by immunocapture prior to reduced mass spectrometry analysis. Spectra are zoomed to show details in the heavy chain (HC) mass region. No significant deconjugation was observed.

FIG. 7.2. Shows rat serum stability of 12G3H11 K274CP1-NNAA PM-MMAE ADC. ADC was incubated in rat serum at 37° C. for 7 days and recovered by immunocapture prior to reduced mass spectrometry analysis. Spectra are zoomed to show details in the heavy chain (HC) mass region. No significant deconjugation was observed, however linker cleavage was observed at the phenyl acetamide group. See appendix 7 for description of the cleavage product.

FIG. 7.3. Shows mouse serum stability of 12G3H11 K274CP1-NNAA AM-MMAE ADC. ADC was incubated in mouse serum at 37° C. for 7 days and recovered by immunocapture prior to reduced mass spectrometry analysis. Spectra are zoomed to show details in the heavy chain (HC) mass region. No significant deconjugation was observed, however nearly complete linker cleavage was observed at the val-cit dipeptide. See appendix 7 for description of the cleavage product.

FIG. 7.4. Shows mouse serum stability of 12G3H11 K274CP1-NNAA PM-MMAE ADC. ADC was incubated in mouse serum at 37° C. for 7 days and recovered by immunocapture prior to reduced mass spectrometry analysis. Spectra are zoomed to show details in the heavy chain (HC) mass region. No significant deconjugation was observed, however nearly complete linker cleavage was observed. See appendix 7 for description of the cleavage products.

FIG. 7.5. Shows the chemical structures of MMAE payloads and their molecular weight.

FIG. 7.6. Shows chemical structures of predominant cleavage products observed following incubation of ADCs in mouse serum. A) and B) show the species remaining on the antibody (CP1-maleimide linkage not shown) for AM-MMAE and PM-MMAE conjugates, respectively. C) Shows the species liberated after val-cit dipeptide cleavage.

FIG. 7.7. Shows the chemical structure of PM-MMAE cleavage products following rat serum incubation. A) species remaining on the antibody and B) liberated species.

FIG. 8.1. General design of spirocyclopentadiene crosslinkers (A) and spirocyclopentadiene NNAA (B) described in example 8.

FIG. 9.1. Shows intact deglycosylated mass spectra before (A) and after (B) reaction with CP2-NHS. Numbers below peaks in (B) indicate the number of CP2-linker groups introduced into the mAb. Estimation of CP2-linker introduction by peak intensities yields 3.29 CP2-linkers per mAb.

FIG. 9.2. Shows reduced deglycosylated mass spectrometry analysis of mAb-CP2-linker before and after reaction with AM-MMAE and PM-MMAE. Spectra are zoomed to show both heavy and light chains.

FIG. 9.3. Shows reduced deglycosylated mass spectra of mAb-CP2-linker maleimido MMAE reaction products. Spectra are zoomed to the antibody heavy chain.

FIG. 10.1. Shows a reduced deglycosylated mass spectra of mAb-CP2-linker and AM-MMAE-reacted mAb-CP2-linker at 4 h and 48 h. Spectra are zoomed in to show the heavy chain only.

FIG. 10.2. Shows a reduced deglycosylated mass spectra of mAb-CP2-linker and PM-MMAE-reacted mAb-CP2-linker at 4 h and 48 h. Spectra are zoomed in to show the heavy chain only.

FIG. 10.3. Shows reaction of mAb-CP2-linker with maleimido-MMAEs. A) Molar concentration of unreacted CP2 diene over time. Unreacted CP2 diene per mAb was determined from the peak intensities of reduced deglycosylated mass spectra. B) Inverse concentration plot used to calculate reaction rates.

FIG. 11.1. Shows titers and cell viability of 12G3H11 K274CP2-NNAA mAb after expression in mammalian cells comprising mutant or wild type tRS.

FIG. 11.2. Shows deglycosylated mass spectra of 1C1 K274CP2-NNAA mAb.

FIG. 11.3. Shows deglycosylated mass spectrometry analysis of 1C1 S239CP2-NNAA mAb.

FIG. 11.4. Shows deglycosylated mass spectrometry analysis of 1C1 wild-type mAb.

FIG. 11.5. Shows SEC analysis of 1C1 K274CP2-NNAA mAb indicating that monomeric product was obtained.

FIG. 11.6. Shows SEC analysis of 1C1 S239CP2-NNAA mAb indicating that monomeric product was obtained.

FIG. 11.7. Shows analysis of 1C1-K274CP2-NNAA mAb and 1C1-S239CP2-NNAA mAb by SDS-PAGE.

FIG. 12.1. Shows general scheme for generation of mAb-CP2-NNAA ADCs and 239C-mAb ADCs.

FIG. 12.2. Shows reduced, glycosylated mass spectrometry analysis of mAb-CP2-NNAA and mAb-cysteine molecules before and after reaction with AM-MMAE. Spectra are zoomed in to show the mAb heavy chain.

FIG. 12.3. Shows reduced, glycosylated mass spectrometry analysis of mAb-CP2-NNAAs and mAb-cysteine molecules before and after reaction with AM-MMAE. Spectra are zoomed in to show the mAb light chain.

FIG. 12.4. Shows hydrophobic interaction chromatography analysis of mAb-CP2-NNAA ADCs and mAb-cysteine ADCs.

FIG. 12.5. Shows reduced reverse-phase high-performance chromaography analysis of mAb-CP2-NNAA ADCs and mAb-cysteine ADCs.

FIG. 12.6. Shows reduced SDS-PAGE analysis of mAb-CP2-NNAA ADCs and mAb-cysteine ADCs.

FIG. 12.7. Shows reduced, deglycosylated mass spectrometry analysis of mAb-CP2-NNAA ADCs before and after incubation in rat serum for 7 days at 37° C. Mass spectra are zoomed to show the heavy chain (HC) only.

FIG. 12.8. Shows quantification of mAb-CP2-NNAA ADC DARs before and after incubation in rat serum for 7 d at 37° C. DARs were calculated from the peak heights of mass spectra shown in FIG. 12.7. Values are reported as the mean±standard deviation, n=3.

FIG. 12.9. Shows cytotoxicity of mAb-CP2-NNAA and mAb-cysteine ADCs towards PC3 cancer cells in vitro.

FIG. 13.1. Shows ester positions in A) CP1-NHS and B) CP1b-NHS linkers.

FIG. 14.1. Shows mass spectrometry analysis of mAb-CP1b conjugates. Numbers above peaks indicate the number of linkers (B and E) or AM-MMAEs (C and F) conjugated to the mAb. All samples were deglycosylated with EndoS prior to analysis.

FIG. 14.2. Shows mass spectrometry analysis of mAb-F2 conjugates. Numbers above peaks indicate the number of linkers (B and E) or AM-MMAEs (C and F) conjugated to the mAb. All samples were deglycosylated with EndoS prior to analysis.

FIG. 14.3. Shows mass spectrometry analysis of mAb-cysteine conjugates. mAb light chain (LC) and heavy chain (HC) are indicated (A-D), as well as the number of MMAEs conjugated (B and D). All samples were deglycosylated with EndoS and reduced prior to analysis.

FIG. 14.4. Shows rRP-HPLC analysis of mAbs, mAb-linker conjugates and ADCs. mAb light chain and heavy chains are indicated, number of MMAEs conjugated to mAbs are also indicated for ADC samples.

FIG. 14.5. Shows SEC analysis of mAbs, mAb-linker conjugates and ADCs. High molecular weight species (HMWS) are indicated.

FIG. 14.6. Shows drug retention on ADCs following incubation in rat serum for 7 d.

FIG. 14.7. Shows in vitro activity of ADCs towards receptor-positive A) NCI-N87 cells and B) SKBR3 cells.

FIG. 14.8. Shows antitumor activity of Herceptin-linker ADCs towards subcutaneous N87 xenograft tumor models in mice.

FIG. 15.1. Shows SDS-PAGE analysis of 1C1 K274CP1-NNAA AZ1508 ADC. A) nonreduced B) reduced.

FIG. 15.2. Shows Reduced glycosylated mass spectrometry analysis of 1C1 K274CP1-NNAA mAb AZ1508 conjugation product. A) Unreacted mAb B) AZ1508 reaction product. Spectra are zoomed to show both antibody heavy chain (HC) and light (LC) chain.

FIG. 15.3. Shows SEC analysis of 1C1 K274CP1-NNAA AZ1508 ADC indicating that high monomeric product was obtained. High molecular weight solids (HMWS) are indicated.

FIG. 16.1. Shows SDS-PAGE analysis of 1C1 CP2-NNAA AZ1508 ADCs and 1C1 cysteine AZ1508 ADCs. A) Non-reduced samples, B) reduced samples.

FIG. 16.2. Shows analytical data for analysis of 1C1 S239CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.3. Shows analytical data for analysis of 1C1 K274CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.4. Shows analytical data for analysis of 1C1 $N_{297}$CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.5. Shows analytical data for analysis of 1C1 S239C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.6. Shows analytical data for analysis of 1C1 K274C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.7. Shows analytical data for analysis of 1C1 N297C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 17.1. Shows representative reduced, glycosylated mass spectra of 1C1 CP2-NNAA ADCs and 1C1 cysteine-AZ1508 ADCs before and after incubation in rat serum. (A) Position S239, (B) Position K274, (C) Position N297. Unconjugated and conjugated species are indicated.

FIG. 17.2. Shows quantification of AZ1508 remaining attached to CP2-NNAA or cysteine-engineered antibodies after incubation in rat serum for 7 d at 37° C. Drug:antibody ratios (DAR) were calculated from reduced glycosylated mass spectra. Data represent the average f standard deviation, n=3.

FIG. 17.3. Shows quantification of AZ1508 remaining attached to CP2-NNAA or cysteine-engineered antibodies after incubation in mouse serum for 7 d at 37° C. Drug:antibody ratios (DAR) were calculated from reduced glycosylated mass spectra. Deacetylated AZ1508 was considered a conjugated species for the analysis. Data represent the average±standard deviation, n=3.

FIG. 18.1. Shows conjugation kinetics of 1C1 CP1-NNAA and 1C1 CP2-NNAA mAbs with AZ1508 measured by reduced glycolsylated mass spectrometry. Data is plotted as the average±absolute error, n=2 1C1 K274CP1-NNAA, 1C1 K274CP2-NNAA, and 1C1 N297CP2-NNAA, and average±standard deviation n=3 for 1C1 S239CP2-NNAA.

FIG. 18.2. Shows inverse concentration plot showing consumption of diene upon reaction of CP1-NNAA and CP2-NNAA mAbs with AZ1508. (A) 1C1 K274CP1-NNAA, (B) 1C1 S239CP2, 1C1 K274CP2-NNAA, and N297CP2-NNAA mAbs. Data is plotted as the average f absolute error, n=2 1C1 K274CP1-NNAA, 1C1 K274CP2-NNAA, and 1C1 N297CP2-NNAA, and average f standard deviation n=3 for 1C1 S239CP2-NNAA.

FIG. 19.1. Shows antitumor activity of 1C1 CP2-NNAA AZ1508 ADCs against PC3 xenograft tumor models in mice.

FIG. 20.1. Shows dynamic light scattering analysis (DLS) of 60 nm maleimide-functionalized gold nanoparticles before and after incubation with 1C1 wild-type (WT) or 1C1 K274CP1-NNAA antibodies (CP1-NNAA mAb) for 2 h at 25° C.

EXAMPLES

Example 1. Furan-Maleimide Reaction for Generation of ADCs

The furan-maleimide reaction was evaluated as a conjugation modality to generate ADCs. Furan-NHS was provided by SynChem, Inc. at 90% purity.

Introduction of furan functionality onto mAbs: Furan diene functionality was installed onto IgG1 mAbs by reaction of lysine primary amines with an NHS-ester activated furan linker. This approach resulted in randomly conjugated, amide-linked furan groups with the modified mAb termed mAb-furan linker. Note that mAb-furan-linker may be denoted as mAb-furan in certain figures, see figure caption for clarification. Mab solution was adjusted to 5 mg/mL (3 mL, 15 mg mAb, 0.1 µmol, 1 eq.) with PBS pH 7.2 followed by addition of 10% v/v 1 M NaHCO₃. This solution was chilled on ice and 30 µL furan-NHS (10 mM stock in DMAc, 0.3 µmol, 3 eq.) was added. The reaction proceeded on ice for 5 minutes and then room temperature for 1 h with continuous mixing. Reaction progress was monitored by mass spectrometry and furan-NHS was added in 30 µL portions until a degree of conjugation of ~2 furans/mAb was achieved. In total, 3 additions of furan-NHS were performed with a total volume of 90 µL (0.9 µmol, 9 eq) added. Reacted mAb was purified by dialysis (Slide-A-Lyzer, 10 kDa MWCO) against PBS, 1 mM EDTA, pH 7.4, 0° C. for 24 h.

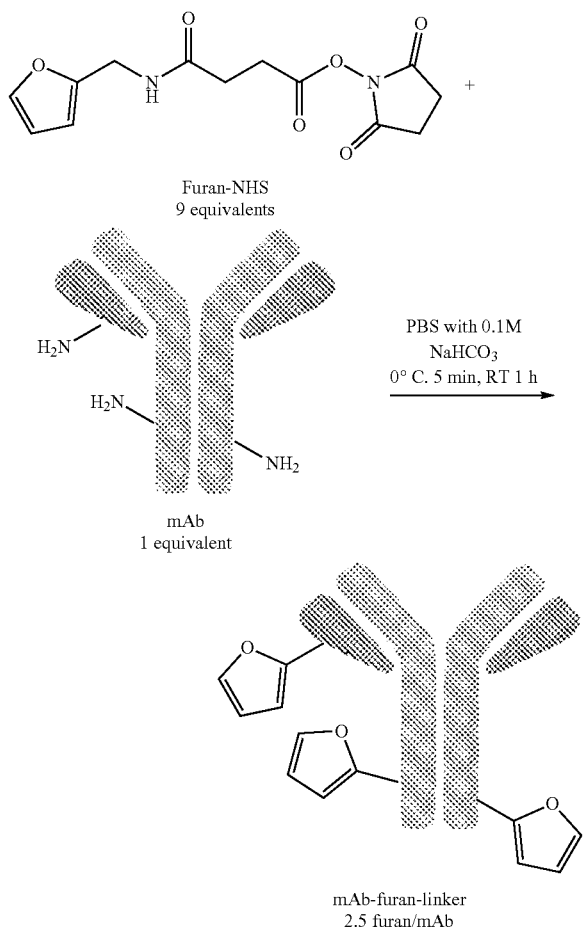

Scheme 1.1. Introduction of furan functionality onto mAbs.

Reaction of furan-modified mAb with maleimido-MMAEs: MMAE ADC payloads were installed onto mAb-furan-linker through Diels-Alder 4+2 cycloaddition coupling of furan groups to either alkyl- or phenyl-maleimide groups contained on MMAE. First, mAb-furan-linker solution (286 µL, 3.5 mg/mL, 6.7 nmol, 1 eq) was combined with 10% v/v NaH₂PO₄ and 20% v/v DMSO. Next, AM-MMAE or PM-MMAE solution (10 μL of a 10 mM stock solution in DMAc, 100 nmol, 15 eq.) was added to the antibody solution. The reaction mixture was capped under ambient atmosphere and the reaction proceeded at 37° C. for 20 h with mixing. After the 20 h reaction period was complete N-acetyl cysteine (8 μL of a 100 mM solution, 8 equivalents) was added and the solution was further incubated at room temperature for 15 minutes to quench maleimide groups. After quenching, conjugates were purified using PD Spin-trap G-25 devices (GE Healthcare Life Sciences) prior to analysis by deglycosylated mass spectrometry as described below. Alloc-lysine was reacted with furan-linker modified mAb as described above using a 200 mM stock solution in 75 mM NaOH (10 PL, 2 μmol, 300 equiv.).

Scheme 1.2.

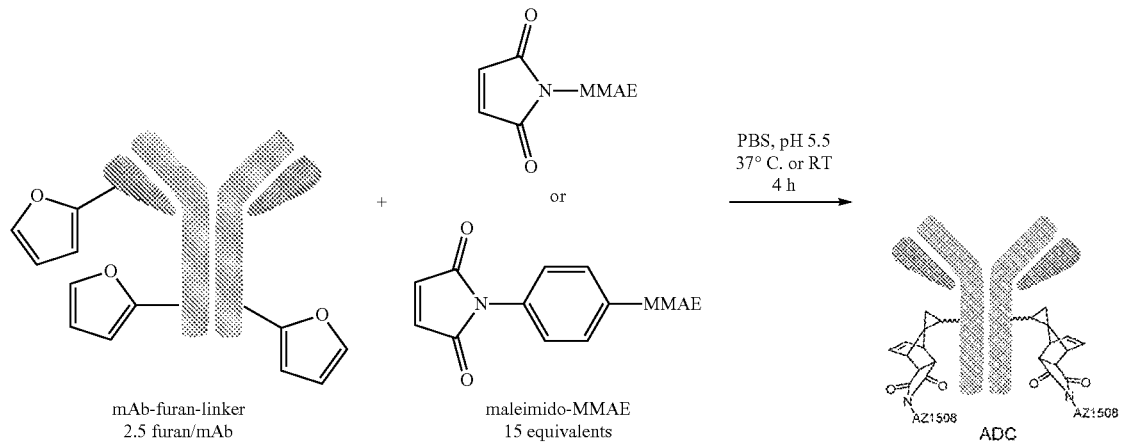

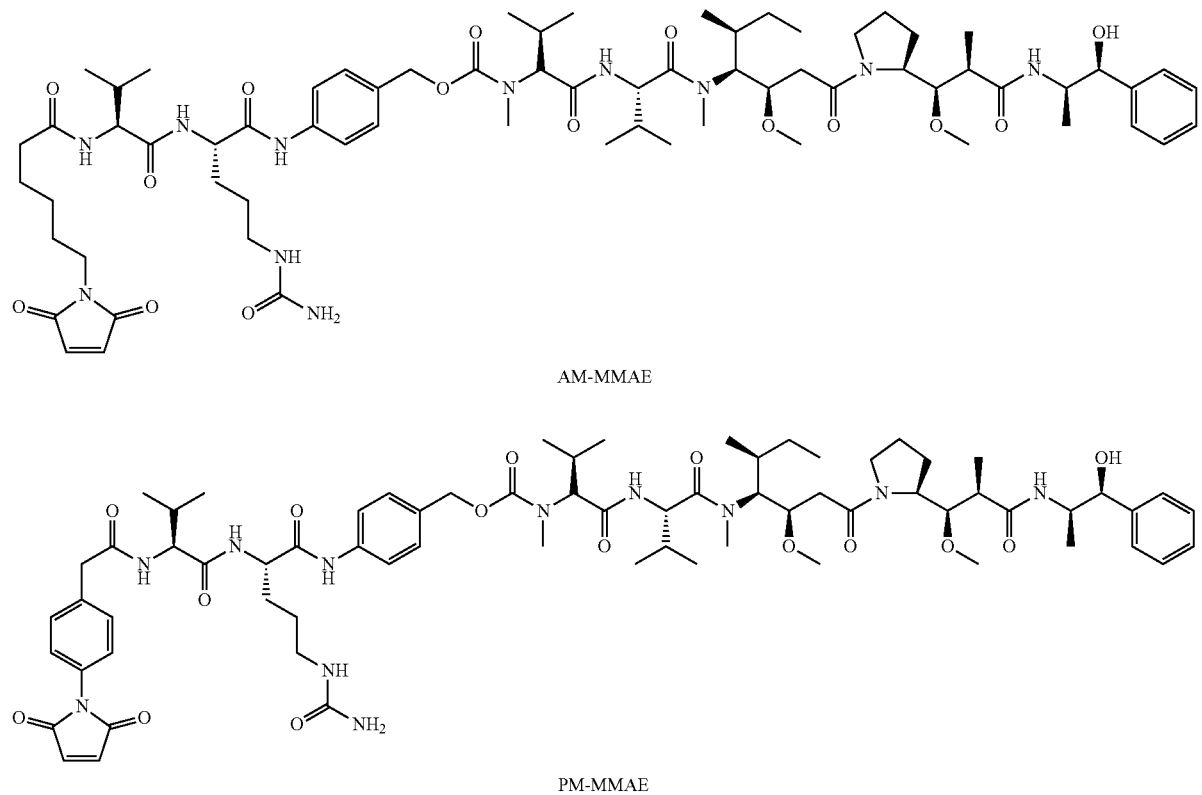

A) Reaction of mAb-furan-linker with maleimido-MMAEs, B) Chemical structure of AM-MMAE and PM-MMAE.

Mass spectrometry analysis: First, mAbs or mAb conjugates were deglycosylated with EndoS (New England BioLabs) by combining 50 μL sample (1 mg/mL mAb) with 5 μL glyco buffer 1 (New England BioLabs) and 5 μL Remove-iT EndoS (1:10 dilution in PBS, 20,000 units/mL, New England BioLabs) followed by incubation for 1 h at 37° C. Reduced samples were prepared by addition of 5 μL Bond-Breaker TCEP solution (0.5 M, Thermo Fisher Scientific) and incubation for 10 min at 37° C. Mass spectrometry analysis was performed using an Agilent 6520B Q-TOF mass spectrometer equipped with a RP-HPLC column (ZORBAX 300 Diphenyl RRHD, 1.8 micron, 2.1 mm×50 mm). High-performance liquid chromatography (HPLC) parameters were as follows: flow rate, 0.5 ml/min; mobile phase A was 0.1% (v/v) formic acid in HPLC-grade $H_2O$, and mobile phase B was 0.1% (v/v) formic acid in acetonitrile. The column was equilibrated in 90% A/10% B, which was also used to desalt the mAb samples, followed by elution in 20% A/80% B. Mass spec data were collected for 100-3000 m/z, positive polarity, a gas temperature of 350° C., a nebulizer pressure of 48 $lb/in^2$, and a capillary voltage of 5,000 V. Data were analyzed using vendor-supplied (Agilent v.B.04.00) MassHunter Qualitative Analysis software and peak intensities from deconvoluted spectra were used to derive the relative proportion of species in each sample.

FIG. 1.1. Intact deglycosylated mass spectrometry before (A) and after (B) reaction of mAb with furan-NHS.

FIG. 1.2. Reduced deglycosylated mass spectra of mAb-furan-linker samples after 20 h reaction with MMAEs. Spectra are zoomed in to show the mass region of mAb heavy chain only. Similar results were observed for mAb light chains. MMAE was observed to add to mAb heavy chain with and without furan, indicating non-specific conjugation.

TABLE 1.1

Summary of mAb-furan-linker reactions at 37° C. for 20 hours

| payload | Equiv*. | pH | [mAb] mg/mL | furan/ mAb | total conjugation to mAb (%) | non-specific conjugation to mAb (%) | specific conjugation to furan (%) |
|---|---|---|---|---|---|---|---|
| AM-MMAE | 15 | 5.5 | 3.5 | 2.5 | 2.4 | 1.1 | 1.3 |
| PM-MMAE | 15 | 5.5 | 3.5 | 2.5 | 16.6 | 12.0 | 4.0 |
| alloc-lysine | 300 | 5.5 | 3.5 | 2.5 | 0 | 0 | 0 |

*(rel to mAb)

FIG. 1.3. Reduced deglycosylated mass spectrometry analysis of mAb-furan linker alloc lysine reaction product. No peaks corresponding to the expected mass of the conjugate were observed. The structure of alloc-lysine is shown below the graph.

Introduction of furan functionality into an antibody was achieved using an amine-reactive furan-NHS molecule. The degree of furan functionality was controlled by the amount of furan-NHS used in the mAb modification reaction. More or less furan could be achieved by adjusting the molar feed ratio accordingly. Reaction of mAb-furan-linker with maleimido-MMAEs was inefficient and non-specific. Neither alkyl- or phenyl-maleimide payloads achieved over 5% specific conjugation, even after 20 h reaction time at 37° C. Non-specific reaction to mAb (presumably through Michael-addition to amines) was 12 times higher for PM-MMAE compared to AM-MMAE, indicating the higher reactivity of this maleimide group. Furthermore, non-specific reaction (presumably to amines) appeared to be higher than specific reaction to furans by ~4-fold for PM-maleimide MMAE payload. Furan-maleimide coupling is not amenable for production of ADCs.

Example 2. Synthesis of Cyclopentadiene (CP1)-Containing Compounds

Crosslinkers and non-natural amino acids (NNAAs) were prepared based on the general design shown in FIG. 2.1.

Materials and Methods: Unless stated otherwise, reactions were conducted under an atmosphere of $N_2$ using reagent grade solvents. DCM, and toluene were stored over 3 Å molecular sieves. THF was passed over a column of activated alumina. All commercially obtained reagents were used as received. Thin-layer chromatography (TLC) was conducted with E. Merck silica gel 60 F254 pre-coated plates (0.25 mm) and visualized by exposure to UV light (254 nm) or stained with p-anisaldehyde, ninhydrin, or potassium permanganate. Flash column chromatography was performed using normal phase silica gel (60 Å, 0.040-0.063 mm, Geduran). $^1$H NMR spectra were recorded on Varian spectrometers (400, 500, or 600 MHz) and are reported relative to deuterated solvent signals. Data for $^1$H NMR spectra are reported as follows: chemical shift (δ ppm), multiplicity, coupling constant (Hz) and integration. $^{13}$C NMR spectra were recorded on Varian Spectrometers (100, 125, or 150 MHz). Data for $^{13}$C NMR spectra are reported in terms of chemical shift (δ ppm). Mass spectra were obtained from the UC Santa Barbara Mass Spectrometry Facility on a (Waters Corp.) GCT Premier high-resolution time-of-flight mass spectrometer with a field desorption (FD) source.

Synthesis of CP1-NNAA (4)

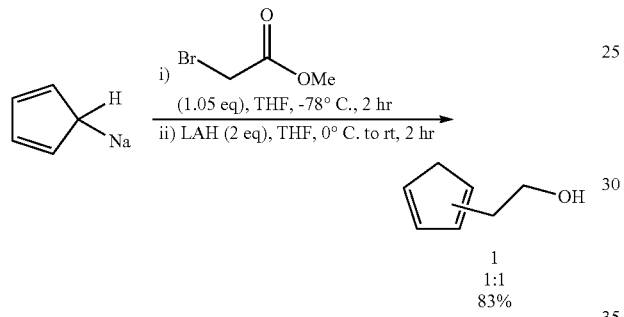

2-(Cyclopentadienyl)ethanol Isomers (1)

Methyl bromoacetate (6.0 mL, 63 mmol, 1.05 eq) was added to THF (60 mL) and cooled to −78° C. Sodium cyclopentadienide (2 M solution in THF, 30 mL, 60 mmol, 1 eq) was added dropwise over 10 min. The reaction was stirred at −78° C. for 2 hr. The reaction was quenched with H$_2$O (6 mL) and silica gel (6 g) and allowed to warm to rt. The reaction mixture was filtered through a plug of silica then rinsed with DCM (100 mL). The organic layers were combined and the solvent removed to yield methyl 2-(cyclopentadienyl)acetate isomers (1:1) as a brown oil, which was used directly in the next step.

LAH (4.55 g, 120. mmol, 2 eq) was added to THF (300 mL) and cooled to 0° C. Crude methyl 2-(cyclopentadienyl)acetate (60 mmol) dissolved in THF (10 mL) was added dropwise in 4 portions over 1 hr. The reaction was allowed to warm to rt and stirred until consumption of starting material (TLC, 2 hr). The reaction was cooled to 0° C. and slowly quenched with H$_2$O (10 mL) dropwise then NaOH (4 M in H$_2$O, 5 mL). H$_2$O (20 mL) was added, the mixture filtered, and rinsed with Et$_2$O (100 mL). The filtrates were combined and the solvent removed. The residue was suspended in brine (100 mL) and extracted with Et$_2$O (3×100 mL). The organic layers were combined, washed with brine (100 mL), dried over MgSO$_4$, filtered, and the solvent removed. The residue was filtered through a plug of silica (Hexane:EtOAc, 2:1) and the solvent removed to yield 1 (5.45 g, 83%) as an amber oil. To prevent dimerization, 1 should be stored frozen in a benzene matrix.

Rf (Hexane:EtOAc, 4:1): 0.11; $^1$H NMR (400 MHz, CDCl$_3$) δ 6.50-6.13 (m, 3H), 3.81 (td, J=6.3, 10.1 Hz, 2H), 3.01 (d, J=1.6 Hz, 1H), 2.95 (d, J=1.6 Hz, 1H), 2.70 (dt, J=1.2, 6.5 Hz, 1H), 2.66 (dt, J=1.4, 6.4 Hz, 1H), 1.52 (s, 1H) ppm.

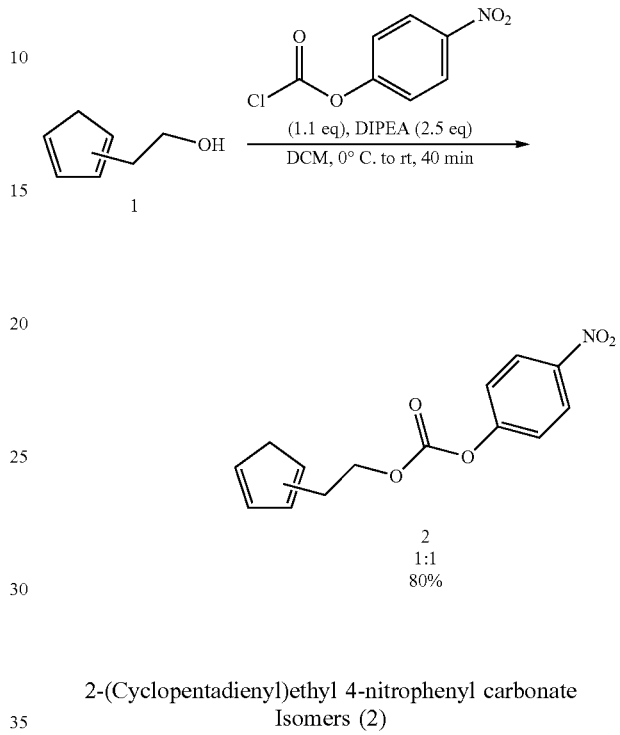

2-(Cyclopentadienyl)ethyl 4-nitrophenyl carbonate Isomers (2)

2 (2.86 g, 26.0 mmol, 1 eq) was added to DCM (100 mL) and cooled to 0° C. Pyridine (5.2 mL, 65 mmol, 2.5 eq) was added followed by 4-nitrophenyl chloroformate (5.76 g, 28.6 mmol, 1.1 eq) in 2 portions over 10 min. The ice bath was removed and the reaction was stirred until consumption of the starting material (TLC, 40 min). The reaction was poured into a separatory funnel and washed with a saturated NH4Cl in H$_2$O (100 mL). The aqueous layer was extracted with DCM (100 mL). The organic layers were combined, washed with brine (50 mL), dried over Na$_2$SO$_4$, filtered, and the solvent removed. The residue was subjected to flash column chromatography (Hexane:EtOAc, 6:1) to yield 2 (5.69 g, 80%) as a yellow oil that solidifies in the freezer.

Rf (Hexane:EtOAc, 4:1): 0.43; $^1$H NMR (400 MHz, CDCl$_3$) δ 8.34-8.24 (m, 2H), 7.40-7.34 (m, 2H), 6.56-6.13 (m, 3H), 4.47 (td, J=6.8, 10.2 Hz, 2H), 3.02 (d, J=0.8 Hz, 1H), 2.98 (d, J=1.2 Hz, 1H), 2.88 (dtd, J=1.0, 6.9, 16.1 Hz, 2H) ppm.

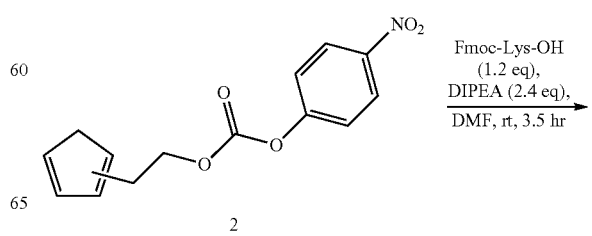

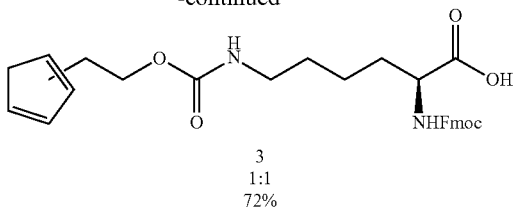

3
1:1
72%

Fmoc-Lys(2-(cyclopentadienyl)ethyl formate)-OH Isomers (3)

2 (3.60 g, 13.1 mmol, 1 eq) was added to DMF (30 mL), followed by Fmoc-Lys-OH (5.78 g, 15.7 mmol, 1.2 eq) and DIPEA (5.4 mL, 32 mmol, 2.4 eq). The reaction was stirred until consumption of the starting material (NMR, 3.5 hr), then poured into EtOAc (100 mL) and H$_2$O (140 mL). The aqueous layer was acidified with HCl (1 M, 60 mL), poured a separatory funnel, and the layers separated. The aqueous layer was extracted with EtOAc (2×100 mL). The organic layers were combined, washed with brine (100 mL), dried over Na$_2$SO$_4$, filtered, and the solvent removed. The residue was subjected to flash column chromatography (Hexane: EtOAc, 3:1 then DCM:MeOH:AcOH, 89:10:1) to yield 3 (4.73 g, 72%) as a white foam.

Rf (DCM:MeOH:AcOH, 89:10:1): 0.50; $^1$H NMR (400 MHz, CDCl$_3$) δ 7.76 (d, J=7.4 Hz, 2H), 7.66-7.56 (m, 2H), 7.39 (t, J=7.4 Hz, 2H), 7.31 (t, J=7.2 Hz, 2H), 6.57-5.96 (m, 3H), 5.85-5.54 (m, 1H), 4.84-4.11 (m, 7H), 3.27-2.61 (m, 6H), 1.99-1.11 (m, 6H) ppm.

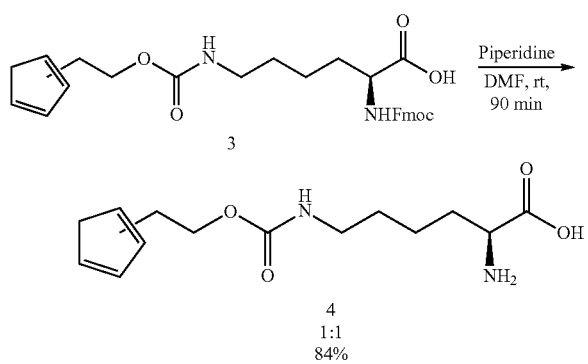

CP1-NNAA (4)

3 (4.61 g, 9.13 mmol, 1 eq) was added to DMF (130 mL), followed by piperidine (14.4 mL). The reaction was stirred until consumption of the starting material (TLC, 90 min), then the solvent was removed. Et$_2$O (100 mL) was added to the residue, and the suspension was sonicated for 5 min. The suspension was filtered and rinsed with Et$_2$O (100 mL). The solid was suspended in MeOH (10 mL), stirred for 10 min, Et$_2$O (40 mL) was added, the suspension filtered and rinsed with Et$_{20}$ (50 mL). The compound was dried under vacuum to yield 4 (2.15 g, 84%) as a tan powder.

$^1$H NMR (400 MHz, Methanol-d4+one drop TFA) δ 6.53-6.07 (m, 3H), 4.29-4.11 (m, 2H), 3.96 (t, J=6.3 Hz, 1H), 3.11 (t, J=1.0 Hz, 2H), 3.01-2.62 (m, 3H), 2.02-1.81 (m, 2H), 1.62-1.35 (m, 4H) ppm; MS (FD) Exact mass cald. for C$_{14}$H$_{22}$N$_2$O$_4$ [M+H]$^+$: 283.17, found: 283.19.

Synthesis of CP1-NHS (6)

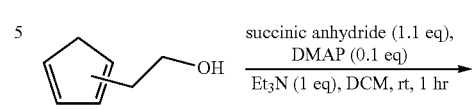

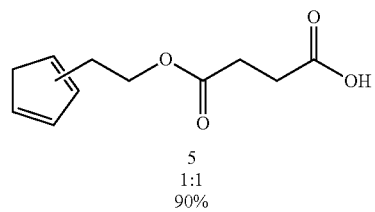

5
1:1
90%

4-(2-(Cyclopentadienyl)ethoxy)-4-oxobutanoic acid Isomers (5)

DCM (1.5 mL) was added to a vial containing 1 (0.33 g, 3.0 mmol, 1 eq). Et$_3$N (0.42 mL, 3.0 mmol, 1 eq), DMAP (37 mg, 0.30 mmol, 0.1 eq) and succinic anhydride (0.33 g, 3.3 mmol, 1.1 eq) were added, the reaction capped under an atmosphere of air, and stirred at rt until consumption of the starting material (TLC, 60 min). The reaction mixture was poured into a separatory funnel with DCM (50 mL) and extracted with aqueous HCl (1 M, 50 mL) then H$_2$O (50 mL). The organic layer was dried over MgSO$_4$, filtered, and the solvent removed to yield 5 (0.57 g, 90%) as a tan powder.

Rf (EtOAc): 0.67; $^1$H NMR (400 MHz, CDCl$_3$) δ 11.49 (br. s., 1H), 6.49-6.05 (m, 3H), 4.27 (td, J=7.0, 9.0 Hz, 2H), 2.94 (d, J=17.6 Hz, 2H), 2.80-2.56 (m, 6H) ppm.

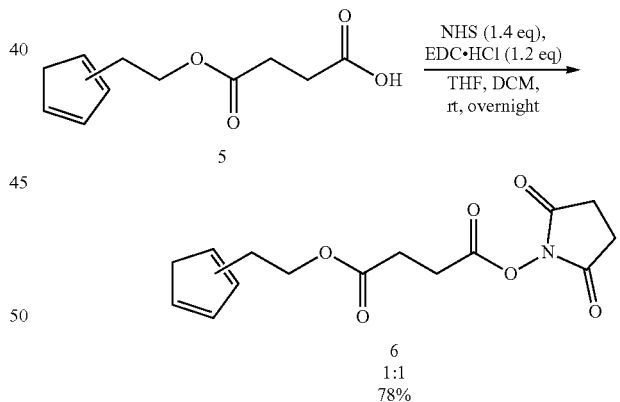

CP1-NHS (6)

THF (10 mL) was added to a vial containing 5 (0.42 g, 2.0 mmol, 1 eq). NHS (0.32 g, 2.8 mmol, 1.4 eq), EDC-HCl (0.46 g, 2.4 mmol, 1.2 eq) and DCM (5 mL) were added, the reaction capped under an atmosphere of air, and stirred at rt overnight. The solvent was removed and the residue was subjected to flash column chromatography (Hexane:EtOAc, 1:1) to yield 6 (0.48 g, 78%) as a clear, viscous oil. CP1-NHS is referred to as CP1-linker after conjugation to antibodies.

Rf (Hexane:EtOAc, 1:1): 0.38; $^1$H NMR (400 MHz, CDCl$_3$) δ 6.49-6.40 (m, 3H), 6.31 (dd, J=1.2, 5.1 Hz, 1H), 6.25 (td, J=1.5, 2.8 Hz, 1H), 6.11 (td, J=1.8, 3.0 Hz, 1H), 4.30 (td, J=7.0, 9.0 Hz, 4H), 3.00-2.90 (m, 8H), 2.85 (br. s., 8H), 2.80-2.68 (m, 8H); $^{13}$C NMR (125 MHz, CDCl$_3$) δ 170.8, 170.8, 168.9, 168.8, 167.6, 167.6, 144.3, 142.3, 134.2, 134.1, 132.3, 131.4, 128.4, 128.0, 64.5, 64.2, 43.5, 41.4, 29.7, 29.0, 28.7, 26.2, 25.5 ppm.

The synthesis of cyclopentadiene (CP) functionalized non-natural amino acid (NNAA) began with the reaction of commercially available NaCp with methyl bromoacetate. The crude ester was reduced with LAH to alcohol 1, which was obtained as a mixture of isomers (~1:1). 1 will dimerize when stored at −20° C., it should be stored frozen in a matrix of benzene or used immediately. The reaction of 1 with 4-nitrophenyl chloroformate produced activated carbamate 2, which can be stored for several weeks at −20° C. The reaction of 2 with copper lysinate was attempted, but isolation of NNAA 4 after treatment with 8-hydroxyquinoline or EDTA was not fruitful. The reaction of 2 with Boc-Lys-OH provided the Boc-protected NNAA in 71% (or directly from 1 using triphosgene in 38%) but efforts to remove the Boc group using TFA, formic acid, or Lewis acid lead to rapid decomposition of the CP ring. Reacting 2 with Fmoc-Lys-OH produces the Fmoc-protected 3, which could be deprotected using piperidine to obtain NNAA 4. Compound 4 has poor solubility in commonly used deuterated solvents. A drop of TFA can be added to increase solubility, but leads to decomposition after several hours. The CP protons in 4 exchange when dissolved in D$_2$O with catalytic NaOH due to sequential [1,5]-hydride shifts.

The synthesis of a CP1-functionalized NHS-ester began with the reaction of 1 with succinic anhydride to produce acid 5. The acid 5 was reacted with EDC-HCl and N-hydroxysuccinimide to yield NHS ester 6. At room temperature the CP ring on 6 will dimerize over several days, but it can be stored for over a month at −20° C.

Example 3. CP1 Diene-Maleimide Conjugation for Preparation of ADCs Via Crosslinker-Modified mAb Cyclopentadiene-maleimide reactions were evaluated for bioconjugation, where cyclopentadiene groups were introduced via a linker.

Introduction of CP1 functionality onto mAbs: CP1 diene functionality was installed onto IgG1 mAbs by reaction of lysine primary amines with CP1-NHS (compound 6). This approach resulted in randomly conjugated, amide-linked cyclopentadiene groups, with the modified mAb termed mAb-CP1-linker. Note that mAb-CP1-linker may also be referred to as mAb-CP1 in some figures, see figure caption for clarification. A typical mAb modification reaction is described as follows. Mab solution was adjusted to 5 mg/mL (3 mL, 15 mg mAb, 100 nmol, 1 eq.) with PBS pH 7.2 followed by addition of 10% v/v 1M NaHCO$_3$. This solution was chilled on ice and 30 μL CP1-NHS (10 mM stock in DMAc, 300 nmol, 3 equivalents) was added. The reaction proceeded on ice for 5 minutes followed by reaction at room temperature for 1 h with continuous mixing. Reacted mAb was purified by dialysis (Slide-A-Lyzer, 10 kDa MWCO) against PBS, 1 mM EDTA, pH 7.4, 0° C. for 24 h. CP1-linker introduction was quantified by intact deglycosylated mass spectrometry as described below and found to be 2.3 CP1 per mAb in this example, which corresponds to 77% conversion of CP1-NHS to antibody conjugate. A summary of results for this reaction performed under various conditions is described in appendix A3.1.

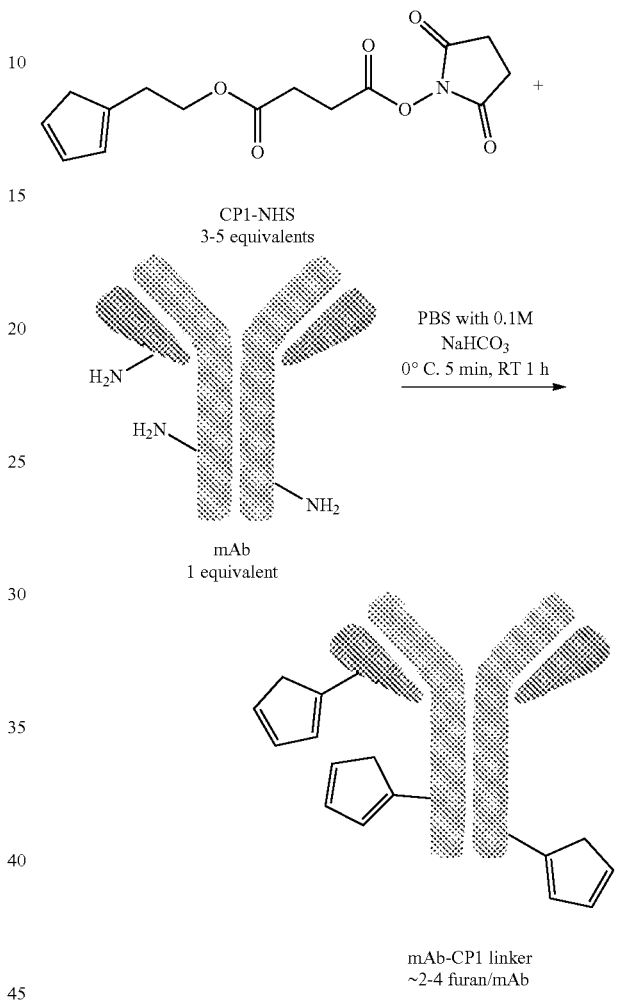

Scheme 3.1. Modification of mAbs with CP1-NHS to generate mAb-CP1-linker.

Reaction of CP1-modified mAb with maleimido-MMAEs: mAb-CP1-linker (2.3 CP1 diene/mAb, 1 mg, 6.7 nmol mAb, 1 equivalent) was diluted with PBS (pH 7.4) to a final concentration of 3.5 mg/mL. Next, DMSO was added to yield a 20% v/v solution followed by addition of 1 M sodium phosphate monobasic to yield a 10% v/v solution. Addition of all solution components yielded a mixture comprising 2.7 mg/mL mAb, 41.4 μM CP1 diene, 1.78 M DMSO, 110 mM sodium phosphate, 100 mM NaCl, pH 5.5. AM-MMAE or PM-MMAE (10 μL of a 10 mM stock solution in DMAc, 100 nmol, 15 equivalents) was added to the antibody solution. The reaction mixture was vortexed briefly and allowed to proceed at 22° C. or 37° C. with mixing. After 4 h reaction, N-acetyl cysteine (8 μL of a 100 mM solution, 120 equivalents) was added to quench unreacted maleimide groups. Samples were then purified using PD Spintrap G-25 devices (GE Healthcare Life Sciences) to remove small molecule components from the mixture. Samples were then analyzed by reduced deglycosylated mass spectrometry as described below.

Scheme 3.2. Reaction of mAb-CP1-linker with maleimido MMAEs.

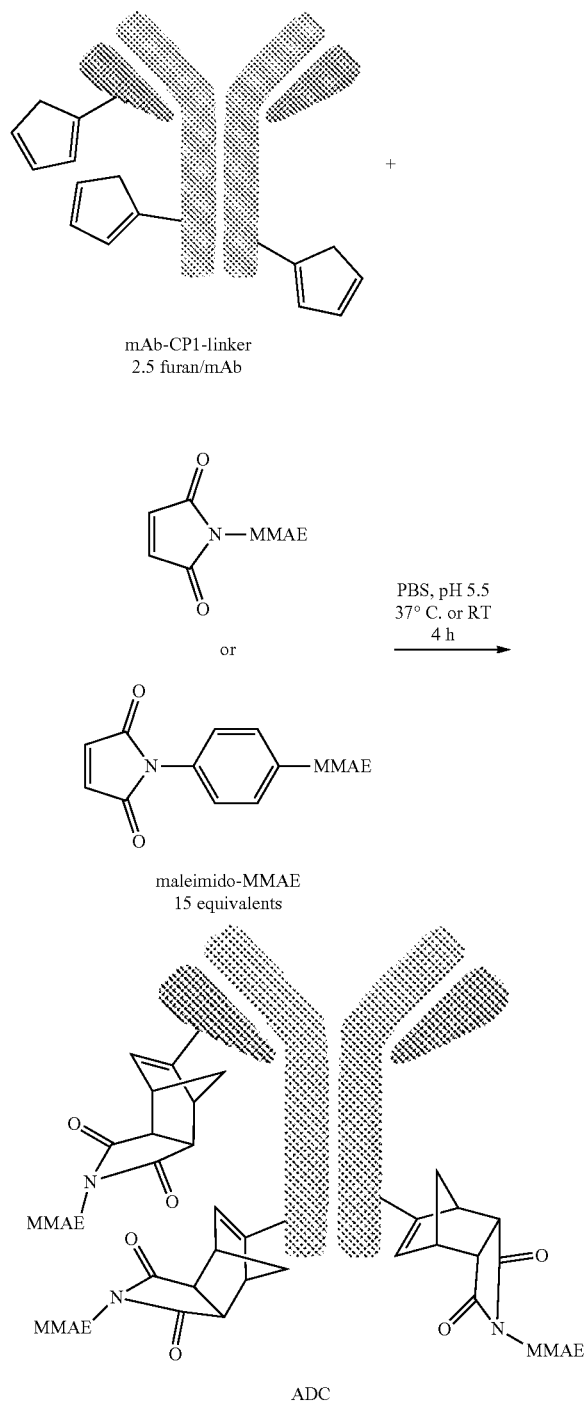

TABLE 3.1

Summary of CP1-NHS mAb reactions

| equivalents CP1-NHS (rel to mAb) | [mAb] mg/nL | CP1-linker per mAb | conversion (%) |
|---|---|---|---|
| 3 | 5 | 2.3 | 77 |
| 5.4 | 3.75 | 3.9 | 74 |
| 4 | 5 | 3.7 | 93 |

FIG. 3.2. Reduced glycosylated mass spectra of mAb-CP1-linker maleimido-MMAE reaction products. Zoomed to show both heavy and light mAb chains.

FIG. 3.3. Reduced deglycosylated mass spectra of mAb-CP1-linker maleimido MMAE reaction products zoomed in to show the mAb heavy chain region. DAR-0 indicates no MMAE conjugated to the mAb heavy chain, DAR-1 indicates one MMAE conjugated to the mAb heavy chain and DAR-2 indicates two MMAEs conjugated to the mAb heavy chain. No unconjugated CP1-linker peaks were detected in the reaction product and all MMAE conjugate peaks tracked from the corresponding heavy chain CP1-linker peaks, indicating that conjugation was specific to CP1-linker groups.

TABLE 3.2

Summary of mAb-CP1-linkermaleimido-MMAE reactions[a]

| Payload | Equivalents (rel to mAb) | pH | temp | MMAE conjugation to mAb-CP1-linker (%) |
|---|---|---|---|---|
| AM-MMAE | 15 | 5.5 | 37° C. | 100 |
|  |  |  | 22° C. | 100 |
| PM-MMAE | 15 | 5.5 | 37° C. | 100 |
|  |  |  | 22° C. | 100 |
| alloc-lysine | 300 | 5.5 | 37° C. | 0 |
|  |  |  | 22° C. | 0 |

[a]All reactions performed at 2.7 mg/mL mAb-CP1-linker for 4 h.

FIG. 3.4. Reduced deglycosylated mass spectrometry analysis of mAb-CP1-linker alloc lysine reaction product. No peaks corresponding to the expected mass of the conjugate were observed.

CP1 diene groups installed onto the surface of antibodies completely reacted with maleimido-MMAE prodrugs within 4 h at room temperature. No non-specific conjugation was observed by mass spectrometry, as all CP1-linker-MMAE conjugate peaks tracked from mAb-CP1-linker peaks, not unmodified mAb peaks (i.e. lacking CP1-linker). This is in stark contrast to reactions of mAb-furan-linker with maleimido MMAE's, where only ~2-20% conjugation was observed including non-specific conjugation after 20 h at 37° C. Diene-maleimide conjugation with mAb-CP1-linker is an improvement over mAb-furan-linker based coupling.

Example 4. Kinetics of mAb-CP1-Linker Conjugation to Maleimido-MMAEs at 0.6 Molar Equivalents Maleimido-MMAE to Diene Groups Contained on CP1-mAb-Linker Reaction kinetics of mAb-CP1-linker with maleimido MMAEs was investigated at the stiociometry of 0.6 molar equivalents of maleimido-MMAE to diene contained on mAb-CP1-linker.

Introduction of CP1 functionality onto mAbs: CP1 diene functionality was installed onto IgG1 mAbs by reaction of lysine primary amines with CP1-NHS (compound 6). This approach resulted in randomly conjugated, amide-linked cyclopentadiene groups. The resulting conjugate was termed Mass spectrometry analysis: Samples were analyzed as described in Example 1.

FIG. 3.1. Intact deglycosylated mass spectrometry before (A) and after (B) reaction of mAb with CP1-NHS. Numbers below peaks in (B) indicate the number of CP1-linker groups introduced into the mAb. Note that the set of higher MW peaks in (A) represent glycosylated mAb. Estimation of CP1-linker introduction by peak intensities yields 2.3 CP1-linkers per mAb.

mAb-CP1-linker and may also be referred to as mAb-CP1, see figure captions for clarification. Mab solution was adjusted to 3.7 mg/mL (3 mL, 11.1 mg mAb, 74 nmol, 1 eq.) with PBS pH 7.2 followed by addition of 10% v/v 1M NaHCO$_3$. This solution was chilled on ice and 40 μL CP1-NHS (10 mM stock in DMAc, 400 nmol, 5.4 equivalents) was added. The reaction proceeded at room temperature for 1 h with continuous mixing. Reacted mAb was purified by dialysis (Slide-A-Lyzer, 10 kDa MWCO) against PBS, 1 mM EDTA, pH 7.4, 0° C. for 24 h. CP1 diene introduction was quantified by intact deglycosylated mass spectrometry as described below and found to be 3.99 CP1 dienes per mAb, which corresponds to 74% conversion of CP1-NHS to antibody conjugate.

Reaction of mAb-CP1-linker with maleimido-MMAEs: CP1-modified mAb (3.99 CP1 diene/mAb, 3 mg, 80 nmol CP1 diene, 1 equivalent) was diluted with PBS (pH 7.4) to a final concentration of 1.7 mg/mL. Next, DMSO was added to yield a 20% v/v solution followed by addition of 1 M sodium phosphate monobasic to yield a 10% v/v solution. Addition of all solution components yielded a mixture comprising 1.3 mg/mL mAb, 34.6 μM CP1 diene, 1.78 M DMSO, 110 mM sodium phosphate, 100 mM NaCl, pH 5.5. AM-MMAE or PM-MMAE (5.2 μL of a 10 mM stock solution in DMSO, 52 nmol, 0.67 equivalents) was added to the antibody solution. The reaction mixture was vortexed briefly and allowed to proceed at 22° C. with mixing. Aliquots (180 μL) were removed at various timepoints and N-acetyl cysteine (2 μL of a 100 mM solution, 38 equivalents) was added to quench maleimide groups. Samples were then purified using PD Spintrap G-25 devices (GE Healthcare Life Sciences) to remove small molecule components from the mixture. Samples were then analyzed by reduced deglycosylated mass spectrometry as described below.

Mass spectrometry analysis: Samples were analyzed as described in Example 1.

Calculation of CP1 diene-maleimide reaction rate constants: Second order rate constants for reaction of maleimido-MMAEs with antibody dienes were determined from peak intensities in deglycosylated, reduced mass spectra. Reaction progress was monitored by both disappearance of mAb-CP1-linker peaks and appearance of mAb-CP1-linker-AM MMAE peaks, but only mAb-CP1-linker peak intensities on the antibody heavy chains were used to calculate relative abundance of reacted CP1 diene. The relative amount of unreacted CP1 diene groups on mAb heavy chains was calculated using the equation below:

$$CP1\ per\ mAb = \left[\frac{b}{a+b+c+d}\times 1\right]+\left[\frac{c}{a+b+c+d}\times 2\right]+\left[\frac{d}{a+b+c+d}\times 3\right]$$

a=peak intensity of unmodified heavy chain
b=sum of peak intensities of heavy chains with one CP1-linker group
c=sum of peak intensities of heavy chains with two CP1-linker groups
d=peak intensity of heavy chain with three CP1-linker groups
Note: maleimido-MMAE-containing heavy chains were also included in the calculation. For example, CP1-linker-2+1 maleimido-MMAE would be included as a CP1-linker-1 species.

Results
FIG. 4.1. Intact deglycosylated mass spectrometry before (A) and after (B) reaction of mAb with CP1-NHS.
FIG. 4.2. Reduced deglycosylated mass spectra of unmodified mAb, mAb-CP1-linker (mAb-CP1) and AM-MMAE-reacted mAb-CP1-linker (mAb-CP1 AM-MMAE) at 15 min and 2.5 h.
FIG. 4.3. Reaction of mAb-CP1-linker with maleimido-MMAEs over time. Unreacted diene was determined from the peak intensities of reduced deglycosylated mass spectra.

TABLE 4.1

Summary of mAb-CP1-linker conjugation results[a]

| payload | feed[b] | reacted diene[c] |
|---|---|---|
| AM-MMAE | 0.65 | 60.0% |
| PM-MMAE | 0.65 | 63.4% |

[a]all conjugation reactions performed at pH 5.5, 20% DMSO, 22° C. and 1.3 mg/mL mAb for 3.5 h
[b]feed calculated as molar equivalent maleimido-MMAE:CP1 diene
[c]calculated from peak intensities of reduced deglycosylated mass spectra.

Reaction of CP1 dienes (contained on mAb-CP1-linker) with maleimido-MMAEs was rapid and specific under aqueous conditions, with complete reaction achieved on the order of 10's of minutes. Calculated molar feed ratios of maleimido-MMAE based match the observed degree of conjugation from intact mass spectra, as MMAE molar feed and conversion of diene to conjugate were essentially the same.

Example 5. Kinetics of mAb-CP1-Linker Conjugation to Maleimido-MMAEs at 1.0 Molar Equivalent Maleimido-MMAE to Diene Groups Reaction kinetics of CP1 dienes with maleimido MMAEs at 22° C. was evaluated.

Introduction of CP1 functionality onto mAbs: CP1 diene functionality was installed onto IgG1 mAbs by reaction of lysine primary amines with CP1-NHS (compound 6). This approach resulted in randomly conjugated, amide-linked cyclopentadiene groups. Mab solution was adjusted to 5 mg/mL (3 mL, 5 mg mAb, 100 nmol, 1 eq.) with PBS pH 7.2 followed by addition of 10% v/v 1 M NaHCO$_3$. This solution was chilled on ice and 40 μL CP1-NHS (10 mM stock in DMAc, 400 nmol, 4 equivalents) was added. The reaction mixture was vortexed briefly and incubated at room temperature for 1 h with continuous mixing. Reacted mAb was purified by dialysis (Slide-A-Lyzer, 10 kDa MWCO) against PBS, 1 mM EDTA, pH 7.4, 0° C. for 24 h. CP1 diene introduction was quantified by intact deglycosylated mass spectrometry as described below and found to be 3.7 CP1 dienes per mAb, which corresponds to 92% conversion of CP1-NHS to antibody conjugate.

Reaction of mAb-CP1-linker with maleimido-MMAEs: mAb-CP1-linker (3.7 CP1 diene/mAb, 3 mg, 74 nmol CP1 diene, 1 equivalent) was diluted with PBS (pH 7.4) to a final concentration of 1.7 mg/mL. Next, DMSO was added to yield a 20% v/v solution followed by addition of 1 M sodium phosphate monobasic to yield a 10% v/v solution. Addition of all solution components yielded a mixture comprising 1.3 mg/mL mAb, 32.3 μM CP1 diene, 1.78 M DMSO, 110 mM sodium phosphate, 100 mM NaCl, pH 5.5. AM-MMAE or PM-MMAE (7.4 μL of a 10 mM stock solution in DMSO, 74 nmol, 1 equivalent) was added to the antibody solution. The reaction mixture was vortexed briefly and allowed to proceed at 22° C. with mixing. Aliquots (180 μL) were removed at various timepoints and N-acetyl cysteine (3 μL of a 100 mM solution, 51 equivalents) was added to quench unreacted maleimide groups. Samples were then purified using PD Spintrap G-25 devices (GE Healthcare Life Sciences) to remove small molecule components from the mixture. Samples were then analyzed by reduced deglycosylated mass spectrometry as described below.

Mass spectrometry analysis: Samples were analyzed as described in Example 1.

Calculation of CP1 diene-maleimide reaction rate constants: Second order rate constants for reaction of maleimido-MMAE with mAb dienes were determined from peak intensities in deglycosylated, reduced mass spectra. Reaction progress was monitored by both disappearance of mAb-CP1-linker peaks and appearance of mAb-CP1-linker-maleimido-MMAE peaks, but only mAb-CP1-linker peak intensities on the antibody heavy chains were used to calculate relative abundance of reacted CP1 dienes. Unreacted CP1 diene groups on mAb-CP1-linker was calculated using the equation below:

$$\text{CP1 dienes per mAb} = \left[\frac{b}{a+b+c+d}\times 1\right] + \left[\frac{c}{a+b+c+d}\times 2\right] + \left[\frac{d}{a+b+c+d}\times 3\right] + \left[\frac{f}{e+f+g}\times 1\right] + \left[\frac{g}{e+f+g}\times 2\right]$$

a=peak intensity of unmodified heavy chain
b=sum of peak intensities of heavy chains with one CP1-linker group
c=sum of peak intensities of heavy chains with two CP1-linker groups
d=peak intensity of heavy chain with three CP1-linker groups
e=peak intensity of unmodified light chain
f=sum of peak intensities of light chains with one CP1-linker group
g=sum of peak intensities of light chains with two CP1-linker groups Conjugation data were further analyzed in units of molar concentration to determine kinetic constants. Second order rate constants were determined from the slopes of curves generated from plotting 1/[CP1] versus time and linear regression analysis. Reaction half-lives were calculated from second-order reaction rate constants using the equation shown below:

$$T_{1/2} = \frac{1}{k_2[CP1]_0}$$

$k_2$=second order rate constant
$[CP1]_0$=CP1 diene concentration at time=0

FIG. 5.1. Intact deglycosylated mass spectrometry before (A) and after (B) reaction of mAb with CP1-NHS. Numbers above peaks indicate the number of CP1 linker groups present on that mAb species.

FIG. 5.2. Reduced deglycosylated mass spectra of unmodified mAb, mAb-CP1-linker (mAb-CP1), and PM-MMAE-reacted mAb-CP1-linker (mAb-CP1 PM-MMAE) at 5 min and 150 min. Spectra are zoomed in to show the heavy chain only.

FIG. 5.3. Reaction of mAb-CP1-linker with maleimido-MMAEs. A) Molar concentration of unreacted CP1 diene over time. Unreacted CP1 diene per mAb was determined from the peak intensities of reduced deglycosylated mass spectra. B) Inverse concentration plot used to calculate reaction rates.

TABLE 5.1

Summary of diene-maleimide coupling kinetics for reaction of mAb-CP1-linker with maleimido MMAEs[a,b,c]

| payload | $2^{nd}$ order rate constant ($M^{-1}s^{-1}$) | $t_{1/2}$ (min) | conversation (%)[d] |
|---|---|---|---|
| AM-MMAE | 36 ± 1.4 | 13.5 | 90 |
| PM-MMAE | 54 ± 1.2 | 8.9 | 97 |

[a]all conjugation reactions performed at pH 5.5, 20% DMSO, 22° C. and 1.3 mg/mL CP1-modified mAb
[b]the molar ratio of MMAE:CP1 diene used was 1:1
[c]calculated from peak intensities of reduced deglycosylated mass spectra
[d]after 150 minutes reaction Reaction of CP1 dienes with maleimido-MMAEs was rapid and specific, with half-live's on the order of several minutes. Reaction conversion was 90% or more for both maleimido-MMAE. Phenyl maleimide reaction rates were slightly higher than alkyl maleimide rates, however, rates and final conversion were comparable between the two types of maleimides.

Example 6. CP1-NNAA Incorporation into an Antibody

CP1-NNAA was incorporated into position K274 of an antibody, the quality of expressed mAb, and reactivity of CP1 diene after antibody incorporation was assessed.

Preparation of CP1-NNAA stock solution: CP1-NNAA (0.5 g, 1.77 mmol) was combined with 6.81 mL H$_2$O and 1.38 mL 1 M NaOH. The resulting slurry was stirred at room temperature until all solids dissolved (10 minutes). After complete dissolution the light yellow solution was passed through a 0.2 μm filter, aliquoted, and stored at −80° C. until use. This procedure resulted in 8.2 mL of 216 mM CP1 and 168 mM NaOH stock solution.

Antibody expression: 12G3H11 or 1C1 IgG1 antibody genes with an amber mutation at Fc position K274 or S239 were cloned into a proprietary pOE antibody expression vector. The construct was transfected into CHO-G22 by PEImax (1.5 L of G22 cells), along with a plasmid encoding PyIRS double mutant (Y306A/Y384F) or wild-type PyIRS and a plasmid containing tandem repeats of the tRNA expression cassette (pORIP 9xtRNA). Four hours post transfection, 3.3% of feed F9 (proprietary) and 0.2% of feed F10 (proprietary) were added to cells and the cells were further incubated at 34° C. CP1-NNAA was added the next day at final concentration of 0.26 mM for 1C1.K274 transfected cells. Cells were fed again on day 3 and day 7 with 6.6% of feed F9 and 0.4% of feed F10. Cells were spun down and supernatant was harvested on day 11. The supernatant was purified by IgSelect affinity column (GE Health Care Life Science). The antibody was eluted with 50 mM glycine, 30 mM NaCl, pH 3.5 elution buffer, neutralized with 1 M Tris buffer pH 7.5, and dialyzed into PBS, pH 7.2. Concentration of antibody eluted was determined by absorbance measurement at 280 nm. The back calculated titer was 47 mg/L for 1C1.K274.12G3H11 mAb was expressed in a similar manner at smaller scale, with CP1-NNAA feed concentration and feeding times varied. Recovered antibody was analyzed by SDS-PAGE using standard methods. Antibody was also analyzed by size exclusion chromatography and mass spectrometry as described below. Antibodies incorporating CP1-NNAA are denoted as mAb-CP1-NNAA to distinguish them from mAb-CP1-linker constructs, or mAb-[position]CP1-NNAA where [position] indicates the amino acid number and amino acid symbol that was mutated to CP1-NNAA.

Size exclusion chromatography (SEC): SEC analysis was performed using an Agilent 1100 Capillary LC system equipped with a triple detector array (Viscotek 301, Viscotek, Houson, Tex.); the wavelength was set to 280 nm, and samples were run on a TSK-GEL G3000SWXL column (Toso Bioscience LLC, Montgomeryville, Pa.) using 100 mM sodium phosphate buffer, pH 6.8 at a flow rate of 1 mL/min.

Conjugation of mAb-CP1-NNAA with maleimido MMAEs: mAb-CP1-NNAA (0.4 mg, 2.7 nmol, 1 equivalent) was adjusted to 3 mg/mL with PBS (0.133 mL). DMSO (27 µL) and 1 M sodium phosphate, monobasic (13 µL) was added to yield ~20% and 10% v/v solution, respectively. Maleimido-MMAE (5 µL of 10 mM stock in DMSO, 13 nmol, 5 equivalents) was added to mAb-CP1-NNAA solution and the mixture was vortexed briefly. ADCs were prepared with both AM-MMAE and PM-MMAE. The reaction proceeded at room temperature for 1 h with continuous mixing. N-acetyl cysteine (1.1 µL of 100 mM, 108 nmol, 40 equivalents) was added and the solution was incubated for an additional 15 min to quench unreacted maleimide groups. Samples were then purified using PD Spintrap G-25 devices (GE Healthcare Life Sciences) to remove small molecule components from the mixture. Samples were subsequently analyzed by reduced mass spectrometry as described below.

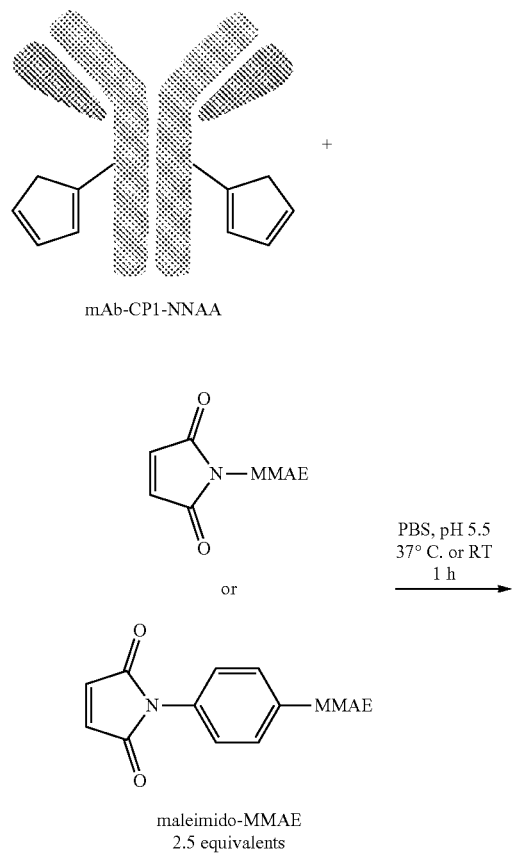

Scheme 6.1. A) Reaction of mAb-CP1-NNAA with maleimido MMAE. CP1-NNAA was incorporated at position K274 by mutation of lysine to CP1-NNAA.

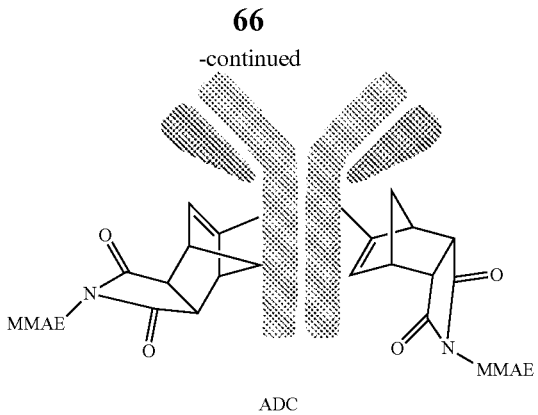

ADC

Mass spectrometry analysis: For deglycosylated mAb analysis, EndoS (5 µL Remove-iT EndoS (1:10 dilution in PBS, 20,000 units/mL, New England BioLabs) was combined with 50 µL sample (1 mg/mL mAb) and 5 µL glyco buffer 1 (New England BioLabs) and followed by incubation for 1 h at 37° C. Reduced samples were prepared by addition of 5 µL Bond-Breaker TCEP solution (0.5 M, Thermo Fisher Scientific) and incubation for 10 min at 37° C. Mass spectrometry analysis was performed using an Agilent 6520B Q-TOF mass spectrometer equipped with a RP-HPLC column (ZORBAX 300 Diphenyl RRHD, 1.8 micron, 2.1 mm×50 mm). High-performance liquid chromatography (HPLC) parameters were as follows: flow rate, 0.5 ml/min; mobile phase A was 0.1% (v/v) formic acid in HPLC-grade H2O, and mobile phase B was 0.1% (v/v) formic acid in acetonitrile. The column was equilibrated in 90% A/10% B, which was also used to desalt the mAb samples, followed by elution in 20% A/80% B. Mass spec data were collected for 100-3000 m/z, positive polarity, a gas temperature of 350° C., a nebulizer pressure of 48 lb/in$^2$, and a capillary voltage of 5,000 V. Data were analyzed using vendor-supplied (Agilent v.B.04.00) MassHunter Qualitative Analysis software and peak intensities from deconvoluted spectra were used to derive the relative proportion of species in each sample as previously described.

FIG. 6.1. Titers of 12G3H11 K274CP1-NNAA mAb after expression in mammalian cells comprising mutant or wt tRNA synthetase (TRS). CP1-NNAA final concentration in media and feeding time was varied as indicated on the x-axis. Note that the structure of non-natural amino acid #50 is shown in FIG. 6.8.

TABLE 6.1

Summary of 1C1 K274CP1-NNAA mAb production

| | |
|---|---|
| CP1 NNAA feed (mM) | 0.26 |
| Volume (L) | 1.7 |
| Mass recovered (mg) | 67 |
| Titer (mg/L) | 39 |
| Monomer (%) | 90.8 |

FIG. 6.2. Reduced glycosylated mass spectrometry analysis of 12G3H11 K274CP1-NNAA mAb. A) Mass range showing mAb light chain (LC) and heavy chain (HC). B) Zoomed spectrum showing mAb heavy chain only. The observed heavy chain mass (51129.55 amu) closely matched the calculated heavy chain mass (51127 amu) assuming incorporation of CP1NNAA into the antibody heavy chain.

FIG. 6.3. SEC analysis of 12G3H11 K274CP1-NNAA mAb indicating that monomeric product was obtained. High molecular weight species (HMWS) are indicated.

FIG. 6.4. Analysis of 1C1-K274CP1-NNAA mAb (1C1.K274CP1) by SDS-PAGE.

FIG. 6.5. Reduced deglycosylated mass spectrometry analysis of 12G3H11 K274CP1-NNAAmAb-MMAE conjugation products. A) unreacted antibody, B) AM-MMAE reaction product, C) PM-MMAE reaction product. Spectra are zoomed in to show only the mAb heavy chain.

FIG. 6.6. Reduced glycosylated mass spectrometry analysis of 1C1 K274CP1-NNAA mAb-AM-MMAE conjugation product. A) unreacted antibody, B) AM-MMAE reaction product. Spectra are zoomed in to show only the mAb heavy chain (HC). Zoomed out spectra showing both heavy and light chains are shown in FIGS. 6.9 and 6.10.

FIG. 6.7. Chemical structure of CP1-NNAA showing compound isomers, which exist as a 1:1 ratio.

FIG. 6.8. Chemical structure of compound 50, a furan analogue of CP1-NNAA described in the literature. This compound was used as a control for expression studies with 12G3H11 mAb.

FIG. 6.9. Reduced deglycosylated mass spectrometry analysis of 12G3H11 K274CP1-NNAA mAb-MMAE conjugation products. A) unreacted antibody, B) AM-MMAE reaction product, C) PM-MMAE reaction product. Spectra are zoomed to show both antibody heavy and light chains.

FIG. 6.10. Reduced glycosylated mass spectrometry analysis of 1C1 K274CP1-NNAA mAb-AM-MMAE conjugation product. A) unreacted antibody, B) AM-MMAE reaction product. Spectra are zoomed to show both antibody heavy and light chains and also high molecular weight species.

imido MMAEs to produce the desired ADC. First, 12G3H11 K274CP1-NNAA mAb (0.4 mg, 2.7 nmol, 1 equivalent) was adjusted to 3 mg/mL with PBS (0.133 mL). DMSO (27 µL) and 1M sodium phosphate, monobasic (13 µL) was added to yield ~20% and 10% v/v solution, respectively. Maleimido-MMAE (5 µL of 10 mM stock in DMSO, 13 nmol, 5 equivalents) was added to 12G3H11 K274CP1-NNAA mAb solution and the mixture was vortexed briefly. The reaction proceeded at room temperature for 1 h with continuous mixing. N-acetyl cysteine (1.1 µL of 100 mM, 108 nmol, 40 equivalents) was added and the solution was incubated for an additional 15 min to quench unreacted maleimide groups. Samples were then purified using PD Spintrap G-25 devices (GE Healthcare Life Sciences) to remove small molecule components from the mixture. Samples were subsequently analyzed by reduced mass spectrometry as described below to confirm conjugation and quantify the drug:antibody ratio.

Serum stability assay: ADC samples were evaluated in whole rat serum (Jackson Immunoresearch cat:012-000-120) and whole mouse serum (Jackson Immunoresearch cat:015-000-120). Lyophilized serum product was reconstituted with sterile water according to the manufacturer's protocol. ADC sample was added to serum to result in a 0.2 mg/mL antibody solution. ADC/serum mixtures were passed through a 0.2 µm filter, capped in an air-tight vial and incubated at 37° C. An aliquot was removed and frozen to serve as a T=0 d reference. Remaining sample was incubated at 37° C. for 7 d, followed by recovery of antibody (conjugated and unconjugated) by immunocapture using Fc-specific anti-human IgG-agarose resin (Sigma-Aldrich).

TABLE 6.2

Summary of K274CP1-NNAA mAb-MMAE conjugation data[a,b,c]

| mAb | payload | Conjugation efficiency (%) | Observed Δ mass (AMU) | Calculated Δ mass (AMU) | DAR[d] | Comments |
|---|---|---|---|---|---|---|
| 12G3H11 | AM-MMAE | 95.7 | 1315.47 | 1316.65 | 1.91 | |
| 12G3H11 | PM-MMAE | 95.1 | 1335.96 | 1336.64 | 1.46 | linker cleavage observed |
| 1C1 | AM-MMAE | 100 | 1317.59 | 1316.65 | 2.0 | unconjugated species not detected |

[a] all conjugation reactions performed at pH 5.5, 20% DMSO, 22° C. and 3 mg/mL CP1-NNAA mAb. CP1-NNAA was incorporated into position K274 in place of lysine
[b] the molar ratio of MMAE:CP1 diene used was 2.5:1
[c] calculated from peak intensities of reduced mass spectra
[d] DAR = drug to antibody ratio, linker cleaved species not included in DAR calculation Incorporation of CP1-NNAA into antibodies at position K274 was confirmed using two different antibody constructs; 12G3H11 and 1C1. Recovered antibody was of high quality, with no truncated product and very little aggregate. Titer achieved for the 1.7 L scale production of 1C1 antibody was reasonably high considering the low amount of CP1-NNAA fed to cells. CP1 diene reactivity was preserved throughout the expression and purification process as indicated by the nearly complete conversion of antibody to ADC.

Example 7. Serum Stability of CP1-NNAA mAb Maleimido MMAE Antibody Drug Conjugates Stability of the 4+2 cycloaddition product (cyclopentadiene-maleimide bond) in physiological milieu ex vivo by incubation in rat and mouse serum for 7 days at 37° C.

Generation of ADCs: 12G3H11 K274CP1-NNAA bearing CP1-NNAA at position K274 was conjugated to male- Resin was rinsed twice with PBS, once with IgG elution buffer, and then twice more with PBS. ADC serum samples were then combined with anti-human IgG resin (100 µL of ADC-serum mixture, 50 µL resin slurry) and gently mixed for 15 minutes at room temperature. Resin was recovered by centrifugation and then washed twice with PBS. The resin pellet was resuspended in 100 µL IgG elution buffer (Thermo Scientific) and further incubated for 5 minutes at room temperature. Resin was removed by centrifugation and then 20 µL of 10× Glyco buffer 1 (New England Biolabs) and 5 µL Endo S (Remove iT EndoS, New England Biolabs) was added to the supernatant followed by incubation for 1 h at 37° C. Deglycosylated human antibody solution was sterile filtered, reduced with TCEP (Bond Breaker 0.5 M TCEP solution, Thermo Fisher Scientific) and analyzed by LC/MS. Percent conjugated antibody and the quantification of linker cleavage products were determined from peak heights of mass spectra.

Mass spectrometry analysis; Samples were analyzed as described in Example 1.

FIG. 7.1. Rat serum stability of 12G3H11 K274CP1-NNAA AM-MMAE ADC. ADC was incubated in rat serum at 37° C. for 7 days and recovered by immunocapture prior to reduced mass spectrometry analysis. Spectra are zoomed to show details in the heavy chain (HC) mass region. No significant deconjugation was observed.

FIG. 7.2. Rat serum stability of 12G3H11 K274CP1-NNAA PM-MMAE ADC. ADC was incubated in rat serum at 37° C. for 7 days and recovered by immunocapture prior to reduced mass spectrometry analysis. Spectra are zoomed to show details in the heavy chain (HC) mass region. No significant deconjugation was observed, however linker cleavage was observed at the phenyl acetamide group. See appendix 7 for description of the cleavage product.

FIG. 7.3. Mouse serum stability of 12G3H11 K274CP1-NNAA AM-MMAE ADC. ADC was incubated in mouse serum at 37° C. for 7 days and recovered by immunocapture prior to reduced mass spectrometry analysis. Spectra are zoomed to show details in the heavy chain (HC) mass region. No significant deconjugation was observed, however nearly complete linker cleavage was observed at the val-cit dipeptide. See appendix 7 for description of the cleavage product.

FIG. 7.4. Mouse serum stability of 12G3H111 K274CP1-NNAA PM-MMAE ADC. ADC was incubated in mouse serum at 37° C. for 7 days and recovered by immunocapture prior to reduced mass spectrometry analysis. Spectra are zoomed to show details in the heavy chain (HC) mass region. No significant deconjugation was observed, however nearly complete linker cleavage was observed. See appendix 7 for description of the cleavage products.

TABLE 7.1

Summary of 12G3H1 K274CP1-NNAA MMAE ADC serum stability data[a,b]

| payload | Species | Deconjugation[c] (%) | Linker cleavage (%)[c] | MMAE DAR[d] |
|---|---|---|---|---|
| AM-MMAE | mouse | 0.52 ± 0.9 | 99.1 ± 0.1[e] | 0 |
| | rat | 0.07 ± 0.4 | none detected | 1.9 ± 0.01 |
| PM-MMAE | mouse | none detected | 78 ± 2[e] | 0.07 ± 0.06 |
| | rat | 1.4 ± 2.4 | 31 ± 1[f] | 1.35 ± .02 |

[a]ADCs prepared with 12G3H11 mAb bearing a K274CP1-NNAA mutation.
[b]samples were incubated for 7 days at 37° C.
[c]calculated from peak intensities of reduced deglycosylated mass spectra.
[d]cleaved linker species not included in DAR calculation. Theoretical DAR = 2.
[e]both val-cit dipeptide cleavage and phenylacetamide cleavage contributed to overall linker cleavage and drug loss.
[f]phenylacetamide cleavage in linker observed, but not val-cit dipeptide cleavage.

FIG. 7.5. Chemical structures of MMAE payloads showing molecular weight.

FIG. 7.6. Chemical structures of predominant cleavage products observed following incubation of ADCs in mouse serum. A) and B) show the species remaining on the antibody (CP1-maleimide linkage not shown) for AM-MMAE and PM-MMAE conjugates, respectively. C) Shows the species liberated after val-cit dipeptide cleavage.

FIG. 7.7. Chemical structure of PM-MMAE cleavage products following rat serum incubation. A) species remaining on the antibody and B) liberated species.

The cyclopentadiene-maleimide conjugation products between mAb-CP1-NNAA and maleimido-MMAE's are stable in rat and mouse serum over a period of 7 days regardless of the type of maleimide contained on the MMAE payload. Other parts of the ADC payload were found to degrade before the maleimide-CP1 diene bond. Specifically, both phenyl maleimide- and alkyl maleimide-MMAE payloads exhibited high val-cit dipeptide cleavage in mouse serum, likely due to enzymatic accessibility to the highly exposed K274 conjugation site. Phenyl-maleimide conjugate showed an additional structural liability at the phenyl acetamide between the phenyl maleimide and val-cit dipeptide. This cleavage was more evident in rat serum than mouse serum. It is unclear at which point in the process that phenylacetamide cleavage occurred, since it did not increase from day 0 to day 7. It is possible that cleavage occurred during immunocapture, which includes a low pH rinsing step. Overall, the stability of cyclopentadiene-maleimide conjugation product in physiological mileau was demonstrated.

Example 8. Synthesis of Spirocyclopentadiene (CP2)-Containing Compounds

Spirocyclopentadiene-containirnt crosslinkers and non-natural amino acids (NNAAs) were prepared with the general structure shown below:

FIG. 8.1. General design of spirocyclopentadiene crosslinkers (A) and spirocyclopentadiene NNAA (B) described in example 8.

Synthesis of CP2-NNAA (10) began with the reaction of a commercially available NaCp solution with epichlorohydrin in a modified version of Carreira's reaction.[1] Racemic epichlorohydrin was used, but 7 can be synthesized in 91% ee using enantiopure epichlorohydrin. The reaction of 7 with 4-nitrophenyl chloroformate produced activated carbamate 8. Reacting 8 with Fmoc-Lys-OH produces the Fmoc-protected 9, which could be deprotected using piperidine to obtain NNAA 10. Compound 10 shows a higher stability to acid compared to 4, and none of the intermediates in its synthesis show dimerization or decomposition when stored at −20° C.

The synthesis of CP2-functionalized NHS-ester 12 began with the reaction of 7 with succinic anhydride to produce acid 11. The acid 7 was reacted with EDC-HCl and N-hydroxysuccinimide to yield NHS ester 12. Compound 12 doesn't appear to dimerize when stored for several days at room temperature.

Materials and Methods: Unless stated otherwise, reactions were conducted under an atmosphere of $N_2$ using reagent grade solvents. DCM, and toluene were stored over 3 Å molecular sieves. THF was passed over a column of activated alumina. All commercially obtained reagents were used as received. Thin-layer chromatography (TLC) was conducted with E. Merck silica gel 60 F254 pre-coated plates (0.25 mm) and visualized by exposure to UV light (254 nm) or stained with p-anisaldehyde, ninhydrin, or potassium permanganate. Flash column chromatography was performed using normal phase silica gel (60 Å, 0.040-0.063 mm, Geduran). $^1$H NMR spectra were recorded on Varian spectrometers (400, 500, or 600 MHz) and are reported relative to deuterated solvent signals. Data for $^1$H NMR spectra are reported as follows: chemical shift (δ ppm), multiplicity, coupling constant (Hz) and integration. $^{13}$C NMR spectra were recorded on Varian Spectrometers (100, 125, or 150 MHz). Data for $^{13}$C NMR spectra are reported in terms of chemical shift (δ ppm). Mass spectra were obtained from the UC Santa Barbara Mass Spectrometry Facility on a (Waters Corp.) GCT Premier high resolution Time-of-flight mass spectrometer with a field desorption (FD) source.

Synthesis of CP2-NNAA (10)

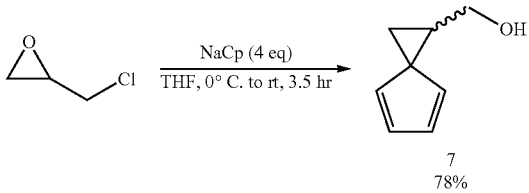 [SMILES: ClCC1CO1 ; OCC1CC12C=CC=C2]

Spiro[2.4]hepta-4,6-dien-1-ylmethanol (7)

Sodium cyclopentadienide (2 M solution in THF, 10 mL, 20 mmol, 4 eq) was added to THF (40 mL) and cooled to 0° C. Epichlorohydrin (0.39 mL, 5.0 mmol, 1 eq) was added dropwise and the reaction was stirred at 0° C. for 1.5 hr then a further 2 hr at rt. The reaction was quenched with $H_2O$ (40 mL) then transferred to a seperatory funnel. A saturated solution of $NaHCO_3$ in $H_2O$ (40 mL) and ether (40 mL) were added and the layers separated. The organic layer was washed with brine (40 mL), dried over $MgSO_4$, filtered, and then the solvent removed. The residue was subjected to flash column chromatography (Hexane:EtOAc, 2:1) to yield 7 (0.48 g, 78%) as a brown oil.

Rf (Hexane:EtOAc, 2:1): 0.22; $^1$H NMR (500 MHz, CDCl$_3$) δ 6.64 (td, J=1.6, 5.1 Hz, 1H), 6.51 (td, J=1.7, 5.1 Hz, 1H), 6.27 (tdd, J=1.0, 2.1, 5.2 Hz, 1H), 6.12 (td, J=1.7, 5.1 Hz, 1H), 4.08-3.88 (m, 1H), 3.59 (dd, J=8.8, 11.7 Hz, 1H), 2.48-2.40 (m, 1H), 1.87 (dd, J=4.3, 8.7 Hz, 1H), 1.69 (dd, J=4.4, 7.0 Hz, 1H), 1.57 (br. s., 1H) ppm; $^{13}$C NMR (125 MHz, CDCl$_3$) δ 139.4, 133.9, 131.7, 128.6, 64.9, 41.9, 30.0, 17.6 ppm.

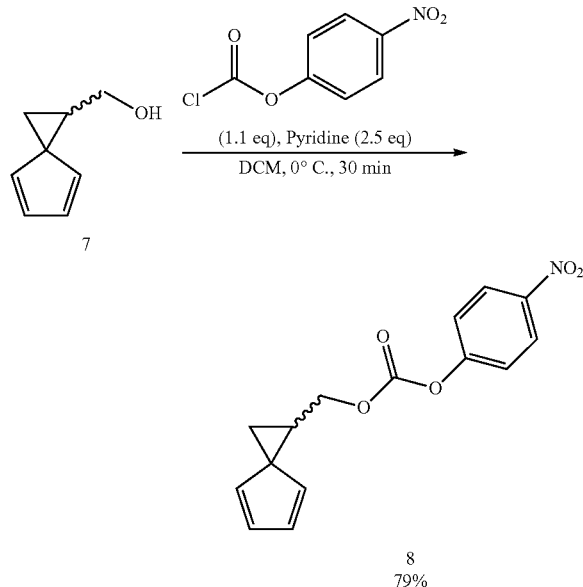

4-Nitrophenyl spiro[2.4]hepta-4,6-dien-1-ylmethyl carbonate (8)

7 (2.80 g, 22.9 mmol, 1 eq) was added to DCM (100 mL) and cooled to 0° C. Pyridine (4.61 mL, 57.3 mmol, 2.5 eq) was added followed by 4-nitrophenyl chloroformate (5.08 g, 25.2 mmol, 1.1 eq). The reaction was stirred at 0° C. until consumption of the starting material (TLC, 30 min). The reaction was poured into a separatory funnel and washed with a saturated solution of $NH_4Cl$ in $H_2O$ (100 mL). The aqueous layer was extracted with DCM (50 mL). The organic layers were combined, washed with brine (50 mL), dried over $Na_2SO_4$, filtered, and the solvent removed. The residue was subjected to flash column chromatography (Hexane:EtOAc, 6:1 to 4:1) to yield 8 (5.17 g, 79%) as an amber oil.

Rf (Hexane:EtOAc, 4:1): 0.28; $^1$H NMR (400 MHz, CDCl$_3$) δ 8.28 (d, J=9.0 Hz, 2H), 7.37 (d, J=9.0 Hz, 2H), 6.62 (td, J=1.7, 5.2 Hz, 1H), 6.53 (td, J=1.7, 4.8 Hz, 1H), 6.25 (td, J=1.8, 5.5 Hz, 1H), 6.11 (td, J=1.6, 5.1 Hz, 1H), 4.53 (dd, J=7.6, 11.5 Hz, 1H), 4.40 (dd, J=7.4, 11.3 Hz, 1H), 2.52 (quin, J=7.6 Hz, 1H), 1.92 (dd, J=4.7, 8.6 Hz, 1H), 1.76 (dd, J=4.7, 6.7 Hz, 1H) ppm; $^{13}$C NMR (100 MHz, CDCl$_3$) δ 155.4, 152.3, 145.3, 138.6, 133.8, 131.7, 129.4, 125.2, 121.7, 70.9, 41.5, 24.6, 16.9 ppm.

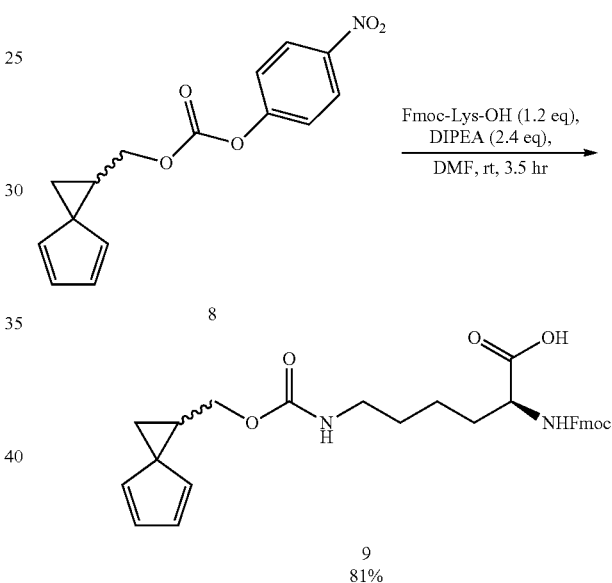

Fmoc-Lys(spiro[2.4]hepta-4,6-dien-1-ylmethyl carbonate)-OH (9)

8 (5.12 g, 17.8 mmol, 1 eq) was added to DMF (40 mL), followed by Fmoc-Lys-OH (7.87 g, 21.4 mmol, 1.2 eq) and DIPEA (7.44 mL, 42.7 mmol, 2.4 eq). The reaction was stirred until consumption of the starting material (NMR, 3.5 hr), then poured into EtOAc (100 mL) and $H_2O$ (140 mL). The aqueous layer was acidified to pH 2-3 with HCl (1 M, 100 mL), poured into a separatory funnel, and the layers separated. The aqueous layer was extracted with EtOAc (2×100 mL). The organic layers were combined, washed with brine (100 mL), dried over $Na_2SO_4$, filtered, and the solvent removed. The residue was subjected to flash column chromatography (Hexane:EtOAc, 3:1 then DCM:MeOH:AcOH, 89:10:1) and the solvent removed. Residual AcOH and DMF was removed by suspending the product in DCM, washing with brine, drying the organic layer over $Na_2SO_4$, filtering, then removing the solvent to yield 9 (7.43 g, 81%) as an eggshell foam.

Rf (DCM:MeOH, 90:10): 0.39; $^1$H NMR (500 MHz, CDCl$_3$) δ 8.62 (br. s., 1H), 7.75 (d, J=7.3 Hz, 2H), 7.66-7.49 (m, 2H), 7.39 (t, J=7.4 Hz, 2H), 7.30 (t, J=7.3 Hz, 2H), 6.54 (br. s., 1H), 6.47 (br. s., 1H), 6.21 (br. s., 1H), 6.04 (br. s., 1H), 5.74 (d, J=7.3 Hz, 1H), 4.91 (br. s., 1H), 4.53-4.00 (m, 5H), 3.21-3.00 (m, 2H), 2.97 (s, 1H), 2.90 (d, J=0.8 Hz, 1H), 2.47-2.31 (m, 1H), 1.95-1.27 (m, 6H) ppm; $^{13}$C NMR (125 MHz, CDCl$_3$) 163.2, 156.7, 143.6, 141.2, 138.9, 134.5, 130.9, 128.9, 127.6, 127.0, 125.1, 119.9, 115.6, 67.0, 66.5, 53.5, 47.1, 41.6, 40.4, 36.8, 31.8, 29.2, 25.7, 22.2, 21.4, 17.1 δ ppm.

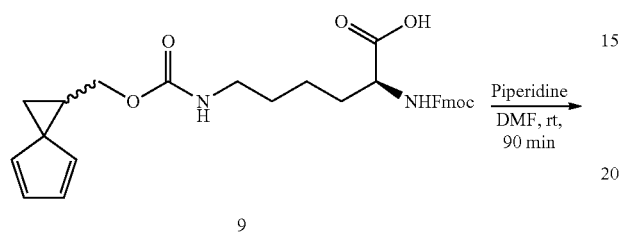

9

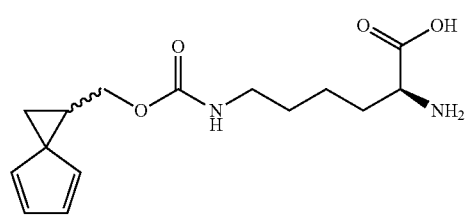

10
71%

CP2-NNAA (10)

9 (5.50 g, 10.6 mmol, 1 eq) was added to DMF (150 mL), followed by piperidine (16.8 mL). The reaction was stirred until consumption of the starting material (TLC, 90 min), then the solvent was removed. Et$_2$O (100 mL) was added to the residue, and the suspension was sonicated for 5 min. The suspension was filtered and rinsed with H$_2$O (2×100 mL) and Et$_2$O (100 mL). The solid was suspended in MeOH (10 mL), stirred for 10 min with gentle warming (~40° C.), Et$_2$O (40 mL) was added, the suspension filtered and rinsed with Et$_2$O (2×50 mL). The compound was dried under vacuum to yield 10 (2.24 g, 71%) as a white powder.

Rf (DCM:MeOH, 85:15): 0.29; $^1$H NMR (400 MHz, DMSO-d$_6$+1 drop TFA) δ 8.20 (br. s., 3H), 7.16 (t, J=5.5 Hz, 1H), 6.48 (td, J=1.8, 5.1 Hz, 1H), 6.40 (d, J=5.1 Hz, 1H), 6.32 (d, J=5.1 Hz, 1H), 6.12 (td, J=1.9, 4.9 Hz, 1H), 4.24 (dd, J=6.7, 11.7 Hz, 1H), 3.99 (dd, J=7.6, 11.5 Hz, 1H), 3.88 (d, J=5.1 Hz, 1H), 2.94 (d, J=5.9 Hz, 2H), 2.37 (quin, J=7.5 Hz, 1H), 1.83-1.63 (m, 4H), 1.44-1.19 (m, 4H) ppm; $^{13}$C NMR (100 MHz, DMSO-d$_6$+1 drop TFA):

171.2, 156.2, 139.3, 135.2, 130.4, 128.3, 65.3, 51.9, 42.0, 29.7, 28.9, 25.7, 21.6, 16.4; MS (EI) Exact mass cald. for C$_{15}$H$_{22}$N$_2$O$_4$ [M]$^+$: 294.1580, found: 294.1571.

Synthesis of CP2-NHS (12)

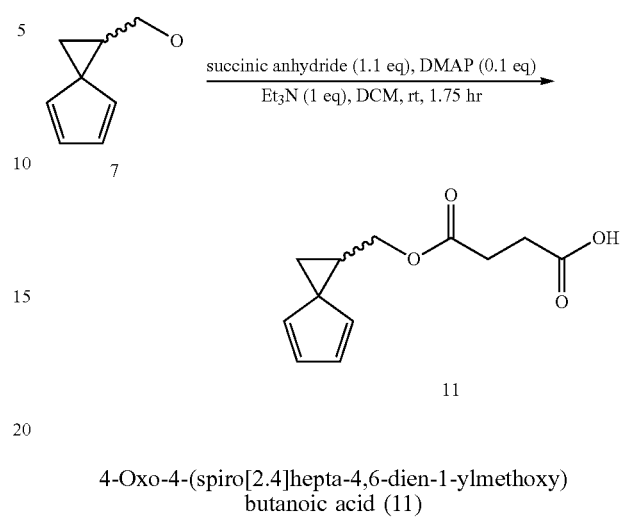

4-Oxo-4-(spiro[2.4]hepta-4,6-dien-1-ylmethoxy) butanoic acid (11)

DCM (1.5 mL) was added to a vial containing 1 (0.37 g, 3.0 mmol, 1 eq). Et$_3$N (0.42 mL, 3.0 mmol, 1 eq), DMAP (37 mg, 0.30 mmol, 0.1 eq) and succinic anhydride (0.33 g, 3.3 mmol, 1.1 eq) were added, the reaction capped under an atmosphere of air, and stirred at rt until consumption of the starting material (TLC, 1.75 hr). The reaction mixture was poured into a separatory funnel with DCM (50 mL) and washed with aqueous HCl (1 M, 50 mL). The aqueous layer was extracted with DCM (50 mL), the organic layers combined, dried over Na$_2$SO$_4$, filtered, and the solvent removed to yield 11 of sufficient purity for the next reaction.

Rf (EtOAc): 0.56; $^1$H NMR (400 MHz, CDCl$_3$) δ 10.60 (br. s., 1H), 6.57 (td, J=1.9, 5.3 Hz, 1H), 6.50 (td, J=1.8, 5.1 Hz, 1H), 6.21 (td, J=1.7, 5.2 Hz, 1H), 6.07 (td, J=1.8, 5.1 Hz, 1H), 4.37 (dd, J=7.4, 11.7 Hz, 1H), 4.20 (dd, J=7.0, 11.7 Hz, 1H), 2.74-2.57 (m, 4H), 2.42 (quin, J=7.8 Hz, 1H), 1.85 (dd, J=4.5, 8.4 Hz, 1H), 1.69 (dd, J=4.3, 7.0 Hz, 1H) ppm.

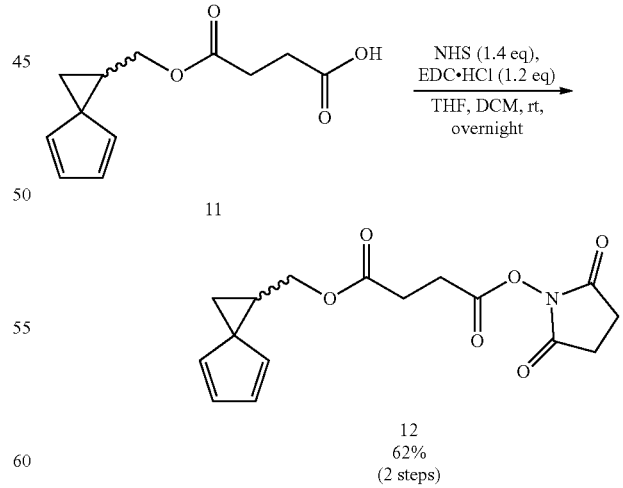

CP2-NHS (12)

THF (10 mL) was added to a vial containing 11 (theo 3.0 mmol, 1 eq). NHS (0.48 g, 4.2 mmol, 1.4 eq), EDC·HCl (0.69 g, 3.6 mmol, 1.2 eq) and DCM (5 mL) were added, the reaction capped under an atmosphere of air, and stirred at rt overnight. The solvent was removed and the residue was subjected to flash column chromatography (Hexane:EtOAc, 1:1) to yield 12 (0.59 g, 62% over two steps) as a colourless, viscous oil.

Rf (Hexane:EtOAc, 1:1): 0.34; $^1$H NMR (400 MHz, CDCl$_3$) δ 6.56 (td, J=1.8, 5.1 Hz, 1H), 6.48 (td, J=1.8, 5.1 Hz, 1H), 6.21 (td, J=1.6, 3.4 Hz, 1H), 6.06 (td, J=1.6, 3.4 Hz, 1H), 4.36 (dd, J=7.4, 11.7 Hz, 1H), 4.21 (dd, J=7.4, 11.7 Hz, 1H), 2.93 (t, J=7.0 Hz, 2H), 2.83 (s, 4H), 2.73 (t, J=7.4 Hz, 2H), 2.42 (quin, J=7.6 Hz, 1H), 1.83 (dd, J=4.3, 8.6 Hz, 1H), 1.68 (dd, J=4.5, 6.8 Hz, 1H) ppm; $^{13}$C NMR (100 MHz, CDCl$_3$) δ 170.8, 168.9, 167.6, 138.8, 134.3, 131.2, 129.0, 66.6, 41.5, 28.6, 26.2, 25.5, 25.1, 17.3 ppm.

1. Ledford, B. E.; Carreira, E. M., Total Synthesis of (+)-Trehazolin: Optically Active Spirocycloheptadienes as Useful Precursors for the Synthesis of Amino Cyclopentitols. *Journal of the American Chemical Society* 1995, 117, 11811-11812.

Example 9. CP2 Diene-Maleimide Conjugation for Preparation of ADCs Via Crosslinker-Modified mAb The feasibility of spirocyclopentadiene-maleimide reactions for bioconjugation was evaluated. Spirocyclopentadiene groups were introduced via an amine-reactive heterobifunctional linker with the same general strategy described in Example 3.

Introduction of CP2 functionality onto mAbs: CP2 diene functionality was installed onto IgG1 mAbs by reaction of lysine primary amines with NHS-ester activated CP2 diene. This approach resulted in randomly conjugated, amide-linked cyclopentadiene groups. The resulting antibody is termed mAb-CP2-linker, but may also be denoted as mAb-CP2 in figures. See figure captions for clarification. A typical mAb modification reaction is described as follows. Mab solution was adjusted to 5 mg/mL (3 mL, 15 mg mAb, 100 nmol, 1 eq.) with PBS pH 7.2 followed by addition of 10% v/v 1 M NaHCO$_3$. This solution was chilled on ice and 35 µL CP2-NHS (10 mM stock in DMAc, 350 nmol, 3.5 equivalents) was added. The reaction proceeded on ice for 5 minutes followed by reaction at room temperature for 1 h with continuous mixing. Reacted mAb was purified by dialysis (Slide-A-Lyzer, 10 kDa MWCO) against PBS, 1 mM EDTA, pH 7.4, 0° C. for 24 h. CP2 introduction was quantified by intact deglycosylated mass spectrometry as described below and found to be 3.29 CP2-linkers (and thus dienes) per mAb in this example, which corresponds to 94% conversion of CP2-NHS to antibody conjugate.

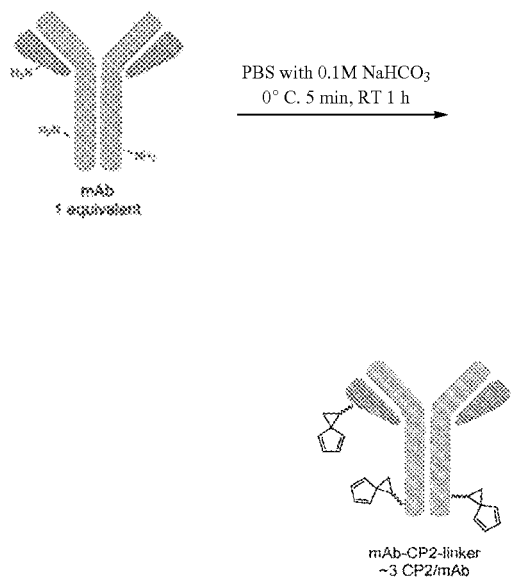

Reaction of CP2-modified mAb with maleimido-MMAEs: mAb-CP2-linker (3.29 CP2 dienes/mAb, 1 mg, 6.7 nmol mAb, 1 equivalent) was diluted with PBS (pH 7.4) to a final concentration of 3.16 mg/mL. Next, DMSO was added to yield a 20% v/v solution followed by addition of 1 M sodium phosphate monobasic to yield a 10% v/v solution. Addition of all solution components yielded a mixture comprising 2.43 mg/mL mAb, 53.3 µM CP2, 1.78 M DMSO, 110 mM sodium phosphate, 100 mM NaCl, pH 5.5. AM-MMAE or PM-MMAE (10 µL of a 10 mM stock solution in DMAc, 100 nmol, 15 equivalents) was added to the antibody solution. The reaction mixture was vortexed briefly and allowed to proceed at 22° C. or 37° C. with mixing. After 4 h reaction, N-acetyl cysteine (8 µL of a 100 mM solution, 120 equivalents) was added to quench unreacted maleimide groups. Samples were purified using PD Spintrap G-25 devices (GE Healthcare Life Sciences) to remove small molecule components from the mixture. Samples were subsequently analyzed by reduced deglycosylated mass spectrometry as described below.

Scheme 9.1. Modification of mAbs with CP2-NHS

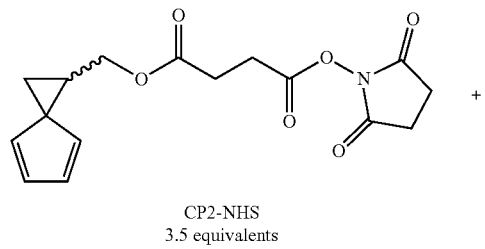

CP2-NHS
3.5 equivalents

Scheme 9.2. Reaction of mAb-CP2-linker with maleimido MMAEs.

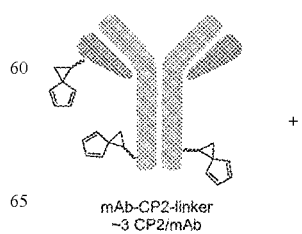

mAb-CP2-linker
~3 CP2/mAb

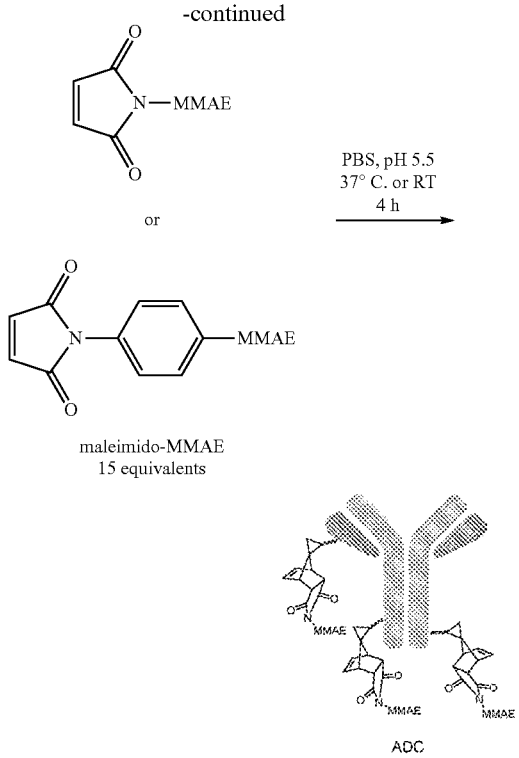

maleimido-MMAE
15 equivalents

Mass spectrometry analysis; Samples were analyzed as described in Example 1.

FIG. 9.1. Intact deglycosylated mass spectra before (A) and after (B) reaction with CP2-NHS. Numbers below peaks in (B) indicate the number of CP2-diene groups introduced into the mAb. Estimation of CP2-linker introduction by peak intensities yields 3.29 CP2-dienes per mAb.

TABLE 9.1

Summary of CP2-NHS mAb reaction

| equivalents CP1-NHS (rel to mAb) | [mAb] mg/nL | CP2-linker per mAb | conversion (%) |
|---|---|---|---|
| 3.5 | 5 | 3.29 | 94 |

FIG. 9.2. Reduced deglycosylated mass spectrometry analysis of mAb-CP2-linker before and after reaction with AM-MMAE and PM-MMAE Spectra are zoomed to show both heavy and light chains.

FIG. 9.3. Reduced deglycosylated mass spectra of mAb-CP2-linker maleimido MMAE reaction products. Spectra are zoomed to show antibody heavy chain. The number of conjugated species is indicated above each peak.

TABLE 9.2

Summary of mAb-CP2-linker maleimido-MMAE reactions[a]

| payload | Equivalents (rel to mAb) | pH | temp | MMAE conjugation (%) |
|---|---|---|---|---|
| AM-MMAE | 15 | 5.5 | 37° C. | 88 |
|  |  |  | 22° C. | 73 |
| PM-MMAE | 15 | 5.5 | 37° C. | 95 |
|  |  |  | 22° C. | 78 |

[a]All reactions performed at 2.43 mg/mL mAb-CP2-linker for 4 h.

CP2 diene groups installed onto the surface of antibodies partially reacted with maleimido-MMAE prodrugs within 4 h at room temperature. No non-specific conjugation was observed by mass spectrometry, as all conjugate peaks tracked from mAb-CP2-linker peaks and not unreacted mAb. This reaction is much more efficient than furan diene, but less efficient than CP1 diene for reaction with maleimido-MMAE payloads. This approach can be used for production of bioconjugates.

Example 10. Kinetics of mAb-CP2-Linker Conjugation to Maleimido-MMAEs at 1.0 Molar Equivalent Maleimido-MMAE to Diene Groups Reaction kinetics of CP2 dienes with maleimido MMAEs at 22° C. was evaluated.

Introduction of CP2 diene functionality onto mAbs: CP2 functionality was installed onto IgG1 mAbs by reaction of lysine primary amines with NHS-ester activated CP2. This approach resulted in randomly conjugated, amide-linked cyclopentadiene groups. A typical mAb modification reaction is described as follows. Mab solution was adjusted to 5 mg/mL (3 mL, 15 mg mAb, 100 nmol, 1 eq.) with PBS pH 7.2 followed by addition of 10% v/v 1 M $NaHCO_3$. This solution was chilled on ice and 35 μL CP2-NHS (10 mM stock in DMAc, 350 nmol, 3.5 equivalents) was added. The reaction proceeded on ice for 5 minutes followed by reaction at room temperature for 1 h with continuous mixing. Reacted mAb was purified by dialysis (Slide-A-Lyzer, 10 kDa MWCO) against PBS, 1 mM EDTA, pH 7.4, 0° C. for 24 h. CP2-linker introduction was quantified by intact deglycosylated mass spectrometry as described below and found to be 3.29 CP2-linkers (and thus dienes) per mAb in this example, which corresponds to 94% conversion of CP2-NHS to antibody conjugate.

Reaction of CP2-modified mAb with maleimido-MMAEs: mAb-CP2-linker (3 mg, 3.29 CP2/mAb, 66 nmol CP2 diene, 1 equivalent) was diluted with PBS (pH 7.4) to a final concentration of 1.7 mg/mL. Next, DMSO was added to yield a 20% v/v solution followed by addition of 1 M sodium phosphate monobasic to yield a 10% v/v solution. Addition of all solution components yielded a mixture comprising 1.3 mg/mL mAb, 32.3 μM CP2 diene, 1.78 M DMSO, 110 mM sodium phosphate, 100 mM NaCl, pH 5.5. AM-MMAE or PM-MMAE (6.6 μL of a 10 mM stock solution in DMSO, 66 nmol, 1 equivalent) was added to the antibody solution. The reaction mixture was vortexed briefly and allowed to proceed at 22° C. with mixing. Aliquots (180 μL) were removed at various timepoints and N-acetyl cysteine (3 μL of a 100 mM solution, 45 equivalents) was added to quench unreacted maleimide groups. Samples were then purified using PD Spintrap G-25 devices (GE Healthcare Life Sciences) to remove small molecule components from the mixture. Samples were then analyzed by reduced deglycosylated mass spectrometry as described below.

Mass spectrometry analysis: Samples were analyzed as described in Example 1.

Calculation of CP2 diene-maleimide reaction rate constants: Second order rate constants for reaction of maleimido-MMAEs with CP2 dienes in mAb-CP2-linker were determined from peak intensities in deglycosylated reduced mass spectra. Reaction progress was monitored by both disappearance of mAb-CP2-linker peaks and appearance of mAb-CP2-linker-MMAE conjugate peaks, but only mAb-CP2-linker peak intensities on the antibody heavy chains were used to calculate relative abundance of reacted CP2 diene. Unreacted CP2 diene groups on mAb heavy chains was calculated using the equation below:

$$CP2 \text{ per } mAb = \left[\frac{b}{a+b+c+d} \times 1\right] + \left[\frac{c}{a+b+c+d} \times 2\right] +$$
$$\left[\frac{d}{a+b+c+d} \times 3\right] + \left[\frac{f}{e+f+g} \times 1\right] + \left[\frac{g}{e+f+g} \times 2\right]$$

a=peak intensity of unmodified heavy chain
b=sum of peak intensities of heavy chains with one CP2 diene group
c=sum of peak intensities of heavy chains with two CP2 diene groups
d=peak intensity of heavy chain with three CP2 diene groups
e=peak intensity of unmodified light chain
f=sum of peak intensities of light chains with one CP2 diene group
g=sum of peak intensities of light chains with two CP2 diene groups Conjugation data were further analyzed in units of molar concentration to determine kinetic constants. Second order rate constants were determined from the slopes of curves generated from plotting 1/[CP2 diene] versus time and linear regression analysis. Reaction half-lives were calculated from Second-order reaction rate constants using the equation shown below:

$$T_{1/2} = \frac{1}{k_2 [CP2]_0}$$

$k_2$=second order rate constant
$[CP2]_0$=CP2 diene concentration at time=0

FIG. 10.1. Reduced deglycosylated mass spectra of mAb-CP2-linker and AM-MMAE-reacted mAb-CP2-linker at 4 h and 48 h. Spectra are zoomed in to show the heavy chain only. Each peak is labelled to indicate the number of species conjugated.

FIG. 10.2. Reduced deglycosylated mass spectra of mAb-CP2-linker and PM-MMAE-reacted CP2-mAb at 4 h and 48 h. Spectra are zoomed in to show the heavy chain only. Each peak is labelled to indicate the number of species conjugated.

FIG. 10.3. Reaction of mAb-CP2-linker dienes with maleimido-MMAEs. A) Molar concentration of unreacted CP2 diene over time. Unreacted CP2 diene per mAb was determined from the peak intensities of reduced deglycosylated mass spectra. B) Inverse concentration plot used to calculate reaction rates.

TABLE 10.1

Summary of kinetic data for reaction of mAb-CP2-linker diene with-maleimido-MMAE [a,b,c]

| payload | 2nd order rate constant (M[−1]s[−1]) | $t_{1/2}$ (min) | conversion (%) |
|---|---|---|---|
| AM-MMAE | 2.2 ± 0.1 | 219 | 73 |
| PM-MMAE | 2.1 ± 0.1 | 230 | 93 |

[a] all conjugation reactions performed at pH 5.5, 20% DMSO, 22° C. and 1.3 mg/mL CP2-modified mAb
[b] the molar ratio of MMAE:CP2 diene used was 1:1
[c] calculated from peak intensities of reduced deglycosylated mass spectra of measurement at 48 h.

Reaction of CP2 diene with maleimido-MMAEs was slower than CP1 dienes, with half-live's on the order of several hours. Unlike CP1 diene, no difference in reaction rate was noted for phenyl- vs. alkyl-maleimide. Reaction conversion was 90% for AM-MMAE, but only 73% for PM-MMAE after 48 h reaction. Given the similar rate constants for both substrates, it is possible that a portion of phenyl maleimides degrade after extended time under these conditions, thus limiting overall conversion.

Example 11. CP2-NNAA Incorporation into Antibodies

Incorporation of CP2-NNAA into position K274 or S239 of an anti EphA2 (1C1) antibody, the quality of expressed mAb, and reactivity of CP2-NNAA diene after antibody incorporation was assessed.

Preparation of CP2 NNAA stock solution: CP2 NNAA (0.5 g, 1.7 mmol) was combined with 7.8 mL 0.2 M NaOH in $H_2O$. The resulting slurry was stirred at room temperature until all solids dissolved (10 minutes). After complete dissolution the light-yellow solution was passed through a 0.2 μm filter, aliquoted, and stored at −80° C. until use. This procedure resulted in 8.2 mL of 216 mM CP2 NNAA stock solution.

Structure of CP2-NNAA

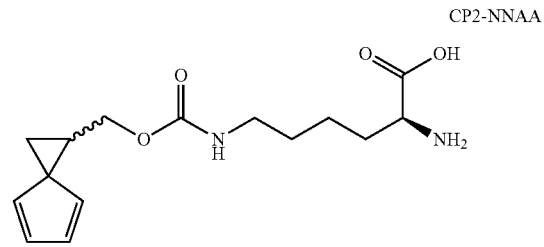

CP2-NNAA

Antibody expression: 12G3H11 or 1C1 IgG1 antibody genes with an amber mutation at Fc position K274 or S239 were cloned into a proprietary pOE antibody expression vector. The construct was transfected into CHO-G22 by PEImax (1.5 L of G22 cells), along with a plasmid encoding PyIRS double mutant (Y306A/Y384F) or wild-type PyIRS and a plasmid containing tandem repeats of the tRNA expression cassette (pORIP 9xtRNA). Four hours post transfection, 3.3% of feed F9 (proprietary) and 0.2% of feed F10 (proprietary) were added to cells and the cells were further incubated at 34 degrees. CP2-NNAA was added the next day at final concentration of 0.26 mM for 1C1 K274 and 1C1 S239 transfected cells. Cells were fed again on day 3 and day 7 with 6.6% of feed F9 and 0.4% of feed F10. Cells were spun down and supernatant was harvested on day 11. The supernatant was purified by IgSelect affinity column (GE Health Care Life Science). The antibody was eluted with 50 mM glycine, 30 mM NaCl, pH 3.5 elution buffer, neutralized with 1 M Tris buffer pH 7.5, and dialyzed into PBS, pH 7.2. Concentration of antibody eluted was determined by absorbance measurement at 280 nm. The back calculated titer was 57 mg/L for 1C1 K274CP2-NNAA and 76 mg/L for 1C1 S239CP2-NNAA. 12G3H11 mAb was expressed in a similar manner at smaller scale, with CP2-NNAA feed concentration varied. Recovered antibody was analyzed by SDS-PAGE using standard methods. Antibody was also analyzed by size exclusion chromatography and mass spectrometry as described below. Antibodies incorporating CP2-NNAA are denoted as mAb-CP1-NNAA to distinguish them from mAb-CP2-linker constructs, or mAb-[position]CP2-NNAA where [position] indicates the amino acid number and amino acid symbol that was mutated to CP2-NNAA.

Size exclusion chromatography: SEC analysis was performed using an Agilent 1100 Capillary LC system equipped with a triple detector array (Viscotek 301, Viscotek, Houson, Tex.); the wavelength was set to 280 nm, and samples were run on a TSK-GEL G3000SWXL column (Toso Bioscience LLC, Montgomeryville, Pa.) using 100 mM sodium phosphate buffer, pH 6.8 at a flow rate of 1 mL/min.

Mass spectrometry analysis: For deglycosylated mAb analysis, EndoS (5 μL Remove-iT EndoS (1:10 dilution in PBS, 20,000 units/mL, New England BioLabs) was combined with 50 μL sample (1 mg/mL mAb) and 5 μL glyco buffer 1 (New England BioLabs) and followed by incubation for 1 h at 37° C. Reduced samples were prepared by addition of 5 μL Bond-Breaker TCEP solution (0.5 M, Thermo Fisher Scientific) and incubation for 10 min at 37° C. Mass spectrometry analysis was performed using an Agilent 6520B Q-TOF mass spectrometer equipped with a RP-HPLC column (ZORBAX 300 Diphenyl RRHD, 1.8 micron, 2.1 mm×50 mm). High-performance liquid chromatography (HPLC) parameters were as follows: flow rate, 0.5 ml/min; mobile phase A was 0.1% (v/v) formic acid in HPLC-grade $H_2O$, and mobile phase B was 0.1% (v/v) formic acid in acetonitrile. The column was equilibrated in 90% A/10% B, which was also used to desalt the mAb samples, followed by elution in 20% A/80% B. Mass spec data were collected for 100-3000 m/z, positive polarity, a gas temperature of 350° C., a nebulizer pressure of 48 lb/in$^2$, and a capillary voltage of 5,000 V. Data were analyzed using vendor-supplied (Agilent v.B.04.00) MassHunter Qualitative Analysis software and peak intensities from deconvoluted spectra were used to derive the relative proportion of species in each sample.

FIG. 11.1. Titers and cell viability of 12G3H11 K274CP2-NNAA mAb after expression in mammalian cells comprising mutant or wild type tRS. CP2-NNAA final concentration in media is indicated in the figure legend. 12G3H11 K274CP2-NNAA mAb expression with mutant tRS was comparable to azido-lysine with wild-type tRS, with minimal toxicity.

TABLE 11.1

Summary of 1C1 K274CP2-NNAA and 1C1 S239CP2-NNAA mAb production

|  | K274 | S239 |
| --- | --- | --- |
| NNAA feed (mM) | 0.5 | 0.5 |
| Volume (L) | 2 | 2 |
| Mass recovered (mg) | 114 | 153 |
| Titer (mg/L) | 57 | 76 |
| Monomer (%) | 93.2 | 99 |

FIG. 11.2. Mass spectrometry analysis of deglycosylated 1C1 K274CP2-NNAA mAb. A) Intact mAb B) Reduced mAb zoomed to show the light chain (LC) and heavy chain (HC). The observed intact mass closely matched the calculated intact mass (147546.03) assuming incorporation of two CP2-NNAAs in the intact mAb structure. The observed heavy chain mass closely matched the calculated heavy chain mass (50325.93) assuming incorporation of one CP2-NNAA into the antibody heavy chain. No incorporation of CP2-NNAA into the mAb light chain was observed. Analogous spectra for 1C1 wild-type mAb are shown in FIG. 11.4.

FIG. 11.3. Mass spectrometry analysis of deglycosylated 1C1 S239CP2-NNAA mAb. A) Intact mAb B) Reduced mAb zoomed to show the light chain (LC) and heavy chain (HC). The observed intact mass closely matched the calculated intact mass (147628.23) assuming incorporation of two CP2 amino acids in the intact mAb structure. The observed heavy chain mass closely matched the calculated heavy chain mass (50367.03) assuming incorporation of CP2-NNAA into the antibody heavy chain. No incorporation of CP2-NNAA into the mAb light chain was observed. Analogous spectra for 1C1 wild-type mAb are shown in FIG. 11.4

FIG. 11.4. Mass spectrometry analysis of deglycosylated 1C1 wild-type mAb. A) Intact mAb B) Reduced mAb zoomed to show the light chain (LC) and heavy chain (HC). A) Mass range showing intact mAb, B) mass range showing light chain (LC) and heavy chain (HC).

TABLE 11.2

Summary of mass spectrometry data for IC1-K274CP2-NNAA and 1C1-S239CP2-NNAA mAbs

|  | K274 | S239 | WT |
| --- | --- | --- | --- |
| Observed intact mass | 147545.85 | 147628.1 | 147249.63 |
| Observed change relative to WT | +296.2 | +378.4 | NA |
| Calculated change relative to WT | +296.4 | +378.6 | NA |
| Observed heavy chain mass | 50325.22 | 50367.71 | 50177.73 |
| Observed change relative to WT | +147.5 | +189.9 | NA |
| Calculated change relative to WT | +148.2 | +189.3 | NA |

FIG. 11.5. SEC analysis of 1C1 K274CP2-NNAA mAb indicating that monomeric product was obtained. High molecular weight species (HMWS) are indicated.

FIG. 11.6. SEC analysis of 1C1 S239CP2-NNAA mAb indicating that monomeric product was obtained.

FIG. 11.7. Analysis of 1C1-K274CP2-NNAA mAb and 1C1-S239CP2-NNAA mAb by SDS-PAGE.

Incorporation of CP2-NNAA into antibodies at positions K274 and S239 was confirmed by mass spectrometry. Recovered antibody was of high quality, with no truncated product and very little aggregate. Titers achieved at 2 L production scale for 1C1 antibody were reasonably high considering the low amount of CP2-NNAA fed to cells.

Example 12. Production and Evaluation of ADCs with 1C1 K274CP2-NNAA and 1C1 S239CP2-NNAA mAbs Reactivity of CP2-NNAA after incorporation into mAbs at position K274 or S239 of an anti EphA2 (1C1) antibody was assessed by conjugation with AM-MMAE. Resulting ADCs were evaluated to determine drug:antibody ratio (DAR), serum stability, and in vitro cytotoxicity.

Preparation of CP2-mAb ADCs: CP2-NNAA mAb ADCs were prepared in one step, simply by mixing antibody with alkyl-maleimide MMAE (AM-MMAE). First, 1C1-S239CP2-NNAA mAb solution (8 mg, 53 nmol, 1 equivalent) was diluted to 2 mg/mL with PBS (4 mL total volume). DMSO (813 μL) and 1 M sodium phosphate, monobasic (407 μL) was added to yield ~20% and ~10% v/v solution, respectively. AM-MMAE (53.3 μL of 10 mM stock in DMSO, 533 nmol, 10 equivalents) was added to 1C1-S239CP2-NNAA mAb solution and the mixture was vortexed briefly. The reaction proceeded at room temperature for 7 h with continuous mixing. N-acetyl cysteine (43 μL of 100 mM stock in water, 4.3 μmol, 80 equivalents) was added and the solution was incubated for an additional 15 min to quench unreacted maleimide groups. The reaction mixture was then diluted 3-fold with distilled water and subjected to CHT chromatography (Bio-Scale Mini Cartridge CHT Type II 40 µm media column). ADC was eluted with a gradient from buffer A (10 mM phosphate, pH 7.0) to buffer B (10 mM phosphate pH 7.0 containing 2M NaCl) over 25 minutes. After CHT chromatography the sample was buffer exchanged to PBS supplemented with 1 mM EDTA, pH 7.4 by dialysis in a slide-a-lyzer cassette at 4° C. 1C1-K274CP2-NNAA mAb was conjugated with AM-MMAE in the same manner, except the reaction proceeded for 17 h at room temperature.

Preparation of site-specific cysteine ADCs: For some experiments, mAb-CP2-NNAA ADCs were compared to cysteine-conjugated ADCs. For this purpose, an antibody was generated comprising a cysteine at position 239 (termed 1C1-239C). Conjugation of AM-MMAE to 1C1-239C was conducted in three steps; i) reduction and dialysis, ii) oxidation, iii) reaction with AM-MMAE. First, antibodies were mildly reduced to generate free sulfhydryls by combining 4 mL of 2.5 mg/mL antibody solution in 10 mM PBS pH 7.4 containing 1 mM EDTA (10 mg antibody, 66.7 nM, 1 eq) with 53 µL of 50 mM TCEP solution in water (2.7 µmol, 40 eq relative to mAb) followed by gentle mixing at 37° C. for 3 h. Reduced antibody was transferred to a slide-a-lyzer dialysis cassette (10K MWCO) and dialyzed against PBS, 1 mM EDTA, pH 7.4, 4° C. for 24 h with several buffer changes. Reduced antibody was oxidized to reform internal disulfides by addition of dehydroascorbic acid (27 µL of 50 mM stock in DMSO, 1.3 µmol, 20 eq) followed by mixing for 4 h at room temperature. Oxidized antibody solution was combined with 20% v/v DMSO followed by addition of AM-MMAE (53 µL of a 10 mM stock in DMSO, 530 nmol, 8 eq). The reaction proceeded at room temperature with mixing for 1 h followed by addition of N-acetyl cysteine (43 µL of 100 mM stock in water, 4.2 µmol, 64 eq) to quench unreacted maleimides. The reaction mixture was then diluted 3-fold with distilled water and subjected to CHT chromatography and dialysis as described above.

FIG. 12.1. Generation of mAb-CP2-NNAA ADCs and mAb-239C ADCs, and structure of AM-MMAE. Note that production of mAb-CP2-NNAA ADC was achieved in one step, whereas production of the mAb-239C ADC occurred in 4 steps. The R group depicted in (B) could be an endogenous thiol-containing small molecule such as cysteine.

Mass spectrometry analysis: Samples were analysed as described in Example 1.

HIC chromatography analysis: ADCs were analyzed by size exclusion chromatography using a Proteomics HIC Butyl NPS column (4.6×35 mm, 5 µm, Sepax) eluted with a gradient of 100% A to 100% B over 22 minutes (mobile phase A: 25 mM Tris pH 8.0, 1.5 M $(NH_4)_2SO_4$, mobile phase B: 25 mM Tris pH 8.0, 5% (v/v) isopropyl alcohol) at room temperature. Protein was detected by UV absorbance at 280 nm. Approximately 50-100 µg protein was injected for each analysis.

rRP-HPLC analysis: For each analysis, the antibodies and ADCs were reduced at 37° C. for 20 minutes using 42 mM dithiothreitol (DTT) in PBS pH 7.2. 10 µg of reduced antibodies and ADCs was loaded onto a PLRP-S, 1000 Å column (2.1×50 mm, Agilent) and eluted at 40° C. at a flow rate of 0.5 mL/min with a gradient of 5% B to 100% B over 25 minutes (mobile phase A: 0.1% trifluoroacetic acid in water, and mobile phase B: 0.1% trifluoroacetic acid in acetonitrile). Percent conjugation was determined using integrated peak areas from the chromatogram.

Serum stability of ADCs: ADCs were incubated in rat serum to challenge the stability of the Diels-Alder conjugate. ADCs were added to normal rat serum (Jackson Immunoresearch) to achieve a final concentration of 0.2 mg/mL (1.33 µM antibody), with the total volume of ADC solution added to serum less than 10%. The ADC-serum mixture was sterile filtered and an aliquot was removed from this mixture and frozen as a t=0 control. The remaining sample was then further incubated at 37° C. in a sealed container without stirring. Conjugated and unconjugated human antibody was recovered from rat serum by immunoprecipitation using Fc-specific anti-human IgG-agarose resin (Sigma-Aldrich). Resin was rinsed twice with PBS, once with IgG elution buffer, and then twice more with PBS. ADC-mouse serum samples were then combined with anti-human IgG resin (100 µL of ADC-serum mixture, 50 µL resin slurry) and mixed for 15 minutes at room temperature. Resin was recovered by centrifugation and then washed twice with PBS. Washed resin was resuspended in 100 µL IgG elution buffer (Thermo Scientific) and further incubated for 5 minutes at room temperature. Resin was removed by centrifugation and then 20 µL of 10× glycobuffer 1 (New England Biolabs) was added to the supernatant. Recovered human antibody solution was sterile filtered, and incubated with EndoS for 1 h at 37° C. Deglycosylated mAbs were then reduced with TCEP and analyzed by LC/MS as described above. Percent conjugated antibody was determined from peak heights of mass spectra.

In vitro cytotoxicity analysis: Human prostate cancer cell line PC3 was obtained from American Type Culture Collection (ATCC). PC3 cells were maintained in RPMI1640 media (Life Technologies) supplemented with 10% heat-inactivated fetal bovine serum (HI-FBS) (Life Technologies) at 37° C. in 5% $CO_2$. Cells were grown to exponential growth phase, harvested by mild trypsinization and seeded into 96-well culture plates at 1500 cells/well. Cells were allowed to adhere for 24 h and then treated with antibodies and ADCs subjected to 4-fold serial dilution at 9 concentrations in duplicate starting from 4000 ng/mL. Treated cells were cultured for 6 days and cell viability was determined using the CellTiter-Glo Luminescent Viability Assay (Promega) following the manufacturer's protocol. Cell viability was calculated as a percentage of control untreated cells. $IC_{50}$ of the cytotoxicity for ADCs was determined using logistic non-linear regression analysis with Prism software (GraphPad).

FIG. 12.2. Reduced, glycosylated mass spectrometry analysis of mAb-CP2-NNAA and mAb-cysteine before and after reaction with AM-MMAE. Spectra are zoomed in to show the mAb heavy chain. Drug:antibody ratio (DAR) 0 and 1 peaks are indicated for ADC samples, one drug per heavy chain (DAR 1) is expected for each construct.

FIG. 12.3. Reduced, glycosylated mass spectrometry analysis of mAb-CP2-NNAAs and mAb-cysteine before and after reaction with AM-MMAE. Spectra are zoomed in to show the mAb light chain. No AM-MMAE light chain conjugates were detected, indicating that conjugation was site-specific the mAb heavy-chain.

TABLE 12.1

Summary of mAb-CP2-NNAA ADC characterization by mass spectrometry[a]

| mAb | payload | Observed Δ mass (AMU) | Calculated Δ mass (AMU) | Conversion[b] | DAR |
|---|---|---|---|---|---|
| 1C1-K274CP2-NNAA | AM-MMAE | 1317.06 | 1316.65 | 98% | 1.96 |

TABLE 12.1-continued

Summary of mAb-CP2-NNAA ADC characterization by mass spectrometry[a]

| mAb | payload | Observed Δ mass (AMU) | Calculated Δ mass (AMU) | Conversion[b] | DAR |
|---|---|---|---|---|---|
| 1C1-S239CP2-NNAA | AM-MMAE | 1316.28 | 1316.65 | 97% | 1.94 |
| 1C1-239C | AM-MMAE | 1316.42 | 1316.65 | 95% | 1.90 |

[a]mAb heavy-chains were analyzed from glycosylated, reduced mass spectra
[b]Calculated from relative peak heights of conjugated and unconjugated species FIG. 12.4. Hydrophobic interaction chromatography analysis of mAb-CP2-NNAA and mAb-cysteine ADCs. Disappearance of the peak corresponding to the retention time of 1C1 CP2-NNAA and appearance of a peak with increased retention time indicates conjugation of AM-MMAE to mAbs. Note that for 1C1 K274CP2-NNAA ADC DAR 1 and DAR 2 species are detected.

FIG. 12.5. Reduced reverse-phase high-performance chromaography analysis of mAb-CP2-NNAA and mAb-cysteine ADCs. Disappearance of the heavy-chain peak in ADCs and appearance of a peak of longer retention time indicates conjugation of AM-MMAE to the heavy chain. Light chain (LC) peak retention time did not change before and after conjugation, indicating that conjugation was specific to the mAb heavy-chain.

TABLE 12.2

Summary of ADC characterization by chromatography methods

| mAb | payload | Conjugaion efficiency HIC[a] | DAR HIC | Conjugation efficiency rRP-HPLC[a] | DAR rRP-HPLC |
|---|---|---|---|---|---|
| 1C1-K274CP2-NNAA | AM-MMAE | 97% | 1.94 | 91% | 1.82 |
| 1C1-S239CP2-NNAA | AM-MMAE | 95% | 1.9 | 97% | 1.94 |
| 1C1-239C | AM-MMAE | 98% | 1.96 | 95% | 1.9 |

[a]Calculated from relative peak areas between conjugated and unconjugated species FIG. 12.6. Reduced SDS-PAGE analysis of mAb-CP2-NNAA and mAb-cysteine ADCs.

FIG. 12.7. Reduced, deglycosylated mass spectrometry analysis of mAb-CP2-NNAA ADCs before and after incubation in rat serum for 7 days at 37° C. Mass spectra are zoomed to show the heavy chain (HC) only. Lack of unconjugated HC signal in serum-incubated samples (D and H) indicates that the Diels-Alder conjugate was stable.

FIG. 12.8. Quantification of mAb-CP2-NNAA ADC DARs before and after incubation in rat serum for 7 d at 37° C. DARs were calculated from the peak heights of mass spectra shown in FIG. 12.7. Values are reported as the mean±standard deviation, n=3. No drug loss was detected under these conditions.

FIG. 12.9. Cytotoxicity of mAb-CP2-NNAA and mAb-cysteine ADCs towards PC3 cancer cells in vitro. mAb-CP2-NNAA AM-MMAE ADCs exhibited similar potencies as the analogous ADC prepared by site-specific cysteine conjugation of AM-MMAE.

CP2-NNAA diene reacted with maleimide contained on AM-MMAE with similar conversions to cysteine sulfhydryl groups. The key difference in preparation of the mAb-CP2-NNAA ADC vs. the mAb-cysteine ADC was reduction in the number of steps in the conjugation process. Cysteine mAb required 3 steps and 2 days for production, whereas CP2-NNAA mAb ADCs were produced in one step in less than 24 h. Resulting mAb-CP2-NNAA ADCs are stable under physiologically relevant conditions and did not show drug loss when incubated in rat serum at 37° C. for 7 days. CP2-NNAA mAb ADCs were potent in vitro, with activities similar to an ADC prepared by site-specific cysteine conjugation.

Example 13. Synthesis of Cyclopentadiene and Furan-Containing Compounds

Materials and Methods:Unless stated otherwise, reactions were conducted under an atmosphere of $N_2$ using reagent grade solvents. DCM, and toluene were stored over 3 Å molecular sieves. THF was passed over a column of activated alumina. All commercially obtained reagents were used as received. Thin-layer chromatography (TLC) was conducted with E. Merck silica gel 60 F254 pre-coated plates (0.25 mm) and visualized by exposure to UV light (254 nm) or stained with p-anisaldehyde, ninhydrin, or potassium permanganate. Flash column chromatography was performed using normal phase silica gel (60 Å, 0.040-0.063 mm, Geduran). $^1H$ NMR spectra were recorded on Varian spectrometers (400, 500, or 600 MHz) and are reported relative to deuterated solvent signals. Data for $^1H$ NMR spectra are reported as follows: chemical shift (δ ppm), multiplicity, coupling constant (Hz) and integration. $^{13}C$ NMR spectra were recorded on Varian Spectrometers (100, 125, or 150 MHz). Data for $^{13}C$ NMR spectra are reported in terms of chemical shift (δ ppm). Mass spectra were obtained from the UC Santa Barbara Mass Spectrometry Facility on a (Waters Corp.) GCT Premier high resolution time-of-flight mass spectrometer with a field desorption (FD) source.

Synthesis of CP3-NHS (13)

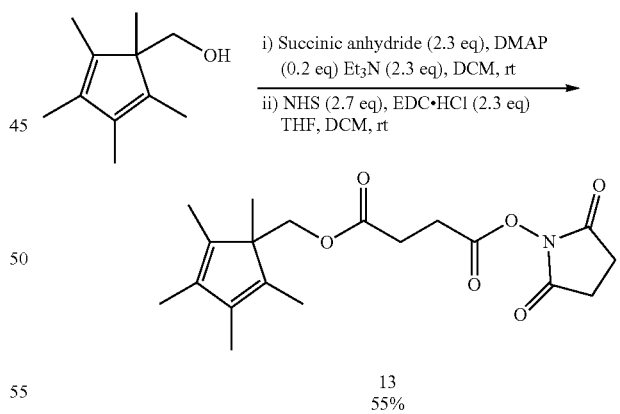

13
55%

2,5-Dioxopyrrolidin-1-yl (1,2,3,4,5-pentamethylcyclopenta-2,4-dienyl)methyl succinate (13): DCM (8 mL) was added to a vial containing (1,2,3,4,5-pentamethylcyclopenta-2,4-dienyl)methanol[1] (0.33 g, 2.0 mmol, 1 eq). Et$_3$N (0.64 mL, 4.6 mmol, 2.3 eq), DMAP (46 mg, 0.38 mmol, 0.2 eq) and succinic anhydride (0.46 g, 4.6 mmol, 2.3 eq) were added, the reaction capped under an atmosphere of air, and stirred at rt overnight. The reaction was quenched with H$_2$O (1 mL) then poured into a separatory funnel. HCl (1 M, 50 mL) was added and extracted with DCM (2×50 mL). The organic layers were combined, washed with brine (50 mL), dried over Na$_2$SO$_4$, filtered, and the solvent removed to yield 4-oxo-4-((1,2,3,4,5-pentamethylcyclopenta-2,4-dienyl)methoxy)butanoic acid which was used directly in the next reaction.

Rf (EtOAc): 0.24; $^1$H NMR (400 MHz, CDCl$_3$) δ 3.98 (s, 2H), 2.64-2.59 (m, 2H), 2.59-2.54 (m, 2H), 1.76 (s, 6H), 1.74 (s, 6H), 0.95 (s, 3H) ppm.

THF (10 mL) was added to a vial containing 4-oxo-4-((1,2,3,4,5-pentamethylcyclopenta-2,4-dienyl)methoxy)butanoic acid (~2 mmol). NHS (0.61 g, 5.3 mmol, 2.7 eq), EDC-HCl (0.87 g, 4.6 mmol, 2.3 eq) and DCM (6 mL) were added, the reaction capped under an atmosphere of air, and stirred at rt overnight. The solvent was removed and the residue was subjected to flash column chromatography (Hexane:EtOAc, 3:1→2:1) to yield 7 (0.39 g, 55% over two steps) as a white solid.

Rf (Hexane:EtOAc, 7:3): 0.27; $^1$H NMR (400 MHz, CDCl$_3$) δ 4.00 (s, 2H), 2.89 (t, J=6.7 Hz, 2H), 2.85 (br. s., 4H), 2.67 (t, J=7.8 Hz, 2H), 1.77 (s, 6H), 1.74 (s, 6H), 0.95 (s, 3H) ppm; $^{13}$C NMR (100 MHz, CDCl$_3$) δ 170.7, 168.9, 167.6, 138.4, 135.0, 68.2, 55.3, 28.6, 26.2, 25.5, 16.8, 11.0, 10.1 ppm; IR (ATR) 2973, 2935, 1815, 1782, 1729, 1208, 1089, 1069, 967 cm$^{-1}$; HRMS (EI) Exact mass cald. for C$_{19}$H$_{25}$NO$_6$ [M]$^+$: 363.1682, found: 363.1676.

Synthesis of F2-NHS (17)

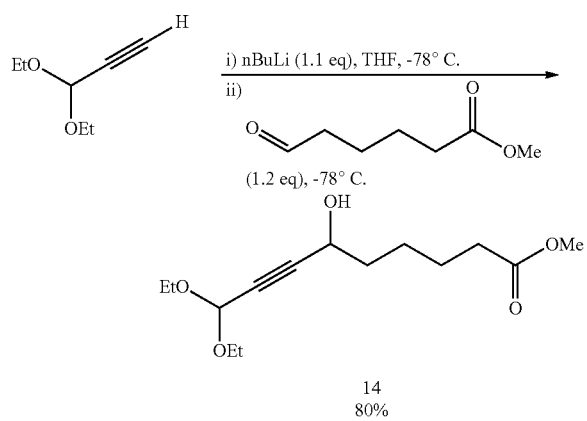

Methyl 9,9-diethoxy-6-hydroxynon-7-ynoate (14)

3,3-Diethoxyprop-1-yne (0.72 mL, 5.0 mmol, 1 eq) was added to THF (15 mL) then cooled to −78° C. nBuLi (2.33 M in hexanes, 2.4 mL, 5.5 mmol, 1.1 eq) was added dropwise then the reaction mixture stirred a further 30 min at −78° C. Methyl 6-oxohexanoate (0.87 g, 6.0 mmol, 1.2 eq) dissolved in THF (5 mL) was added dropwise then the reaction mixture stirred at −78° C. for 1 hr. The reaction mixture was poured into a separatory funnel containing a saturated aqueous solution of sodium bicarbonate (100 mL) then extracted with Et$_2$O (2×50 mL). The combined organic layers were washed with brine (50 mL), dried over MgSO$_4$, filtered, the solvent removed, and the residue subjected to flash column chromatography (Hexane:EtOAc, 2:1) to yield 14 (1.1 g, 80%) as a clear and colourless oil.

Rf (Hexane:EtOAc, 6:4): 0.41; $^1$H NMR (400 MHz, CDCl$_3$) δ 5.28 (d, J=1.6 Hz, 1H), 4.47-4.36 (m, J=3.5 Hz, 1H), 3.76-3.67 (m, 2H), 3.67-3.63 (m, 3H), 3.56 (qd, J=7.0, 9.4 Hz, 2H), 2.34-2.27 (m, 3H), 1.76-1.59 (m, 4H), 1.54-1.42 (m, 2H), 1.21 (t, J=7.0 Hz, 6H) ppm; $^{13}$C NMR (100 MHz, CDCl$_3$) δ 174.0, 91.2, 86.2, 80.0, 61.8, 60.8, 60.8, 51.5, 36.9, 33.8, 24.6, 24.4, 15.0 ppm; IR (ATR) 3451, 2932, 1736, 1437, 1328, 1135, 1051, 1012 cm$^1$; HRMS (EI) Exact mass cald. for C$_{14}$H$_{23}$O$_5$ [M−H]$^+$: 271.1545, found: 271.1546.

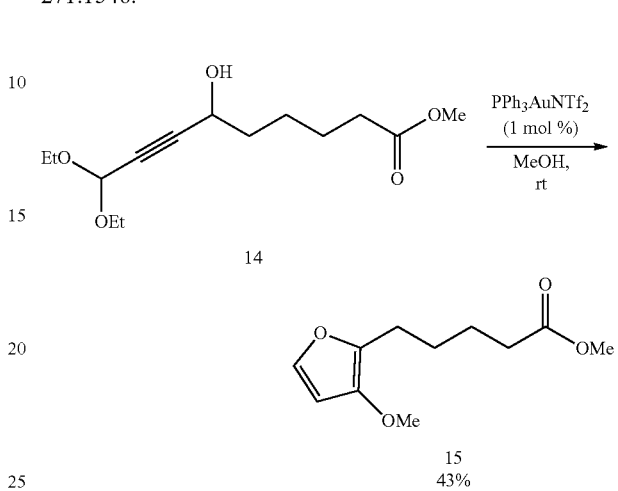

Methyl 5-(3-methoxyfuran-2-yl)pentanoate (15)

MeOH (3.9 mL) was added to a vial containing 14 (1.06 g, 3.89 mmol, 1 eq). PPh$_3$AuNTf$_2$ (29 mg, 0.039 mmol, 0.01 eq) was added, the reaction capped under an atmosphere of air, and stirred at rt overnight. The reaction mixture was poured into a separatory funnel containing brine (50 mL) then extracted with DCM (2×50 mL). The combined organic layers were washed with brine (50 mL), dried over Na$_2$SO$_4$, filtered, the solvent removed, and the residue subjected to flash column chromatography (Hexane:EtOAc, 15:1→9:1) to yield 15 (0.35 g, 43%) as a clear and colourless oil.

Rf (Hexane:EtOAc, 9:1): 0.35; $^1$H NMR (400 MHz, CDCl$_3$) δ 7.11 (d, J=2.0 Hz, 1H), 6.27 (d, J=2.0 Hz, 1H), 3.72 (s, 3H), 3.66 (s, 3H), 2.61 (t, J=6.8 Hz, 2H), 2.33 (t, J=7.2 Hz, 2H), 1.69-1.60 (m, 4H) ppm; $^{13}$C NMR (100 MHz, CDCl$_3$) δ 174.1, 143.3, 139.2, 138.9, 102.9, 59.4, 51.4, 33.7, 27.5, 24.5, 24.3 ppm; IR (ATR) 2950, 1734, 1662, 1600, 1230, 1179, 1111 cm$^1$; HRMS (EL) Exact mass cald. for C$_{11}$H$_{16}$O$_4$ [M]$^+$: 212.1049, found: 212.1045.

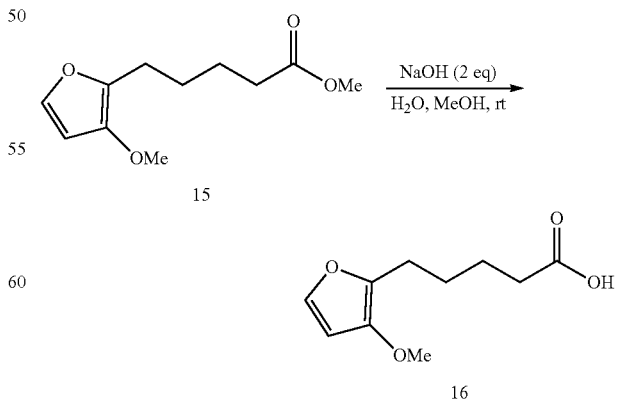

5-(3-Methoxyfuran-2-yl)pentanoic acid (16)

To a vial containing 15 (0.331 g, 1.56 mmol, 1 eq) dissolved in MeOH (4 mL) was added a solution of NaOH (0.125 g, 3.12 mmol, 2 eq) in H$_2$O (4 mL). The reaction was capped under an atmosphere of air, and stirred at rt 30 min. The reaction mixture was poured into a separatory funnel containing H$_2$O (50 mL) and HCl (1 M in H$_2$O) was added to pH 2-3 (~4 mL). The aqueous layer was extracted with DCM (2×50 mL). The combined organic layers were washed with brine (50 mL), dried over Na$_2$SO$_4$, filtered, the solvent removed to yield 16 (0.280 g, 90%) as a clear and colourless oil.

Rf (Hexane:EtOAc, 1:1): 0.55; $^1$H NMR (400 MHz, CDCl$_3$) δ 10.37 (br. s., 1H), 7.12 (d, J=2.0 Hz, 1H), 6.28 (d, J=2.0 Hz, 1H), 3.73 (s, 3H), 2.62 (t, J=6.5 Hz, 2H), 2.38 (t, J=6.5 Hz, 2H), 1.73-1.61 (m, 4H) ppm; $^{13}$C NMR (100 MHz, CDCl$_3$) δ 179.8, 143.4, 139.1, 139.0, 102.9, 59.4, 33.7, 27.4, 24.4, 24.0 ppm; IR (ATR) 3133, 2940, 1706, 1662, 1454, 1411, 1279, 1236, 1109 cm$^{-1}$; HRMS (EI) Exact mass cald. for C$_{10}$H$_{14}$O$_4$ [M]$^+$: 198.0892, found: 198.0890.

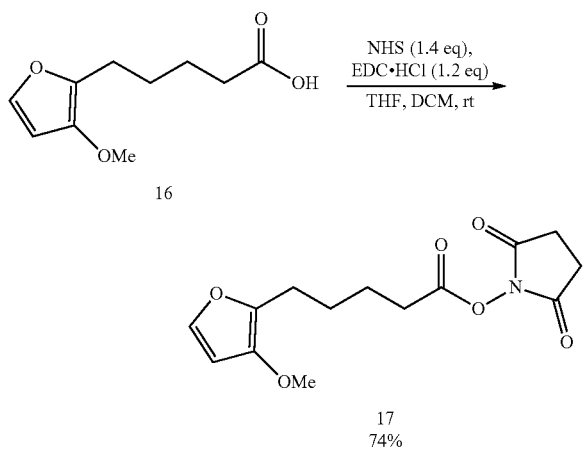

2,5-Dioxopyrrolidin-1-yl 5-(3-methoxyfuran-2-yl)pentanoate (17)

THF (5 mL) was added to a vial containing 16 (0.265 g, 1.34 mmol, 1 eq). NHS (0.216 g, 1.87 mmol, 1.4 eq), EDC-HCl (0.308 g, 1.61 mmol, 1.2 eq) and DCM (3 mL) were added, the reaction capped under an atmosphere of air, and stirred at rt overnight. The solvent was removed and the residue was subjected to flash column chromatography (Hexane:EtOAc, 2:1→1:1) to yield 17 (0.293 g, 74%) as a colourless, viscous oil.

Rf (Hexane:EtOAc, 2:1): 0.33; $^1$H NMR (400 MHz, CDCl$_3$) δ 7.11 (d, J=2.0 Hz, 1H), 6.27 (d, J=2.0 Hz, 1H), 3.72 (s, 3H), 2.82 (br. s., 4H), 2.69-2.54 (m, 4H), 1.81-1.60 (m, 4H) ppm; $^{13}$C NMR (100 MHz, CDCl$_3$) δ 169.1, 168.5, 143.5, 139.1, 138.7, 102.8, 59.3, 30.5, 27.0, 25.5, 24.2, 23.8 ppm; IR (ATR) 2948, 1814, 1735, 1638, 1413, 1206, 1058, 1046 cm$^{-1}$; HRMS (EI) Exact mass cald. for C$_{14}$H$_{17}$NO$_6$ [M]$^+$: 295.1056, found: 295.1062.

Synthesis of CP1b-NHS (19)

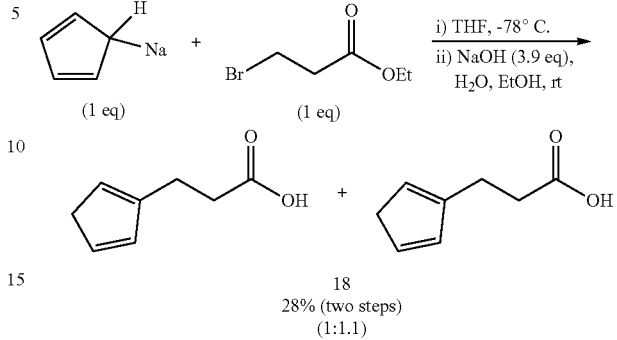

3-(Cyclopenta-1,3-dienyl)propanoic acid & 3-(cyclopenta-1,4-dienyl)propanoic acid (12)

Ethyl 3-bromopropionate (1.65 mL, 12.9 mmol, 1 eq) was added to THF (30 mL) and cooled to −78° C. Sodium cyclopentadienide (2 M solution in THF, 6.45 mL, 12.9 mmol, 1 eq) was added dropwise over 5 min and the reaction was stirred at −78° C. for 3.5 hr. The reaction was poured into DCM (20 mL) and silica gel was added (6 g). The reaction mixture was filtered through silica gel with DCM (100 mL) and the solvent removed to yield ethyl 3-(cyclopentadienyl)propanoate isomers as a yellow oil.

Spectral data matched that of literature reported data.[3]

Rf (Hexane:EtOAc, 9:1): 0.45; $^1$H NMR (400 MHz, CDCl$_3$) δ 6.47-6.02 (m, 3H), 4.17-4.11 (m, 2H), 2.96 (s, 0.31H), 2.91 (d, J=1.4 Hz, 1.69H), 2.78-2.68 (m, J=1.7 Hz, 2H), 2.59-2.53 (m, 2H), 1.26 (t, J=7.1 Hz, 3H).

To a solution of ethyl 3-(cyclopentadienyl)propanoate isomers (~12.9 mmol) dissolved in EtOH (20 mL) was added a solution of NaOH (2.0 g, 50 mmol, 3.9 eq) in H$_2$O (20 mL). The reaction stirred at rt for 15 min. The reaction mixture was poured into a separatory funnel containing H$_2$O (50 mL) and DCM (50 mL). The aqueous layer was acidified with HCl (1 M in H$_2$O) to pH 2 (~70 mL). The layers were separated then the aqueous layer extracted with DCM (50 mL). The combined organic layers were washed with brine (50 mL), dried over Na$_2$SO$_4$, filtered, the solvent removed to yield 18 (0.50 g, 28% two steps) as a brown solid.

Rf (Hexane:EtOAc, 1:2): 0.69; $^1$H NMR (400 MHz, CDCl$_3$) δ 10.57 (br. s., 1H), 6.49-6.02 (m, 3H), 2.97 (d, J=1.6 Hz, 1.07H), 2.92 (d, J=1.2 Hz, 0.93H), 2.82-2.68 (m, 2H), 2.68-2.58 (m, 2H) ppm; $^{13}$C NMR (100 MHz, CDCl$_3$) δ 179.7, 179.7, 147.1, 144.9, 134.2, 134.1, 132.3, 131.1, 127.0, 126.4, 43.3, 41.3, 33.9, 33.3, 25.5, 24.7 ppm; IR (ATR) 3070, 2926, 1705, 1412, 1283, 1205, 913 cm-1; HRMS (EI) Exact mass cald. for C$_8$H$_{10}$NO$_2$ [M]$^+$: 138.0681, found: 138.0678.

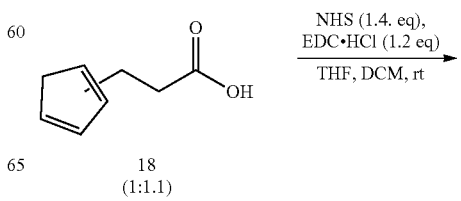

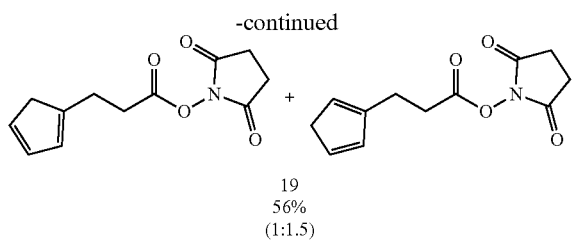

19
56%
(1:1.5)

2,5-Dioxopyrrolidin-1-yl 3-(cyclopenta-1,3-dienyl) propanoate & 2,5-dioxopyrrolidin-1-yl 3-(cyclopenta-1,4-dienyl)propanoate (19)

THF (10 mL) was added to a vial containing 18 (0.460 g, 3.33 mmol, 1 eq). NHS (0.537 g, 4.66 mmol, 1.4 eq), EDC-HCl (0.766 g, 4.00 mmol, 1.2 eq) and DCM (6 mL) were added, the reaction capped under an atmosphere of air, and stirred at rt overnight. The solvent was removed and the residue was subjected to flash column chromatography (Hexane:EtOAc, 2:1→1:1) to yield 19 (0.438 g, 56%) as an eggshell powder.

Rf (Hexane:EtOAc, 2:1): 0.29; $^1$H NMR (400 MHz, CDCl$_3$) δ 6.47-6.08 (m, 3H), 2.97 (d, J=1.2 Hz, 1.2H), 2.92 (d, J=1.6 Hz, 0.8H), 2.90-2.75 (m, 8H); $^{13}$C NMR (100 MHz, CDCl$_3$) δ 169.1, 168.2, 168.1, 145.7, 143.9, 134.4, 133.8, 132.2, 131.4, 127.7, 127.1, 43.2, 41.4, 30.8, 30.2, 25.5, 25.3, 24.5; IR (ATR) 2947, 1810, 1779, 1735, 1420, 1366, 1204, 1062, 1046 cm$^{-1}$; HRMS (EI) Exact mass cald. for $C_{12}H_{13}NO_4$ [M]$^+$: 235.0845, found: 235.0848.

An attempt to synthesize a pentamethylcyclopentadiene (CP3) NHS-derivative using Cp*Li and ethyl 3-bromopropionate failed, instead undergoing elimination to ethyl acrylate. The reaction of CP*Li with methyl bromoacetate was successful, but after ester hydrolysis and reacidification the compound underwent an unexpected cyclization. Our third strategy used Boydston's (1,2,3,4,5-pentamethylcyclopenta-2,4-dienyl)methanol,[1] which was reacted with succinic anhydride to produce the intermediate acid, which was used without further purification. The reaction with EDC-HCl and N-hydroxysuccinimide yielded NHS ester 13. The furan (F2) NHS-derivative's design and synthesis were inspired by Sheppard's work on 3-alkoxyfurans.[2] The lithium salt of 3,3-diethoxyprop-1-yne was added to methyl 6-oxohexanoate to form alcohol 14, which was cyclized using catalytic gold (I) in methanol to yield 3-methoxyfuran 15. The ester of 15 was hydrolyzed then reacted with EDC-HCl and N-hydroxysuccinimide to yield NHS ester 17.

The synthesis of a CP1 NHS-derivative that doesn't contain an internal ester (CP1b) began with the reaction of NaCP with ethyl 3-bromopropionate, then ester hydrolysis to yield acid 12. The reaction with EDC-HCl and N-hydroxysuccinimide yielded NHS ester 19. Structural differences between CP1 and CP1 b are shown in FIG. 13.1.

FIG. 13.1. Overview of ester positions in A) CP1-NHS and B) CP1b-NHS linkers.

1. Peterson, G. I.; Church, D. C.; Yakelis, N. A.; Boydston, A. J., 1,2-oxazine linker as a thermal trigger for self-immolative polymers. *Polymer* 2014, 55, 5980-5985.
2. Foster, R. W.; Benhamou, L.; Porter, M. J.; Bučar, D.-K.; Hailes, H. C.; Tame, C. J.; Sheppard, T. D., Irreversible endo-Selective Diels-Alder Reactions of Substituted Alkoxyfurans: A General Synthesis of endo-Cantharimides. *Chemistry* (Weinheim an Der Bergstrasse, Germany) 2015, 21, 6107-6114.
3. Honzíček, J.; Mukhopadhyay, A.; Santos-Silva, T.; Romão, M. J.; Romão, C. C., Ring-Functionalized Molybdenocene Complexes. *Organometallics* 2009, 28, 2871-2879.

Example 14. Evaluation of ADCs Prepared with Linker-Modified Antibody

The stability and potency of ADCs generated by Diels-Alder conjugation of AM-MMAE to linker-modified antibody were evaluated. Diels-Alder conjugates were compared to cysteine-conjugates.

Materials. All antibodies (IgG1 format) were expressed and purified using standard molecular biology methods. All reagents were purchased from commercial vendors unless noted otherwise. Furan-2-ylmethyl Succinamic acid NHS ester (F1-NHS) and maleimidocaproyl-valine-citrulline-p-aminobenzyloxycarbonyl-monomethyl-auristatin-E (AM-MMAE) were purchased from SynChem, Inc. (Elk Grove Village, Ill.).

Preparation of mAb-linker conjugates: Diene functionality was randomly incorporated into antibodies by reaction of the NHS ester-containing linkers 17 and 19 (F2 and CP1b) described above with lysine amines. Degree of mAb modification was controlled by the amount of NHS-linker used in the reaction and different linker densities were targeted depending on the experiment. A general procedure for modification of mAb with CP1 is described as follows: First, mAb solution was adjusted to 5 mg/mL (3 mL, 15 mg mAb, 100 nmol, 1 eq.) with PBS pH 7.2 followed by addition of 10% v/v 1 M NaHCO$_3$. This solution was chilled on ice and 30 μL CP1b-NHS (10 mM stock in DMAc, 300 nmol, 3 equivalents, also termed CP1-linker) was added. The reaction proceeded on ice for 5 minutes followed by reaction at room temperature for 1 h with continuous mixing. Reacted mAb was purified by dialysis (Slide-A-Lyzer, 10 kDa MWCO) against PBS, 1 mM EDTA, pH 7.4, 4° C. for 24 h. CP1-linker introduction was quantified by intact deglycosylated mass spectrometry as described below.

Scheme 14.1 Preparation of mAb-CP1b-linker and mAb-F2-linker conjugates.

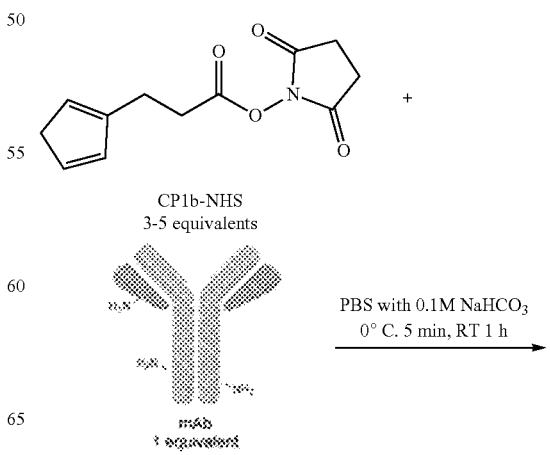

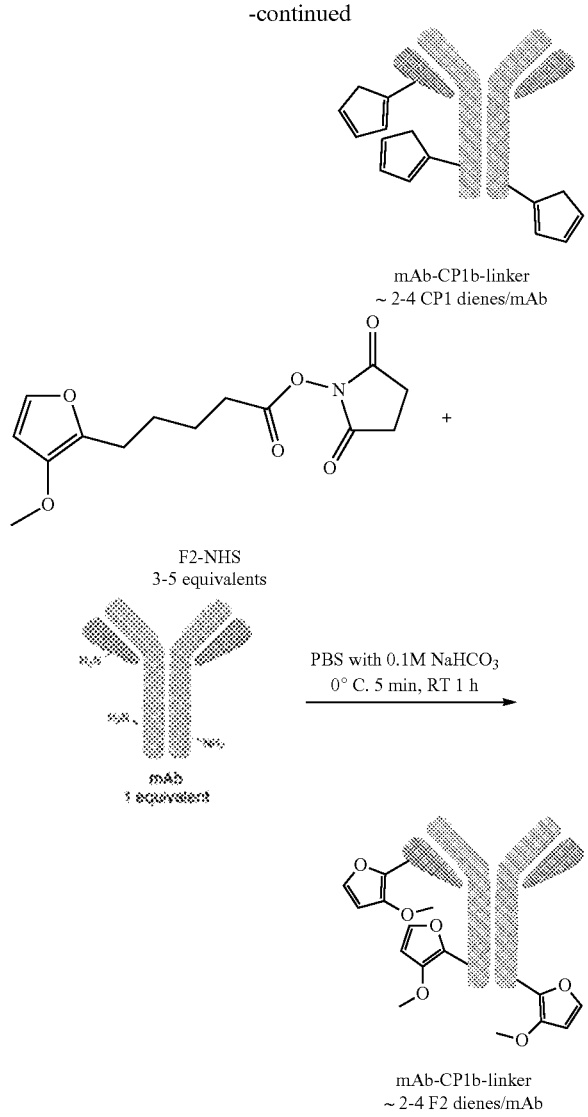

Preparation of ADCs; Antibody drug-conjugates were prepared from Herceptin (on-target) or IgG-1 isotype control-1 (off-target) mAbs using both Diels-Alder conjugation via linkers and direct conjugation to antibody cysteine thiols. Diels-Alder ADCs were prepared from CP1b-NHS (compound 19) and F2-NHS (compound 17) linker-modified antibodies using the same general procedure described for mAb-CP1b-linker as follows: mAb-CP1b-linker (10 mg, 67 nmol, 1 equivalent) was diluted to 4.27 mg/mL with PBS, pH 7.4, followed by addition of DMSO (493 μL) and 1 M sodium phosphate monobasic (247 μL) to yield ~20% and 10% v/v solutions respectively. AM-MMAE (53.3 μL of 10 mM stock in DMSO, 530 nmol, 8 equivalents) was added to the antibody solution and the reaction continued at room temperature with mixing for 4 h. N-acetyl cysteine (43 μL of a 100 mM solution in water, 4.3 μmol, 64 equivalents) was added to quench unreacted maleimides. ADC was purified from the reaction mixture using CHT chromatography. ADC solution was diluted 3-fold with distilled water and loaded onto a Bio-Scale Mini Cartridge CHT Type II 40 μm media column. ADC was eluted with a gradient from buffer A (10 mM phosphate, pH 7.0) to buffer B (10 mM phosphate pH 7.0 containing 2M NaCl) over 25 minutes at a flow rate of 5 mL/min. After CHT chromatography ADC sample was buffer exchanged to PBS using a slide-a-lyzer cassette at 4° C. The same procedure was followed for ADCs prepared with mAb-F2-linker constructs, with the exception that the AM-MMAE conjugation reaction continued for 24 h at room temperature. Note that diene content for each mAb prior to reaction with AM-MMAE is provided in Table 14.1. 8 equivalents of AM-MMAE relative to mAb used for the conjugation reaction corresponds to approximately 2 molar equivalents of AM-MMAE relative to diene.

ADCs were also prepared by conjugation of AM-MMAE to cysteine thiols contained in the antibody hinge region. First, antibody (10 mg, 67 nmol, 1 equivalent) solution was adjusted to 2.5 mg/mL with PBS containing 1 mM EDTA. Next, TCEP (10 μL of 50 mM solution in water, 500 nmol, 7.5 equivalents) was added to reduce hinge disulfides, and the mixture was incubated at 37° C. with mixing for 1 h. Next, DMSO (410 μL, 10% v/v final concentration in reaction) was added and the reaction continued at room temperature with mixing for 1 h.

N-acetyl cysteine was added to quench unreacted maleimide groups and ADC was purified by CHT chromatography and dialysis as described above. ADCs prepared by conjugation to hinge cysteines are denoted with Cys in the name, for example: Herceptin-Cys-MMAE. rRP-HPLC analysis: For each analysis, the antibodies and ADCs were reduced at 37° C. for 20 minutes using 42 mM dithiothreitol (DTT) in PBS pH 7.2. 10 μg of reduced antibodies and ADCs was loaded onto a PLRP-S, 1000 Å column (2.1×50 mm, Agilent) and eluted at 40° C. at a flow rate of 0.5 mL/min with a gradient of 5% B to 100% B over 60 minutes (mobile phase A: 0.1% trifluoroacetic acid in water, and mobile phase B: 0.1% trifluoroacetic acid in acetonitrile). Percent conjugation was determined using integrated peak areas from the chromatogram.

Size exclusion chromatography analysis: SEC analysis was performed using an Agilent 1100 Capillary LC system equipped with a triple detector array (Viscotek 301, Viscotek, Houson, Tex.); the wavelength was set to 280 nm, and samples (50 μg) were run on a TSK-GEL G3000SWXL column (Toso Bioscience LLC, Montgomeryville, Pa.) using 100 mM sodium phosphate buffer, 10% isopropyl alcohol, pH 6.8 at a flow rate of 1 mL/min.

Serum stability analysis: ADCs were incubated in rat serum to challenge the stability of the antibody-payload linkage. ADCs were added to normal rat serum (Jackson Immunoresearch) to achieve a final concentration of 0.2 mg/mL (1.33 μM antibody), with the total volume of ADC solution added to serum less than 10%. The ADC-serum mixture was sterile filtered and an aliquot was removed from this mixture and frozen as a t=0 control. Remaining sample was then further incubated at 37° C. in a sealed container for 7 d. Conjugated and unconjugated human antibody was recovered from rat serum by immunoprecipitation using Fc-specific anti-human IgG-agarose resin (Sigma-Aldrich). Resin was rinsed twice with PBS, once with IgG elution buffer, and then twice more with PBS. ADC-mouse serum samples were then combined with anti-human IgG resin (100 μL of ADC-serum mixture, 50 μL resin slurry) and mixed for 15 minutes at room temperature. Resin was recovered by centrifugation and then washed twice with PBS. Washed resin was resuspended in 100 μL IgG elution buffer (Thermo Scientific) and further incubated for 5 minutes at room temperature. Resin was removed by centrifugation and then 20 μL of 10×glycobuffer 1 (New England Biolabs) was added to the supernatant. Recovered human antibody solution was sterile filtered, and incubated with EndoS for 1 h at 37° C. Deglycosylated mAbs were then reduced with TCEP and analyzed by LC/MS as described above. Percent conjugated antibody was determined from peak heights of mass spectra as described in Example 12.

Mass spectrometry analysis: Samples were analysed as described in Example 1.

In vitro cytotoxicity analysis: SKBR3 and N87 cancer cell lines were obtained from American Type Culture Collection (ATCC). Cells were maintained in RPMI 1640 media (Life Technologies) supplemented with 10% heat-inactivated fetal bovine serum (HI-FBS) (Life Technologies) at 37° C. in 5% $CO_2$. SKBR3 and NCI-N87 cells harvested in exponential growth phase were seeded in 96-well culture plates at 2500 and 2000 cells/well and allowed to adhere overnight. Cells were then treated on the following day with ADCs at 4-fold serial dilutions from 4000 and 64,000 ng/mL (9 concentrations) in duplicate. The treated cells were cultured for 6 days and cell viability was determined using the CellTiter-Glo Luminescent Viability Assay (Promega) following the manufacturer's protocol. Cell viability was calculated as a percentage of untreated control cells. $IC_{50}$ values were determined using logistic non-linear regression analysis with Prism software (GraphPad).

Tumor growth inhibition in vivo: Herceptin-MMAE ADCs prepared with F2 and CP1 b linker-modified mAbs were further evaluated for antitumor activity in vivo in a subcutaneous N87 xenograft model in mice. Tumors were prepared by inoculation of N87 cells (5 million N87 cells in 50% Matrigel) subcutaneously into 4-6 week old female athymic nude mice. When tumors reached approximately 200 $mm^3$, mice were randomly assigned into groups, 5 mice per group. ADCs were administered IV at the indicated doses and dosed at day 5 post cell inoculation. Tumor dimensions (long axis and short axis) were measured twice weekly with calipers. Tumor volume was calculated using the equation:

$$V = \tfrac{1}{2} a \times b^2$$

Where,
a=tumor long axis in mm
b=tumor short axis in mm

FIG. 14.1. Mass spectrometry analysis of mAb-CP1b-linker conjugates. Numbers above peaks indicate the number of linkers (B and E) or AM-MMAEs (C and F) conjugated to the mAb. All samples were deglycosylated with EndoS prior to analysis.

FIG. 14.2. Mass spectrometry analysis of mAb-F2-linker conjugates. Numbers above peaks indicate the number of linkers (B and E) or AM-MMAEs (C and F) conjugated to the mAb. All samples were deglycosylated with EndoS prior to analysis.

FIG. 14.3. Mass spectrometry analysis of mAb-cysteineys conjugates. mAb light chain (LC) and heavy chain (HC) are indicated (A-D), as well as the number of AM-MMAEs conjugated (B and D). All samples were deglycosylated with EndoS and reduced prior to analysis.

FIG. 14.4. rRP-HPLC analysis of mAbs, mAb-linker conjugates and ADCs. mAb light chain and heavy chains are indicated, number of AM-MMAEs conjugated to mAbs are also indicated for ADC samples.

FIG. 14.5. SEC analysis of mAbs, mAb-linker conjugates and ADCs. High molecular weight species (HMWS) are indicated.

FIG. 14.6. A) Reduced, deglycosylated mass spectrometry analysis of ADCs following incubation in rat serum for 7 d. Spectra are zoomed to show the heavy chain only. Drug loss is indicated as a decrease of DAR-1 and DAR-2 species peak heights relative to the DAR-0 peak height. B) Quantification of remaining drug (%) using mass spectrometry data. Data is shown as the average+/−the standard deviation, n=3.

FIG. 14.7. In vitro activity of ADCs towards A) NCI-N87 cells and B) SKBR3 cells.

FIG. 14.8. Tumor growth inhibition activity of Herceptin-linker MMAE ADCs towards subcutaneous N87 tumor models in mice.

TABLE 14.1

Summary of linker-conjugated and cysteine-conjugated ADCs

| mAb | Linker | Conjugation reaction | Linker DAR (MS) | MMAE DAR (MS) | MMAE DAR (rRP-HPLC) | Monomer (%) |
|---|---|---|---|---|---|---|
| Herceptin | CP1b | Diels-Alder | 4.1 | 3.9 | 3.5 | 98.7 |
| IgG isotype control | CP1b | Diels-Alder | 3.7 | 3.2 | 3.4 | 98.4 |
| Herceptin | F2 | Diels-Alder | 4.0 | 3.5 | 4.5 | 97.7 |
| IgG isotype control | F2 | Diels-Alder | 3.8 | 3.2 | 3.5 | 98.1 |
| Herceptin | none | Michael addition | N/A | 3.2 | 3.5 | 97.4 |
| IgG isotype control | none | Michael addition | N/A | 2.9 | 3.1 | 98.5 |

[a]ADCs prepared without linkers were conjugated to native cysteines

TABLE 14.2

In vitro potency of linker-conjugated and cysteine-conjugated ADCs.

| ADC | MMAE DAR[a] | N87 $IC_{50}$ (ng/mL) | SKBR3 $IC_{50}$ (ng/mL) |
|---|---|---|---|
| Herceptin-CP1b-MMAE | 3.7 | 2 | 2 |
| IgG isotype control-CP1b-MMAE | 3.3 | 8230 | 1811 |
| Herceptin-F2-MMAE | 4 | 3 | 1.6 |
| IgG isotype control-F2-MMAE | 3.4 | 9990 | ~2000 |
| Herceptin-Cys-MMAE | 3.4 | 3.6 | 2.8 |
| IgG isotype control-Cys-MMAE | 3 | 8177 | >2000 |

[a]average DAR calculated from MS and rRP-HPLC values reported in Table 14.1

ADCs were prepared via Diels-Alder reaction or Michael addition of maleimido-MMAE to Herceptin and IgG isotype control mAbs. Diels-Alder reactive groups were introduced onto lysine amines via crosslinkers followed by reaction with AM-MMAE whereas Michael addition of AM-MMAE occurred with native cysteine thiols (termed Cys-ADCs). Both conjugation methods yielded heterogeneous ADCs with a drug content of 3-4 MMAE drugs per mAb.

Diels-Alder addition of AM-MMAE to CP1b- and F2 linker-modified mAb was efficient, with nearly quantitative conversion confirmed by mass spectrometry. Furthermore, modification of mAbs with cyclopentadiene or methoxyfuran linkers and subsequent attachment of AM-MMAE by Diels-Alder reaction did not increased aggregate content in conjugate products as indicated by SEC analysis. Overall, ADCs produced by Diels-Alder conjugation were of high quality.

Analysis of ADC stability in rat serum by mass spectrometry demonstrated that Diels-Alder constructs prepared with mAb-CP1 b-linker and mAb-F2-linker were more stable than constructs generated by Michael addition to cysteine thiols. Incubation in rat serum for 7 days at 37° C. resulted in 60% drug loss for mAb-cysteine ADC, whereas mAb-CP1b-linker and mAb-F2-linker ADCs showed less than 10% drug loss under the same conditions. Herceptin mAb-CP1b-linker and Herceptin mAb-F2-linker ADCs were potent inhibitors of cell proliferation towards Her2 positive N87 and SKBR3 cell lines, with $IC_{50}$ values similar to the corresponding cysteine-linked ADC. Non-targeting isotype control ADCs were 2000-4000-fold less potent than on target Herceptin constructs, with similar in vitro potencies observed for Diels-Alder and cysteine ADC constructs. Finally, Herceptin ADCs prepared with CP1 b and F2 linker-modified mAbs were potent inhibitors of tumor growth in vivo. Complete tumor stasis for 30 days was observed in N87 subcutaneous tumor models at an ADC dose of 3 mg/kg. This result confirms that ADCs produced by Diels-Alder reaction are sufficiently stable in vivo to elicit a therapeutic effect.

Example 15. Comparison of Diels-Alder Reaction Rate Constants in Aqueous Buffer and Organic Solvent Kinetics of small molecule diene-maleimide reactions in organic conditions were determined for comparison with antibody-based reactions in aqueous conditions. Reaction rate constants between dienes on linker-modified mAbs and maleimide were determined for; mAb-CP1b-linker, mAb-CP2-linker, mAb-CP3-linker and mAb-F2-linker.

Determination of diene-maleimide reaction rate in organic solvents: Diene and N-ethylmaleimide in $CDCl_3$ were combined in an NMR tube (final concentration 0.01 M each) and monitored by $^1H$ NMR at room temperature. The concentration of starting material [A] was calculated using the integration of N-ethylmaleimide's ethyl peaks (3.59 or 1.20 ppm) and the DA-conjugate's ethyl peak(s) (typically 4.40 or 1.05 ppm).

$[A]=0.01$ M*(integration of starting material)/(integration of starting material+product)

The inverse concentration (1/[A]) was plotted against time (s). The second order reaction rate ($M^{-1}s^{-1}$) was obtained from the best fit line. The average rate and standard deviation of three experiments was used.

Preparation of mAb-linker conjugates: Diene functionality was randomly incorporated into antibodies by reaction of the NHS ester-containing linkers CP1b-linker (compound 19), CP2-linker (compound 12), CP3-linker (compound 13), and F2-linker (compound 17) described in Example 9 and Example 14. Reaction of CP3-NHS with mAb is shown in Scheme 15.1. Degree of mAb modification was controlled by the amount of NHS-linker used in the reaction and different linker densities were targeted depending on the experiment. The number of linkers (and thus dienes) per mAb were determined by intact deglycosylated mass spectrometry as described in Example 1.

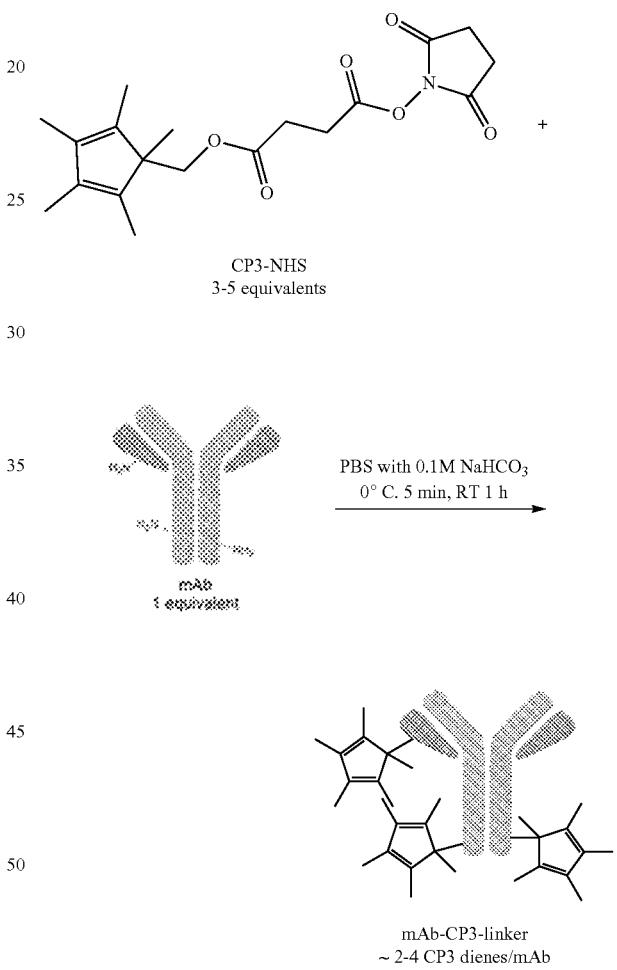

Scheme 15.1. Preparation of mAb-CP3-linker.

Reaction of linker-modified mAb with maleimido-MMAEs: Dienes contained in linker-modified mAbs were reacted with 1 molar equivalent AM-MMAE (diene:maleimide) in aqueous buffer as described in Example 10.

Calculation of mAb-linker diene-maleimide reaction rate constants: Second order rate constants for reaction of maleimido-MMAEs with dienes in mAb-linkers were determined from peak intensities in deglycosylated reduced mass spectra as described in Example 10. For one sample only heavy-chain peaks were analyzed as described in Example 4.

TABLE 15.1

Summary of reaction rates of AM-MMAE with diene linker-modified mAbs
in aqueous buffer and N-ethyl maleimide with diene linkers in $CDCl_3$.

| Experiment | mAb-Linker | mAb-linker Diels-Alder rate in buffer[a,b] | | | Linker Diels-Alder Rate in $CDCl_3$[c] | Aqueous rate acceleration |
| --- | --- | --- | --- | --- | --- | --- |
| | | LAR | $k_2(H_2O)$ $(M^{-1}s^{-1})$[d] | Half-life (min) | $k_2(CDCl_3)$ $(1000 \times M^{-1}s^{-1})$[e] | $k_2(H_2O)/$ $k_2(CDCl_3)$ |
| 1 | IgG-CP1-linker[f] | 3.7 | 35.7[h] | 14 | 97 ± 7[f] | 368 |
| 2 | IgG-CP1-linker[f] | 3.74 | 77 | 7 | | 794 |
| 3 | IgG-CP1-linker[f] | 3.21 | 119 | 4 | | 1227 |
| 4 | IgG-CP1-linker[f] | 3.21 | 116 | 5 | | 1196 |
| 1 | IgG-CP2-linker | 3.29 | 2.6 | 214 | 8.7 ± 0.6 | 299 |
| 2 | IgG-CP2-linker | 3.29 | 2.7 | 215 | | 310 |
| 3 | IgG-CP2-linker | 2.63 | 3.0 | 192 | | 345 |
| 4 | IgG-CP2-linker | 2.63 | 2.3 | 318 | | 264 |
| 1 | IgG-CP3-linker | 3.04 | 10.2 | 59 | 12.1 ± 0.1 | 843 |
| 2 | IgG-CP3-linker | 3.04 | 16.1 | 39 | | 1331 |
| 3 | IgG-CP3-linker | 2.81 | 24.1 | 24 | | 1992 |
| 1 | IgG-F2-linker | 2.95 | 6.6 | 94 | 12.6 ± 0.7 | 524 |
| 2 | IgG-F2-linker | 2.95 | 2.3 | 210 | | 183 |
| 3 | IgG-F2-linker | 3.03 | 5.5 | 117 | | 437 |
| 1 | IgG-furan | 2.5 | ND[g] | >1200 | ~0.1 | ND |

[a] All conjugation reactions were performed in PBS supplemented with 100 mM sodium phosphate monobasic, 20% DMSO, pH 5.5.
[b] All reactions were performed with 1 eq AM-MMAE relative to diene. mAb concentration was 1.3 mg/mL ± 0.35 mg/mL for all reactions.
[c] All reactions were performed in $CDCl_3$ with diene-linker (0.01M) and N-ethylmaleimide (0.01M) at room temperature.
[d] $k_2(H_2O)$ was calculated from the concentration of unreacted mAb-linker peaks (deglycosylated and reduced mass spectrometry analysis). Both heavy and light chains were analyzed.
[e] $k_2(CDCl_3)$ was calculated from the integration of diagnostic peaks in $^1H$ NMR spectra. The values are the average of 3 runs and the standard deviation.
[f] CP1b linker was used.
[g] ND, not determined.
[h] Only heavy chain was analysed.

Comparison of reaction rate constants between maleimide compounds and diene compounds in antibody/aqueous conditions and small molecule/organic solvent conditions demonstrates several key features of this reaction for bioconjugation applications. First, unmodified furan is insufficiently reactive for conjugation of maleimide compounds to antibodies under typical bioconjugation conditions. This is evidenced by lack of conjugation of AM-MMAE to IgG-furan, which showed minimal reaction after 20 h and also the ~100-1000-fold decrease in rate constant for reaction with maleimide in organic conditions compared to other dienes. Second, acceleration of the Diels-Alder reaction in aqueous conditions in the context of antibody conjugation was confirmed. Reaction rate acceleration is crucial for practical application of this chemistry for production of bioconjugates, consideration of organic condition rate constants alone would make the Diels-Alder reaction unattractive for all dienes described here. For example, cyclopentadiene contained in CP1-linker exhibited a reaction half-life of approximately 10 minutes in aqueous antibody-based reaction with maleimide (AM-MMAE) whereas the corresponding organic-phase reaction would require 3.6 days. Finally, results demonstrate that diene reactivity is tunable, where modification of chemical structure can increase or decrease reaction rate with dienophile. Altogether, cyclopentadiene and modified furan functional groups are amenable to efficient bioconjugation reactions between antibodies and maleimido compounds under mild conditions at antibody concentrations in the ~1-2 mg/mL range, whereas simple unmodified furan is not.

Example 15. ADC Production with 1C1-K274CP1 NNAA mAb and AZ1508 Drug-Linker

The feasibility of preparing ADCs with CP1-NNAA incorporated into position K274 of an antibody with AZ1508 drug-linker was assessed.

Antibody generation. CP1-NNAA was incorporated into 1C1 antibody using the methods described in Example 6.

Conjugation of 1C1 K274CP1-mAb with AZ1508: K274CP1 NNAA-mAb (0.4 mg, 2.7 nmol, 1 equivalent) was adjusted to 3 mg/mL with PBS (0.133 mL). DMSO (27 µL) and 1 M sodium phosphate, monobasic (13 µL) was added to yield ~20% and 10% v/v solution, respectively. AZ1508 (5 µL of 10 mM stock in DMSO, 13 nmol, 5 equivalents) was added to 1C1 K274CP1-mAb solution and the mixture was vortexed briefly. The reaction proceeded at room temperature for 17 h with continuous mixing. N-acetyl cysteine (1.1 µL of 100 mM, 108 nmol, 40 equivalents) was added and the solution was incubated for an additional 15 min to quench unreacted maleimide groups. Samples were then diluted 3-fold with water and purified using CHT chromatography. Samples were subsequently analyzed by reduced mass spectrometry and SEC as described in Examples 6 and 12.

Scheme 15.1. A) Reaction of K274CP1-NNAA mAb with AZ1508. B) Structure of AZ1508.

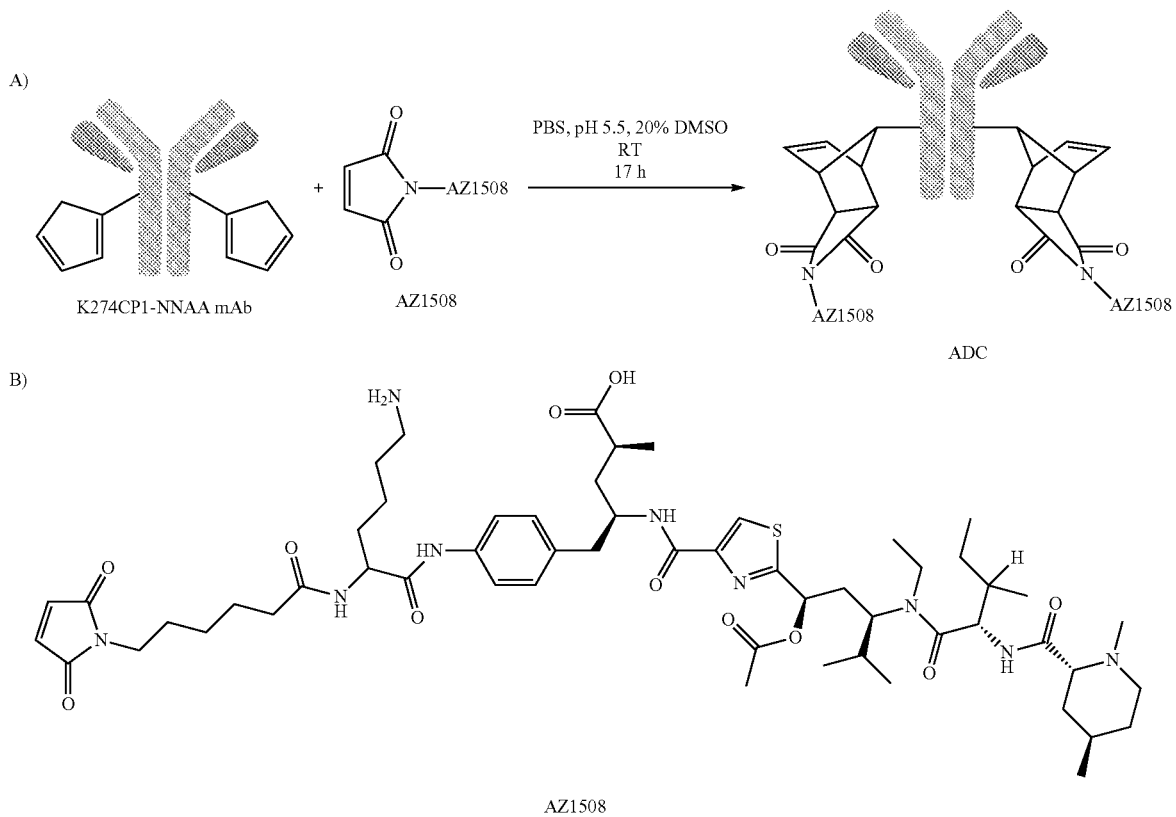

AZ1508

Characterization of 1C1 K274CP1-NNAA ADCs: Samples were analyzed by reduced mass spectrometry and SEC as described in Examples 6 and 12. In vitro activity in PC3 cells was performed as described in Example 12.

FIG. 15.1. SDS-PAGE analysis of 1C1 K274CP1-NNAA AZ1508 ADC. A) nonreduced B) reduced.

FIG. 15.2. Reduced glycosylated mass spectrometry analysis of 1C1 K274CP1-NNAA mAb AZ1508 conjugation product. A) Unreacted mAb B) AZ1508 reaction product. Spectra are zoomed to show both antibody heavy chain (HC) and light (LC) chain.

FIG. 15.3. SEC analysis of 1C1 K274CP1-NNAA AZ1508 ADC indicating that high monomeric product was obtained. High molecular weight solids (HMWS) are indicated.

TABLE 15.1

Summary of 1C1 K274CP1-NNAA AZ1508 ADC properties[a,b,c]

| Conjugated efficiency (%) | Observed Δ mass (AMU) | Calculated Δ mass (AMU) | DAR[d] | Monomer (%) | EC50[e] (ng/mL) |
|---|---|---|---|---|---|
| 96 | +1094.1 | +1092.4 | 1.91 | 95 | 9.75 |

[a] all conjugation reactions performed at pH 5.5, 20% DMSO, 22° C. and 3 mg/mL 1C1 K274CP1-NNAA mAb. CP1-NNAA was incorporated into position K274 in place of lysine
[b] the molar ratio of AZ1508:CP1 diene used was 2.5:1
[c] calculated from peak intensities of reduced mass spectra
[d] DAR = drug to antibody ratio
[e] Determined in EphA2 receptor positive PC3 cells Reactivity of CP1-NNAA diene towards AZ1508 following incorporation at position K274 of the 1C1 antibody was confirmed. ADC product was of high quality, with >95% conjugation and very little aggregate. The resulting ADC was active towards receptor positive PC3 cells.

Example 16. Generation of ADCs with 1C1 S239CP2-NNAA, 1C1 K274CP2-NNAA and 1C1 N297CP2-NNAA Antibodies with AZ1508 Drug-Linker and Comparison with Analogous Cysteine-Linked Site-Specific AZ1508 ADCs ADCs bearing AZ1508 drug-linker were prepared with 1C1 antibodies incorporating CP2-NNAA at positions S239, K274, and $N_{297}$ by mutation of the native amino acid codon to an amber stop codon in the expression plasmid. CP2-NNAA was incorporated into each position on separate antibodies.

Antibody generation: CP2-NNAA was incorporated into 1C1 antibodies and expressed using the methods described in Example 6. Cysteine was incorporated into 1C1 antibodies by site-directed mutagenesis using standard molecular biology techniques.

Conjugation of 1C1 CP2-NNAA mAbs with AZ1508: The same conjugation method was performed for all three CP2-NNAA antibody constructs, using the procedure described in Example 12, with the only difference being AM-MMAE was replaced with AZ1508. Note that drug-linker conjugation is achieved by simply mixing AZ1508 with CP2-NNAA mAb followed by mixing.

Scheme 16.1.

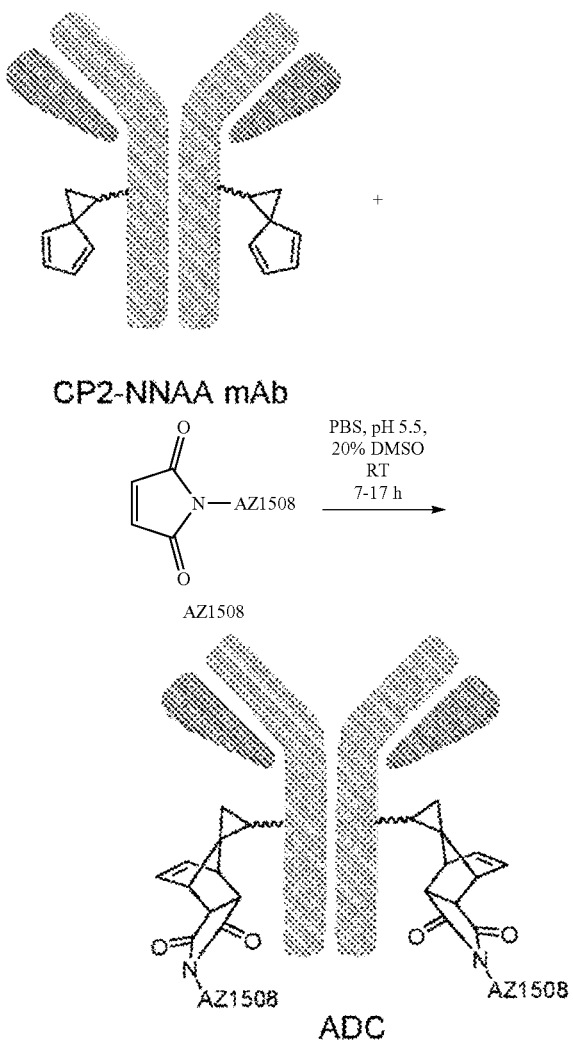

A) Reaction of CP2-NNAA mAb with AZ1508. See scheme 15.1 for structure of AZ1508.

Conjugation of 1C1 cysteine-engineered mAbs with AZ1508. Site-specific cysteine-linked AZ1508 ADCs were prepared using the same method described in Example 12 with the only difference being AM-MMAE was substituted with AZ1508. Note that cysteine-mAb must be reduced, dialyzed, and oxidized prior to addition of AZ1508.

Characterization of 1C1 CP2-NNAA ADCs and 1C1 cysteine-engineered ADCs. Samples were analyzed by SDS-PAGE, reduced mass spectrometry, HIC, rRP-HPLC and SEC as described in Examples 6 and 12. In vitro activity in cultured PC3 cells was performed as described in Example 12.

FIG. 16.1. SDS-PAGE analysis of 1C1 CP2-NNAA AZ1508 ADCs and 1C1 cysteine AZ1508 ADCs. A) Non-reduced samples, B) reduced samples.

FIG. 16.2. Analysis of 1C1 S239CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.3. Analysis of 1C1 K274CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.4. Analysis of 1C1 N297CP2-NNAA AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.5. Analysis of 1C1 S239C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.6. Analysis of 1C1 K274C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

FIG. 16.7. Analysis of 1C1 N297C AZ1508 ADC. A) Reduced glycosylated mass spectrometry analysis of unreacted mAb. B) Reduced glycosylated mass spectrometry analysis of AZ1508 reaction product. C) HIC analysis of unreacted antibody and AZ1508 conjugation product, D) SEC analysis of AZ1508 reaction product. Spectra are zoomed to show both antibody heavy (HC) and light (LC) chains in (A) and (B).

TABLE 16.1

Summary of 1C1 CP2-NNAA and cysteine mAb ADCs[a,b]

| Position | Mutation | Titer mg/L | mAb monomer (%)[c] | ADC DAR MS[d,e] | ADC DAR HIC[d,f] | ADC Δ mass (AMU)[g] | ADC monomer (%)[c] | ADC EC50 (ng/mL)[h] |
|---|---|---|---|---|---|---|---|---|
| S239 | CP2-NNAA | 76–82 | 99 | 1.96 | ND | +1089.5 | 97 | 9 |
|  | Cys | 792 | 96 | 1.96 | ND | +1093.7 | 97 | 7 |
| K274 | CP2-NNAA | 54–69 | 92 | 1.96 | 1.87 | +1089.0 | >99 | 7 |
|  | Cys | 468 | 97 | 1.88 | 1.84 | +1092.9 | 97 | 8 |

TABLE 16.1-continued

Summary of 1C1 CP2-NNAA and cysteine mAb ADCs[a,b]

| Position | Mutation | Titer mg/L | mAb monomer (%)[c] | ADC DAR MS[d,e] | ADC DAR HIC[d,f] | ADC Δ mass (AMU)[g] | ADC monomer (%)[c] | ADC EC50 (ng/mL)[h] |
|---|---|---|---|---|---|---|---|---|
| N297 | CP2-NNAA | 42 | 79 | 1.96 | ND | +1091.0 | >99 | 10 |
|  | Cys | 594 | 93 | 1.60 | ND | +1092.3 | 86 | 4 |

[a]all CP2 NNAA conjugation reactions performed at pH 5.5, 20% DMSO, 22° C. and 3 mg/mL mAb.
[b]the molar ratio of AZ1508:CP2 used was 2.5:1
[c]determined by peak areas in SEC traces
[d]DAR = drug to antibody ratio
[e]calculated from peak intensities of reduced mass spectra
[f]determined by peak areas following analysis of intact ADCs
[g]determined by reduced mass spectra
[h]Determined in EphA2 receptor positive PC3 cells.

CP2-NNAA was incorporated into three positions of the 1C1 antibody and reactivity towards AZ1508 was confirmed. Note that CP2-NNAA was incorporated into each position on separate antibodies. ADCs prepared with CP2-NNAA mAbs were of high quality, with >95% conjugation and very little aggregate. Resulting CP2-NNAA AZ1508 ADCs were active towards receptor positive PC3 cells.

Comparison of CP2-NNAA ADCs with corresponding cysteine-engineered antibodies revealed that position N297 is amenable to mutation with CP2-NNAA but not cysteine. Introduction of cysteine at this position results in disulfide scrambling during the conjugation procedure, as evidenced by SDS-PAGE results. No disulfide scrambling was observed for the N297CP2-NNAA ADC. This demonstrates that CP2-NNAA can be introduced into positions not suitable for cysteine incorporation, where cysteine may impact native disulfides in the antibody framework.

Example 17. Stability of CP1-NNAA and CP2-NNAA AZ1508 ADCs in Mouse and Rat Serum Serum stability of AZ1508 ADCs prepared by Diels-Alder conjugation was evaluated. Stability of ADCs was assessed relative to the chemical bond between the antibody and payload (i.e. the Diels-Alder adduct). Stability of analogous cysteine-linked (thiosuccinimide) ADCs is also presented for comparison.

Method: 1C1 AZ1508 ADCs were incubated in mouse serum or rat serum, ex vivo for 7 d at 37° C., recovered by immunocapture, and analyzed by mass spectrometry as described in Example 7. Relative amounts of conjugated and unconjugated antibody were determined by peak heights in mass spectra as described in Example 7. For mouse serum-incubated samples, deacetylation of AZ1508 was observed. Deacetylated AZ1508 was considered as a conjugated species for calculation of DAR.

FIG. 17.1. Representative reduced, glycosylated mass spectra of 1C1 CP2-NNAA- and 1C1 cysteine-AZ1508 ADCs before and after incubation in rat serum. Natural amino acids were mutated to CP2-NNAA or cysteine as indicated at (A) Position S239, (B) Position K274, (C) Position N297. Unconjugated and conjugated species are indicated.

FIG. 17.2. Quantification of AZ1508 remaining attached to CP2-NNAA or cysteine-engineered antibodies after incubation in rat serum for 7 d at 37° C. Drug:antibody ratios (DAR) were calculated from reduced glycosylated mass spectra. Data represent the average t standard deviation, n=3.

FIG. 17.3. Quantification of AZ1508 remaining attached to CP2-NNAA or cysteine-engineered antibodies after incubation in mouse serum for 7 d at 37° C. Drug:antibody ratios (DAR) were calculated from reduced glycosylated mass spectra. Deacetylated AZ1508 was considered a conjugated species for the analysis. Data represent the average±standard deviation, n=3.

FIG. 17.4. Quantification of AZ1508 remaining attached to CP1-NNAA antibodies after incubation in rat serum for 7 d at 37° C. Drug:antibody ratios (DAR) were calculated from reduced glycosylated mass spectra. Data represent the average±standard deviation, n=3.

Analysis of 1C1 CP2-NNAA AZ1508 ADCs following incubation in rat or mouse serum for 7 d at 37° C. demonstrated that the Diels-Alder adduct was stable, as no drug loss was observed. 1C1 CP1-NNAA AZ1508 prepared at position K274 also showed no drug loss in rat serum after 7 d incubation at 37° C., however, significant drug loss was observed for the analogous cysteine-linked ADCs subjected to the same conditions. Cysteine-linked ADC stability was position-dependent, with position S239 being stable and positions K274 and N297 were not. In the case of cysteine-linked ADCs, AZ1508 is coupled to the antibody via a thiosuccinimide linkage, which may undergo the retro-Michael deconjugation reaction, leading to drug loss. This process impacts exposed positions more than buried positions, thus position-dependent stability is observed for cysteine-linked ADCs. Diels-Alder adducts on the other hand were stable at positions unstable for thiosuccinimides, for both CP1 and CP2 dienes. Thus, Diels-Alder conjugation to cycopentadiene NNAAs represents an advantage over thiol-based conjugation strategies in terms of conjugate stability.

Example 18. Reaction Kinetics of 1C1 mAb Containing CP1-NNAA or CP2-NNAA with AZ1508

Reactivity of diene NNAAs were evaluated following incorporation into positions S239, K274, or N297 in the 1C1 antibody framework.

Methods: 1C1 CP1-NNAA or CP2-NNAA antibodies (3 mg, 1.3 mg/mL mAb, 17.4 µM diene, 1 equivalent) were reacted with AZ1508 (4 µL of 10 mM stock in DMSO, 40 nmol, 1 equivalent) in 0.1 M sodium phosphate, 0.15 M NaCl, 20% DMSO, pH 5.5, 22° C. Aliquots (100 µL) were removed from the reaction mixture at predetermined time-points and N-acetyl cysteine (3 µL of 100 mM in water, 8 equivalents) was added followed by incubation for 15 minutes at room temperature to quench unreacted maleimides. Samples were then purified using PD Spintrap G-25 devices (GE Healthcare Life Sciences) to remove small molecule components from the mixture and subsequently analyzed by reduced glycosylated mass spectrometry. Mass spectrometry analysis procedures and kinetic constant calculations are described in Examples 5 and 10.

FIG. 18.1. Conjugation kinetics of 1C1 CP1-NNAA and 1C1 CP2-NNAA mAbs with AZ1508 measured by reduced glycolsylated mass spectrometry. Data is plotted as the average±absolute error, n=2 1C1 K274CP1-NNAA, 1C1 K274CP2-NNAA, and 1C1 N297CP2-NNAA, and average+standard deviation n=3 for 1C1 S239CP2-NNAA.

FIG. 18.2. Inverse concentration plot showing consumption of diene upon reaction of CP1-NNAA and CP2-NNAA mAbs with AZ1508. (A) 1C1 K274CP1-NNAA, (B) 1C1 S239CP2, 1C1 K274CP2-NNAA, and N297CP2-NNAA mAbs. Data is plotted as the average f absolute error, n=2 1C1 K274CP1-NNAA, 1C1 K274CP2-NNAA, and 1C1 $N_{297}$CP2-NNAA, and average+standard deviation n=3 for 1C1 S239CP2-NNAA.

TABLE 18.1

Summary of kinetic data for reaction of 1C1 CP1-NNAA and CP2-NNAA mAbs with AZ1508.[a,b,c]

| Position | Mutation | $k_2$ $(M^{-1}s^{-1})$ | $R^{2d}$ | $T_{1/2}$ $(min)^e$ |
|---|---|---|---|---|
| K274 | CP1-NNAA | 73.2 ± 6.9[b] | 0.99 | 12 ± 1 |
| S239 | CP2-NNAA | 2.6 ± 0.5[c] | 0.99 | 383 ± 84 |
| K274 | CP2-NNAA | 1.8 ± 0.4[c] | 0.99 | 545 ± 108 |
| N297 | CP2-NNAA | 5.4 ± 1.1[c] | 0.99 | 183 ± 41 |

[a]All conjugation reactions were performed in PBS supplemented with 100 mM sodium phosphate monobasic, 20% DMSO, pH 5.5.
[b]The molar ratio of AZ1508:CP1-NNAA or CP2-NNAA diene used was 1:1. The mAb concentration was 1.3 mg/mL (17.3 μM diene) for all reactions.
[c]Reaction of deine was monitored by reduced glycosylated mass spectrometry.
[d]determined from bestfit line of inverse diene concentration (M) vs time (s) plot.
[e]calculated using the half-life equation shown in Examples 5 and 10.

Antibodies bearing CP1-NNAA or CP2-NNAA reacted with the maleimide containing drug-linker AZ1508 at 1:1 molar equivalent of diene:maleimide. Reaction half-lives of 12 minutes for CP1-NNAA mAb and 3-10 hours for CP2-NNAA mAb. Final conversions achieved after the 48 h measurement period ranged from 87-100%.

Example 19. Antitumor Activity of ADCs Prepared with CP2-NNAA mAb and AZ1508

ADCs prepared with 1C1 CP2-NNAA and AZ1508 drug-linker were evaluated for their ability to inhibit tumor growth of PC3 xenografts in mice.

ADC preparation: ADCs were prepared with 1C1 mAbs as described in Example 16. Non-EphA2 binding ADCs were prepared with isotype control antibody (termed R347). CP2-NNAA was incorporated into positions S239 and N297 for 1C1 mAbs and position S239 for R347 mAb.

In vivo methods: Tumor growth inhibition studies were performed at Charles River Discovery Services North Carolina (CR Discovery Services) in accordance with the recommendations of the Guide for Care and Use of Laboratory Animals with respect to restraint, husbandry, surgical procedures, feed and fluid regulation, and veterinary care. PC3 xenograft tumor models were established in mice by inoculation of PC3 cells (10 million cells in 50% Matrigel) subcutaneously into 8-9 week old female athymic nude mice. Seventeen days later, designated as day 1 of the study, tumor volumes reached~150-200 $mm^3$ and mice were randomly assigned into groups, 8 mice per group. On day 1 of the study, dosing was initiated and ADC was administered at 3 mg/kg via tail vein injection. ADC was dosed once weekly at 3 mg/kg over three weeks for a total of three doses. Tumor dimensions (long axis and short axis) were subsequently measured twice weekly with calipers. Tumor volume was calculated using the equation in Example 14.

FIG. 19.1. Tumor growth inhibition of PC3 xenografts in mice following administration of CP2-NNAA AZ1508 ADCs. On-target 1C1 mAb ADCs were prepared with CP2-NNAA incorporated at position S239 or N297 whereas non-targeting isotype control R347 mAb ADC was prepared with CP2 incorporated at position S239. ADCs were dosed intravenously at 3 mg/kg on days 0, 7 and 14 (indicated with arrows). Data is represented as the average±standard deviation, N=8.

1C1 CP2-NNAA AZ1508 ADCs were effective at inhibiting tumor growth in EphA2-positive PC3 xenograft models in mice for at least 60 days in mice following the first injection of ADC. The off-target ADC prepared with non-binding R347 mAb was not as potent as on-target ADCs.

Example 20. Conjugation of CP1-NNAA Antibody to Maleimide Functionalized Nanoparticles 1C1 K274CP1-NNAA antibody was reacted with 60 nm maleimide-functionalized gold nanoparticles.

Method: Maleimide-functionalized 60 nm gold nanoparticles were prepared from a commercial kit (Sigma Aldrich, catalogue #9009465) according to the manufacturer's instructions. First, the lyophilized maleimide-functionalized gold nanoparticle product was resuspended in 100 μL of reaction buffer provided in the kit. Next, solutions of wild-type (WT) or K274CP1-NNAA 1C1 antibodies were prepared at 0.5 mg/mL in PBS. Nanoparticle solution (10 μL) and antibody solution (10 μL) were combined and mixed by pipetting up and down several times. The conjugation reaction continued for 2 h at 25° C. followed by light scattering analysis using a Zetasizer-Nano ZS (Malvern Instruments, UK). Each conjugation reaction was performed in triplicate.

Scheme 20.1. Reaction of 1C1 K274CP1-NNAA mAb with maleimide-functionalized gold nanoparticles.

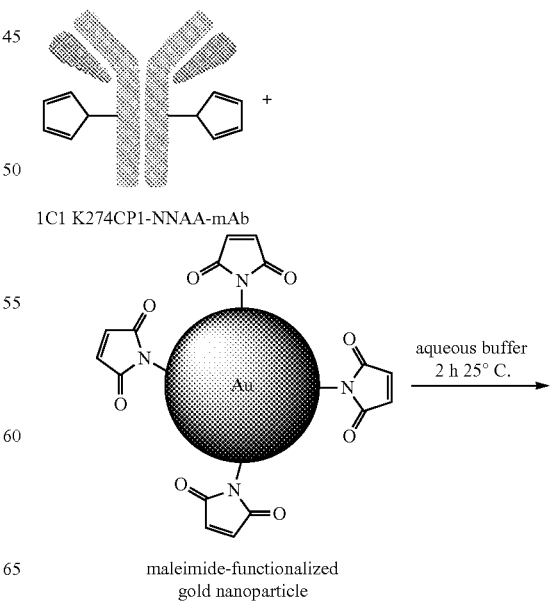

-continued

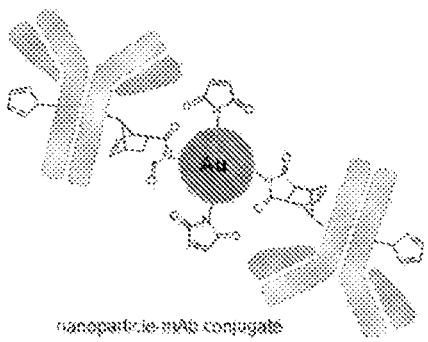

FIG. 20.1. Dynamic light scattering analysis (DLS) of 60 nm maleimide-functionalized gold nanoparticles before and after incubation with 1C1 wild-type (WT) or 1C1 K274CP1-NNAA antibodies (CP1-NNAA mAb) for 2 h at 25° C.

TABLE 1

Summary of light scattering data for nanoparticles and nanoparticle-mAb conjugates.

| Sample[a] | Size (d. nm)[b] | PDI |
|---|---|---|
| 60 nm Au nanoparticle control sample 1 | 61.5 | 0.136 |
| 60 nm Au nanoparticle control sample 2 | 57.7 | 0.146 |
| 60 nm Au nanoparticle control sample 3 | 60.8 | 0.112 |
| 1C1 WT mAb reaction sample 1 | 63.3 | 0.102 |
| 1C1 WT mAb reaction sample 2 | 59.5 | 0.115 |
| 1C1 WT mAb reaction sample 3 | 59.0 | 0.121 |
| 1C1 K274CP1-NNAA mAb reaction sample 1 | 71.8 | 0.07 |
| 1C1 K274CP1-NNAA mAb reaction sample 2 | 73.4 | 0.06 |
| 1C1 K274CP1-NNAA mAb reaction sample 3 | 70.8 | 0.08 |

[a]Each reaction sample represents an independent experiment.
[b]Size is reported as the number average diameter in nanometers.

Antibody incorporating CP1-NNAA conjugated to maleimide-functionalized nanoparticles via a Diels-Alder reaction.

The invention claimed is:

1. An antibody or binding fragment thereof conjugated to a payload, wherein the conjugation reaction linking the antibody or binding fragment thereof to the payload was via a Diels-Alder reaction between a diene and a dieneophile to form a cyclohexene ring, and wherein the resulting conjugate is represented by formula (IVa):

(IVa)

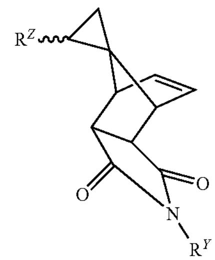

wherein $R^Y$ represents the payload; and $R^Z$ represents the antibody or binding fragment thereof; or wherein the resulting conjugate is represented by formula (IVb):

(IVb)

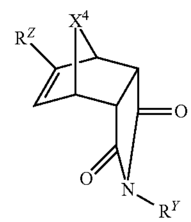

wherein $R^Y$ represents the payload;

$R^Z$ represents the antibody or binding fragment thereof, and $X^4$ represents $—CH_2—$.

2. The antibody or binding fragment thereof conjugated to a payload according to claim 1, wherein the payload is selected from:

a. an auristatin, b. a maytansinoid, c. a toxin, and d. a polymer.

3. A pharmaceutical composition comprising the antibody or binding fragment thereof conjugated to a payload according to claim 1 and a diluent, carrier and/or excipient.

4. A method of treating a patient comprising administering a therapeutically effective amount of the antibody or binding fragment thereof conjugated to a payload according to claim 1.

5. A method of treating a patient comprising administering a therapeutically effective amount of the pharmaceutical composition according to claim 3.

* * * * *